(12) United States Patent
Johnson et al.

(10) Patent No.: US 11,718,660 B2
(45) Date of Patent: Aug. 8, 2023

(54) RECOMBINANT POLYCLONAL PROTEINS TARGETING ZIKA AND METHODS OF USE THEREOF

(71) Applicant: GigaGen, Inc., South San Francisco, CA (US)

(72) Inventors: David Scott Johnson, San Francisco, CA (US); Sheila Keating, South San Francisco, CA (US); Adam Shultz Adler, Belmont, CA (US); Michael Asensio, South San Francisco, CA (US); Kacy Stadtmiller, San Francisco, CA (US); Emily Benzie, San Francisco, CA (US); Ariel Niedecken, Sunnyvale, CA (US); Angelica V. Medina-Cucurella, Mountain View, CA (US); Rena Aviva Mizrahi, Pacifica, CA (US); Yoong Wearn Lim, South San Francisco, CA (US)

(73) Assignee: GigaGen, Inc., San Carlos, CA (US)

( * ) Notice: Subject to any disclaimer, the term of this patent is extended or adjusted under 35 U.S.C. 154(b) by 0 days.

(21) Appl. No.: 17/469,493

(22) Filed: Sep. 8, 2021

(65) Prior Publication Data

US 2022/0064268 A1  Mar. 3, 2022

Related U.S. Application Data

(63) Continuation of application No. PCT/US2021/044523, filed on Aug. 4, 2021.

(60) Provisional application No. 63/061,730, filed on Aug. 5, 2020.

(51) Int. Cl.
  *C07K 14/00* (2006.01)
  *C07K 16/10* (2006.01)
  *A61P 31/14* (2006.01)

(52) U.S. Cl.
  CPC .......... *C07K 16/1081* (2013.01); *A61P 31/14* (2018.01); *C07K 2317/52* (2013.01); *C07K 2317/565* (2013.01); *C07K 2317/622* (2013.01)

(58) Field of Classification Search
  None
  See application file for complete search history.

(56) References Cited

U.S. PATENT DOCUMENTS

| | | |
|---|---|---|
| 2004/0009168 A1 | 1/2004 | Kaisheva et al. |
| 2010/0310558 A1 | 12/2010 | Oleksiewicz et al. |
| 2018/0258422 A1 | 9/2018 | Johnson et al. |

FOREIGN PATENT DOCUMENTS

| | | |
|---|---|---|
| WO | WO 2004/061104 A2 | 7/2004 |
| WO | WO 2009/030237 A2 | 3/2009 |
| WO | WO 2016/200577 A1 | 12/2016 |
| WO | WO 2018/170013 A1 | 9/2018 |
| WO | WO 2020/223573 A2 | 11/2020 |
| WO | WO 2021/253002 A1 | 12/2021 |
| WO | WO 2022/031834 A1 | 2/2022 |

OTHER PUBLICATIONS

Wang et al. (Science Translational Medicine, Dec. 14, 2016, vol. 8, issue 369) (Year: 2016).*
Adler, A.S. et al. "Rare, high-affinity anti-pathogen antibodies from human repertoires, discovered using microfluidics and molecular genomics," mAbs, Sep. 22, 2017, vol. 9, Iss. 8, pp. 1282-1296, XP55784902.
Bendig, M.M., "Humanization of Rodent Monoclonal Antibodies by CDR Grafting," Methods: A Companion to Methods in Enzymology, 1995; 8:83-93.
Bloch et al., "Deployment of convalescent plasma for the prevention and treatment of COVID-19," The Journal of Clinical Investigation, vol. 130, No. 6, Jun. 1, 2020 (Jun. 1, 2020), pp. 2757-2765, XP055815868, GB Issn: 0021-9738, DOI: 10.1172/JCI138745.
Branche, E. et al., "Human Polyclonal Antibodies Prevent Lethal Zika Virus Infection in Mice", Scientific Reports, vol. 9, Article No. 9857, Jul. 8, 2019 (Jul. 8, 2019), pp. 1-12, XP055664845.
Colman. P.M., "Effects of amino acid sequence changes on antibody-antigen interactions," Research in Immunology, 1994, 145:33-36.
Cross, "Searching for a coronavirus cure in the blood," Chemical & Engineering New, Apr. 7, 2020 (Apr. 7, 2020), XP055850922, 7 pages, Retrieved from the Internet: URL:https://cen.acs.org/pharmaceuticals/biologics/Searching-coronavirus-cure-blood/98/i14 [retrieved on Oct. 31, 2021].
Ferrara, F. et al., "Recombinant renewable polyclonal antibodies," mAbs, Jan. 14, 2015, vol. 7, Iss. 1, pp. 32-41, XP55784903.
Frandsen, T.P. et al., "Consistent manufacturing and quality control of a highly complex recombinant polyclonal antibody product for human therapeutic use", Biotechnology and Bioengineering, vol. 108, Issue 9, Sep. 2011, pp. 2171-2181, XP071108999.
GIGAGEN Press Release, "COVID-19 Antibody Therapy: GigaGen Initiates Development of rCIG," Outbreak News Today, Mar. 30, 2020 (Mar. 30, 2020), 4 pages, XP055850665, Retrieved from the Internet: URL:http://outbreaknewstoday.com/covid-19-antibody-therapy-gigagen-initiates-development-of-rcig-21518/ [retrieved on Oct. 12, 2021].
Goldstein et al., "Massively parallel single-cell B-cell receptor sequencing enables rapid discovery of diverse antigen-reactive antibodies," Communications Biology, vol. 2, Article No. 304, Aug. 9, 2019 (Aug. 9, 2019), pp. 1-10, XP055758874, DOI: 10.1038/s42003-019-0551-y.
Hammarström et al., "Development of passive immunity against SARS-CoV-2 for management of immunodeficient patients—a perspective," Journal of Allergy and Clinical Immunology, Elsevier, Amsterdam, NL, vol. 146, No. 1, May 12, 2020 (May 12, 2020), pp. 58-60, P086207336, ISSN: 0091-6749, DOI: 10.1016/J.JACI.2020.04.043 [retrieved on May 12, 2020].

(Continued)

*Primary Examiner* — Meera Natarajan
(74) *Attorney, Agent, or Firm* — Fenwick & West LLP

(57) ABSTRACT

Provided herein are compositions comprising recombinant polyclonal protein (RPP) derived from mammalian plasma cells and plasmablasts. Specifically, RPPs specific to Zika virus are provided. Also provided are the methods of using the RPP for treatment of viral infection and the methods of making the RPPs.

6 Claims, 117 Drawing Sheets

Specification includes a Sequence Listing.

(56) References Cited

OTHER PUBLICATIONS

International Preliminary Report on Patentability, Patent Cooperation Treaty Application No. PCT/US2020/030878, dated Nov. 2, 2021, 8 pages.
International Search Report and Written Opinion, Patent Cooperation Treaty Application No. PCT/US2020/030878, dated Dec. 21, 2020, 13 pages.
International Search Report and Written Opinion, Patent Cooperation Treaty Application No. PCT/US2021/037232, dated Nov. 8, 2021, 16 pages.
International Search Report and Written Opinion, Patent Cooperation Treaty Application No. PCT/US2021/044523, dated Nov. 18, 2021, 19 pages.
Keating, S.M. et al., "Capturing and Recreating Diverse Antibody Repertoires as Multivalent Recombinant Polyclonal Antibody Drugs," bioRxiv, preprint, Aug. 6, 2020, 78 pages.
Keating, S.M. et al., "Generation of recombinant hyperimmune globulins from diverse B-cell repertoires," nature biotechnology, vol. 39, No. 8, Aug. 2021, pp. 989-999, XP037534475.
Khantasup, K. et al., "Design and Generation of Humanized Single-chain Fv Derived from Mouse Hybridoma for Potential Targeting Application," *Monoclonal Antibodies in Immunodiagnosis and Immunotherapy*, 2015, 34(6): 404-417.
Lou, Y. et al., "Cross-neutralization antibodies against SARS-CoV-2 and RBD mutations from convalescent patient antibody libraries," bioRxiv, posted on Jun. 6, 2020, 32 pages.
Murphy, C et al., "Enhancing recombinant antibody performance by optimally engineering its format," *Journal of Immunological Methods*, vol. 463, Dec. 2018, pp. 127-133.
Non-final Office Action, U.S. Appl. No. 17/386,504, filed Mar. 2, 2022, 27 pages.
Paul, W.E. (ed), Fundamental Immunology, 3rd Edition, Chapter 9, Structure and Function of Immunoglobulins, 1993, pp. 292-295.
Ravichandran, S. et al., Antibody repertoire induced by SARS-CoV-2 spike protein immunogens, bioRxiv, posted on May 13, 2020, 34 pages.
Reason, D.C et al. "Human Fab Fragments Specific for the Haemophilus influenzae b Polysaccharide Isolated from a Bacteriophage Combinatorial Library Use Variable Region Gene Combinations and Express an Idiotype That Mirrors In Vivo Expression," *Infection and Immunity*, Jan. 1997, vol. 65, No. 1, pp. 261-266.
Rudikoff, S. et al., "Single amino acid substitution altering antigen-binding specificity," Proc. Natl. Acad. Sci. USA, 1982, 79(6):1979-1983.
Shen et al., "Treatment of 5 Critically Ill Patients With COVID-19 With Convalescent Plasma," JAMA the Journal of the American Medical Association, vol. 323, No. 16, Mar. 27, 2020 (Mar. 27, 2020), pp. 1582-1589, XP055725009, US ISSN: 0098-7484, DOI: 10.1001/jama.2020.4783.
Sheridan, "Convalescent serum lines up as first-choice treatment for coronavirus," Nature Biotechnology, Gale Group Inc, New York, vol. 38, No. 6, May 1, 2020 (May 1, 2020), pp. 655-658, XP037167671, ISSN: 1087-0156, DOI: 10.1038/D41587-020-00011-1 [retrieved on May 1, 2020].
Tanno et al. "A facile technology for the high-throughput sequencing of the paired VH:VL and TCR:TCRα repertoires," *Science Advances*, Apr. 22, 2020, vol. 6, Issue 17, 8 pages, XP55851688, Retrieved from the Internet: URL:https://www.science.org/doi/pdf/10.1126/sciadv.aay9093 [retrieved on Oct. 15, 2021].
Tiberghien et al., "Collecting and evaluating convalescent plasma for COVID-19 treatment why and how?", Vox Sanguinis, vol. 115, No. 6, May 3, 2020 (May 3, 2020), pp. 488-494, XP055815870, CH ISSN: 0042-9007, DOI: 10.1111/vox.12926.
World Health Organization, "Landscape analysis of therapeutics as Feb. 17, 2020," Feb. 25, 2020 (Feb. 25, 2020), XP055809736, Retrieved from the Internet: URL:https://web.archive.org/web/20200225223659/https://www.who.int/blueprint/priority-diseases/key-action/Table_of_therapeutics_Appendix_17022020.pdf?ua=1, pp. 26,28.
Yuan, A.Q. et al., Isolation of and Characterization of Neutralizing Antibodies to COVID-19 from a Large Human Naïve scFv Phage Display Library, bioRxiv, posted on May 19, 2020, 15 pages.
Chi, X., et al., "A neutralizing human antibody binds to the N-terminal domain of the Spike protein of SARS-CoV-2," *Science*, Jun. 22, 2020, vol. 369, Issue 6504, pp. 650-655.
Partial Supplementary European Search Report, European Patent Application No. 20799387.7, dated Jan. 4, 2023, 33 pages.
United States Office Action, U.S. Appl. No. 17/386,504, filed Dec. 7, 2022, 22 pages.
Wang, B., et al., "Functional Interrogation and Mining of Natively-Paired Human VH:VL Antibody Repertoires," *Nature Biotechnology*, author manuscript, Feb. 2018; 36(2): 152-155, 14 pages.

\* cited by examiner

| GigaGen donor ID | Race | Sex | Age | Symptoms | Date of symptoms onset | Days between symptoms onset and blood draw | Presumed/ Confirmed | Spike antigen EC50 (mg/ml) | Spike antigen peak OD signal | RBD antigen EC50 (mg/ml) | RBD antigen peak OD signal | Library ID | PBMC CoV-2 RNA qPCR |
|---|---|---|---|---|---|---|---|---|---|---|---|---|---|
| CSS-1902 | AA | Male | 67 | Fever, SOB | 2/28/20 | 32 | Confirmed | 0.0056 | 3.15 | 0.039 | 2.46 | Library 1 | Negative |
| CSS-1905 | White | Male | 71 | Fever, Cough, SOB | 3/16/20 | 15 | Presumed | 0.019 | 3.22 | 0.12 | 2.34 | Library 1 | Negative |
| CSS-1907 | AA | Female | 66 | Fever, Cough | 3/14/20 | 17 | Presumed | 0.063 | 2.98 | 0.091 | 1.41 | Library 2 | Negative |
| CSS-1911 | White | Female | 61 | Fever, ST, SOB | 3/9/20 | 22 | Presumed | 0.10 | 2.80 | 0.13 | 0.75 | Library 2 | Negative |
| CSS-1921 | White | Female | 30 | Fever, ST, Cough, SOB | 3/17/20 | 15 | Confirmed | 0.021 | 2.95 | 0.11 | 1.81 | Library 3 | Negative |
| CSS-1920 | White | Female | 57 | Fever, Cough, SOB | 3/16/20 | 16 | Confirmed | 0.022 | 2.81 | 0.066 | 1.52 | Library 3 | Negative |
| CSS-1928 | White | Female | 63 | Fever, Cough | 3/14/20 | 19 | Presumed | 0.025 | 2.95 | 0.076 | 1.96 | Library 4 | Negative |
| CSS-1924 | White | Female | 31 | Fever, ST, Cough, Pneumonia | 3/21/20 | 12 | Confirmed | 0.16 | 2.63 | 0.23 | 2.30 | Library 4 | Negative |
| CSS-1944 | White | Female | 49 | ST, Cough, SOB | 3/15/20 | 24 | Confirmed | 0.014 | 3.21 | 0.053 | 2.17 | Library 5 | Negative |
| CSS-1943 | White | Female | 52 | Fever, ST, Cough, SOB | 3/16/20 | 23 | Confirmed | 0.014 | 3.15 | 0.067 | 1.85 | Library 5 | Negative |
| CSS-1937 | White | Female | 35 | Fever, ST, Cough, SOB | 3/17/20 | 21 | Confirmed | 0.009 | 3.17 | 0.027 | 1.71 | Library 6 | Negative |
| CSS-1936 | White | Female | 23 | Fever, Cough, SOB | 3/7/20 | 31 | Confirmed | 0.011 | 3.16 | 0.088 | 2.01 | Library 6 | Negative |
| CSS-1901 | White | Male | 67 | Fever, Cough | 3/15/20 | 16 | Confirmed | 0.010 | 3.09 | 0.085 | 2.37 | Library 7 | Negative |
| CSS-1940 | White | Female | 40 | Fever, Cough | 3/18/20 | 21 | Confirmed | 0.012 | 3.07 | 0.057 | 1.99 | Library 7 | Negative |

FIG. 3A

| GigaGen donor ID | Race | Sex | Age | Symptoms | Date of symptoms onset | Days between symptoms onset and blood draw | Presumed/ Confirmed | Spike antigen EC50 (mg/ml) | Spike antigen peak OD signal | RBD antigen EC50 (mg/ml) | RBD antigen peak OD signal | Library ID | PBMC CoV-2 RNA qPCR |
|---|---|---|---|---|---|---|---|---|---|---|---|---|---|
| CSS-1939 | White | Female | 24 | Fever, ST, Cough, SOB | 3/8/20 | 30 | Confirmed | 0.037 | 3.10 | 0.073 | 1.37 | Library 8 | Negative |
| CSS-1949 | White | Male | 47 | Fever, Cough | 3/21/20 | 19 | Confirmed | 0.13 | 2.79 | 0.32 | 2.32 | Library 8 | Negative |
| CSS-1945 | White | Female | 31 | Fever, ST, Cough, SOB | 3/20/20 | 19 | Confirmed | 0.051 | 3.09 | 0.15 | 1.03 | | |
| CSS-1931 | White | Female | 35 | Fever, ST, Cough, SOB | 3/24/20 | 13 | Confirmed | 0.11 | 2.45 | 0.27 | 1.22 | | |
| CSS-1933 | White | Female | 43 | Fever, Cough | 2/25/20 | 42 | Confirmed | 0.13 | 3.23 | 0.27 | 1.16 | | |
| CSS-1932 | White | Female | 33 | Fever, SOB | 3/18/20 | 20 | Confirmed | 0.13 | 3.09 | 0.11 | 1.05 | | |
| CSS-1935 | White | Female | 45 | ST, Cough, SOB | 3/22/20 | 16 | Confirmed | 0.16 | 3.07 | 0.14 | 1.22 | | |
| CSS-1948 | White | Female | 45 | Fever, Cough, SOB | 3/25/20 | 15 | Confirmed | 0.17 | 2.64 | 0.091 | 0.97 | | |
| CSS-1938 | White | Female | 37 | Fever, ST, Cough, SOB | 3/22/20 | 16 | Confirmed | 0.20 | 3.20 | 0.25 | 0.82 | | |
| CSS-1929 | AA | Male | 49 | Fever, Cough, SOB | 2/28/20 | 34 | Presumed | 0.23 | 0.92 | 0.041 | 1.31 | | |
| CSS-1922 | White | Male | 54 | Fever, Cough, SOB | 2/28/20 | 34 | Presumed | 0.24 | 0.34 | 0.14 | 0.45 | | |
| CSS-1914 | White | Female | 65 | Fever, Cough, SOB | 2/26/20 | 35 | Presumed | 0.37 | 1.54 | 0.39 | 2.76 | | |
| CSS-1925 | White | Male | 63 | Fever, Cough, SOB, ST | 3/10/20 | 23 | Presumed | 0.65 | 0.68 | 0.17 | 0.75 | | |
| CSS-1946 | White | Female | 50 | ST, Cough | 3/19/20 | 21 | Confirmed | 0.67 | 2.50 | 0.69 | 1.66 | | |
| CSS-1930 | White | Female | 47 | Fever, Cough | 3/10/20 | 23 | Presumed | 0.69 | 0.45 | 1.29 | 0.94 | | |

FIG. 3B

| GigaGen donor ID | Race | Sex | Age | Symptoms | Date of symptoms onset | Days between symptoms onset and blood draw | Presumed/ Confirmed | Spike antigen EC50 (mg/ml) | Spike antigen peak OD signal | RBD antigen EC50 (mg/ml) | RBD antigen peak OD signal | Library ID | PBMC CoV-2 RNA qPCR |
|---|---|---|---|---|---|---|---|---|---|---|---|---|---|
| CSS-1934 | White | Female | 42 | Fever, ST, Cough | 3/21/20 | 17 | Confirmed | 0.75 | 3.17 | 0.74 | 1.11 | | |
| CSS-1926 | White | Female | 59 | Fever, Cough, SOB, ST | 3/8/20 | 25 | Presumed | 0.77 | 0.55 | 0.70 | 0.80 | | |
| CSS-1915 | White | Male | 59 | Fever, ST, SOB | 3/11/20 | 21 | Presumed | 0.83 | 0.81 | 0.61 | 0.85 | | |
| CSS-1941 | White | Female | 69 | ST, Cough | 3/11/20 | 28 | Confirmed | 0.91 | 2.93 | 0.55 | 0.94 | | |
| CSS-1917 | White | Male | 67 | Fever, Cough | 3/10/20 | 22 | Presumed | 0.91 | 0.64 | 0.69 | 0.77 | | |
| CSS-1904 | White | Female | 20 | Fever, ST, Cough | 3/11/20 | 20 | Confirmed | 0.96 | 0.64 | 0.63 | 0.86 | | |
| CSS-1916 | White | Male | 70 | Fever, SOB | 2/27/20 | 34 | Presumed | 1.00 | 0.69 | 0.15 | 1.00 | | |
| CSS-1947 | AA | Female | 52 | Fever, Cough | 3/21/20 | 19 | Confirmed | 1.25 | 2.68 | 0.81 | 0.99 | | |
| CSS-1918 | White | Female | 59 | Fever, Cough, SOB | 3/2/20 | 30 | Presumed | 1.32 | 1.55 | 0.38 | 0.91 | | |
| CSS-1923 | White | Female | 57 | Fever, Cough | 2/25/20 | 37 | Presumed | 1.33 | 0.62 | 0.92 | 1.35 | | |
| CSS-1919 | White | Female | 53 | Fever, ST, SOB | 3/13/20 | 19 | Confirmed | 1.34 | 0.80 | 0.30 | 0.76 | | |
| CSS-1913 | White | Female | 57 | Fever, Cough | 3/5/20 | 26 | Presumed | 1.47 | 1.69 | 0.23 | 0.88 | | |
| CSS-1927 | AA | Female | 55 | Cough, ST | 3/2/20 | 31 | Presumed | 1.60 | 0.92 | 0.72 | 1.18 | | |
| CSS-1909 | White | Female | 70 | Fever, Cough, SOB | 2/25/20 | 35 | Presumed | 1.88 | 0.92 | 0.13 | 0.75 | | |
| CSS-1912 | White | Female | 46 | Fever, Cough, SOB | 3/8/20 | 23 | Confirmed | 2.20 | 0.76 | 0.10 | 0.67 | | |
| CSS-1906 | White | Male | 58 | Fever, ST, SOB, Cough | 2/25/20 | 35 | Presumed | 2.59 | 1.28 | 1.46 | 1.31 | | |
| CSS-1908 | White | Female | 57 | Fever, Cough, SOB | 2/24/20 | 36 | Presumed | 2.60 | 0.82 | 0.46 | 0.72 | | |

FIG. 3C

| GigaGen donor ID | Race | Sex | Age | Symptoms | Date of symptoms onset | Days between symptoms onset and blood draw | Presumed/Confirmed | Spike antigen EC50 (mg/ml) | Spike antigen peak OD signal | RBD antigen EC50 (mg/ml) | RBD antigen peak OD signal | Library ID | PBMC CoV-2 RNA qPCR |
|---|---|---|---|---|---|---|---|---|---|---|---|---|---|
| CSS-1910 | White | Female | 25 | Fever, ST, Cough, SOB | 3/4/20 | 27 | Presumed | 2.84 | 1.27 | 1.12 | 1.23 | | |
| CSS-1942 | White | Female | 39 | Fever, Cough | 3/24/20 | 15 | Confirmed | 2.89 | 2.03 | 1.88 | 2.31 | | |
| CSS-1903 | White | Female | 52 | Fever, Cough, SOB, Fatigue | 3/1/20 | 30 | Presumed | 3.47 | 0.84 | 1.25 | 0.99 | | |
| CSS-1900 | White | Female | 69 | Fever, Cough | 3/6/20 | 25 | Presumed | 9.94 | 0.73 | 3.11 | 1.00 | | |
| GAMUNEX C IVIG | n/a | n/a | n/a | n/a | n/a | n/a | n/a | 1.41 | 1.99 | 1.27 | 2.26 | | |

FIG. 3D

| Assay | Category | Requirement |
| --- | --- | --- |
| Anti-HLA | Safety | Comparable to or better than plasma-derived IVIG |
| Agglutination | Safety | Comparable to or better than plasma-derived IVIG |
| Human tissue microarrays | Safety | No detectable binding at physiologically relevant concentration |
| Anti-complement | Safety | Comparable to or better than plasma-derived IVIG |
| Spike:ACE2-inhibition ELISA | Potency | >5,000-fold better than plasma-derived IVIG |
| Live virus neutralization | Potency | >5,000-fold better than plasma-derived IVIG |
| Pseudotype virus neutralization | Potency | >5,000-fold better than plasma-derived IVIG |
| Antibody RNA-seq | Diversity | >1,000 antibodies |

FIG. 5

| Sample / Library | S1 binding $EC_{50}$ (mg/ml) | S1 binding fold over serum | RBD binding $EC_{50}$ (mg/ml) | RBD binding fold over serum | Plate-based neutralization $IC_{50}$ (mg/ml) | Plate-based neutralization over serum | Pseudotype neutralization $IC_{50}$ (mg/ml) | Pseudotype neutralization over serum | Anti-RBC (agglutination) | Anti-HLA | % RBD-specific scFv (1st yeast sort) | # antibodies (2nd yeast sort) |
|---|---|---|---|---|---|---|---|---|---|---|---|---|
| GAMUNEX-C IVIG | 1.41 | --- | 1.27 | --- | 114 | --- | No neutralization | --- | --- | --- | --- | --- |
| SARS-CoV-2 mAb | 0.00012 | --- | 0.0001 | --- | 0.75 | --- | Not tested | --- | --- | --- | --- | --- |
| Library 1 | 0.00017 | 147.1 | 0.00013 | 192.3 | 0.0026 | 269.2 | 0.00044 | 36.4 | Negative | Negative | 1.02% | 149 |
| Library 1 serum pool | 0.025 | 1.0 | 0.025 | 1.0 | 0.7 | 1.0 | 0.016 | 1.0 | --- | --- | --- | --- |
| Library 2 | 0.00037 | 297.3 | 0.00018 | 722.2 | 0.0053 | 241.5 | 0.0044 | 206.8 | Negative | Negative | 0.57% | 167 |
| Library 2 serum pool | 0.11 | 1.0 | 0.13 | 1.0 | 1.28 | 1.0 | 0.91 | 1.0 | --- | --- | --- | --- |
| Library 3 | 0.00016 | 337.5 | 0.000047 | 723.4 | 0.0021 | 128.6 | 0.0018 | 31.1 | Negative | In progress | 1.60% | 123 |
| Library 3 serum pool | 0.054 | 1.0 | 0.034 | 1.0 | 0.27 | 1.0 | 0.056 | 1.0 | --- | --- | --- | --- |
| Library 4 | 0.00014 | 392.9 | 0.00015 | 366.7 | 0.0016 | 1500.0 | 0.0011 | 32.7 | Negative | negative | 0.42% | 209 |
| Library 4 serum pool | 0.055 | 1.0 | 0.055 | 1.0 | 2.4 | 1.0 | 0.036 | 1.0 | --- | --- | --- | --- |
| Library 5 | 0.00019 | 263.2 | 0.000061 | 344.3 | 0.0017 | 164.7 | 0.00082 | 60.0 | Negative | In progress | 2.29% | 140 |
| Library 5 serum pool | 0.05 | 1.0 | 0.021 | 1.0 | 0.28 | 1.0 | 0.049 | 1.0 | --- | --- | --- | --- |
| Library 6 | 0.00013 | 307.7 | 0.000054 | 314.8 | 0.0018 | 194.4 | 0.00034 | 115.3 | Negative | In progress | 0.95% | 108 |
| Library 6 serum pool | 0.04 | 1.0 | 0.017 | 1.0 | 0.35 | 1.0 | 0.039 | 1.0 | --- | --- | --- | --- |
| Library 7 | 0.00011 | 290.9 | 0.000044 | 218.2 | 0.0023 | 139.1 | 0.00032 | 74.4 | Negative | In progress | 1.37% | 83 |
| Library 7 serum pool | 0.032 | 1.0 | 0.0096 | 1.0 | 0.32 | 1.0 | 0.024 | 1.0 | --- | --- | --- | --- |
| Library 8 | 0.000038 | 1394.7 | 0.000027 | 592.6 | 0.00014 | 2500.0 | 0.00017 | 361.4 | Negative | In progress | 0.88% | 122 |
| Library 8 serum pool | 0.053 | 1.0 | 0.016 | 1.0 | 0.35 | 1.0 | 0.061 | 1.0 | --- | --- | --- | --- |

FIG. 6

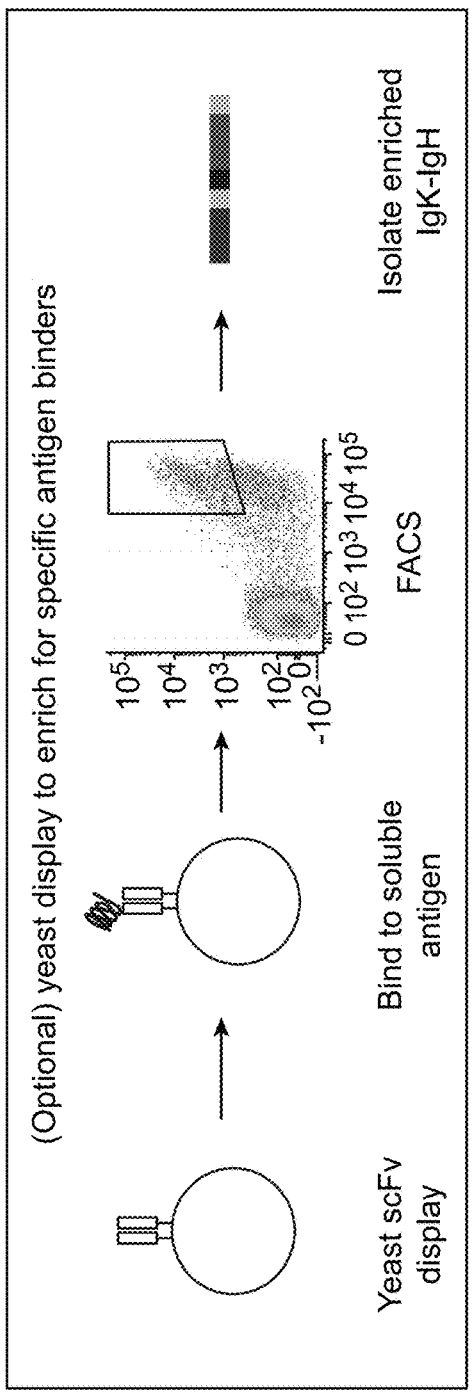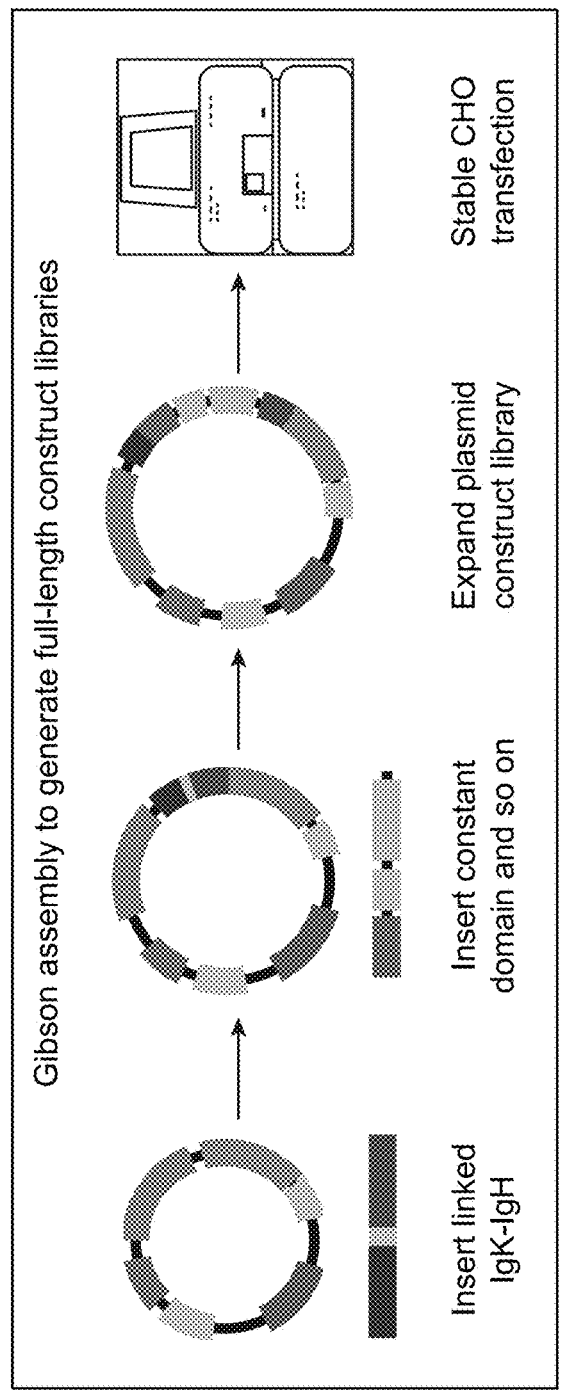

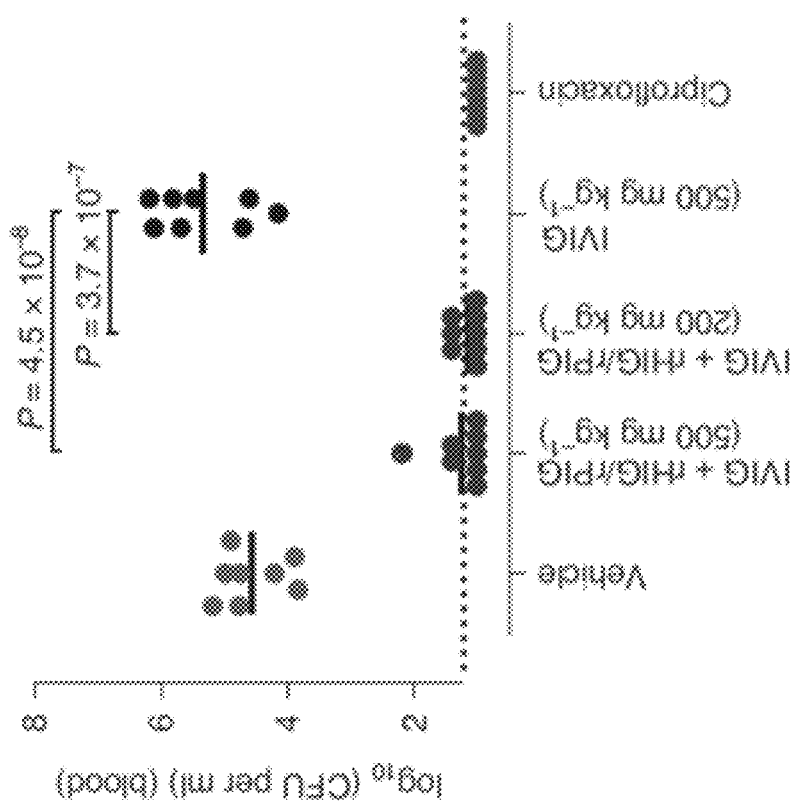
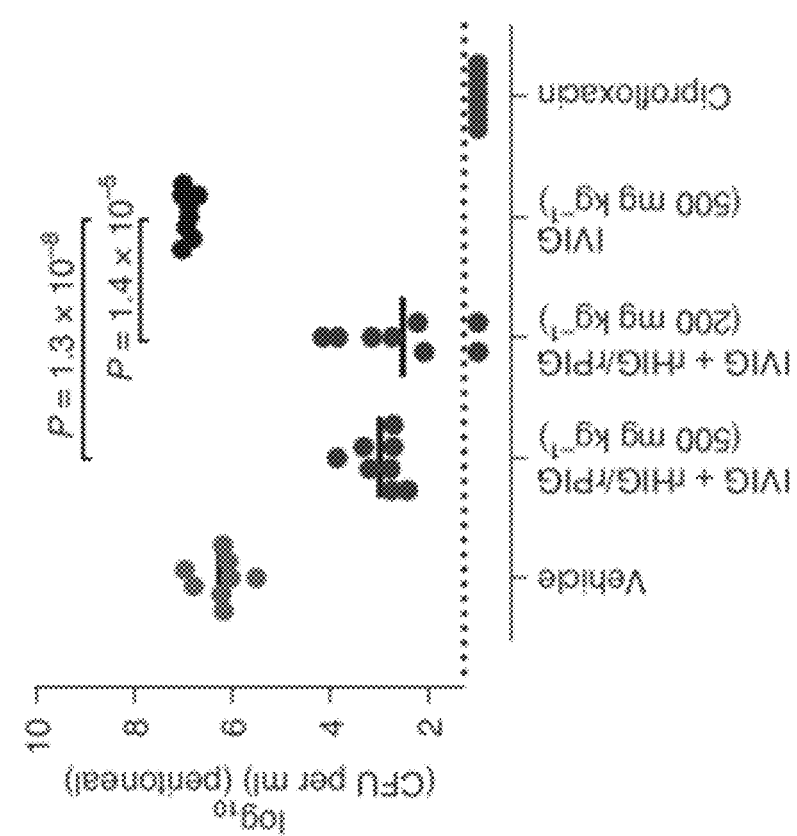
FIG. 10E

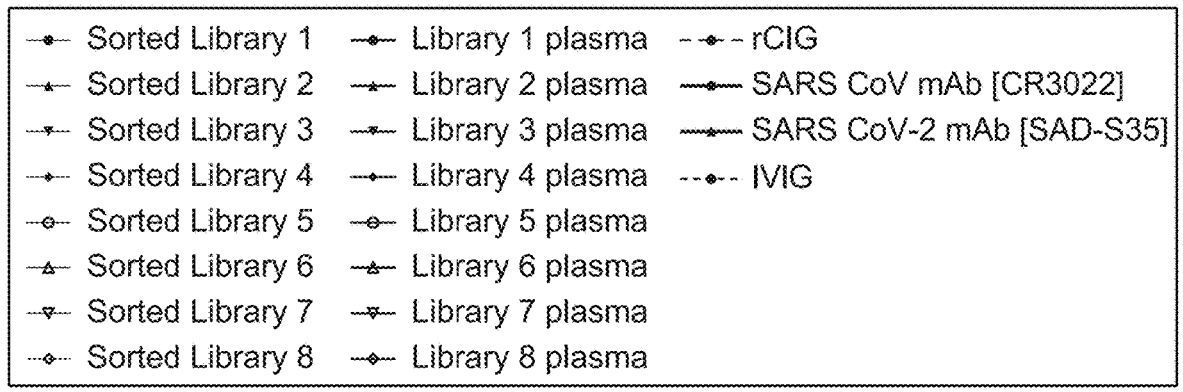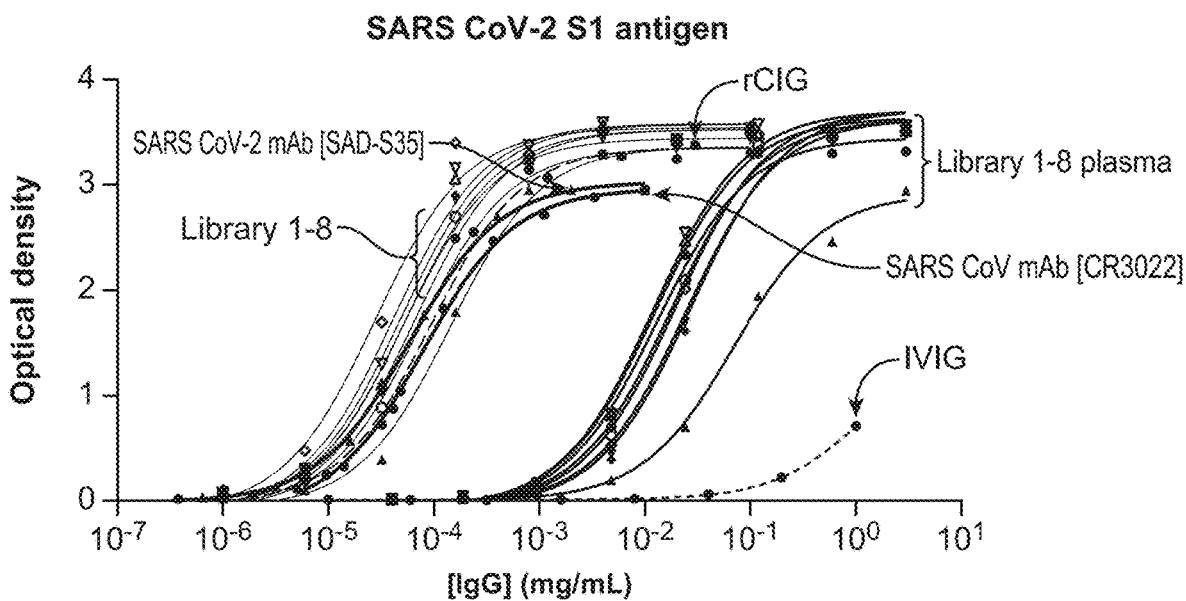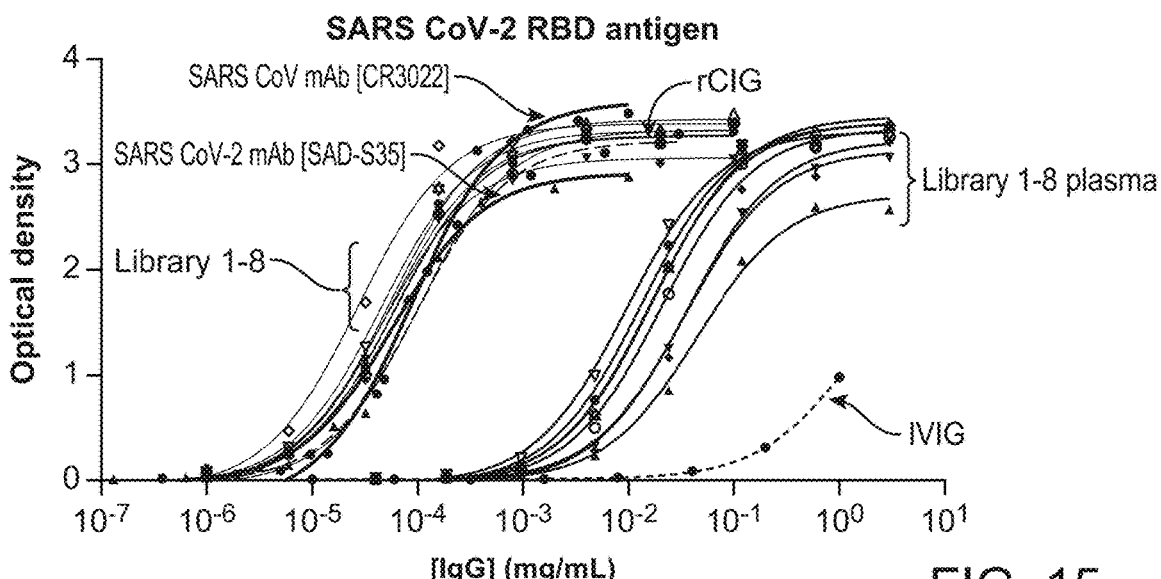
FIG. 15

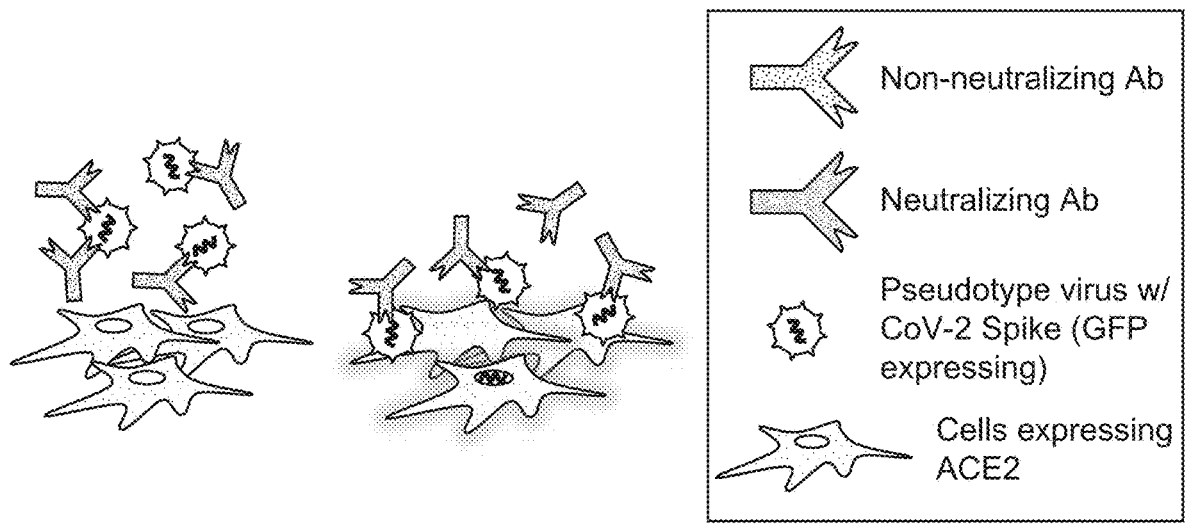
FIG. 17A
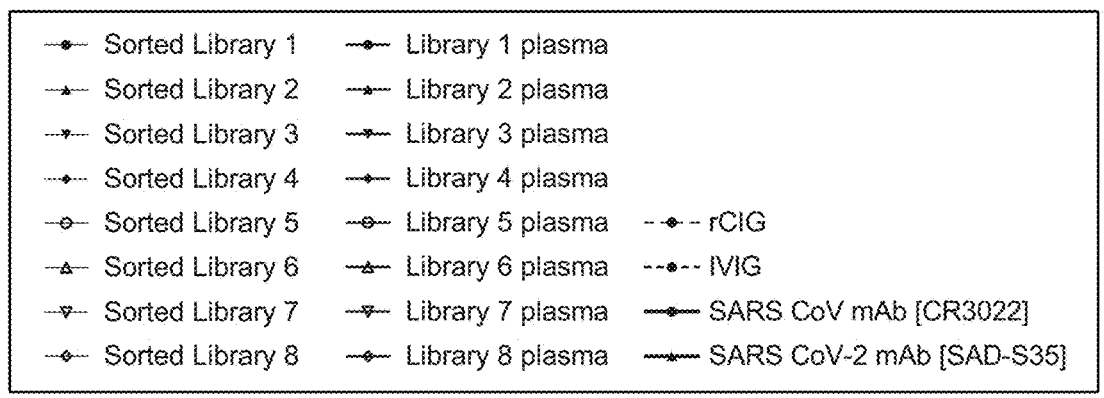
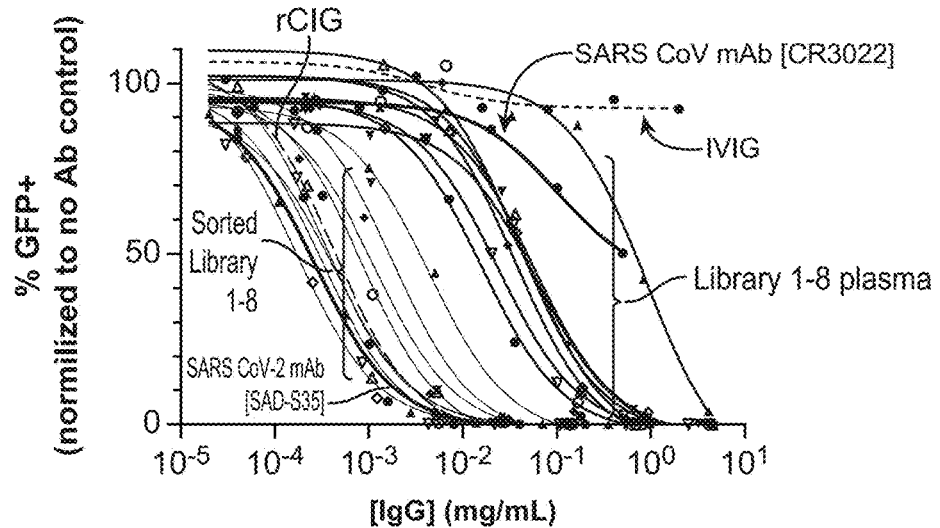
FIG. 17B

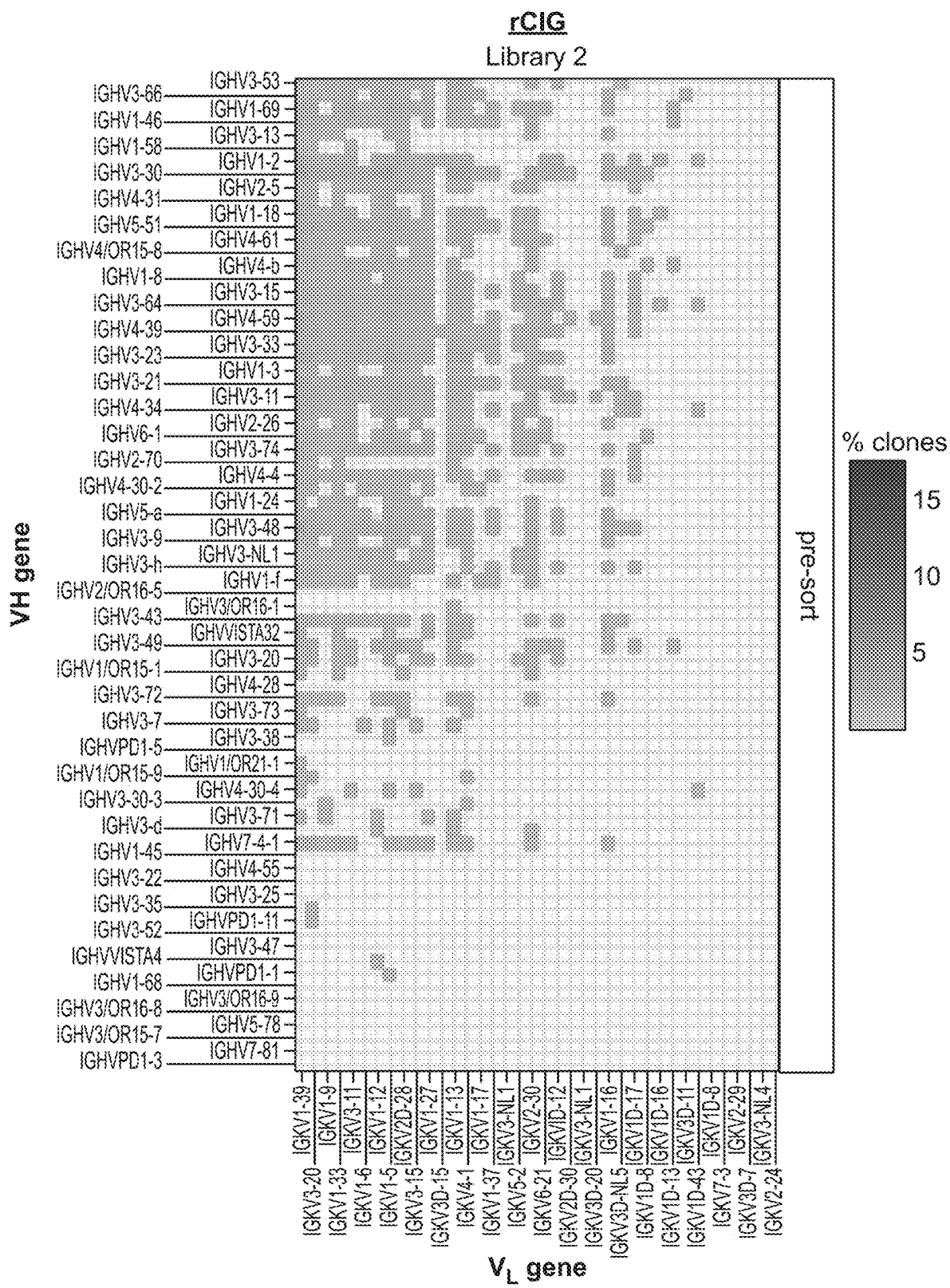
FIG. 21A (Cont. 1)

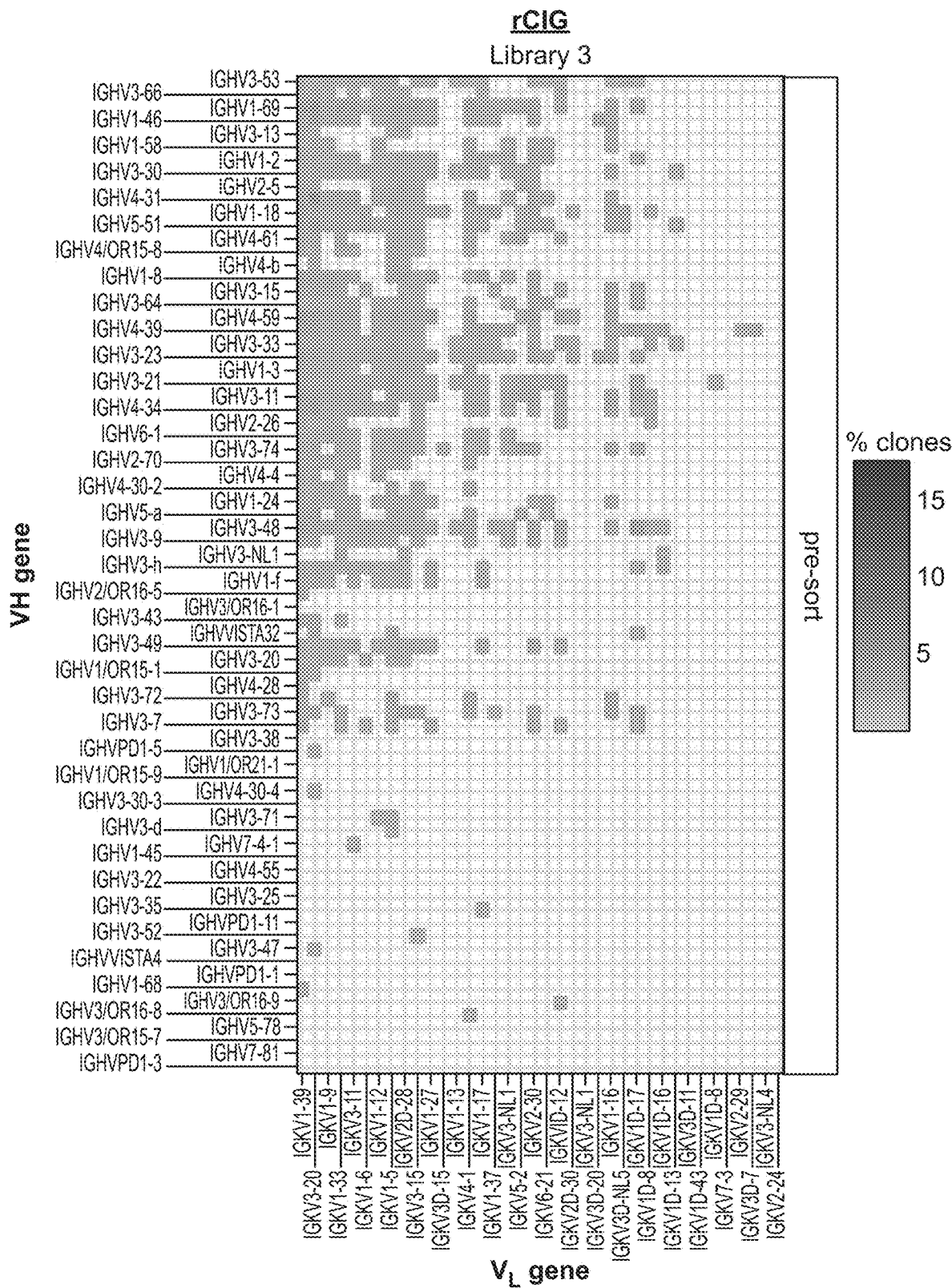
FIG. 21A (Cont. 2)

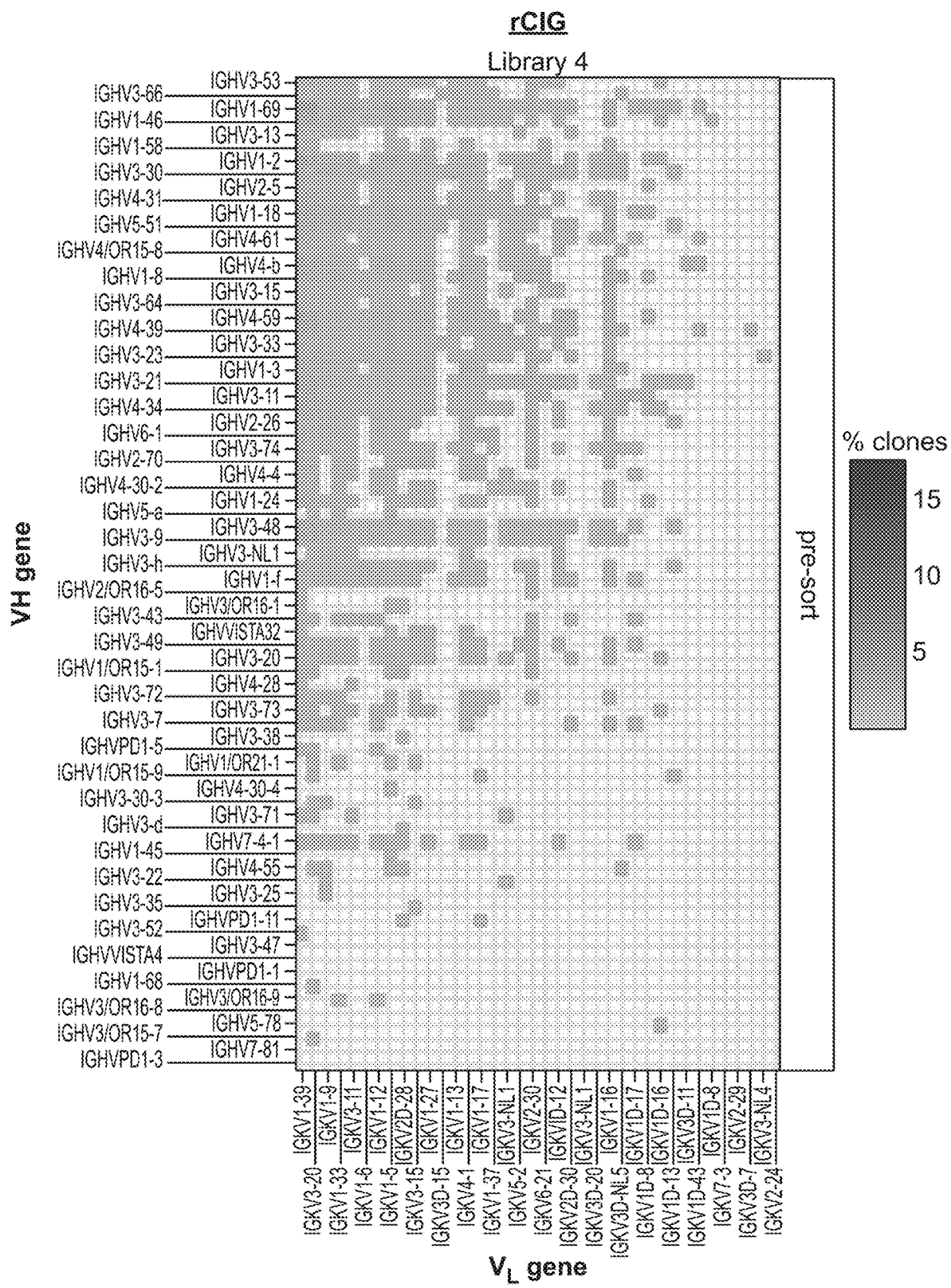
FIG. 21A (Cont. 3)

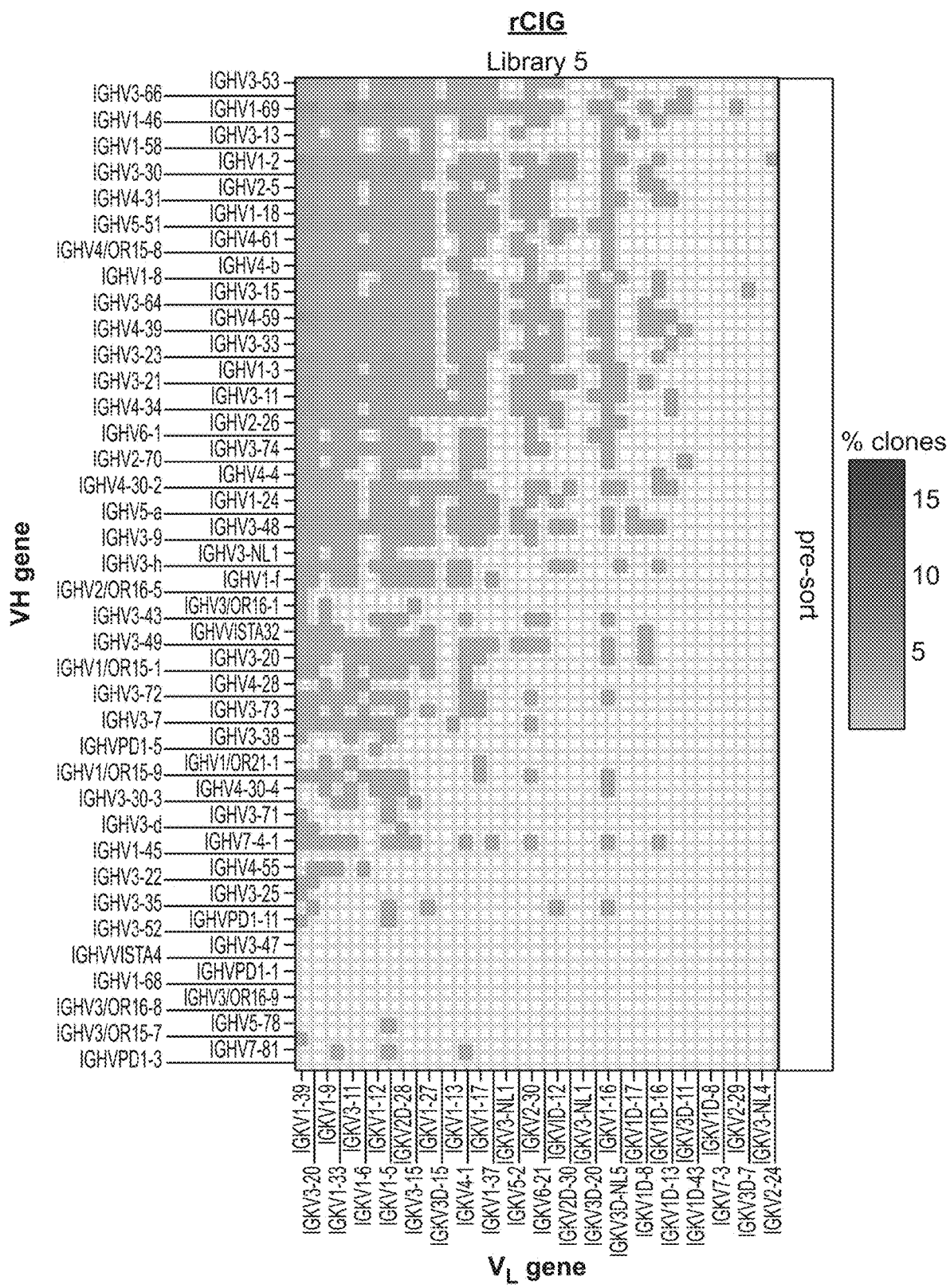
FIG. 21A (Cont. 4)

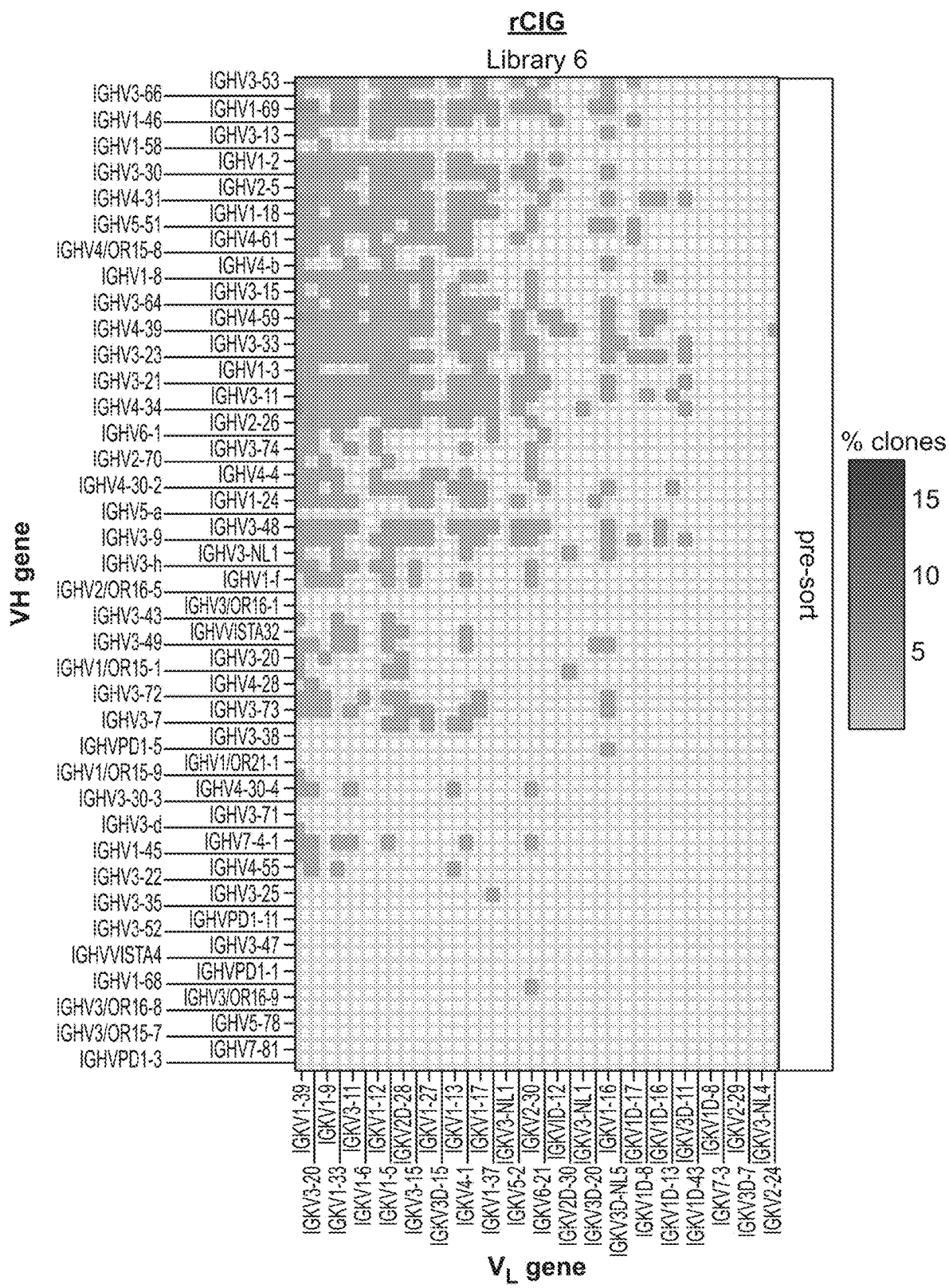
FIG. 21A (Cont. 5)

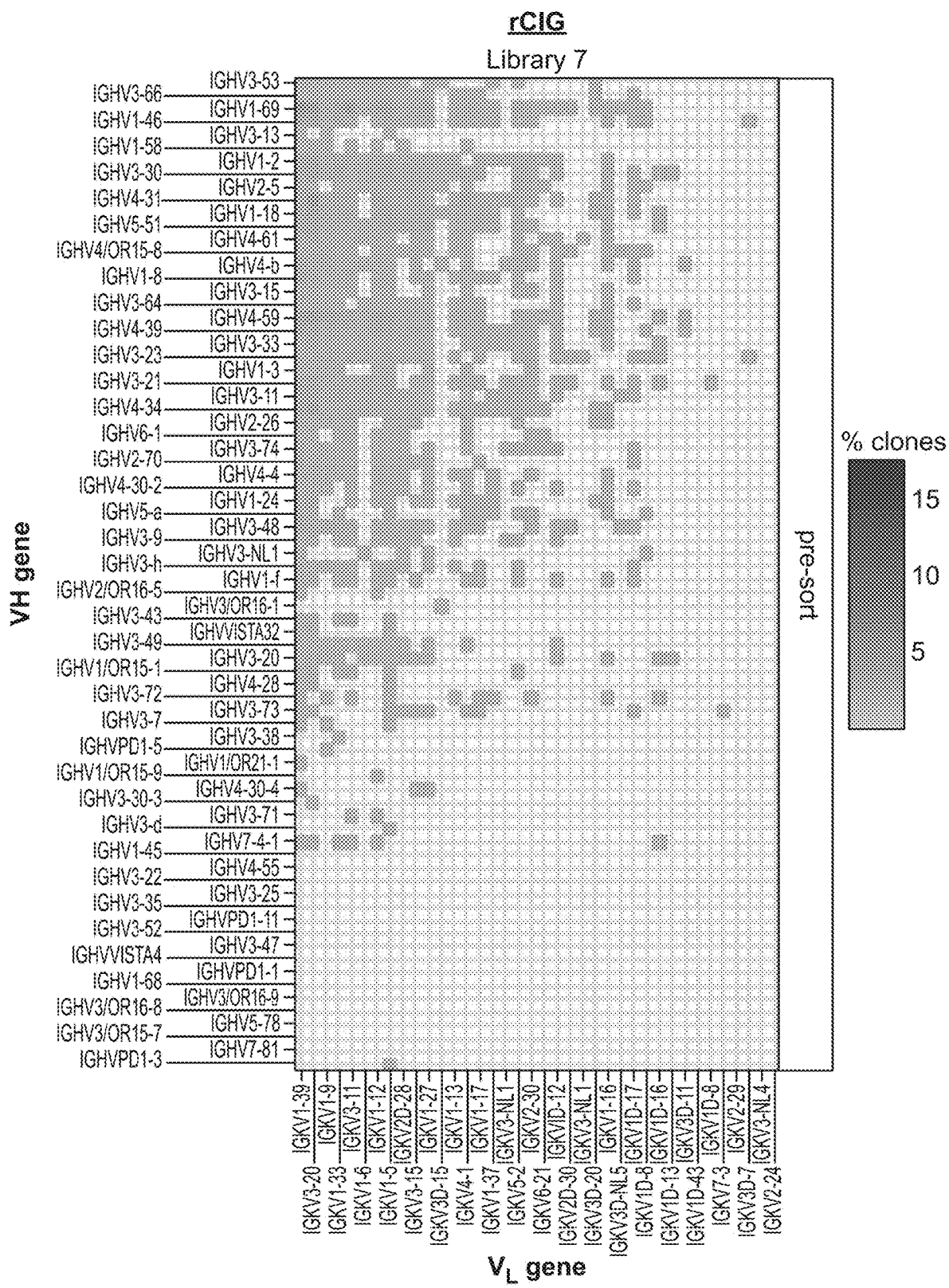
FIG. 21A (Cont. 6)

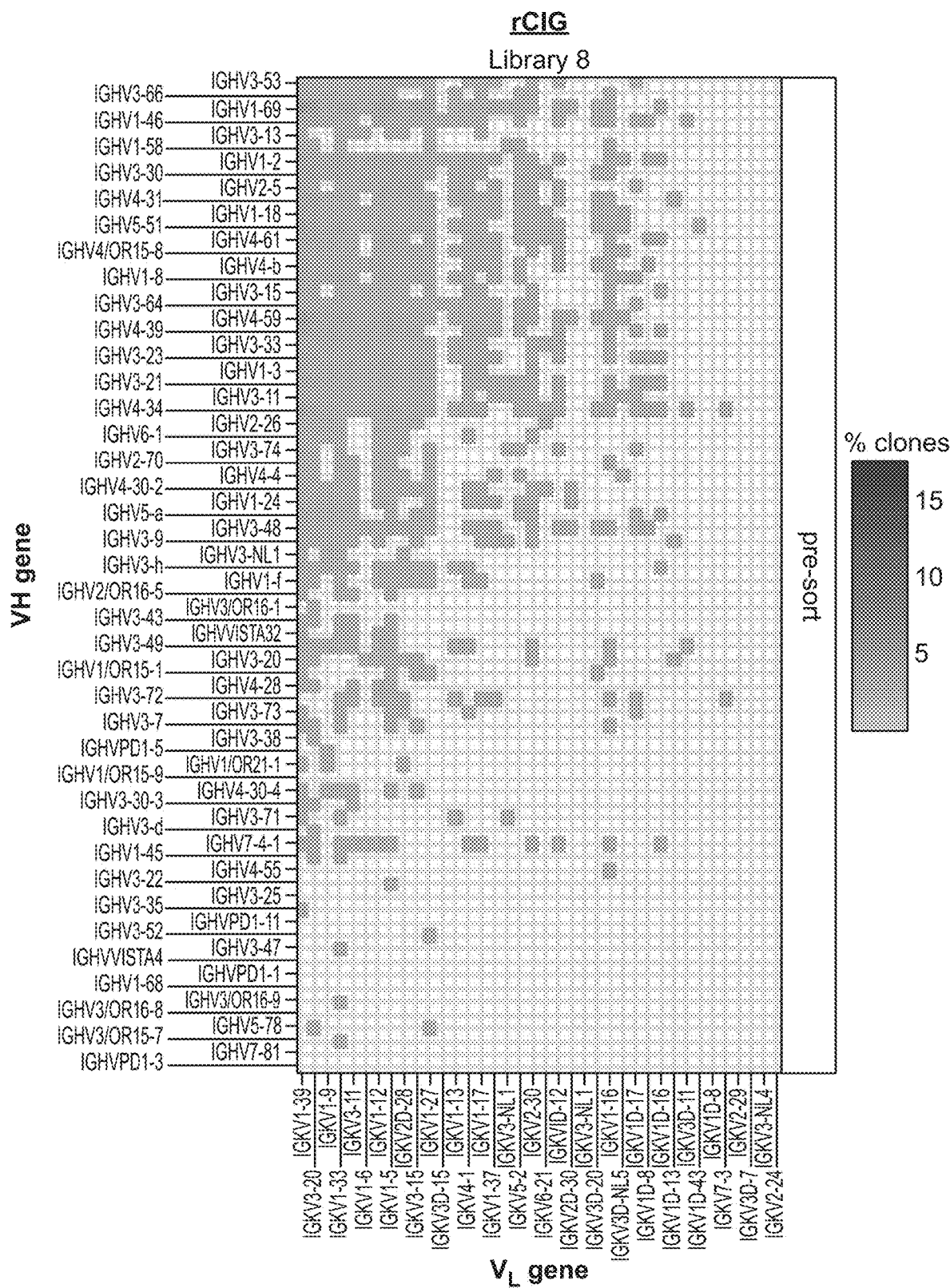
FIG. 21A (Cont. 7)

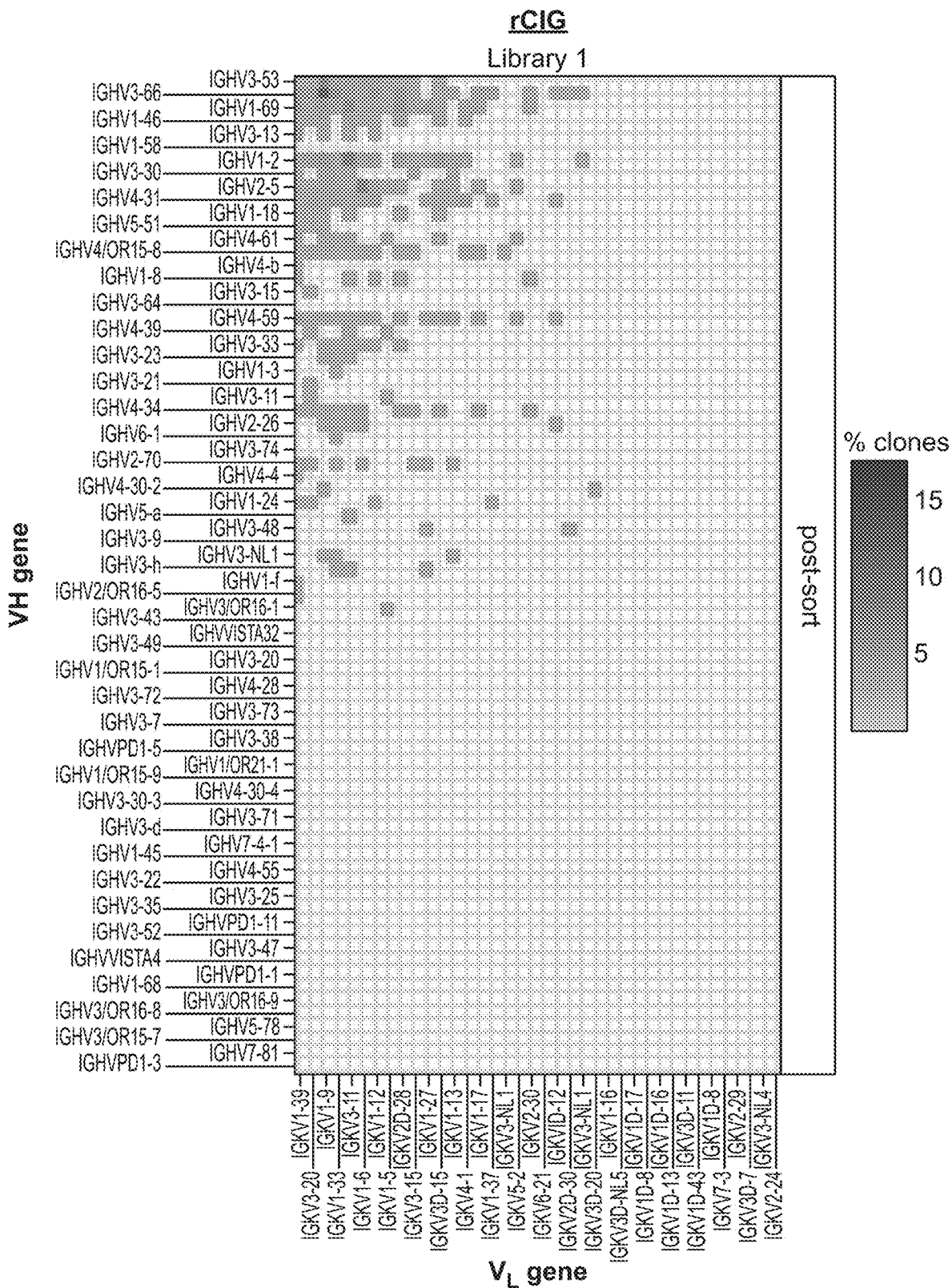
FIG. 21A (Cont. 8)

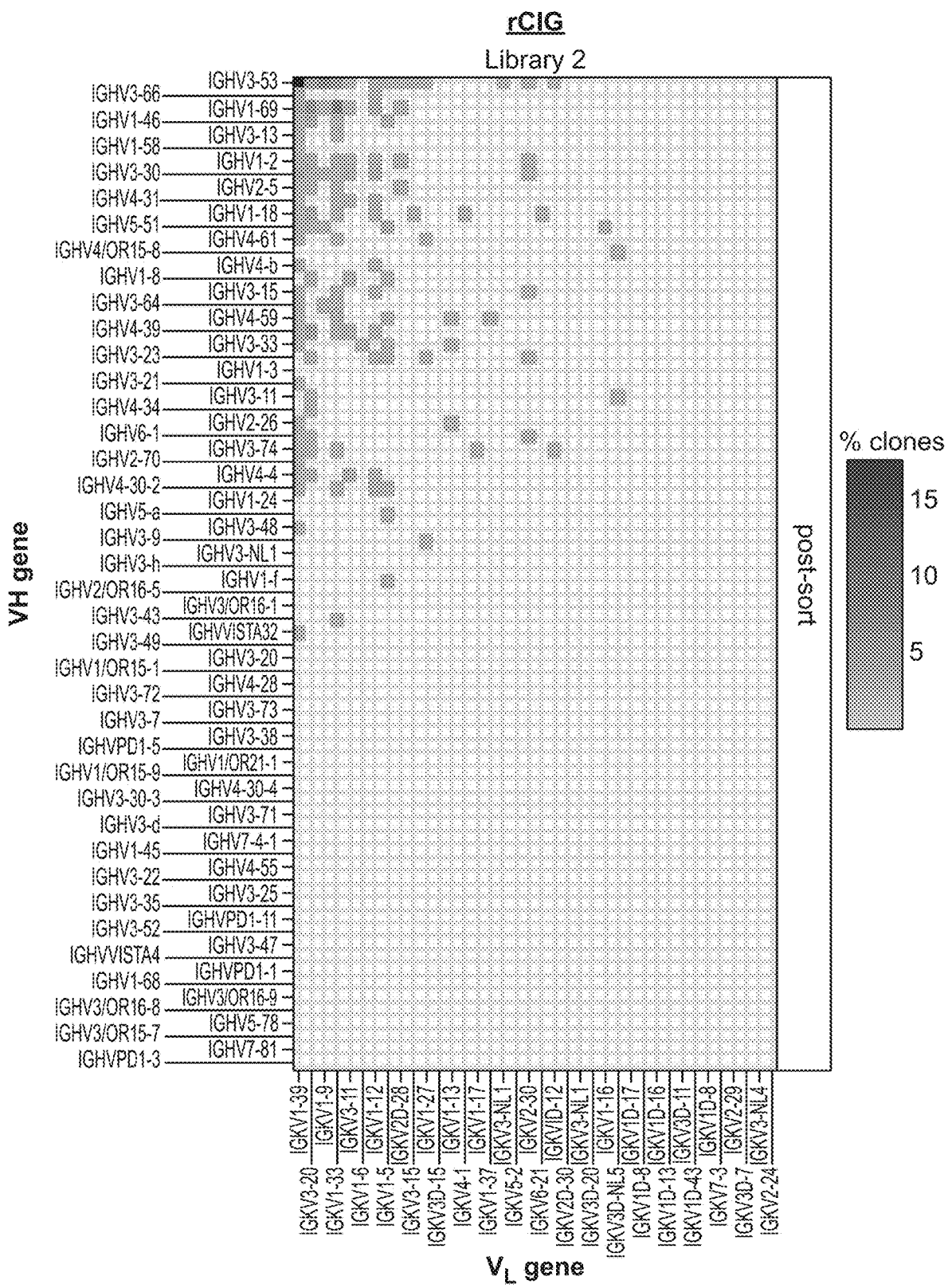
FIG. 21A (Cont. 9)

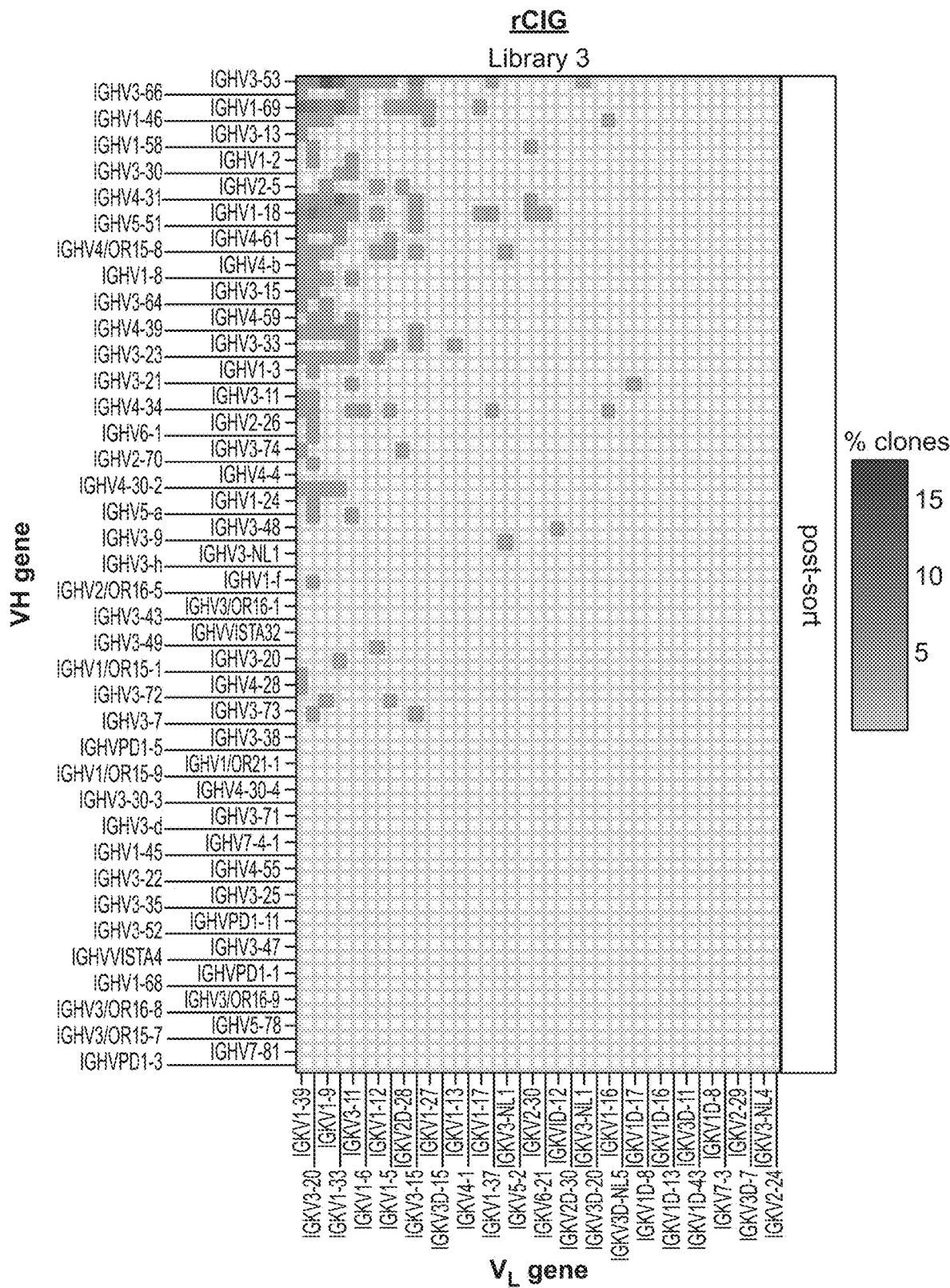
FIG. 21A (Cont. 10)

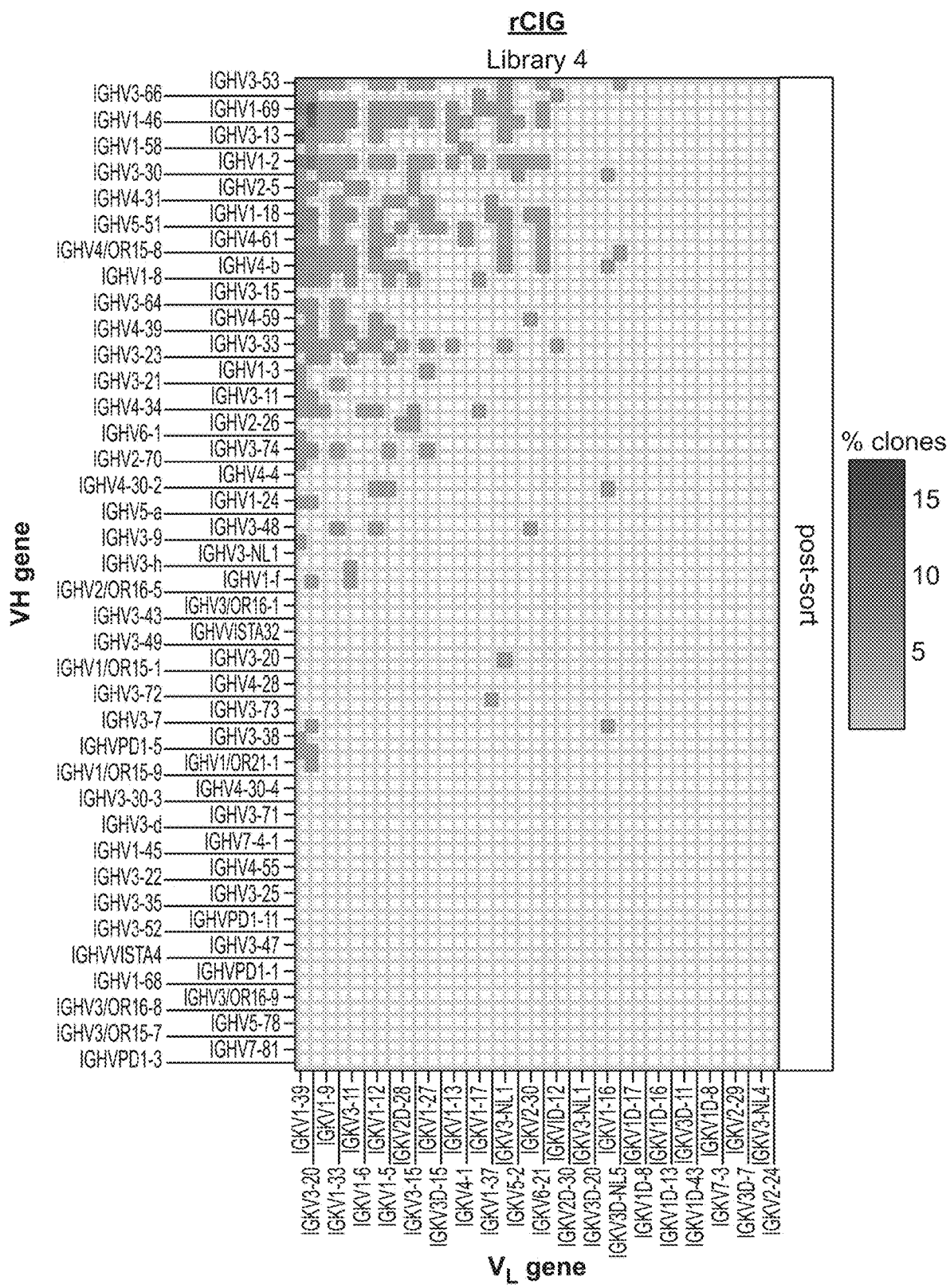
FIG. 21A (Cont. 11)

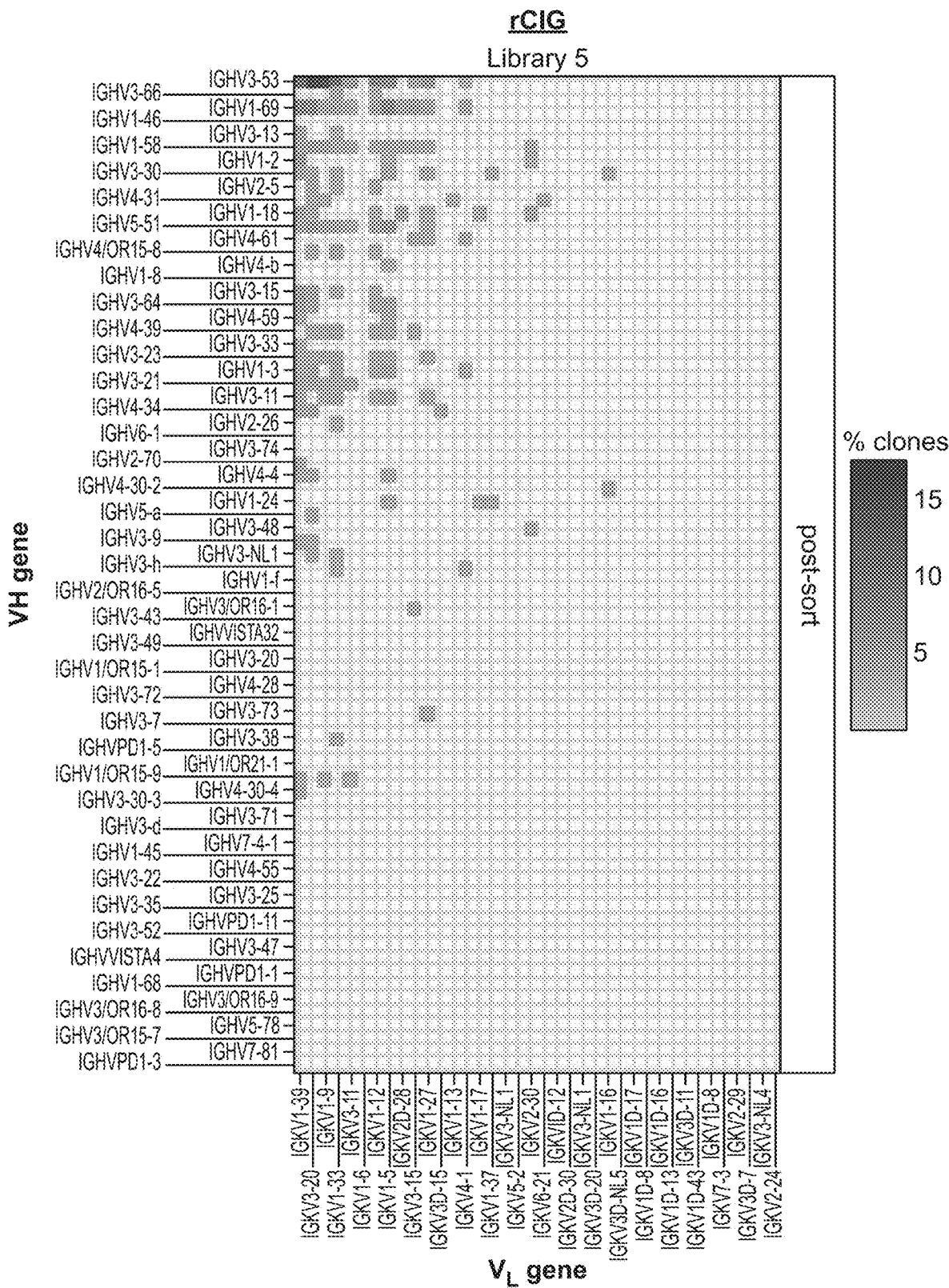
FIG. 21A (Cont. 12)

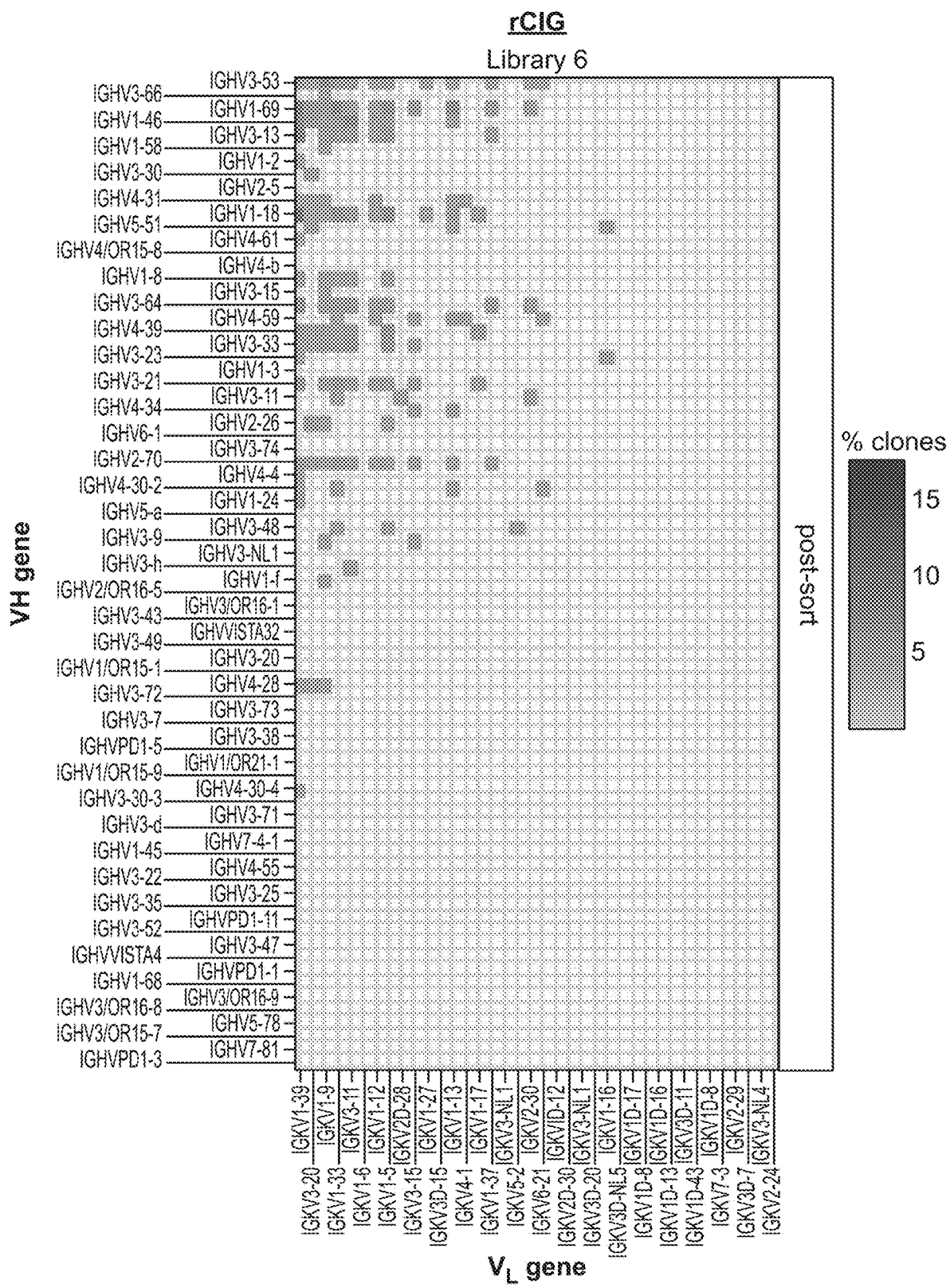
FIG. 21A (Cont. 13)

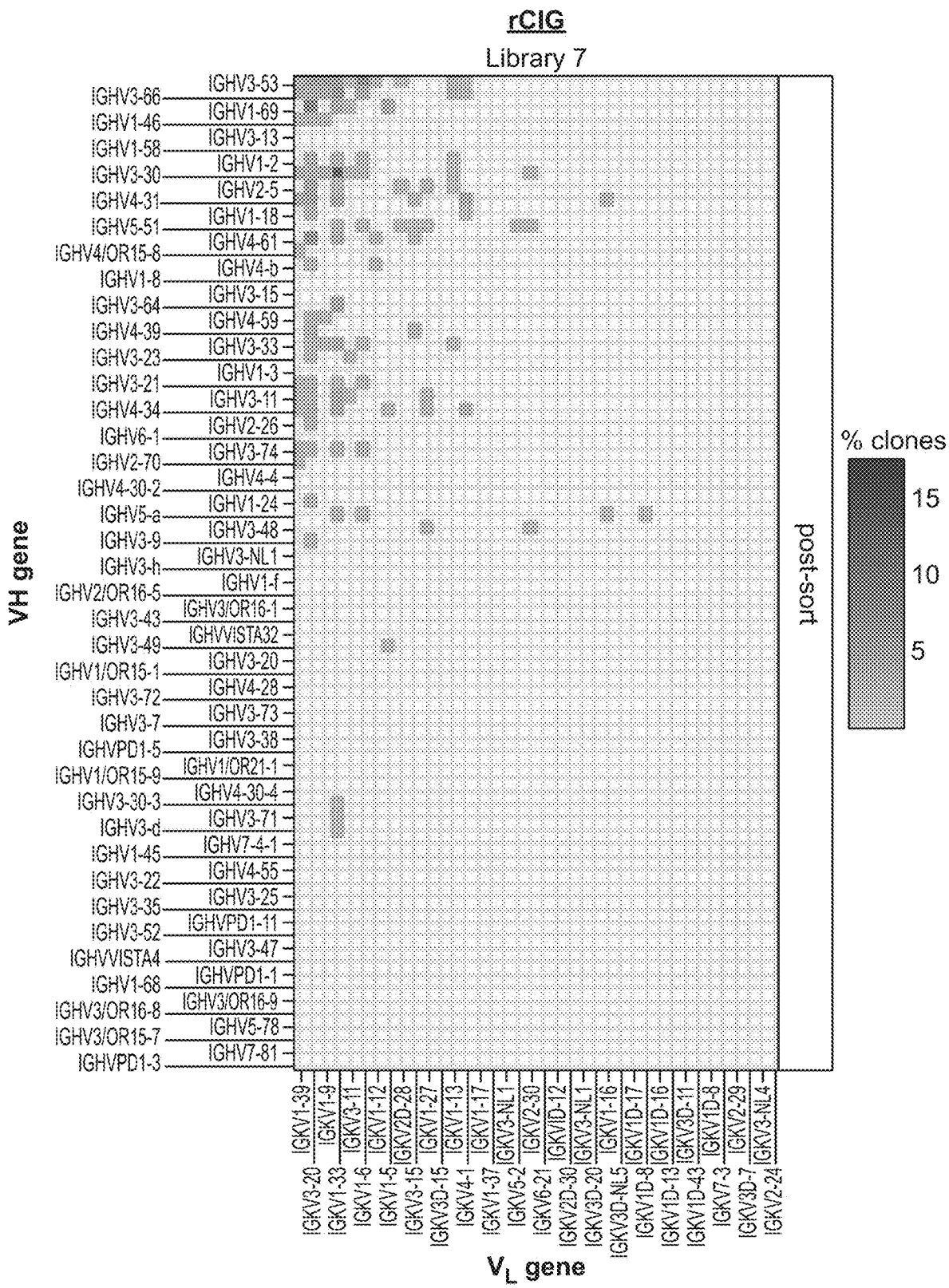
FIG. 21A (Cont. 14)

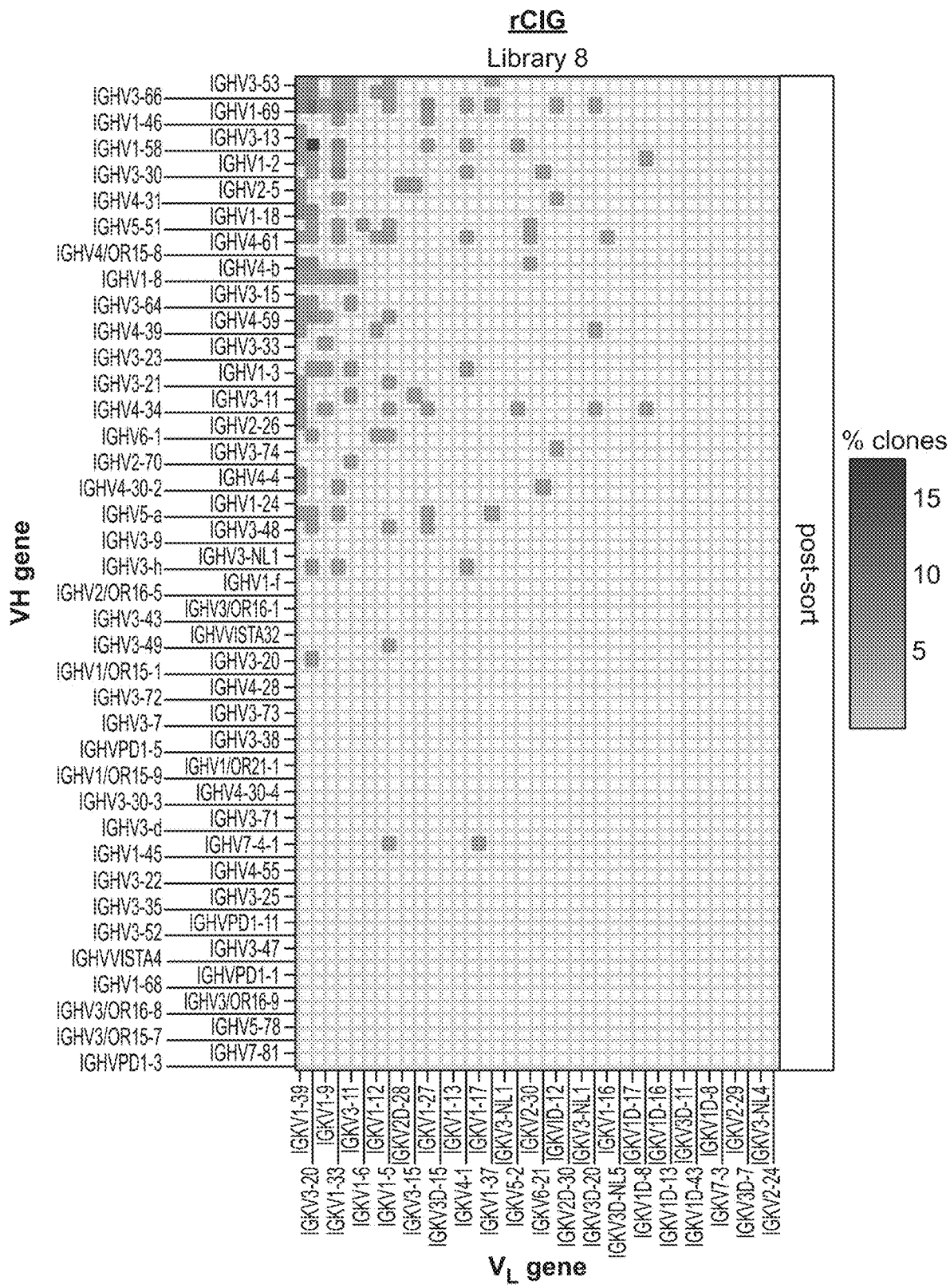
FIG. 21A (Cont. 15)

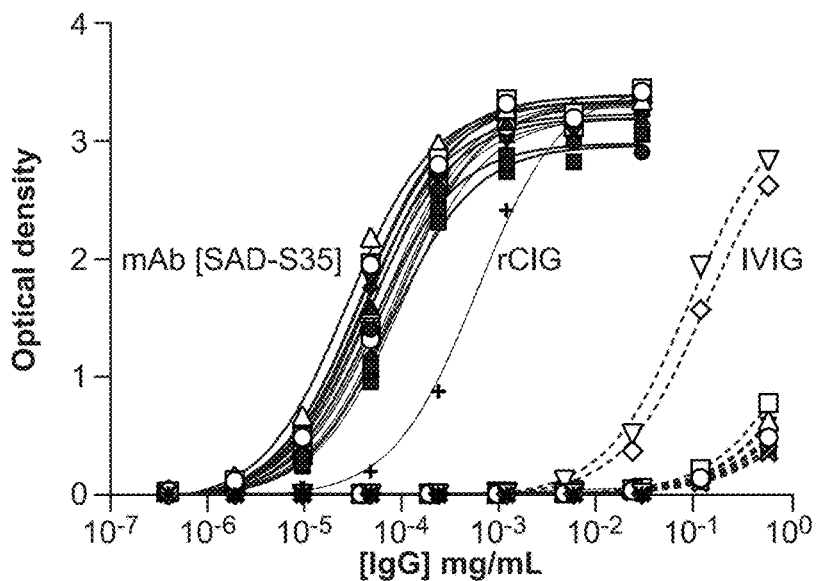
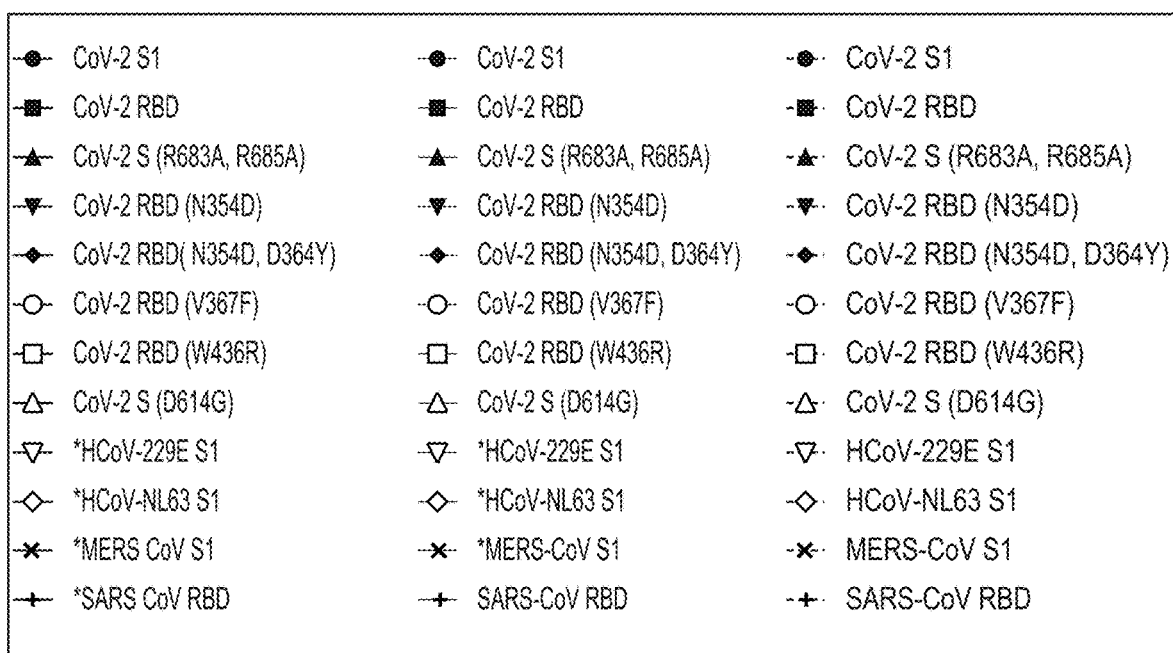
FIG. 22

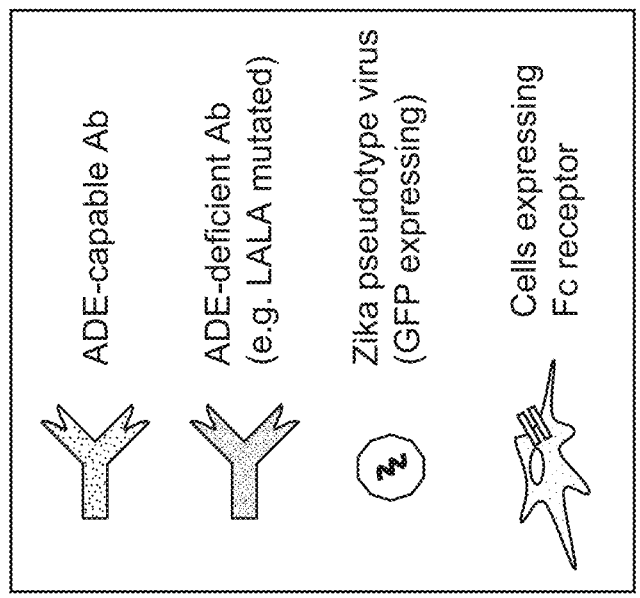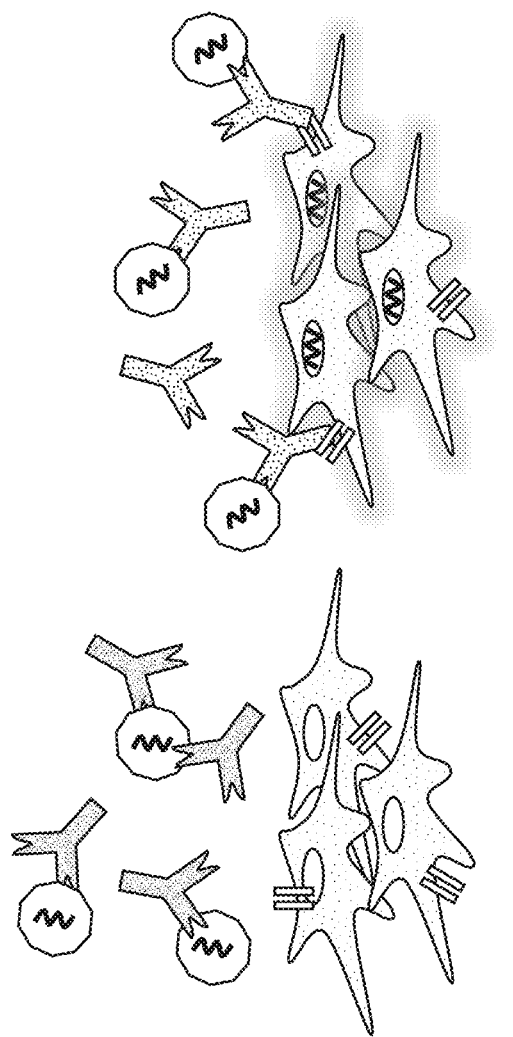
FIG. 32

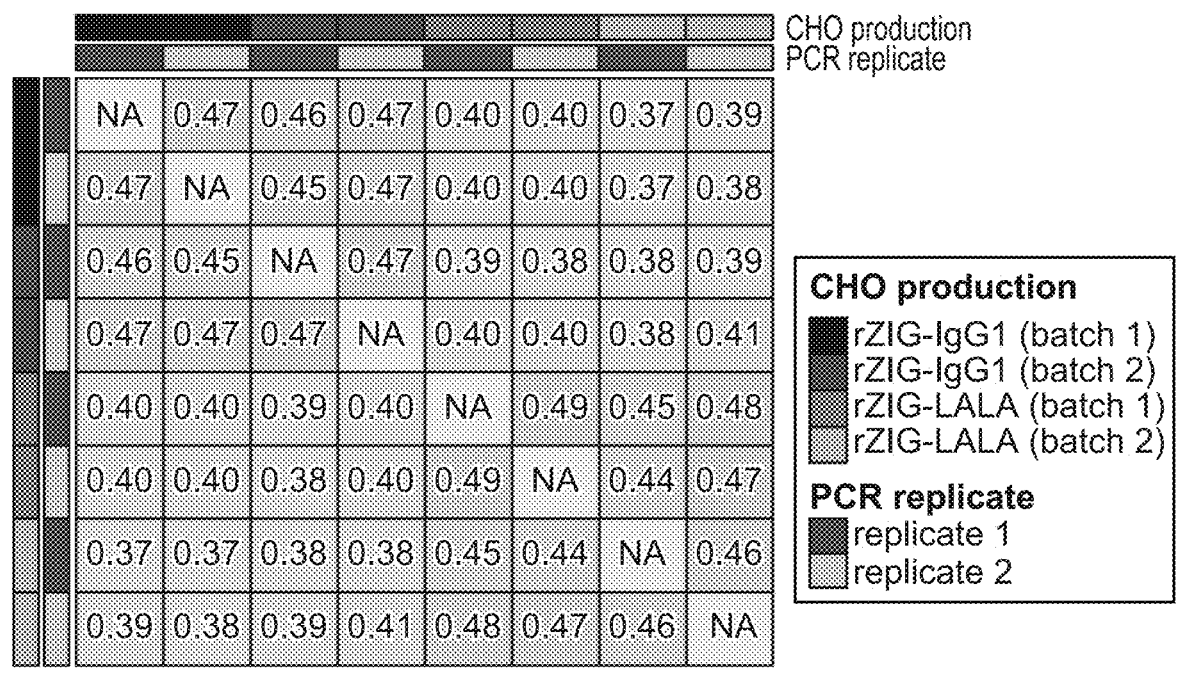
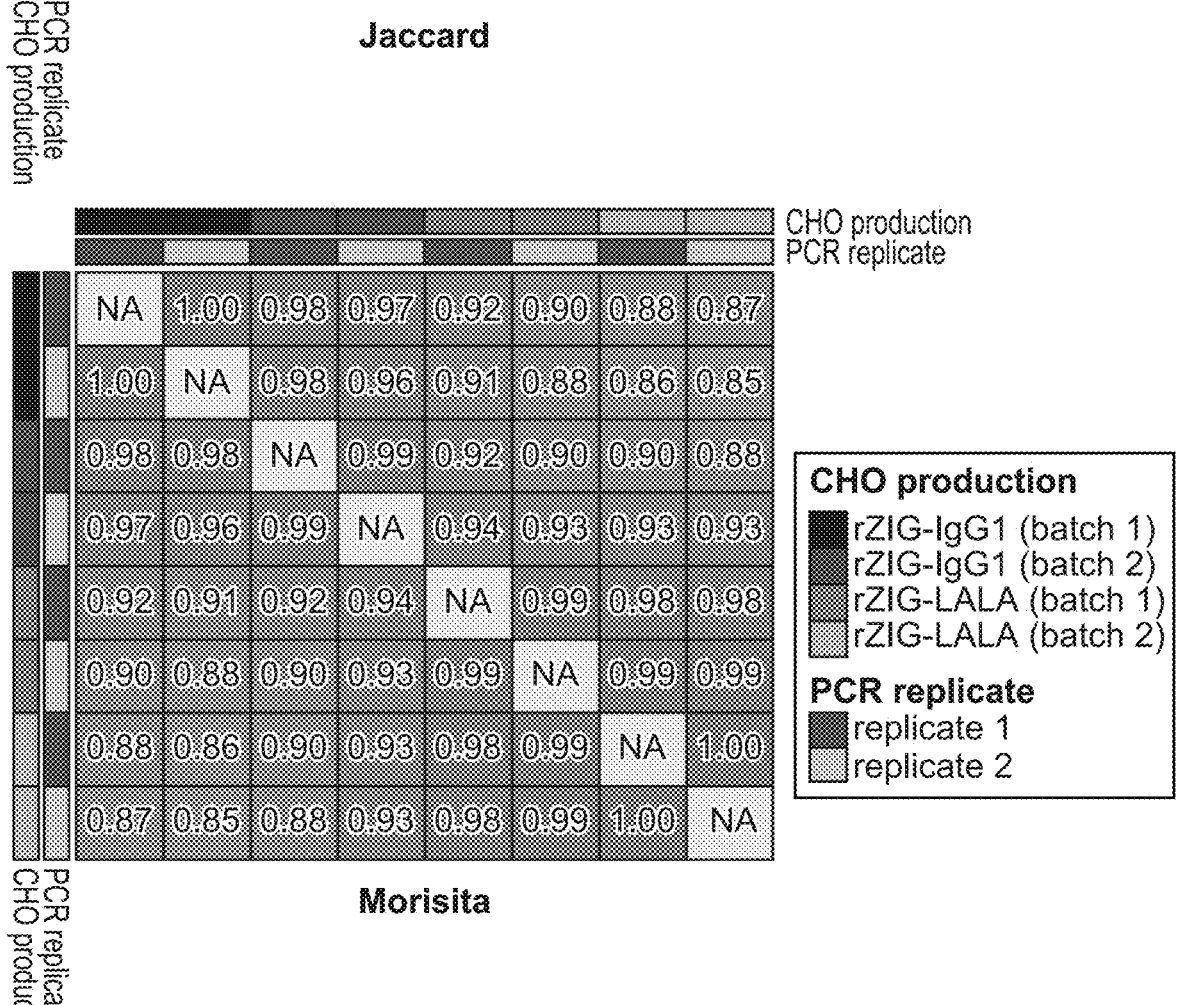
FIG. 33A

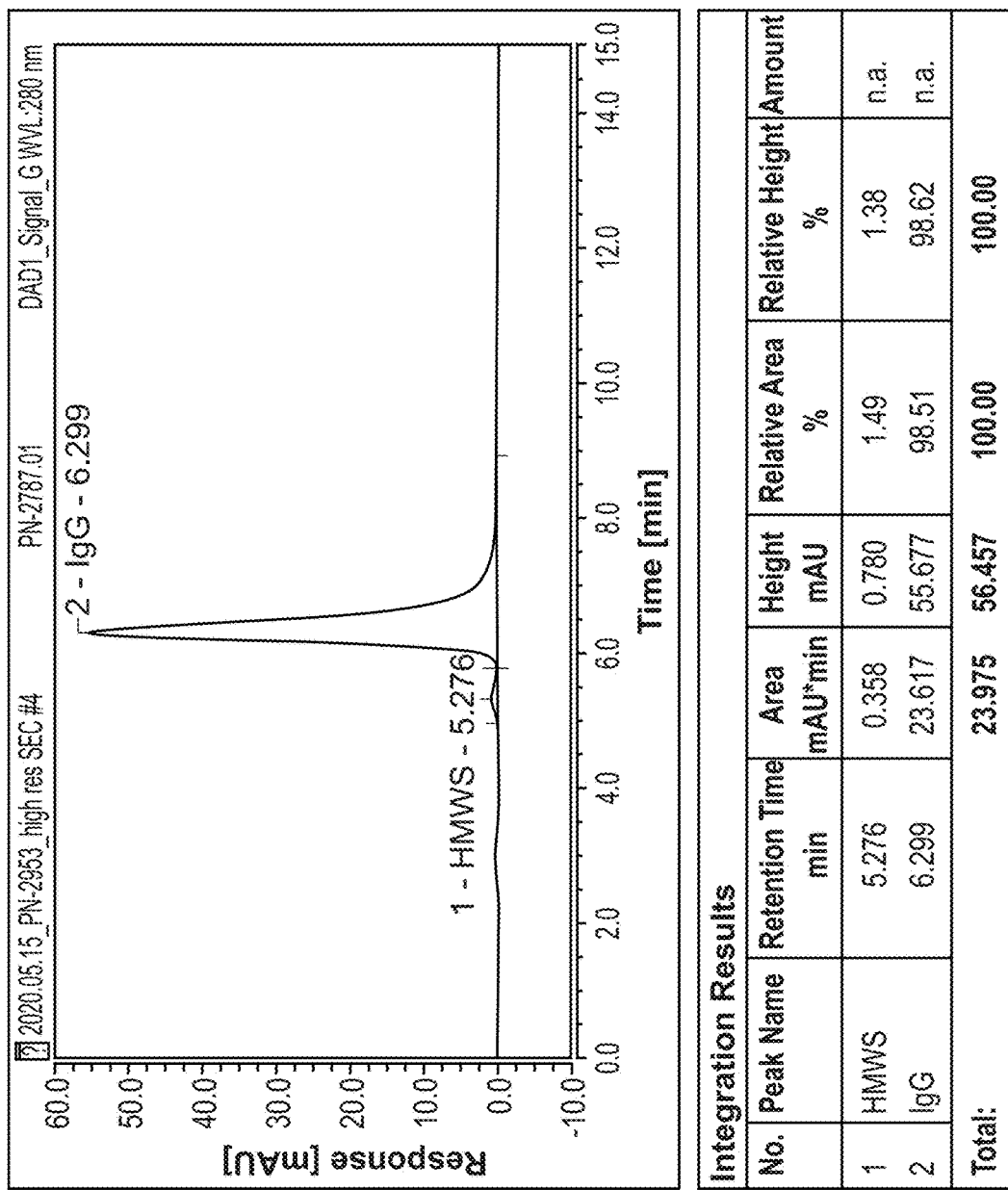
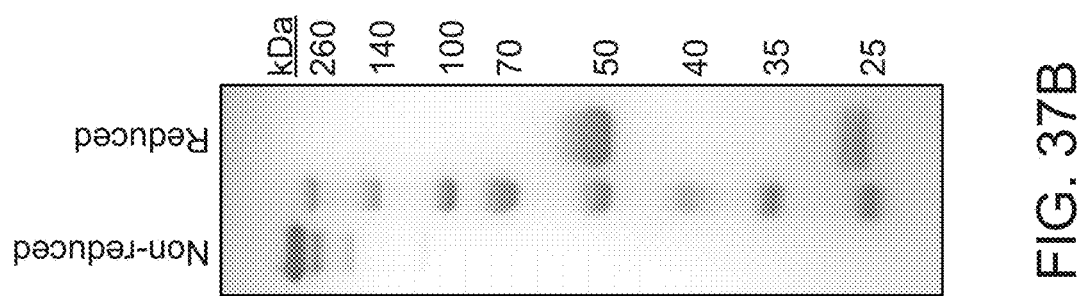
FIG. 37A
FIG. 37B

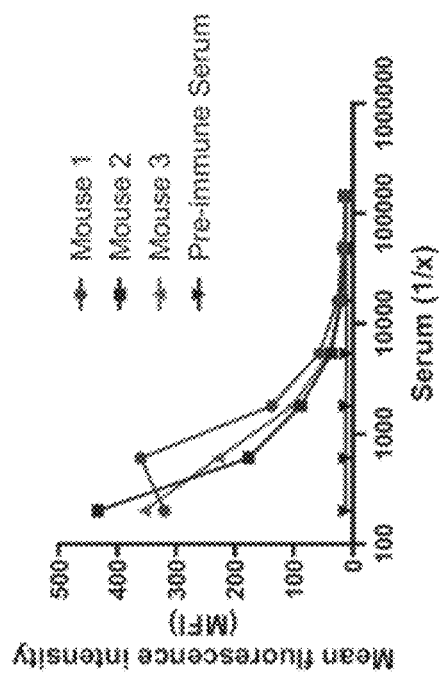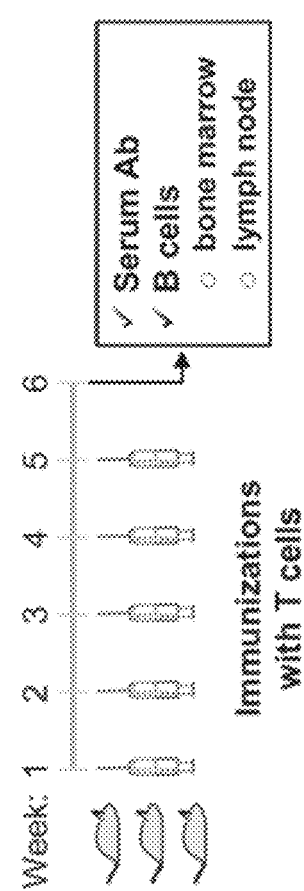
FIG. 43A

RECOMBINANT POLYCLONAL PROTEINS TARGETING ZIKA AND METHODS OF USE THEREOF

1. CROSS REFERENCE TO RELATED APPLICATIONS

The present application is a continuation of PCT/US2021/044523, which claims the benefit of U.S. Provisional Patent Application No. 63/061,730 filed on Aug. 5, 2020 which is hereby incorporated by reference in its entirety.

2. SEQUENCE LISTING

The instant application contains a Sequence Listing with 25975 sequences which has been submitted via EFS-Web and is hereby incorporated by reference in its entirety. Said ASCII copy, created on Mar. 7, 2022, is named 49570US CRF sequencelisting.txt, and is 6,030,864 bytes in size.

3. FIELD

Provided herein are recombinant polyclonal protein composition (RPP), also called Recombinant Zika Immune Globulin (rZIG), recombinant polyclonal antibody proteins, recombinant hyperimmune globulins, or simply recombinant hyperimmunes, with binding specificity for Zika virus. Included are, e.g., therapeutics, vaccines, and libraries, and compositions comprising such RPPs, including pharmaceutical compositions. Also provided are methods of making RPPs, and methods of using RPPs, for example, for therapeutic purposes.

4. BACKGROUND

A major outbreak of the mosquito-borne flavivirus, Zika, spread across Latin America in 2015-2016. Though Zika virus has been less widespread and less deadly than SARS CoV-2, Zika can spread from mother to a fetus in utero, resulting in birth defects such as microcephaly. As of July 2020, there was no FDA-approved vaccine or therapy for Zika virus. Zika virus disease is complicated by antibody-dependent enhancement (ADE) (Katzelnick et al., 2017; Priyamvada et al., 2017), a phenomenon in which poorly neutralizing antibodies enhance viral infection by bringing virus particles to cells that express Fc receptor (FcR). This problem is particularly troublesome for those previously infected with a related flavivirus, Dengue, since many anti-Dengue antibodies are poor neutralizers against Zika virus, and vice versa (Stettler et al., 2016). ADE is a safety concern in the development of plasma-derived hyperimmune compositions and vaccines (Langerak et al., 2019).

Many diseases, such as those caused by infectious viruses or bacteria with many variants or serotypes, are best treated by drugs that target multiple epitopes. An established therapeutic modality is multispecific (multivalent) antibodies derived from human or animal plasma, such as intravenous immunoglobulin (IVIG). Polyclonal antibody drugs with higher potency, known as hyperimmune globulins, are often derived from the plasma of recently vaccinated human donors, for example, HepaGam B against hepatitis B virus (HBV) and BabyBIG against infant botulism. In diseases for which human vaccination is not possible, hyperimmune globulins can be generated by immunizing animals, for example, rabbit-derived thymoglobulin ('rabbit-ATG') against human thymocytes for transplant tolerance. For rapid response to emerging pathogens with poorly characterized neutralizing epitopes, many groups have developed hyperimmune globulins derived from immunized animal plasma or convalescent human serum, for example, Zika virus hyperimmune globulin or severe acute respiratory syndrome coronavirus-2 (SARS-CoV-2).

Plasma-derived antibody therapeutics have substantial drawbacks. First, demand for normal and convalescent donor plasma often outstrips supply. Plasma-derived drugs have suffered from impurities, including infectious viruses and dotting factors, that have resulted in serious adverse events. Antibody drugs derived from animal plasma occasionally cause allergic reactions, lead to antidrug antibodies and have suboptimal effector properties. Because they are derived from naturally occurring proteins, plasma-derived drugs are not easily engineered; for example, it is not possible to modify Fc sequences to improve mechanism of action or drug half-life. Finally, each batch of plasma-derived drug is usually derived from a different cohort of human donors or animals, resulting in batch-to-batch variation.

Many of these problems could be solved by generating multivalent hyperimmune globulins using recombinant DNA technology. However, this strategy presents substantial technical hurdles. Most important, a recombinant hyperimmune globulin technology would have to isolate significant numbers of B cells from donors or animals, natively pair heavy and light chain immunoglobulin at a single-cell level, and then clone the sequences into recombinant expression libraries for manufacturing. Conventionally, most production cell lines for recombinant antibody drugs are generated by random integration of expression constructs into mammalian cell genomes. Pioneering work used 96-well plates to capture antibody sequences from B cells isolated from human donors immunized with Rho(D)$^+$ erythrocytes and then engineer multivalent recombinant antibodies, but this approach produced drug candidates with <30 antibodies, complicating broad application and reducing potential for polyvalence.

There is a need in the art for multivalent hyperimmune globulins with specificity for Zika virus, and methods of using such RPPs, e.g., as human therapeutics.

5. SUMMARY

Provided herein are rZIG (recombinant anti-Zika hyperimmune gammaglobulin), i.e., novel RPPs (novel recombinant polyclonal proteins, also called recombinant polyclonal antibody proteins, recombinant hyperimmune globulins, or recombinant hyperimmunes) with binding specificity to Zika antigens, and methods of using such RPPs, e.g., as human therapeutics. The RPPs are recombinant, and their sequences are derived from peripheral blood plasma cells or plasmablasts. The peripheral blood plasma cells or plasmablasts are mobilized by, e.g., infection of a donor with Zika virus, and the peripheral blood B cells, plasma cells or plasmablasts are specifically separated from other peripheral blood cells. The peripheral blood cells can come from any mammal, for example a mouse, a rat, a human, a monkey, a horse, or a cow.

Accordingly, the present disclosure provides a recombinant polyclonal protein composition (RPP) (also called a Recombinant Zika Immune Globulin (rZIG)), comprising at least 100 antigen binding proteins (ABPs), each of the ABPs comprising a cognate pair of heavy chain CDR3 and light chain CDR3, wherein each of the ABPs specifically binds an antigen of Zika virus.

In some embodiments, each of the ABPs comprises a heavy chain CDR3 having a sequence selected from SEQ ID Nos: 2, 4, 6, through 25838 (even numbers) and SEQ ID NO: 25851-25860, and a light chain CDR3 has a sequence selected from SEQ ID Nos: 1, 3, 5, through 25837 (odd numbers).

In some embodiments, the RPP comprises an ABP comprising a heavy chain CDR1 having the sequence of GFTFX1X2X3X4 (SEQ ID NO: 25839). In some embodiments, the RPP comprises an ABP comprising a heavy chain CDR1 having the sequence of GFTF[S/D][S/D][Y/H/D][A/G/Y/F] (SEQ ID NO: 25840). In some embodiments, the RPP comprises an ABP comprising a heavy chain CDR1 having a sequence selected from the group consisting of: a. GFTFSSYA (SEQ ID NO: 25841); b. GFTFSSYG (SEQ ID NO: 25842); c. GFTFDD[Y/H]G (SEQ ID NO: 25843); and d. GFTFSD[Y/D][Y/F] (SEQ ID NO: 25844).

In some embodiments, the RPP comprises an ABP comprising a heavy chain CDR2 having the sequence of IX1X2X3G X3X4X5 (SEQ ID NO: 25845). In some embodiments, each of the RPP comprises an ABP comprising a heavy chain CDR2 having the sequence of I[W/S/N][G/Y/W] [S/D/N] G[G/S/D/Y] [S/N/T] [T/K/I] (SEQ ID NO: 25846).

In some embodiments, the RPP comprises an ABP comprising a heavy chain CDR2 having a sequence selected from the group consisting of: a. ISGSGGST (SEQ ID NO: 25847); b.I[W/S]YDGSNK (SEQ ID NO: 25848); c.INWNG[G/D]ST (SEQ ID NO: 25849) and d.ISGSG[S/Y]TI (SEQ ID NO: 25850).

In some embodiments, the RPP comprises an ABP comprising a heavy chain CDR3 having a sequence selected from a. AKEGMVLRYFDWLWDY (SEQ ID NO: 25851); b. RX1X2X3SGX4SX5FDY (SEQ ID NO: 25852); c. AX1X2X3X4X5X6VX7X8X9Y (SEQ ID NO: 25853); d. ARX1X2GSX3X4X5X6DX7FDX8 (SEQ ID NO: 25854); and e. ARDEGYX1GYX2LDX3 (SEQ ID NO: 25855).

In some embodiments, the RPP comprises an ABP comprising a heavy chain CDR3 having a sequence selected from a. AKEGMVLRYFDWLWDY (SEQ ID NO: 25856); b. R[D/E][R/L][SN/L]SG[P/W]S[G/H]FDY (SEQ ID NO: 25857); c. A[K/E/R][E/T][Q/L/T][L/W/I][LN/W/N][G/L]V[V/P/L][F/L/N][D/N]Y (SEQ ID NO: 25858); d. AR[D/N][R/G]GS[S/T][G/S/W/F][W/F/Y][R/F/Y]D[W/A]FD[P/I] (SEQ ID NO: 25859); and e. ARDEGY[R/S]GY[V/N]LD[T/N/S] (SEQ ID NO: 25860).

In some embodiments, the RPP comprises at least 20, 40, 50, 100 or 200 ABPs comprising: a. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of AKEGMVLRYFDWLWDY (SEQ ID NO: 25856); b. a heavy chain CDR1 having the sequence of GFTFSSYG (SEQ ID NO: 25842), a heavy chain CDR2 having the sequence of I[W/S]YDGSNK (SEQ ID NO: 25848), and a heavy chain CDR3 having the sequence of R[D/E][R/L][SN/L]SG[P/W]S[G/H]FDY (SEQ ID NO: 25857); c. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of A[K/E/R][E/T][Q/L/T][L/W/I][LN/W/N][G/L]V[V/P/L][F/L/N][D/N]Y (SEQ ID NO: 25858); d. a heavy chain CDR1 having the sequence of GFTFDD[Y/H]G (SEQ ID NO: 25843), a heavy chain CDR2 having the sequence of INWNG[G/D]ST (SEQ ID NO: 25849), and a heavy chain CDR3 having the sequence of AR[D/N][R/G]GS[S/T][G/S/W/F][W/F/Y][R/F/Y]D[W/A]FD[P/I] (SEQ ID NO: 25859); or e. a heavy chain CDR1 having the sequence of GFTFSD[Y/D][Y/F] (SEQ ID NO: 25844), a heavy chain CDR2 having the sequence of ISGSG[S/Y]TI (SEQ ID NO: 25850), and a heavy chain CDR3 having the sequence of ARDEGY[R/S]GY[V/N]LD[T/N/S] (SEQ ID NO: 25860).

In some embodiments, each of at least 5%, 10%, 25%, or 50% of the total ABPs in the RPP comprises: a. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of AKEGMVLRYFDWLWDY (SEQ ID NO: 25856); b. a heavy chain CDR1 having the sequence of GFTFSSYG (SEQ ID NO: 25842), a heavy chain CDR2 having the sequence of I[W/S]YDGSNK (SEQ ID NO: 25848), and a heavy chain CDR3 having the sequence of R[D/E][R/L][SN/L]SG[P/W]S[G/H]FDY (SEQ ID NO: 25857); c. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of A[K/E/R][E/T][Q/L/T][L/W/I][LN/W/N][G/L]V[V/P/L][F/L/N][D/N]Y (SEQ ID NO: 25858); d. a heavy chain CDR1 having the sequence of GFTFDD[Y/H]G (SEQ ID NO: 25843), a heavy chain CDR2 having the sequence of INWNG[G/D]ST (SEQ ID NO: 25849), and a heavy chain CDR3 having the sequence of AR[D/N][R/G]GS[S/T][G/S/W/F][W/F/Y][R/F/Y]D[W/A]FD[P/I] (SEQ ID NO: 25859); or e. a heavy chain CDR1 having the sequence of GFTFSD[Y/D][Y/F] (SEQ ID NO: 25844), a heavy chain CDR2 having the sequence of ISGSG[S/Y]TI (SEQ ID NO: 25850), and a heavy chain CDR3 having the sequence of ARDEGY[R/S]GY[V/N]LD[T/N/S] (SEQ ID NO: 25860).

In some embodiments, each of the ABPs comprises a unique heavy chain CDR3 and a unique light chain CDR3 sequence.

In some embodiments, the RPP comprises 100 to 500 ABPs. In some embodiments, the RPP comprises 500 to 1000 ABPs. In some embodiments, the RPP comprises 1000 to 2500 ABPs. In some embodiments, the RPP comprises more than 2500 ABPs.

In some embodiments, each of the ABPs is an scFv. In some embodiments, each of the ABPs is a full-length antibody. In some embodiments, each of the ABPs is an IgG1 subtype.

In some embodiments, each of the ABPs is produced in eukaryotic cell culture. In some embodiments, each of the ABPs is produced in a CHO cell. In some embodiments, each of the ABPs is produced in yeast cells. In some embodiments, each of the ABPs is recombinantly produced using sequences derived from B cells, plasma cells, or plasmablasts in a sample from a donor injected with one or more Zika antigens or Dengue antigens, or infected with Zika virus or Dengue virus. In some embodiments, the donor is a human. In some embodiments, each of the ABPs is recombinantly produced using sequences derived from B cells, plasma cells, or plasmablasts in a sample from more than one donor injected with one or more Zika antigens or Dengue antigens, or infected with Zika virus or Dengue virus, optionally wherein the donors are humans.

In some embodiments, an average binding titer of the RPP is at least 50 times higher than an average binding titer of antibodies in a serum sample from the same donor or donors, wherein the binding titer is measured by ELISA against Zika. In some embodiments, an average binding titer of the RPP is at least 100, 200, 300, 400, 500, 600, 700, 800, 900, or 1000 times higher than an average binding titer of antibodies in a serum sample from the same donor or donors, wherein the binding titer is measured by ELISA against Zika.

In some embodiments, an average neutralization titer of the RPP is at least 50 times higher than an average neutralization titer of antibodies in a serum sample from the same donor or donors, wherein the neutralization titer is measured by an in vitro assay. In some embodiments, an average neutralization titer of the RPP is at least 100, 200, 300, 400, 500, 600, 700, 800, 900, or 1000 times higher than an average neutralization titer of antibodies in a serum sample from the same donor or donors, wherein the neutralization titer is measured by an in vitro assay.

In some embodiments, an average activity of the RPP is at least 50 times higher than an average activity of antibodies in a serum sample from the same donor or donors, wherein the activity is measured by an in vitro pathogen neutralization assay or an in vitro binding to antigen assay or an in vivo efficacy assay. In some embodiments, an average activity of the RPP is at least 100, 200, 300, 400, 500, 600, 700, 800, 900, or 1000 times higher than an average activity of antibodies in a serum sample from the same donor or donors, wherein the activity is measured by an in vitro pathogen neutralization assay or an in vitro binding to antigen assay or an in vivo efficacy assay.

In one aspect, the present disclosure provides a pharmaceutical composition comprising the RPP provided herein and a pharmaceutically acceptable excipient.

In yet another aspect, the present disclosure provides a method of treating a subject in need thereof, the method comprising administering to the subject an effective amount of the RPPs or the pharmaceutical composition of the present disclosure. In some embodiments, the subject has a viral infection, optionally a Zika virus infection.

In some embodiments, the method further comprises administration of one or more agents.

In one aspect, the present disclosure provides a plurality of isolated polynucleotides, each polynucleotide encoding an ABP of the RPP described herein. In another aspect, the present disclosure provides a plurality of isolated vectors, each vector comprising a polynucleotide encoding an ABP of the RPP described herein. In some embodiments, the vector is an expression vector.

In yet another aspect, the present disclosure provides a plurality of host cells comprising the plurality of isolated polynucleotides or the plurality of the isolated vectors. In some embodiments, the method comprises culturing the host cells under conditions for expression of the RPP and isolating the RPP. In some embodiments, the RPP comprises full-length antibodies and the host cells are CHO cells. In some embodiments, the RPPs comprises scFv and the host cells are CHO cells. In some embodiments, host cells are production host cells.

The present disclosure also provides an isolated polypeptide comprising a cognate pair of heavy chain CDR3 and light chain CDR3, wherein the heavy chain CDR3 has a sequence selected from SEQ ID Nos: 2, 4, 6, through 25838 (even numbers) and the light chain CDR3 has a sequence selected from SEQ ID Nos: 1, 3, 5, through 25837 (odd numbers).

In some embodiments, the isolated polypeptide comprises a heavy chain CDR3 having the sequence of SEQ ID NO: [n+1] and a light chain CDR3 having the sequence of SEQ ID NO: [n], wherein n is an odd number from 1 to 25837.

In one aspect, the present disclosure provides an isolated polypeptide comprising a cognate pair of heavy chain and light chain, wherein a. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of AKEGMVLRYFDWLWDY (SEQ ID NO: 25856); b. a heavy chain CDR1 having the sequence of GFTFSSYG (SEQ ID NO: 25842), a heavy chain CDR2 having the sequence of I[W/S]YDGSNK (SEQ ID NO: 25848), and a heavy chain CDR3 having the sequence of R[D/E][R/L][SN/L]SG[P/W]S[G/H]FDY (SEQ ID NO: 25857); c. a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of A[K/E/R][E/T][Q/L/T][L/W/I][LN/W/N][G/L]V[V/P/L][F/L/N][D/N]Y (SEQ ID NO: 25858); d. a heavy chain CDR1 having the sequence of GFTFDD[Y/H]G (SEQ ID NO: 25843), a heavy chain CDR2 having the sequence of INWNG[G/D]ST (SEQ ID NO: 25849), and a heavy chain CDR3 having the sequence of AR[D/N][R/G]GS[S/T][G/S/W/F][W/F/Y][R/F/Y]D[W/A]FD [P/I] (SEQ ID NO: 25859); or e.a heavy chain CDR1 having the sequence of GFTFSD[Y/D][Y/F] (SEQ ID NO: 25844), a heavy chain CDR2 having the sequence of ISGSG[S/Y]TI (SEQ ID NO: 25850), and a heavy chain CDR3 having the sequence of ARDEGY[R/S]GY[V/N]LD[T/N/S] (SEQ ID NO: 25860).

In one aspect, the present disclosure provides an isolated polynucleotide encoding the isolated polypeptide of described herein.

In one aspect, the present disclosure provides a cell comprising the isolated polypeptide.

In one aspect, the present disclosure provides a method of generating a recombinant polyclonal proteins (RPP) (also called a Recombinant Zika Immune Globulin (rZIG)), comprising a. providing B cells, plasma cells, or plasmablasts of a donor exposed to an antigen of Zika or Dengue virus; b. amplifying a cognate pair of polynucleotides encoding a light chain variable region and a heavy chain variable region from a single cell out of the plasma cells or plasmablasts by overlap extension reverse transcriptase polymerase chain reaction (OE-RT-PCR); c. cloning polynucleotides obtained from the amplification into expression vectors, thereby obtaining constructs encoding the RPP; d. expressing the RPP from the constructs; e. enriching a subset of the constructs based on activity of the RPP or a member of the RPP against Zika; and f obtaining the RPP (also called a Recombinant Zika Immune Globulin (rZIG)).

In another aspect, the present disclosure provides an RPP (also called a Recombinant Zika Immune Globulin (rZIG)) obtained by the method described herein. The present disclosure also provides a Recombinant Zika Immune Globulin (rZIG) produced using the methods described in Example 2. The present disclosure further provides a method for producing an rZIG as described in Example 2. In one aspect, the present disclosure provides an rZIG produced using the methods described in Example 3. It also provides a method for producing an rZIG as described in Example 3.

6. DESCRIPTION OF THE DRAWINGS AND TABLES

FIG. 1 illustrates construct PMD-4681 used for random integration into CHOZN cells.

FIGS. 2A and 2B summarize the steps used to generate libraries of scFv constructs. (FIG. 2A) First, IgH and IgK mRNA transcripts are reverse transcribed into cDNA and then amplified with a pool of VH, VK, CH1, and CK1 primers. (FIG. 2B) The CK1 and VH primers have linkers, which drive fusion of the individual IgH and IgK amplicons into a linked scFv construct. This construct is used for cloning into antibody expression construct libraries.

FIG. 3A to 3D are tables with characteristics of the donors used to create candidate RPP libraries. SOB=shortness of breath; ST=sore throat.

FIG. 5 is a table with a list of assays used to characterize the rCIG RPP candidate.

FIG. 6 is a table with results of assays used to characterize rCIG RPPs.

FIG. 7C illustrates the process of enriching binders to a soluble antigen using a yeast scFv display system.

FIG. 7D illustrates the two-step process comprising (i) Gibson assembly of converting the scFv fragment to full-length antibody expression constructs and (ii) stably integrating the constructs into CHO cells following electroporation and selection.

Figure 8A:
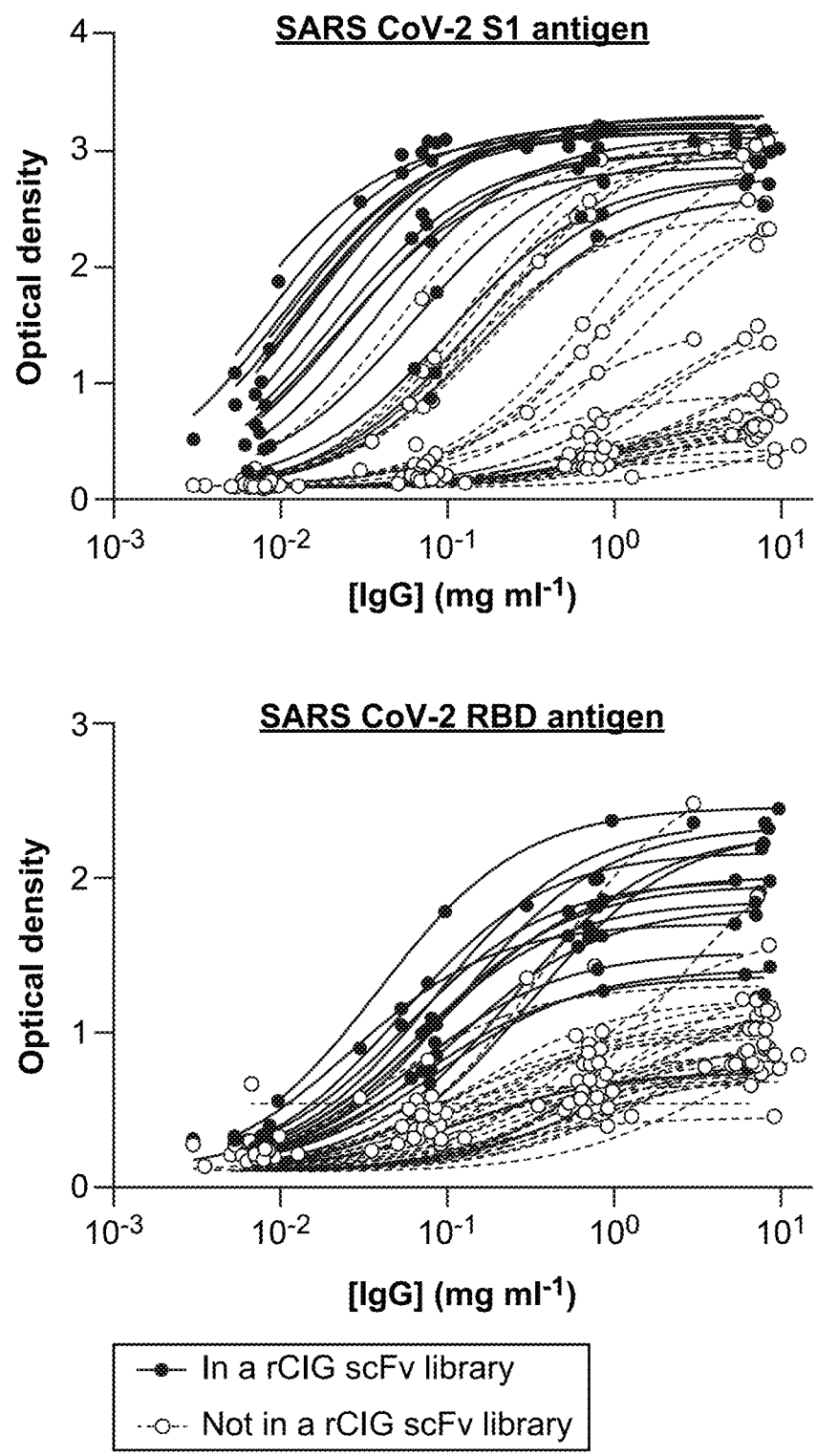

FIG. 8A provides optical density measured by ELISA of individual human plasma donors against SARS-CoV-2 S1 antigen (top) or RBD antigen (bottom). Each data point represents a single measurement at a single test article dilution in a single experiment.

Figure 8B:
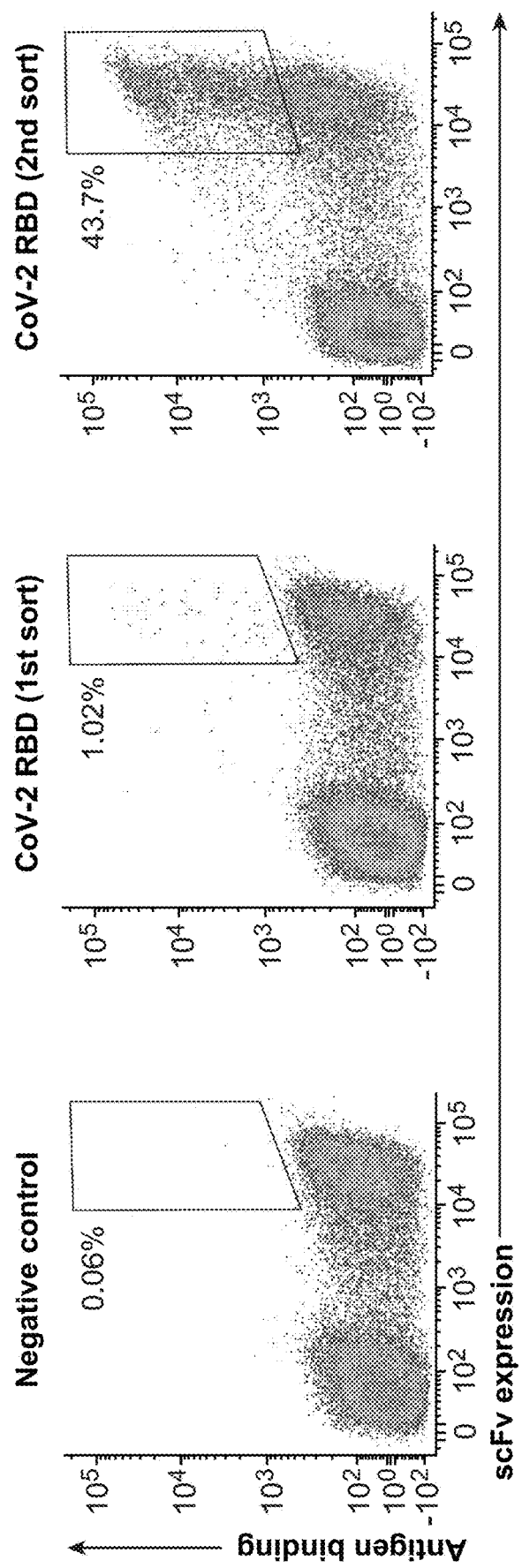

FIG. 8B shows FACS enrichment of scFv against CoV-2 RBD from library 1 using yeast display. The x axis measures presence of a C-terminal c-Myc tag, indicating expression of an scFv on the surface of the cell. They axis measures binding of antigen to the scFv-expressing cells. The gates used for yeast selection (double positive) are indicated, with the percentage of scFv-expressed antigen binders in grey-scale. Each plot summarizes a single FACS experiment with one yeast scFv library.

Figure 8C:
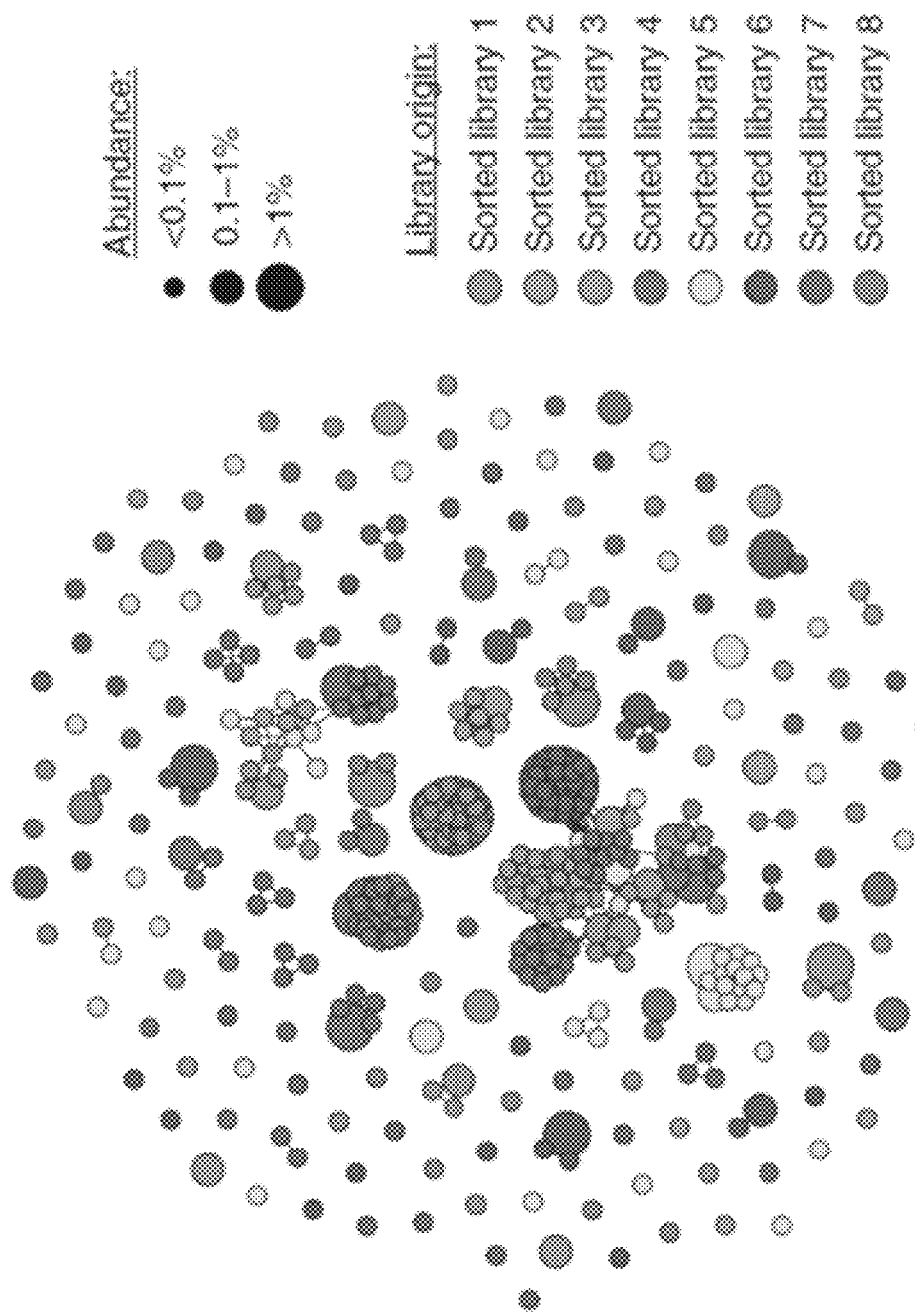

FIG. 8C provides clonal cluster analysis of rCIG antibodies. Each node represents an antibody clone (full-length heavy chain). The greyscale shades of the nodes indicate the sorted scFv library from which the CHO antibody clones were derived. The size of the nodes reflects the frequency of the clones in the final CHO cell bank (only clones ≥0.01% are plotted). The total number of amino acid differences between each pairwise alignment, and edges indicate ≤5 amino acid differences were computed.

Figure 8D:
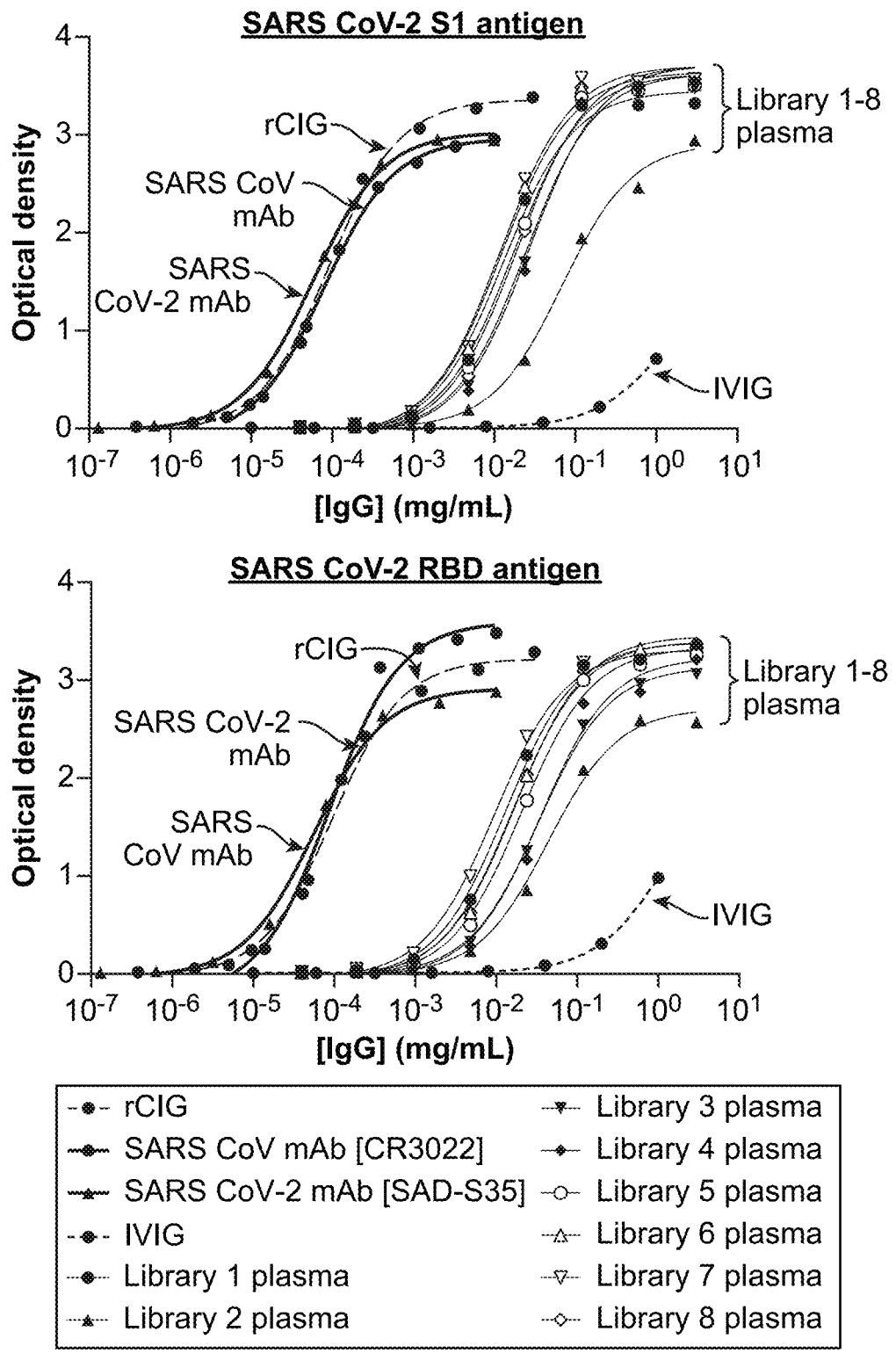

FIG. 8D provides optical density measured by ELISA of the indicated samples against SARS-CoV-2 S1 antigen (top) or RBD antigen (bottom). Each data point represents a single measurement at a single test article dilution, in a single experiment.

Figure 8E:
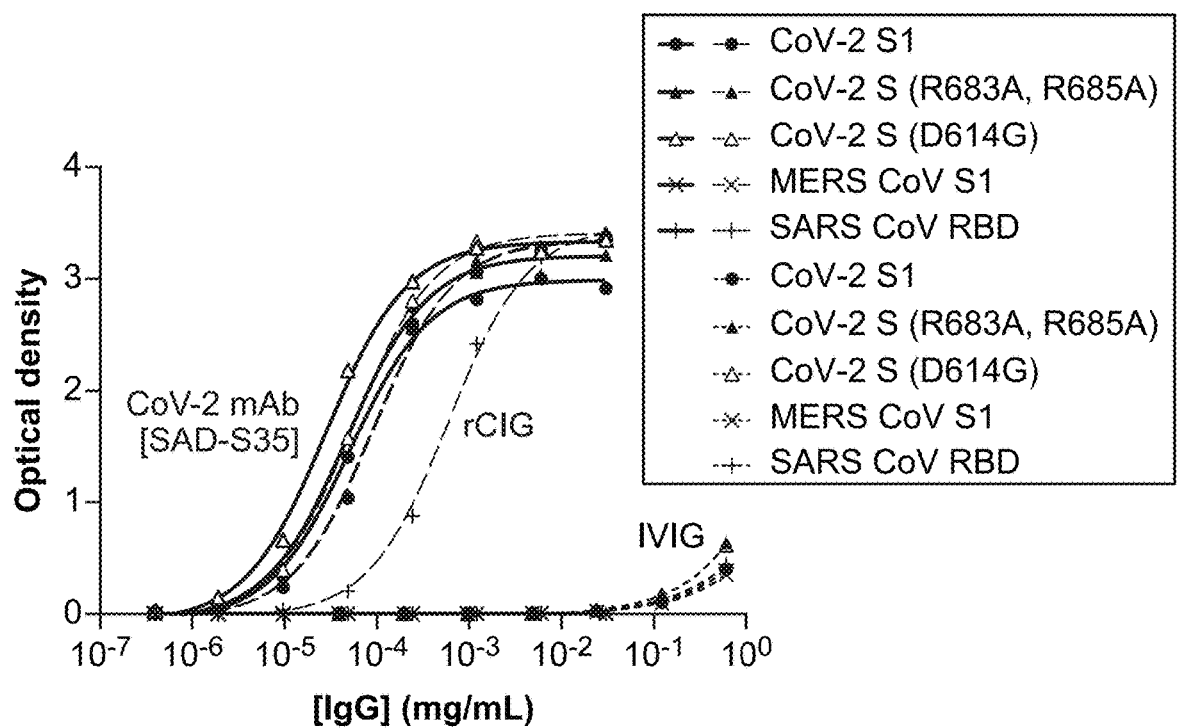

FIG. 8E provides optical density measured by ELISA of the indicated samples against the indicated antigens (different shapes). For rCIG, no binding was observed against MERS CoV S1. For the CoV-2 mAb (SAD-S35), no binding was observed against MERS CoV S1 and SARS-CoV RBD. Each data point represents a single measurement at a single test article dilution, in a single experiment.

Figure 8F:
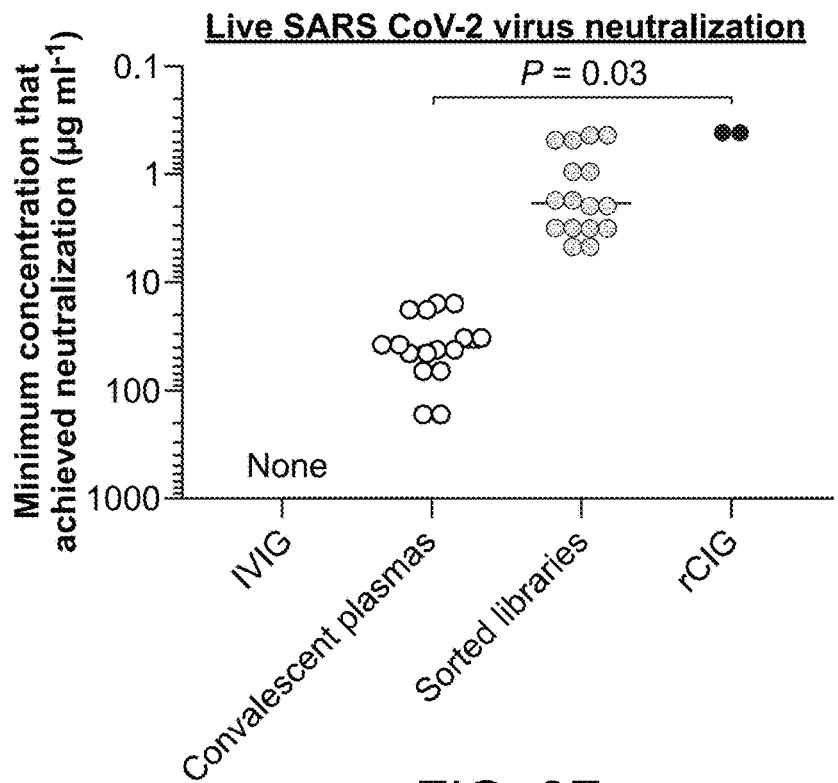

FIG. 8F shows live virus neutralization. Individual dots are separate test articles that represent the minimum antibody concentration that achieved neutralization. Bars represent median measurements for each test article category. Each test article was run in duplicate using different aliquots of cells and virus, in a single experiment, with the same result observed for each replicate. No neutralization was seen for IVIG. A Wilcoxon rank sum test was used to compare the minimum concentration to achieve SARS-CoV-2 live virus neutralization between convalescent plasma measurements (n=16) and rCIG measurements (n=2).

Figure 9A:
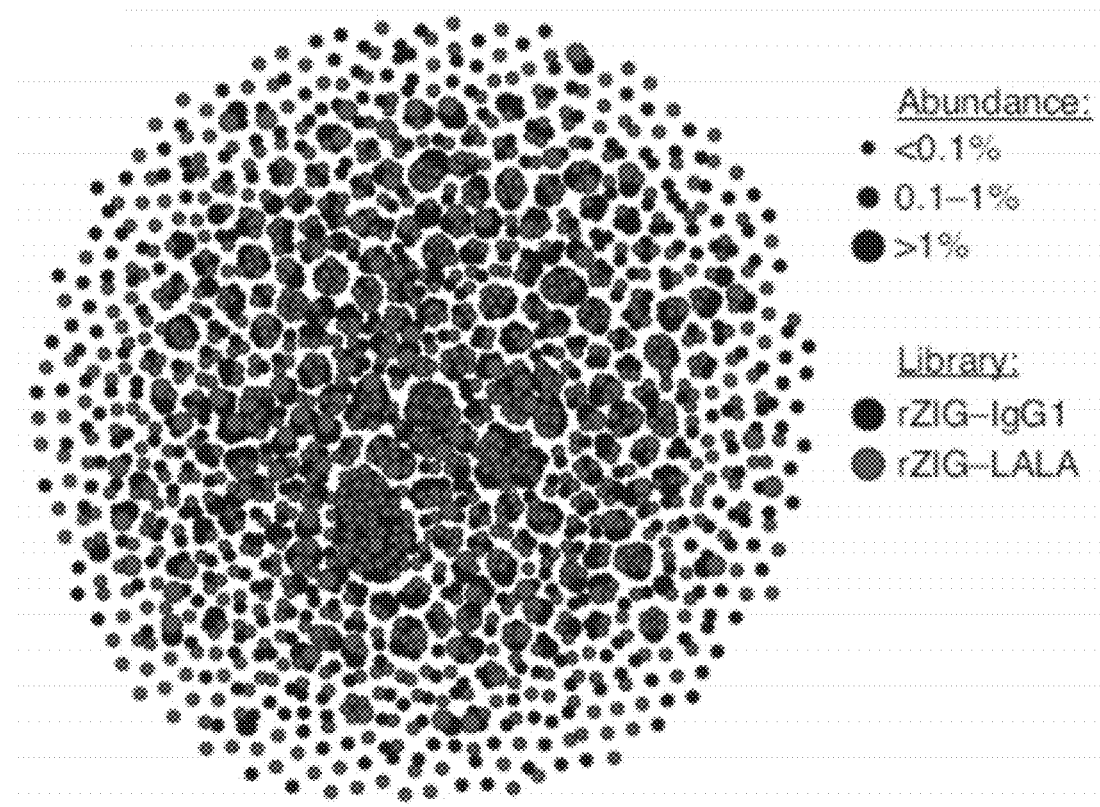

FIG. 9A shows clonal cluster analysis of rZIG-IgG1 and rZIG-LALA antibodies. Each node represents an antibody clone (full-length heavy chain). The size of the nodes reflects the frequency of the clones in the final CHO cell bank (only clones ≥0.01% are plotted). The total number of amino acid differences between each pairwise alignment was computed after combining both libraries together, and edges indicate ≤5 amino acid differences.

Figures 9B, 9C:
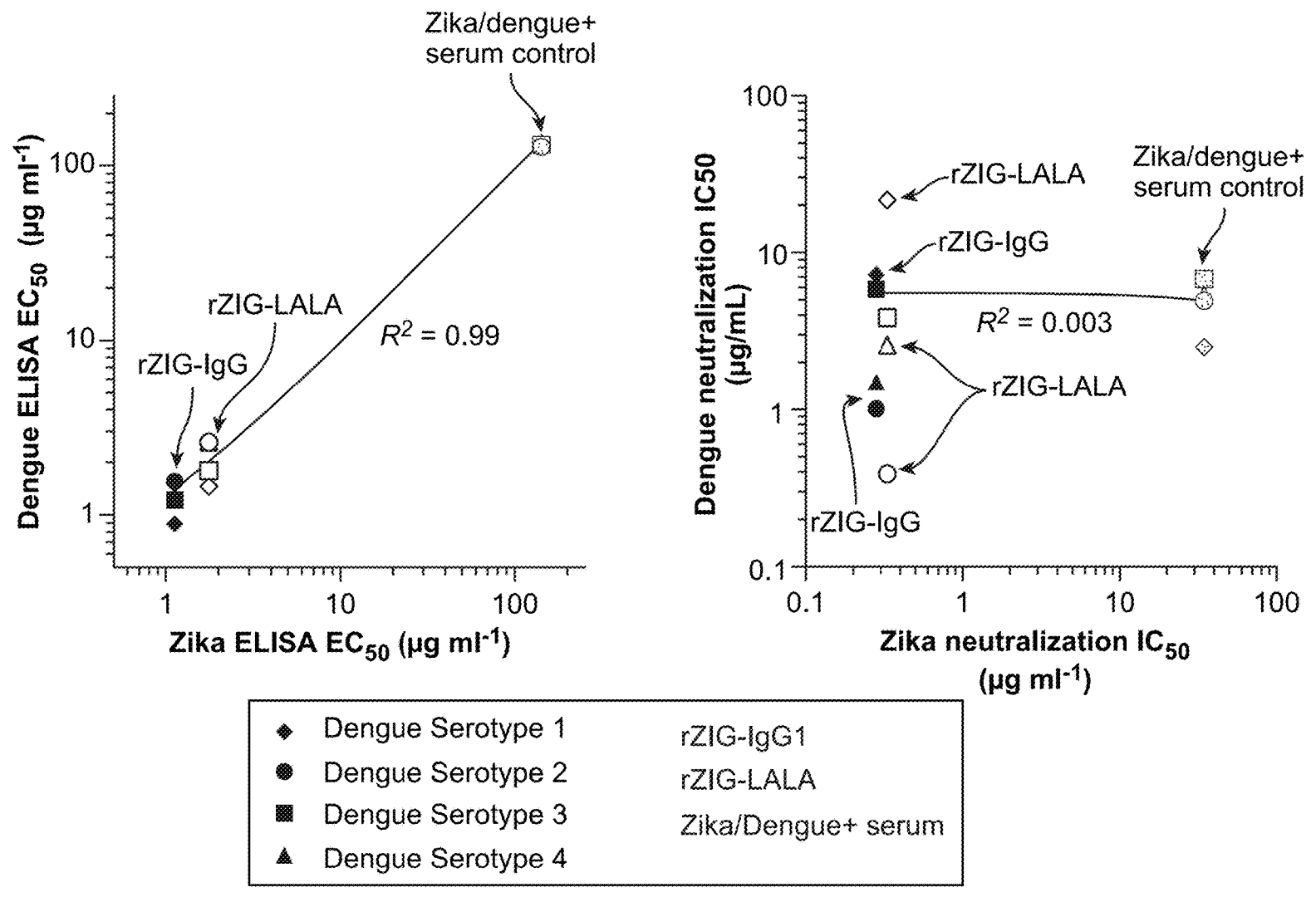

FIG. 9B provides ELISA results of rZIG-IgG1, rZIG-LALA, and Zika/dengue+ serum control for dengue serotypes 1-4 (y axis, indicated by shape) and Zika virus antigen (x axis). Each data point represents a single test article measured against a single dengue serotype. Linear regression trendline is indicated in black. Simple linear regression was used to calculate the coefficient of determination (R2) between Zika and dengue ELISA $EC_{50}$ values (n=7, in a single experiment). EC50 values for all dengue serotypes were pooled for the analysis. Significance of the regression model was determined using an F-statistic with 1 and 10 d.f.

FIG. 9C shows pseudotype neutralization by rZIG-IgG1, rZIG-LALA, and Zika/dengue+ serum control for dengue serotypes 1-4 (y axis, indicated by shape) and Zika virus antigen (x axis). Each data point represents a single test article measured against a single dengue serotype, in a single experiment. Linear regression trendline is indicated in black. Simple linear regression was used to calculate the coefficient of determination (R2) between Zika and dengue pseudotype neutralization $IC_{50}$ values (n=11). $IC_{50}$ values for all dengue serotypes were pooled for the analysis. Significance of the regression model was determined using an F-statistic with 1 and 10 d.f.

Figure 9D:
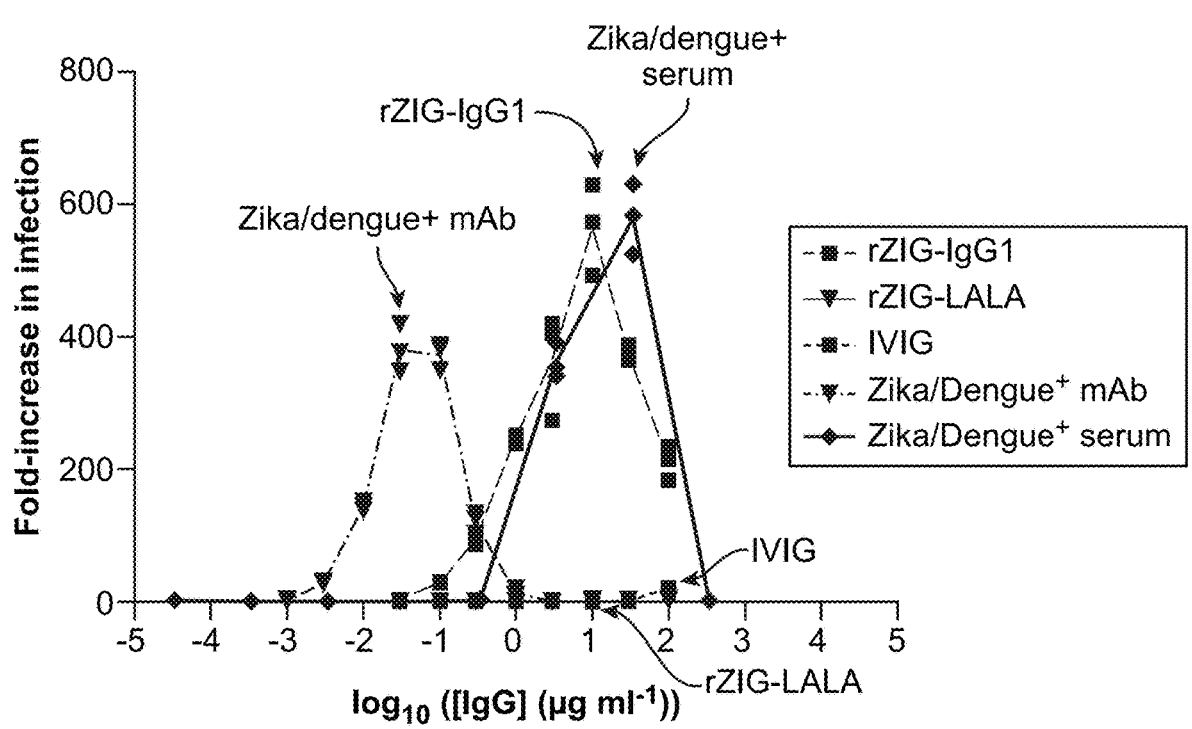

FIG. 9D shows Zika pseudotype virus ADE assay results for rZIG-IgG1, rZIG-LALA, and positive and negative controls. Test article concentration is on the x axis. Fold-increase infection is on they axis, which was the infection-induced luciferase signal observed in the presence of antibody divided by the luciferase signal observed with a no-antibody control. Each data point represents a single measurement at a single test article dilution, in a single experiment.

Figure 10A:
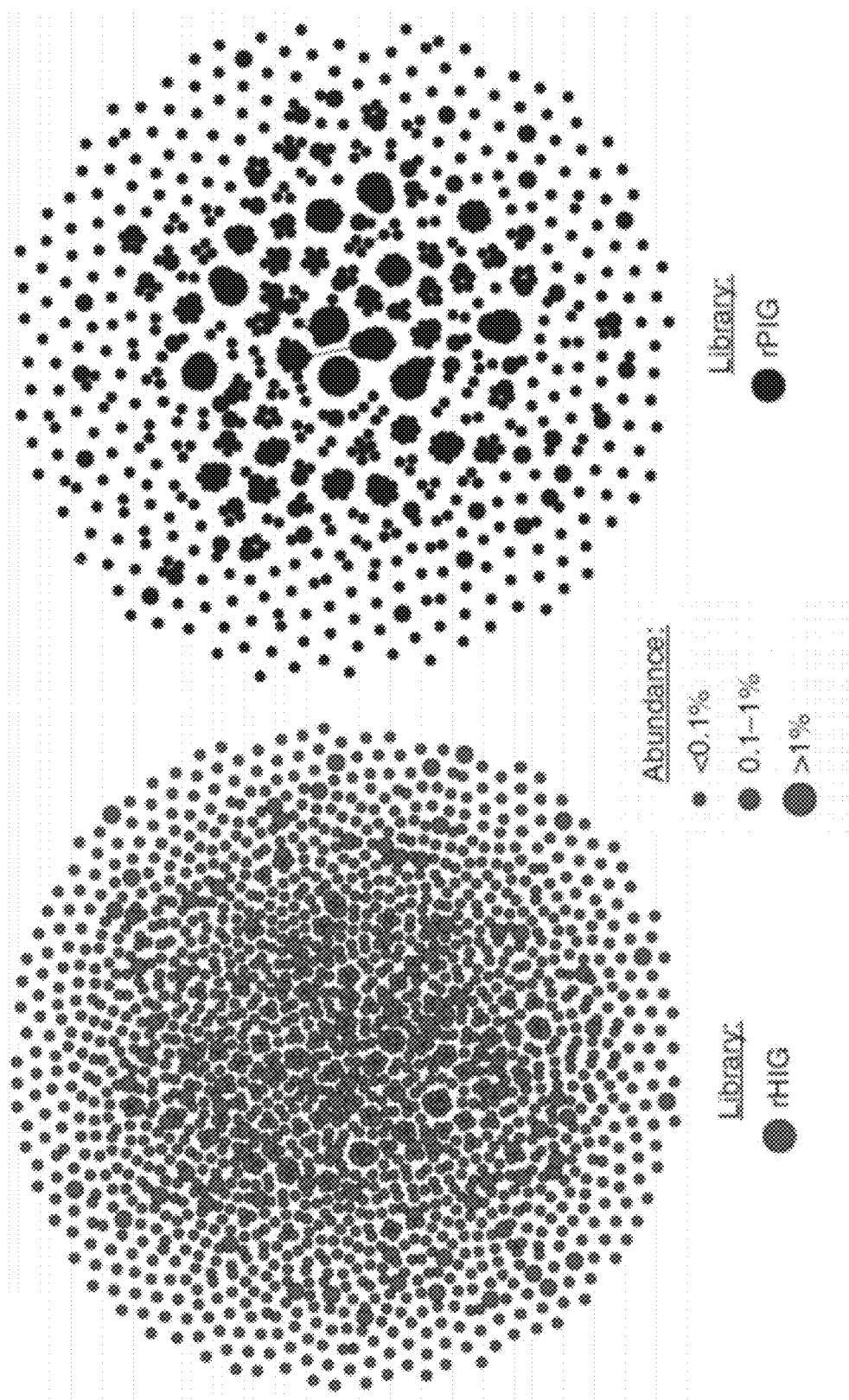

FIG. 10A shows clonal cluster analysis of rHIG and rPIG antibodies. Each node represents an antibody clone (full-length heavy chain). The size of the nodes reflects the frequency of the clones in the final CHO cell bank (only clones ≥0.01% are plotted). The total number of amino acid differences between each pairwise alignment, and edges indicate ≤5 amino acid differences were computed.

Figure 10B:
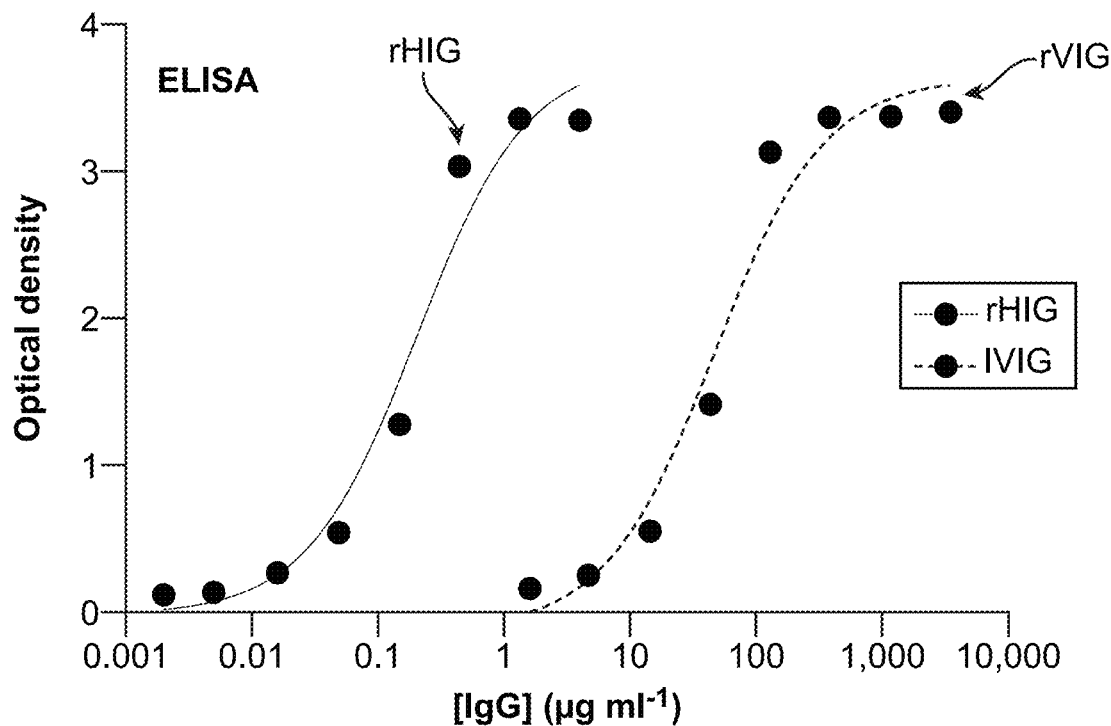

FIG. 10B shows optical density (y-axis) measure by Anti-Hib ELISA for rHIG and IVIG. Each data point represents a single measurement at a single test article dilution, in a single experiment.

Figure 10C:
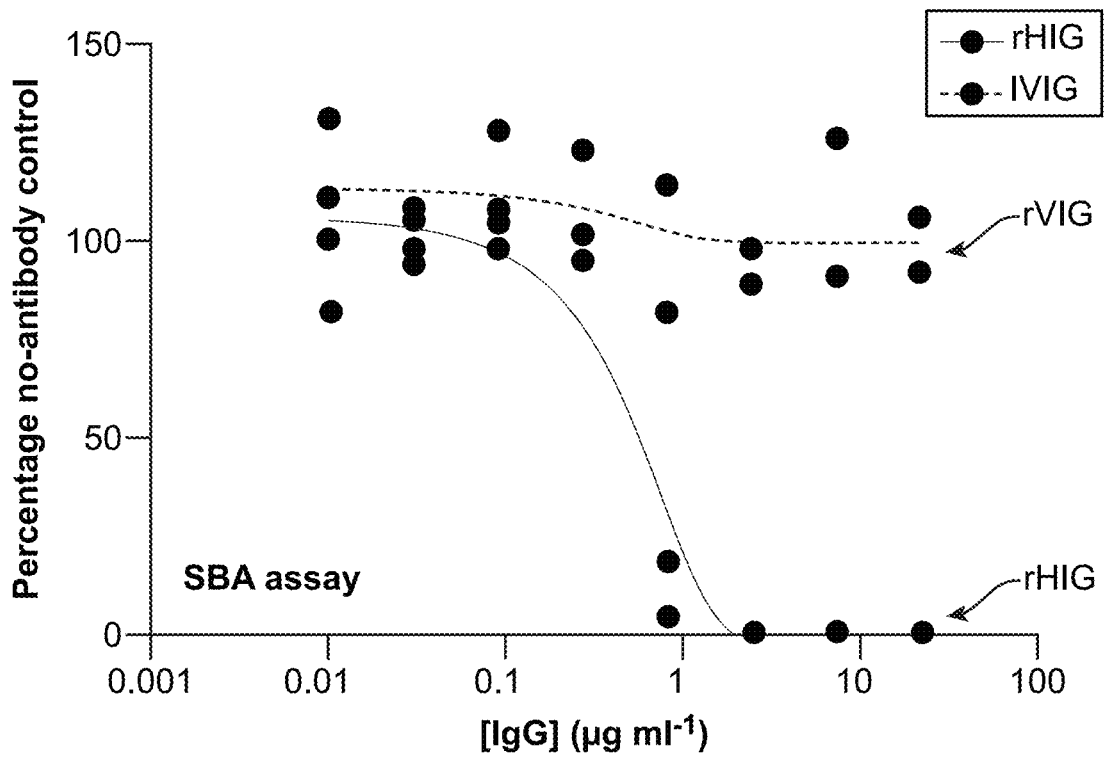

FIG. 10C shows results from serum bactericidal assay (SBA) for rHIG and IVIG with the ATCC 10211 Hib strain. Percentage of no-antibody control (y axis) was computed as the number of bacterial colonies in the test sample divided by the number of bacterial colonies in a no-antibody control sample. Each data point represents a single measurement at a single test article dilution, in a single experiment.

Figure 10D:
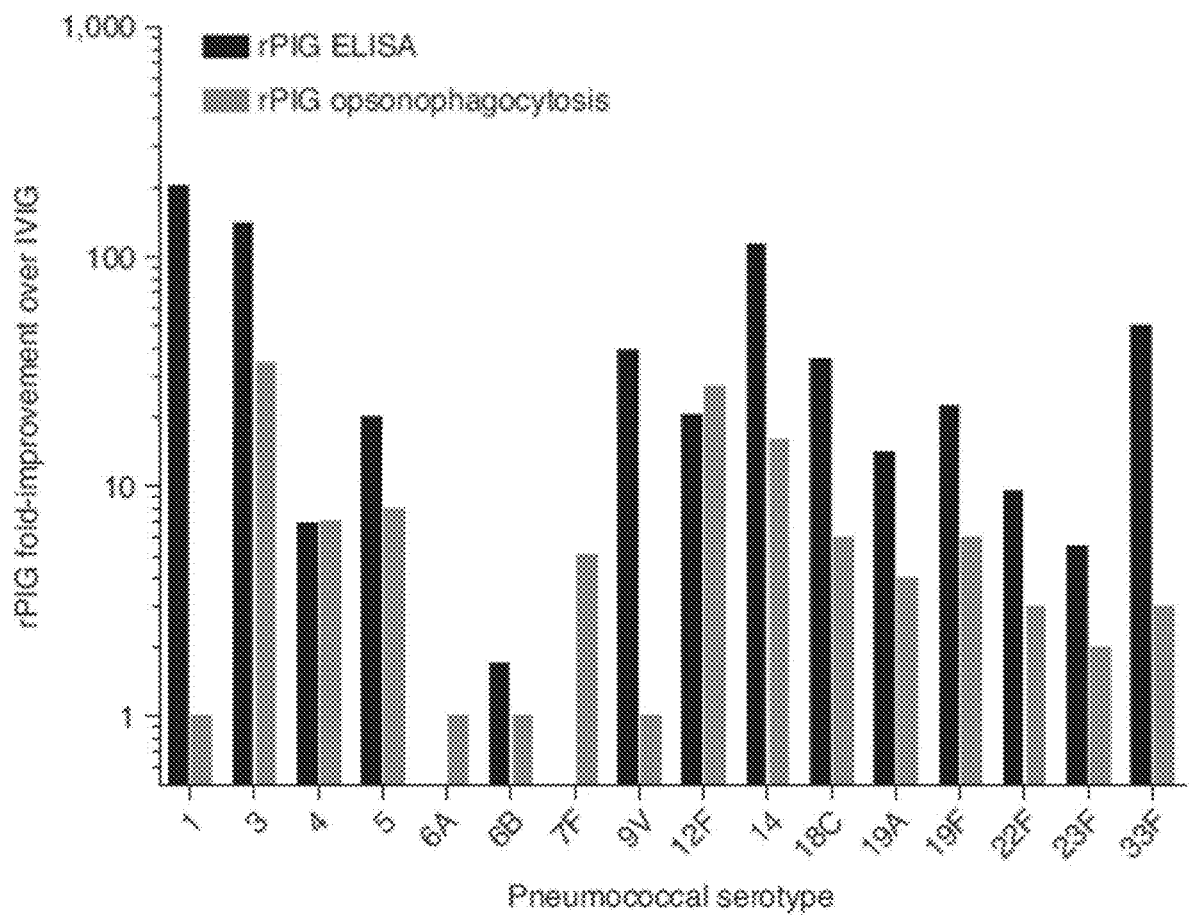

FIG. 10D shows rPIG fold-improvement over IVIG (y-axis) with respect to ELISA binding to (dark shade) or opsonophagocytosis of (light shade) the indicated pneumococcal serotype (x-axis). Fold improvement in binding/activity over IVIG was computed as a mean of duplicate measurements for rPIG divided by a mean of duplicate measurements for IVIG (based on the binding concentration for ELISA and the number of bacterial colonies for opsonophagocytosis). Fold improvement over IVIG, by assay (ELISA or opsonophagocytosis) was tested using a one-sample Wilcoxon signed rank test, with the null hypothesis that the median equals 1, that is, $H_0=1$. For each assay, all individual serotypes were pooled a single Wilcoxon signed rank test. Values for each individual serotype were generated by dividing the mean of duplicate rPIG measurements by the mean of duplicate IVIG measurements.

FIG. 10E provides in vivo assay data with ATCC 10211 Hib strain. Each circle represents CFU Hib per ml (y axis) from either peritoneal fluid or blood from a single mouse in a given test group. Black bars represent mean of the CFU Hib per ml. Dotted lines represent the lower limit of detection for CFU quantification. Welch's t-tests were used to compare CFU Hib per ml between test groups (n=8 mice per group, in a single experiment). d.f. were 7.87 for IVIG+rHIG/rPIG (500 mg kg$^{-1}$) and 7.13 for IVIG+rHIG/rPIG (200 mg kg$^{-1}$) in peritoneal fluid. d.f. were 10.87 for IVIG+rHIG/Rpig (500 mg kg$^{-1}$) and 8.03 for IVIG+rHIG/rPIG (200 mg kg$^{-1}$) in blood.

Figure 11A:
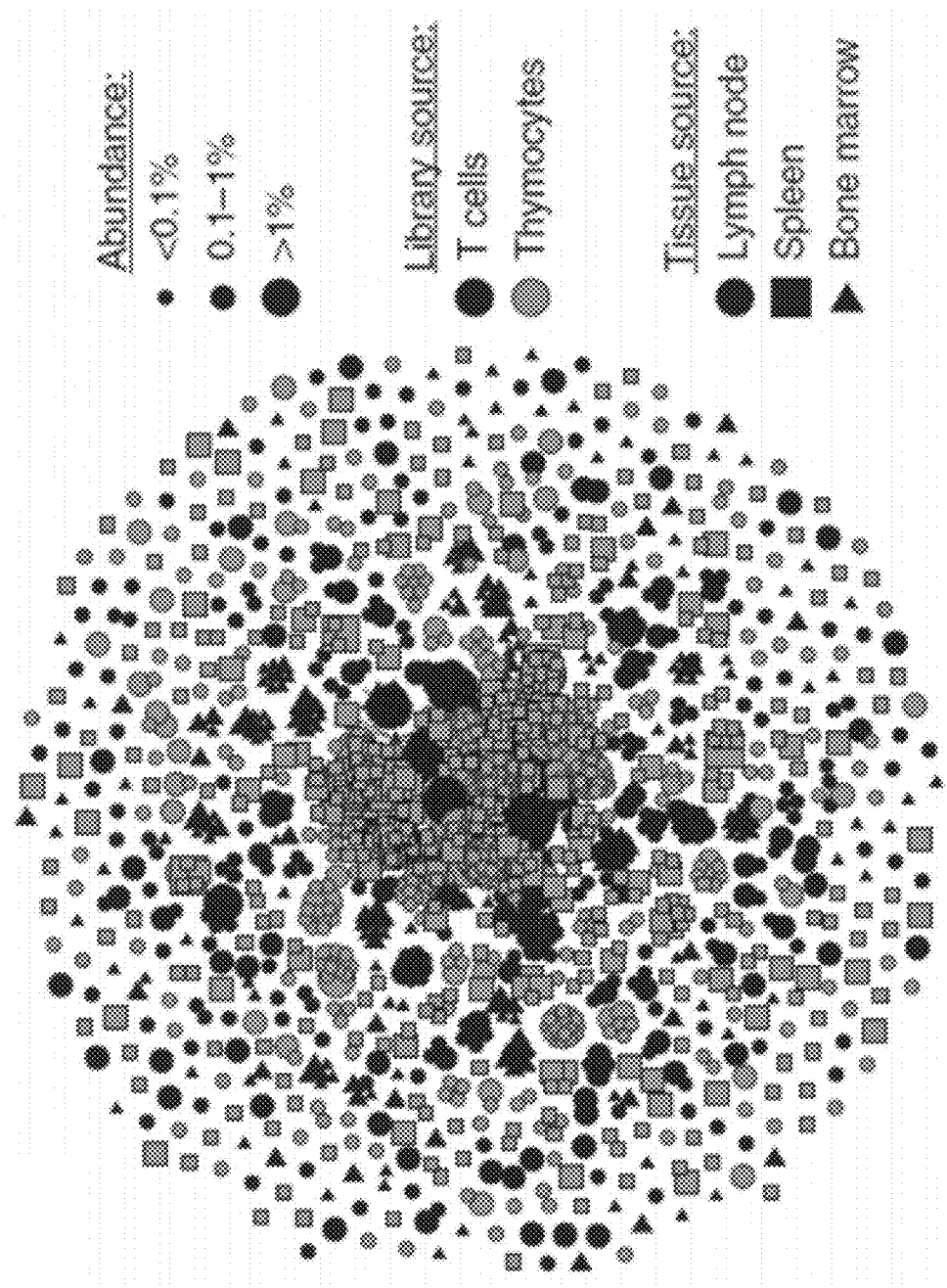

FIG. 11A provides clonal cluster analysis of rhATG antibodies. Each node represents an antibody clone (full-length heavy chain). The color of the nodes indicates the immunized library source. The shape of the nodes indicates the mouse tissue origin. The size of the nodes reflects the frequency of the clones in the final CHO cell bank (only clones ≥0.01% are plotted). The total number of amino acid differences between each pairwise alignment, and edges indicate ≤5 amino acid differences were computed.

Figure 11B:
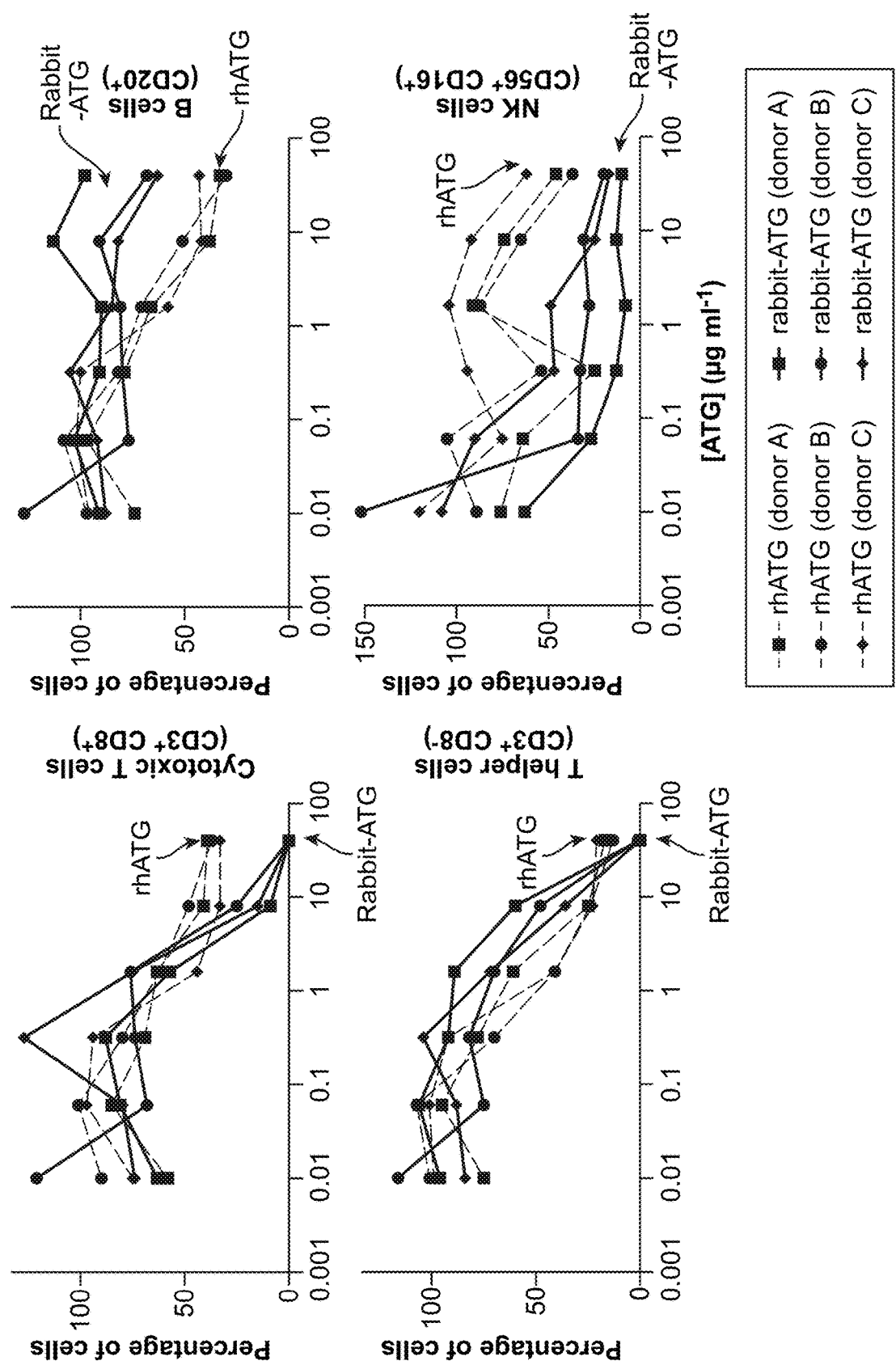

FIG. 11B shows results from cell killing assays of a dilution series of rabbit-ATG and rhATG with three PBMC donors. They axis (% cells) was determined by dividing the number of cells of the indicated cell type present after overnight incubation with the indicated amount of antibody by the number of cells of that cell type present in a no-antibody control. Each data point represents a single measurement at a single test article dilution, in a single experiment. Linear mixed effects models were used to compute P values for each of the four cell types, with group and concentration as fixed effects and PBMC donor as a random effect to account for the dependence of repeated measures. d.f. were 31 for each of the four models. NK, natural killer.

Figures 11C, 11D:
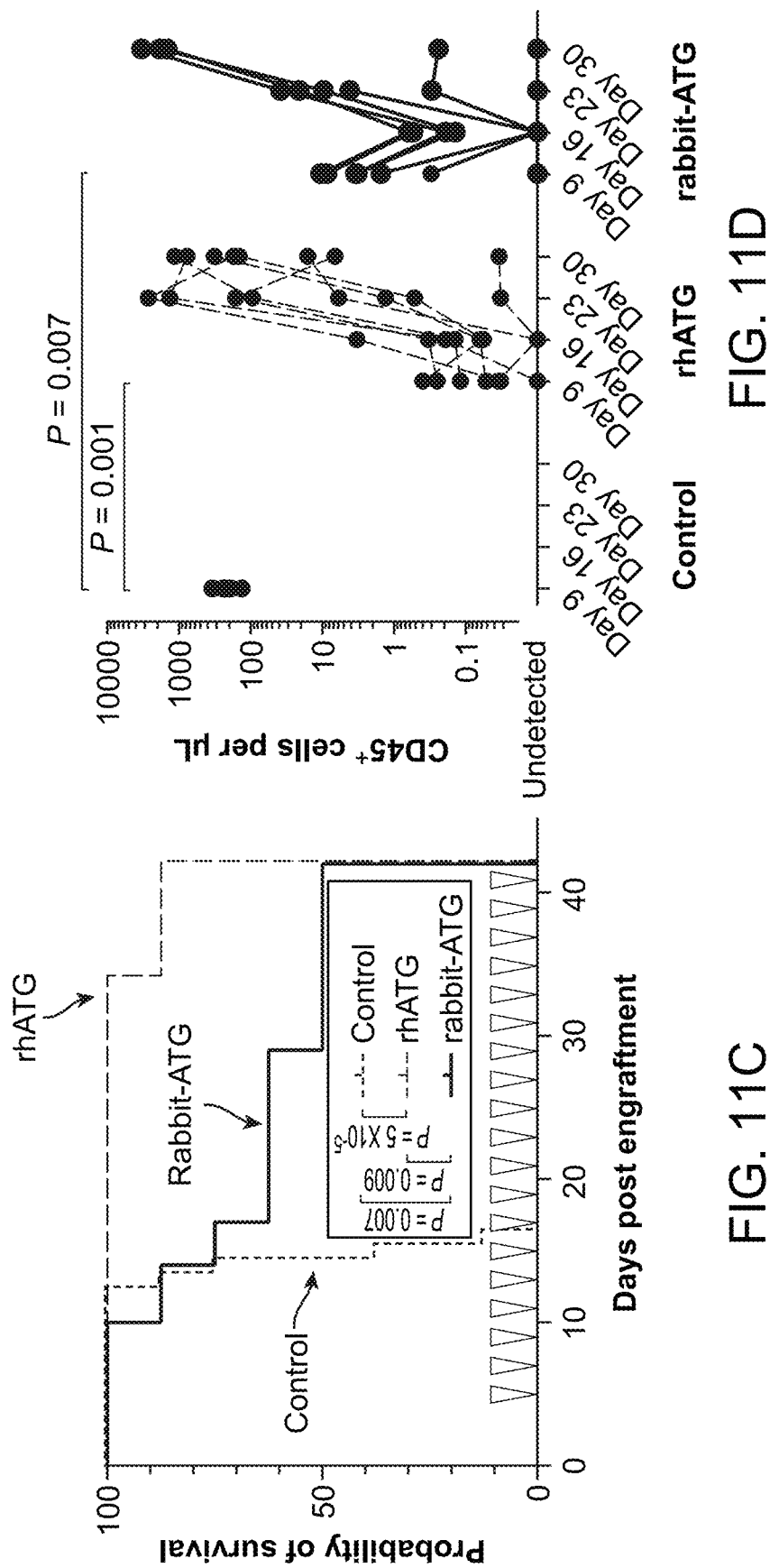

FIG. 11C shows survival of mice (n=8 per treatment group, in a single experiment) in the GVH study using PBMC donor 1 treated every other day with a negative vehicle control, rabbit-ATG or rhATG. Treatment days are indicated by green triangles. Kaplan-Meier survival models were fit on time to mortality and pairwise log-rank tests were performed to compare median survival between treatment groups.

FIG. 11D shows the concentration of CD45+ cells determined by flow cytometry in each alive mouse on days 9, 16, 23 and 30 of the GVH study from FIG. 11C for negative vehicle control, rhATG or rabbit-ATG. Lines connect measurements from each mouse. No CD45+ cells were observed where circles intercept the x axis. Linear mixed effects models were used to compute P values for trends in CD45+ cell counts in each of the four GVH experiments (2 PBMC donors×2 drug dosing regimens=4 experiments) with day as a fixed effect and PBMC donor as a random effect to account for the dependence of repeated measures. A Wilcoxon rank sum test was used to compare CD45+ cell counts on day 9 for saline negative control versus rhATG and saline negative control versus rabbit-ATG, in each of the four GVH experiments (2 PBMC donors×2 drug dosing regimens=4 experiments).

Figure 12A:
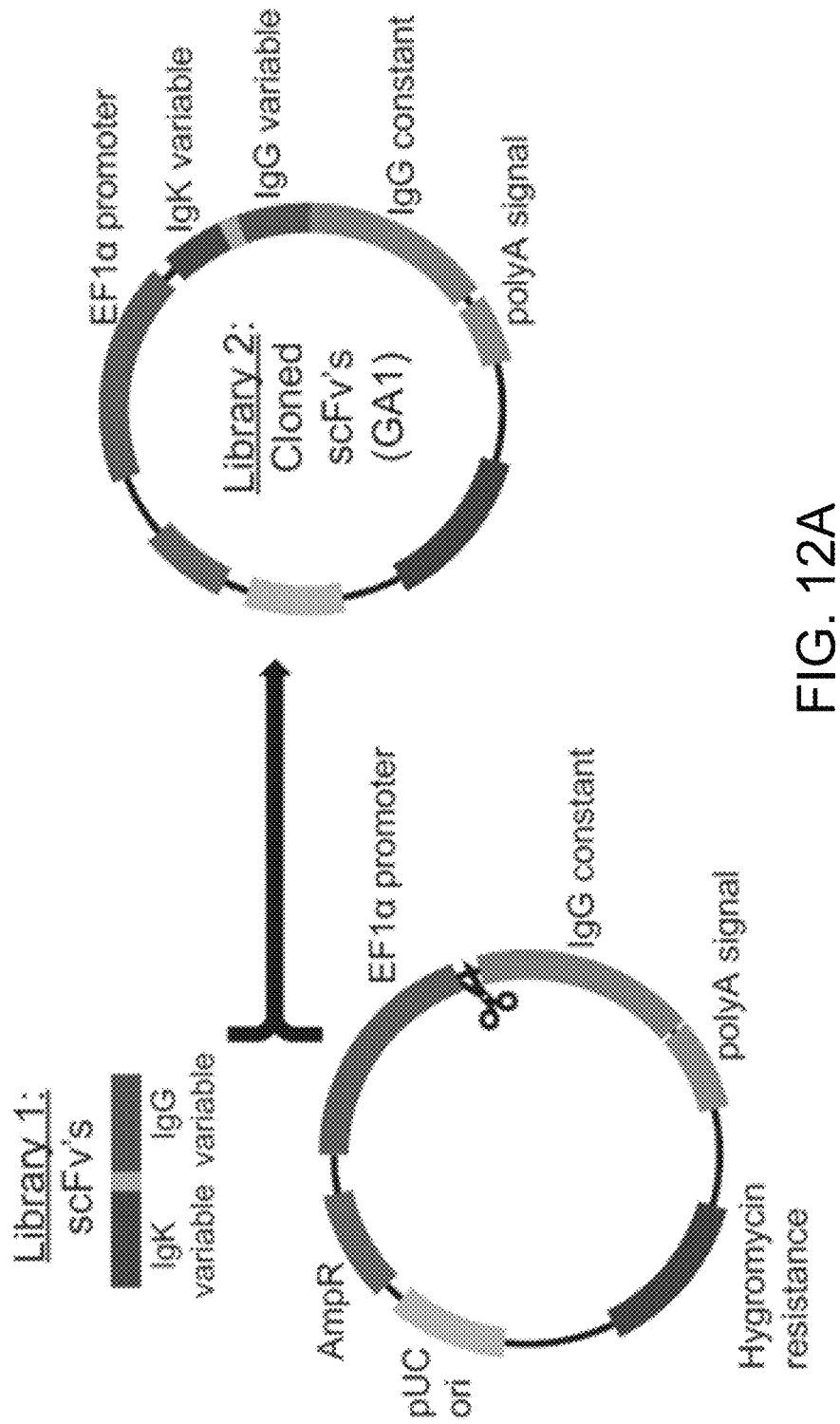
Figure 12B:
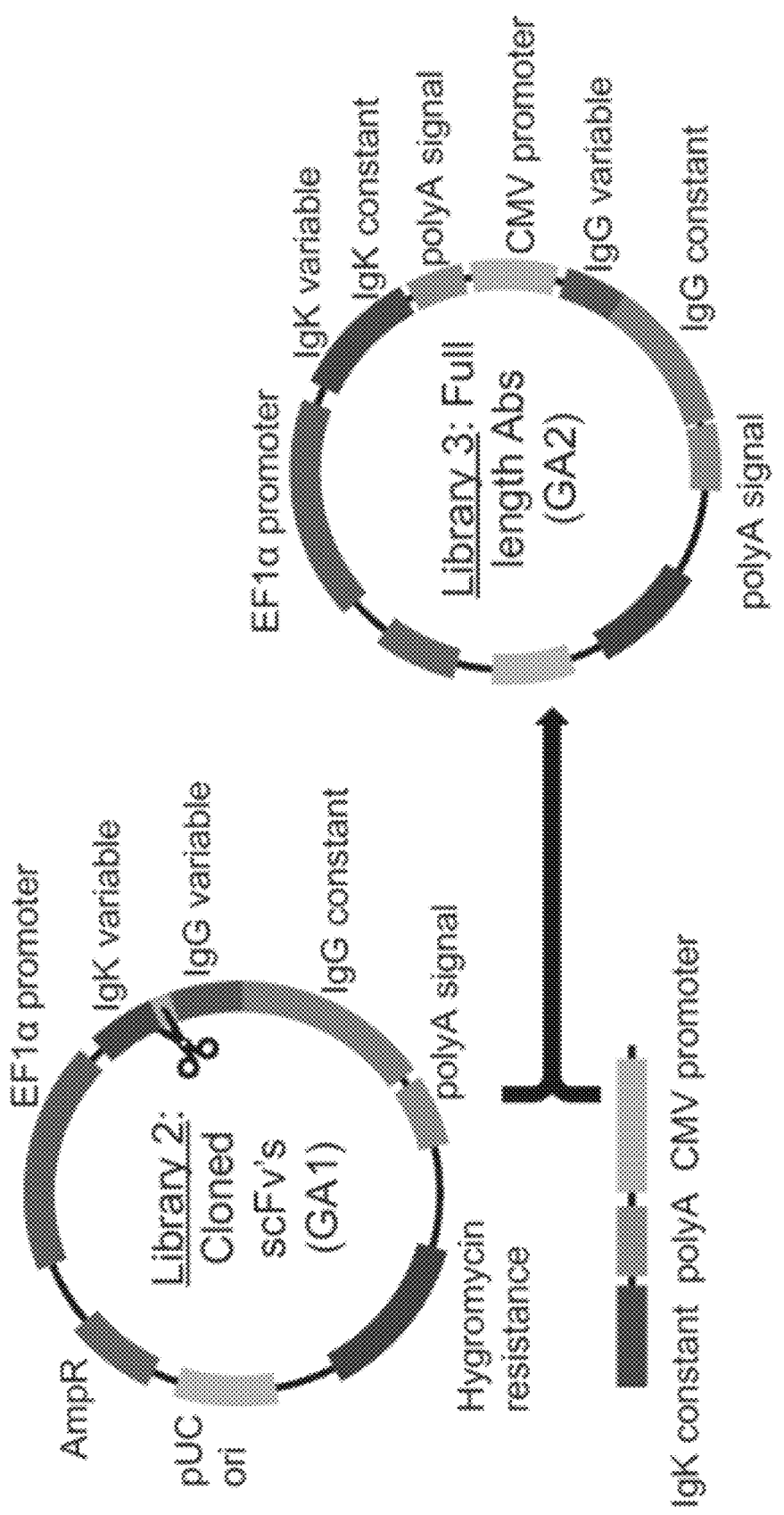

FIGS. 12A and 12B provide schematic of Gibson assembly processes. (FIG. 12A) Product of Gibson Assembly 1 (GA1), comprising the based plasmid vector with an scFv (from Library 1) cloned between the EF1α promoter and the IgG constant domain sequence. (FIG. 12B) Product of Gibson Assembly 2 (GA2), with the scFv linker excised and replaced with a sequence that comprises an IgK constant domain sequence, a poly(A) signal sequence, and a CMV promoter.

Figure 13A:
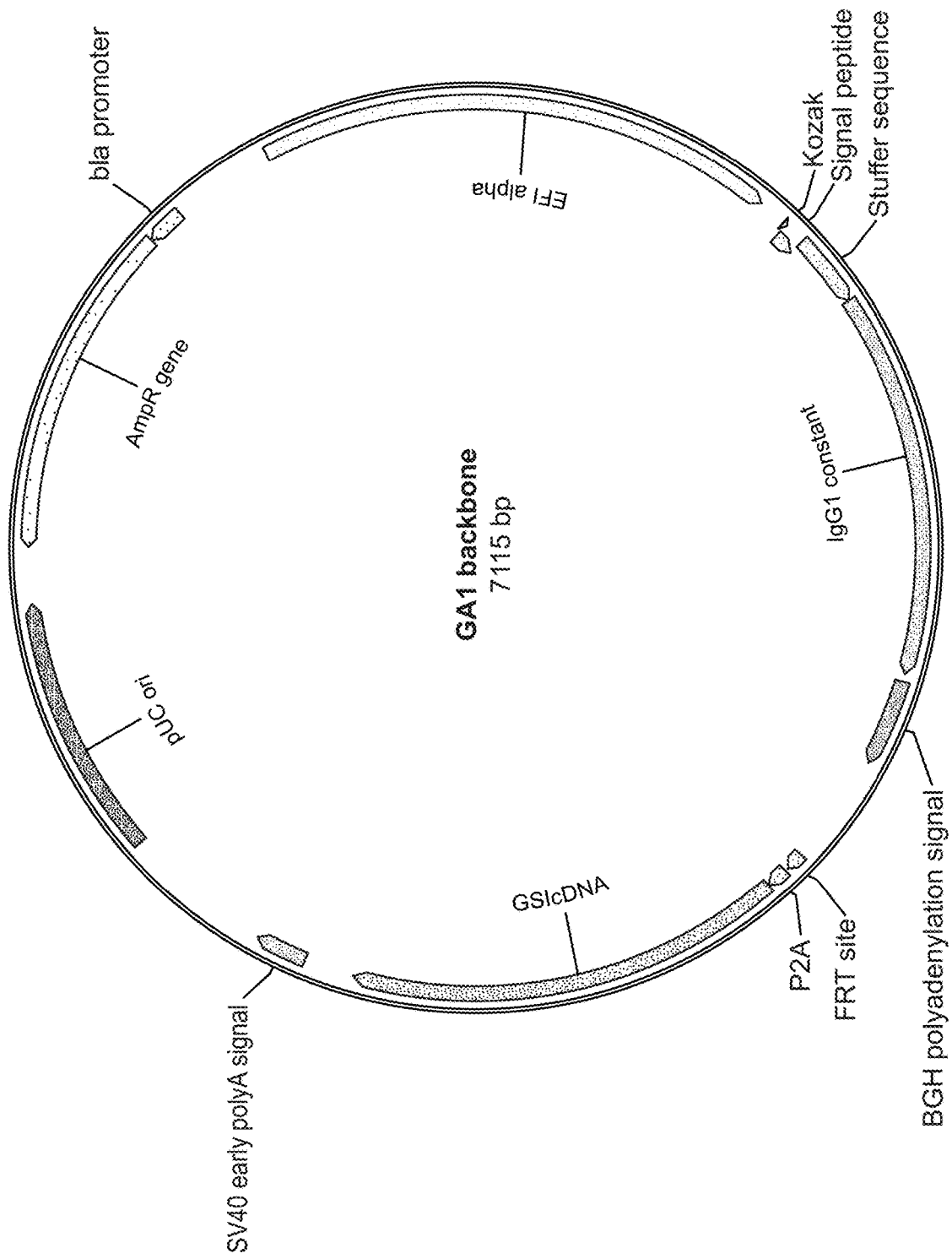

FIG. 13A Gibson Assembly 1 (GA1) backbone (GenBank accession MW079271).

Figure 13B:
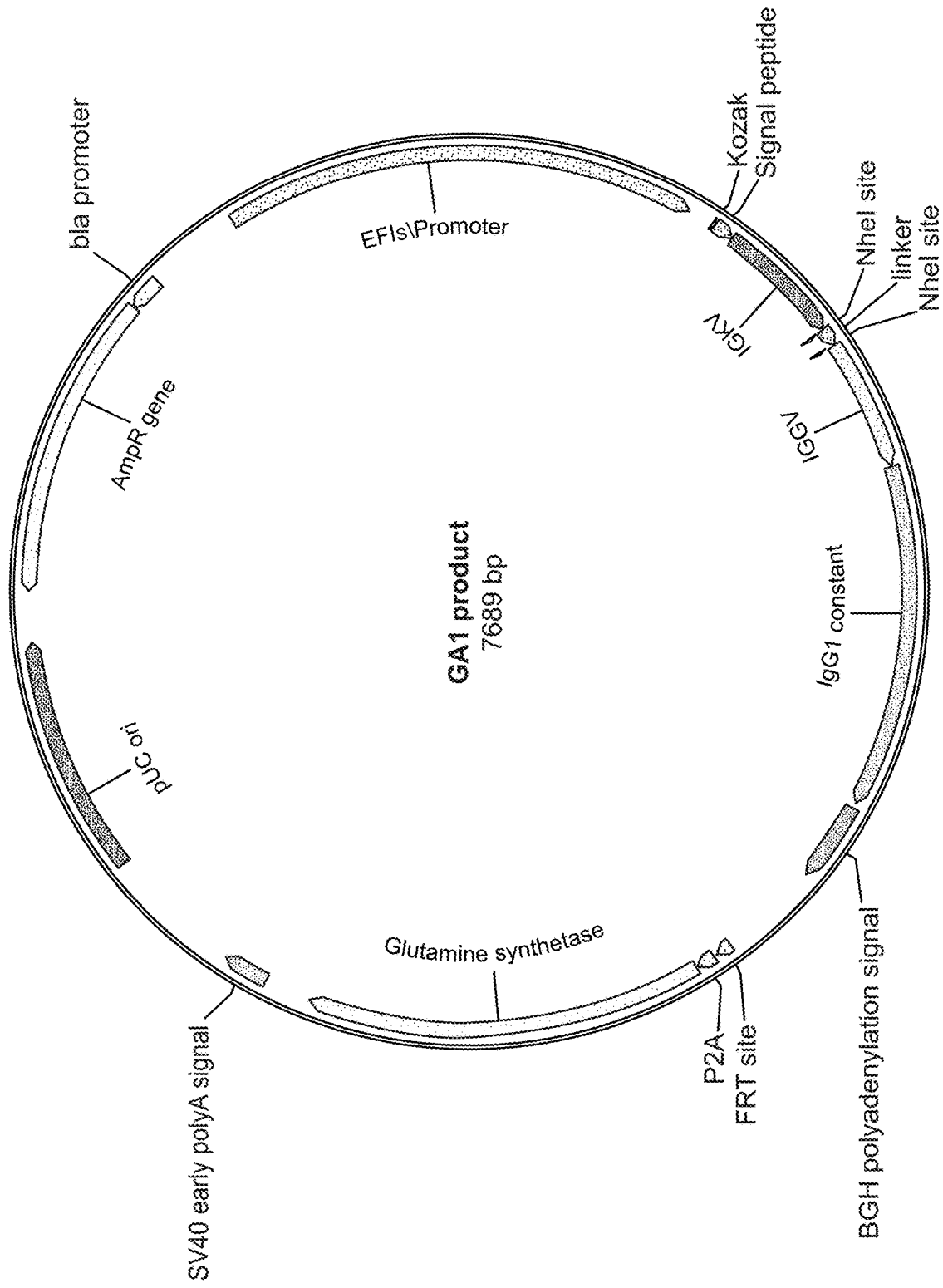

FIG. 13B Product of Gibson Assembly 1 (GA1) after insertion of an scFv sequence (GenBank accession MW079272).

Figure 13C:
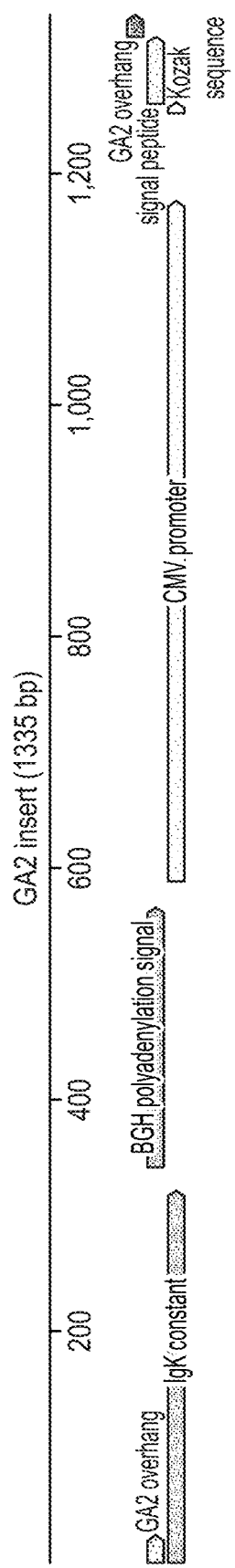

FIG. 13C The linear Gibson Assembly 2 (GA2) insert sequence (GenBank accession MW079275).

Figure 13D:
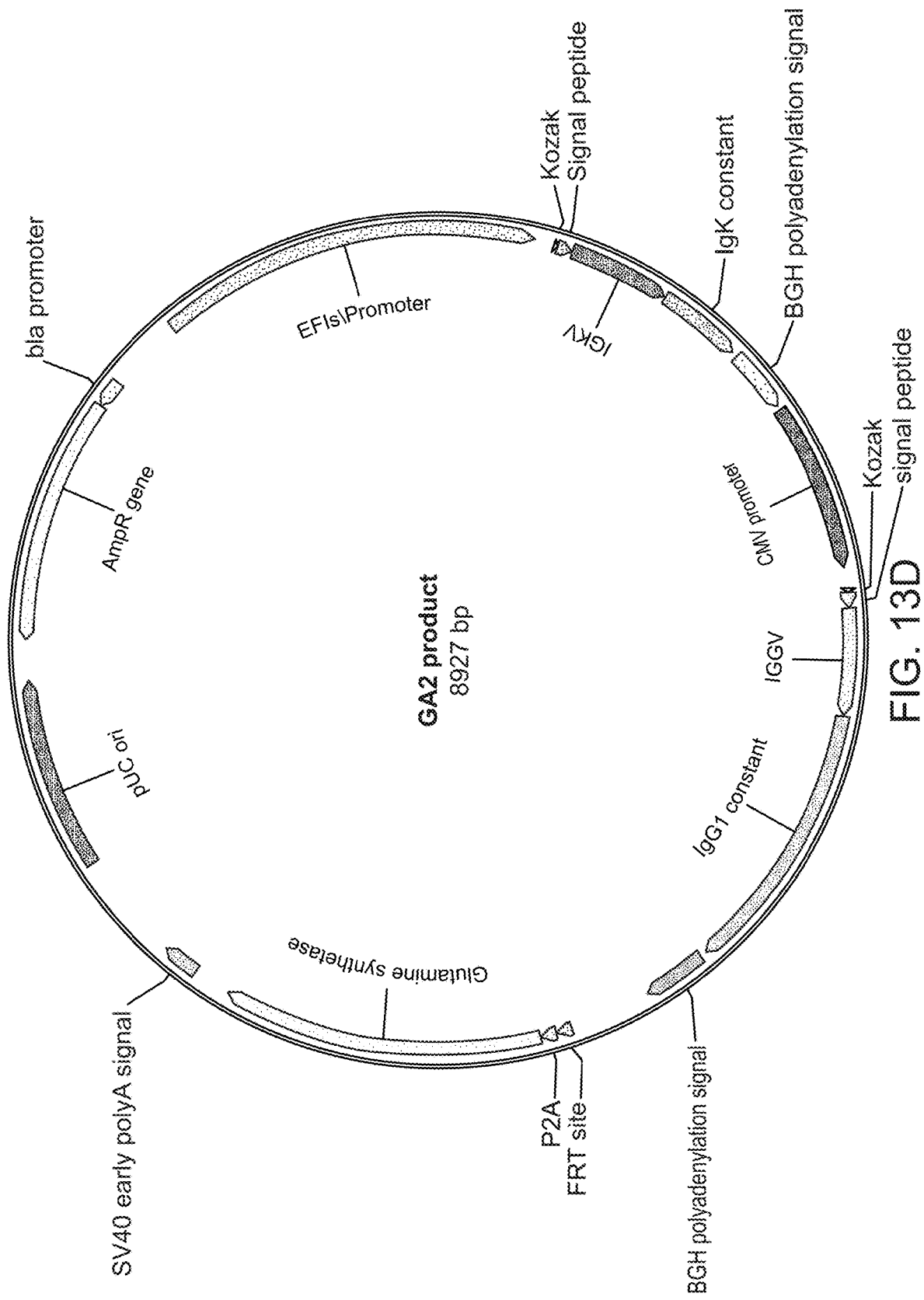

FIG. 13D Product of Gibson Assembly 2 (GA2) after insertion of the GA2 insert (GenBank accession MW079273).

Figure 13E:
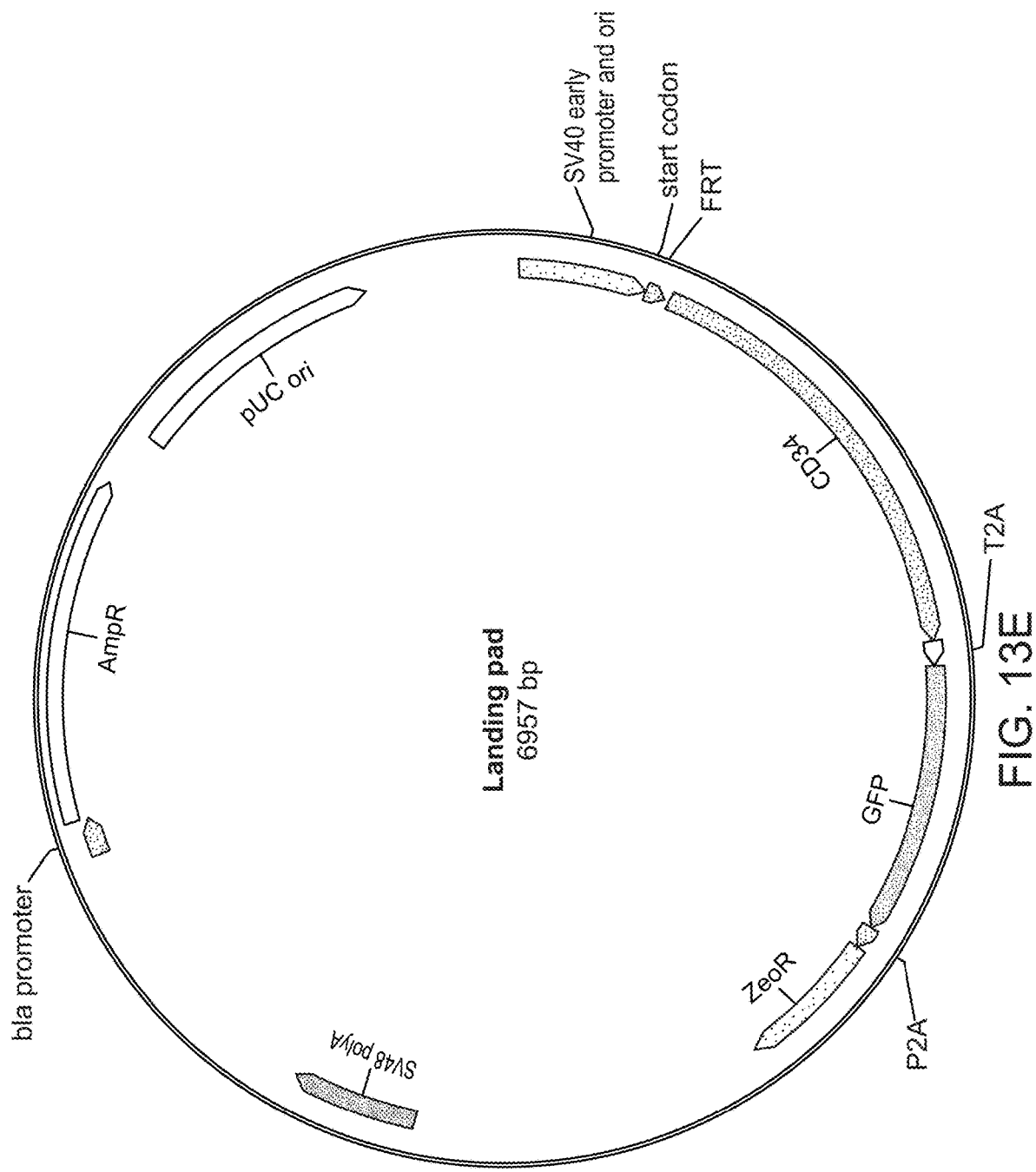

FIG. 13E Landing pad plasmid used to generate a custom CHO landing pad cell line (GenBank accession MW079274).

Figure 14A:
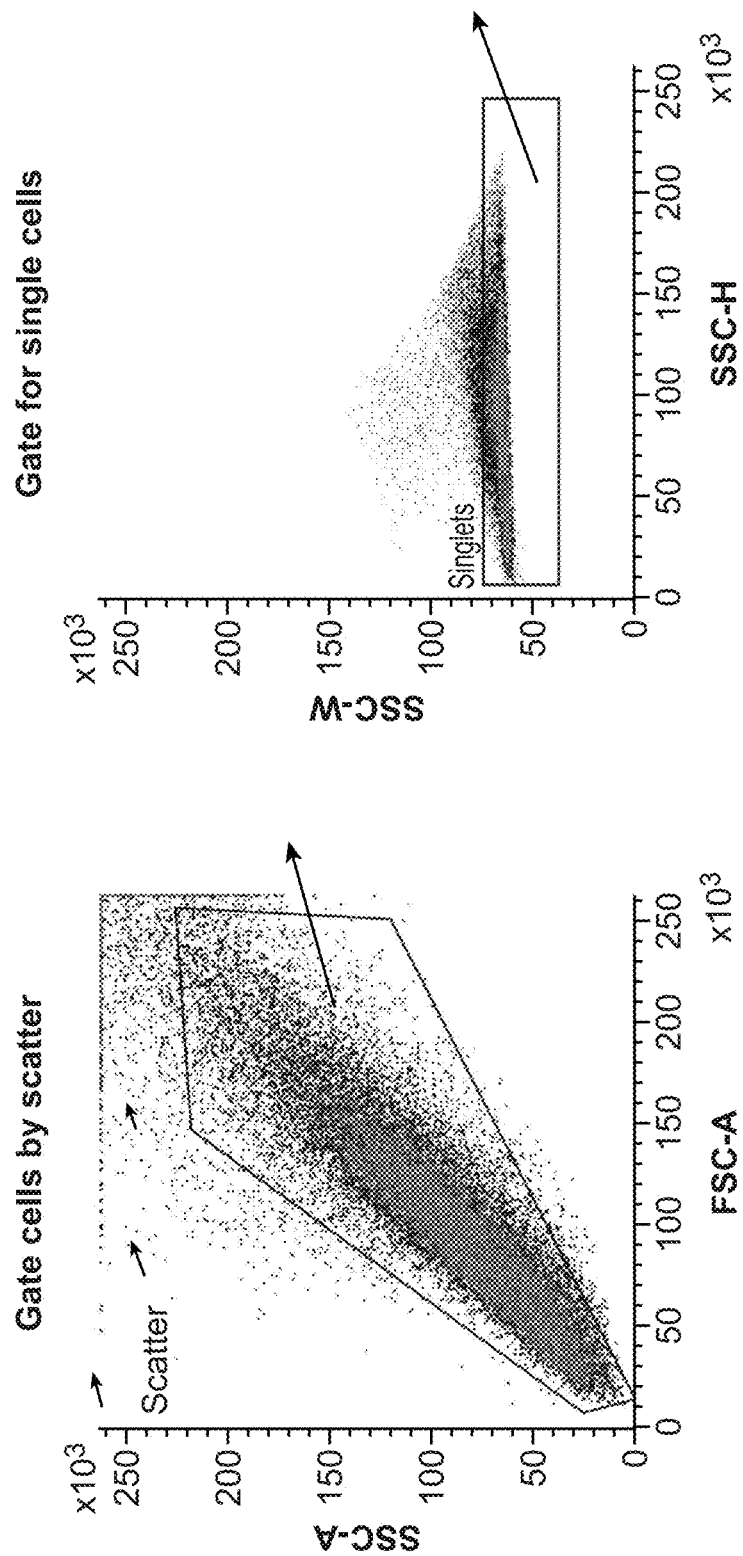
Figure 14A:
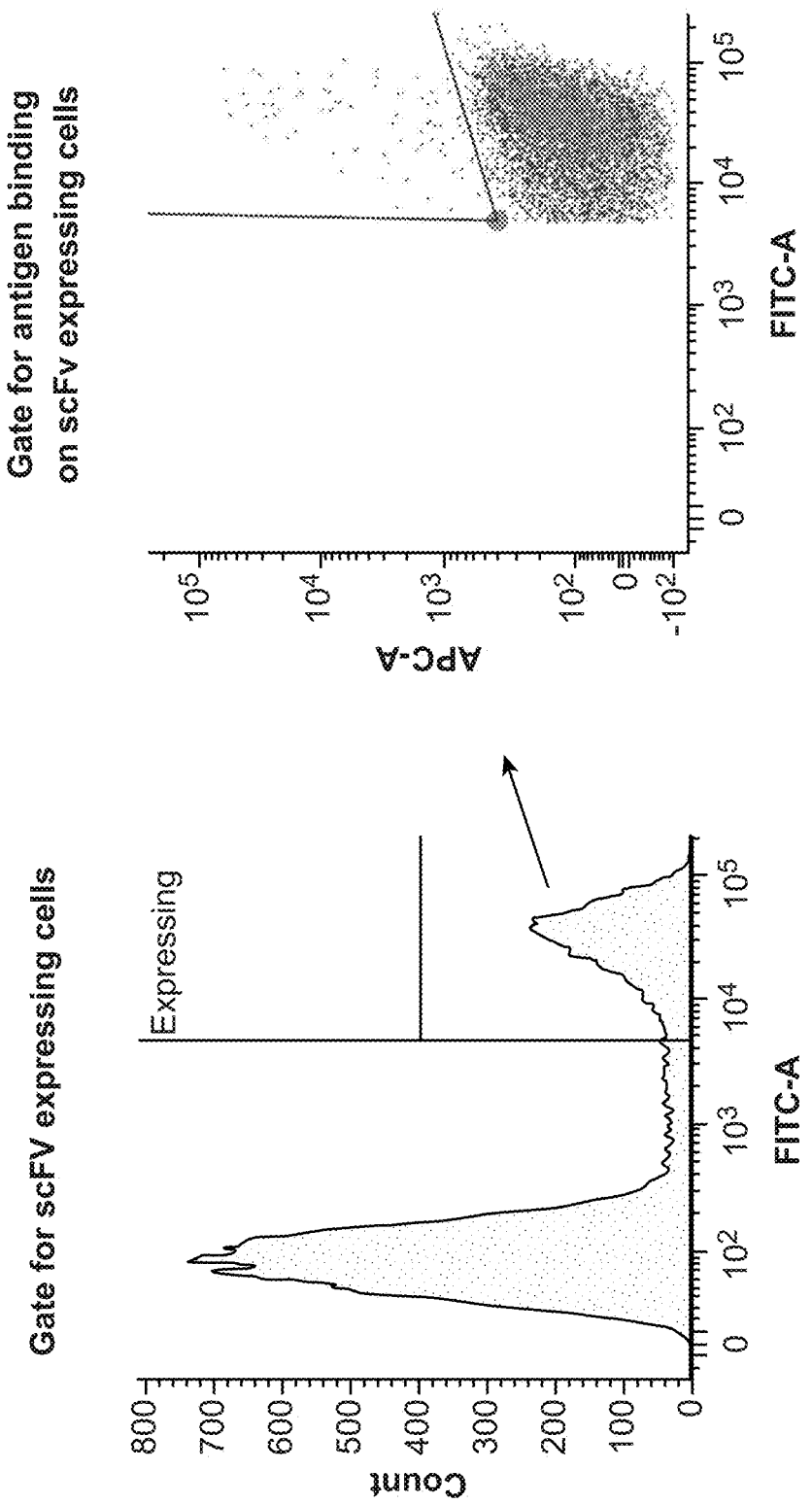

FIG. 14A shows flow sorting for SARS-CoV-2 specific antibodies using yeast scFv display. Gating strategy was used for each yeast sort.

Figure 14B:
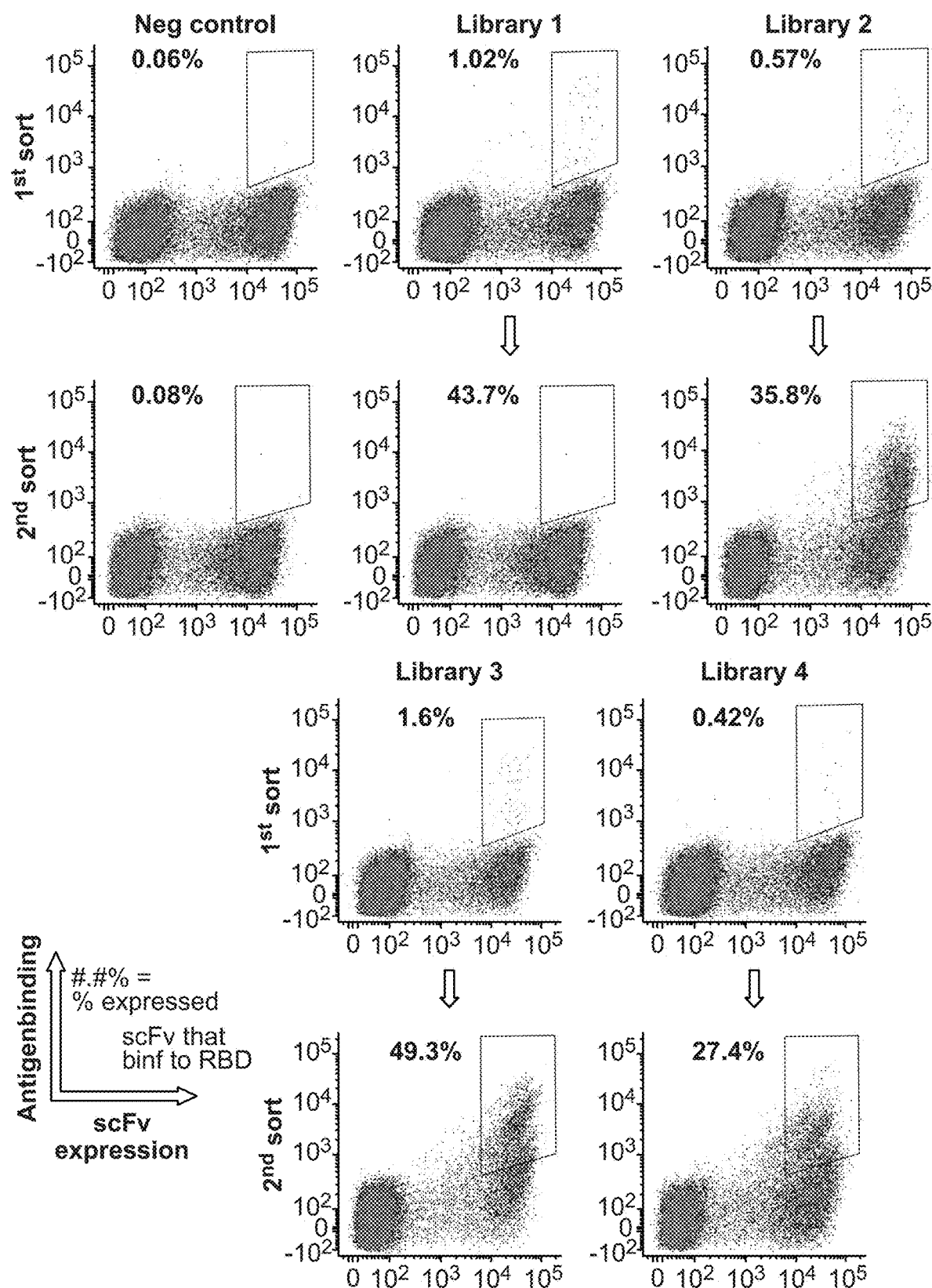
Figure 14B:
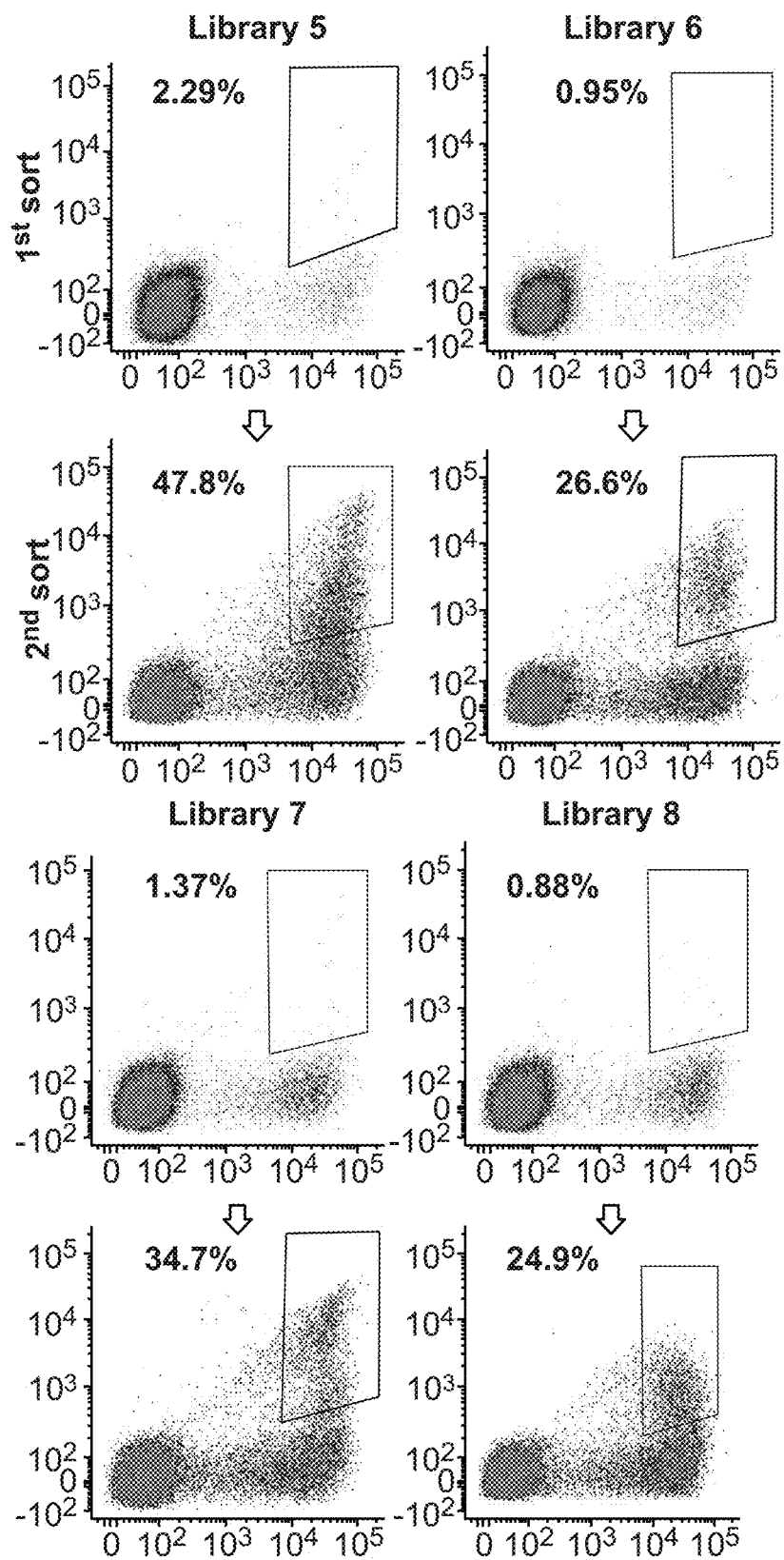

FIG. 14B shows detection of a C-terminal c-Myc tag (x-axis), indicating expression of an scFv on the surface of the cell. The y-axis measures binding of antigen to the scFv-expressing cells. The gates used for yeast selection (double positive) are indicated, with the percentage of scFv-expressed RBD binders. A negative control and the eight rCIG convalescent donor libraries were stained with 1200 nM biotinylated CoV-2 RBDHis. An average of 1.1% of the expressed antibodies were RBD-specific on the first sort. After the second sort, the RBD-specific scFv were amplified and then cloned into full-length antibody expression plasmids.

FIG. 15 shows CoV-2 S1- and RBD-specific antibody binding measured by ELISA. rCIG, the 8 recombinant libraries, the 8 plasma pools from donors that made up rCIG, neutralizing SARS-CoV-2 mAb, nonneutralizing SARS-CoV mAb, and IVIG were titrated relative to total IgG concentration.

Figure 16A:
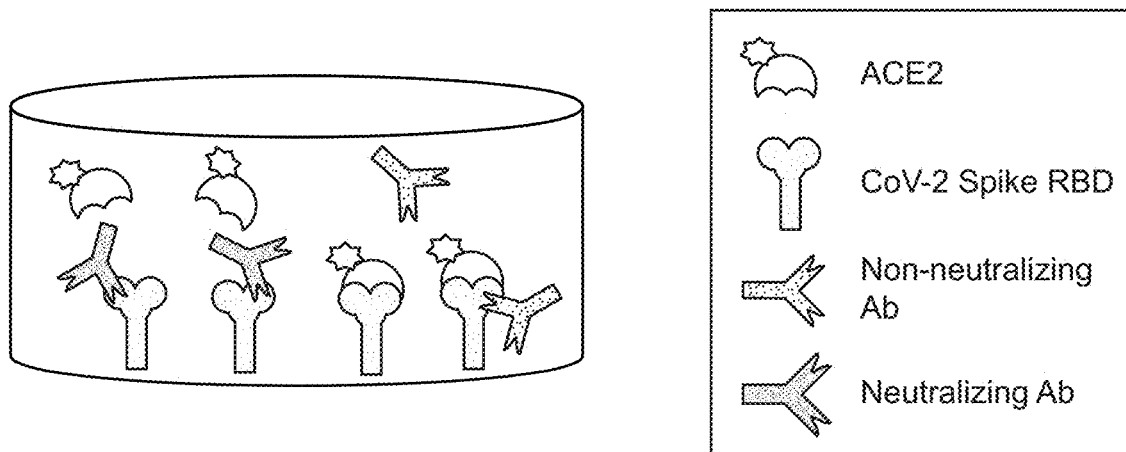

FIG. 16A illustrates ACE2 inhibition assay. The blocking ability of SARS-CoV-2 specific antibodies were measured using a plate-based ELISA method. Spike RBD was used to coat the plate and after the antibody samples are coincubated, ACE2 was added and measured for binding to RBD; antibodies that block the interaction demonstrate low or no binding of ACE2 and are considered neutralizing.

Figure 16B:
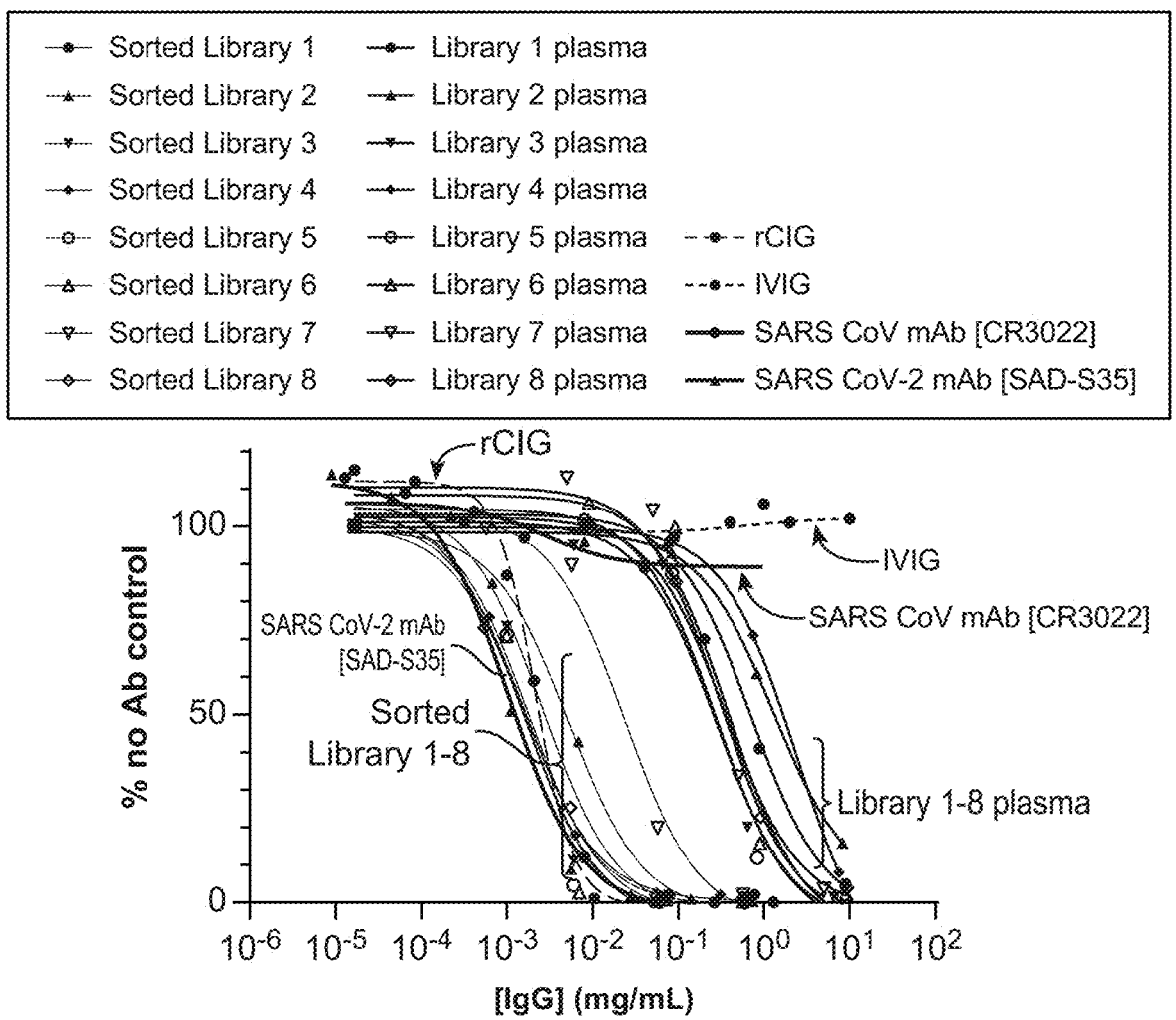

FIG. 16B shows results from the ACE2 inhibition assay. The recombinant polyclonal rCIG, the 8 recombinant antibody libraries, the 8 plasma pools from donors that make up rCIG, neutralizing SARS-CoV-2 mAb, non-neutralizing SARS-CoV mAb, and IVIG were titrated and added to the RBD coated plate. The data are reported as "% no Ab control", i.e., dividing the signal of the test article by the signal of a no Ab control.

FIG. 17A illustrates CoV-2 pseudotype virus neutralization assay. A pseudotype virus expressing the SARS-CoV-2 spike proteins can infect ACE2-expressing target cells (which then turn due to GFP expression from the pseudotype virus), which is used to demonstrate whether antibodies specific to SARS-CoV-2 can neutralize infection.

FIG. 17B shows results from the CoV-2 pseudotype virus neutralization assay. The recombinant polyclonal rCIG, the 8 recombinant antibody libraries, the eight plasma pools from donors that make up rCIG, neutralizing SARS-CoV-2 mAb, non-neutralizing SARS-CoV mAb, and IVIG were titrated and added to ACE2-expressing cells in the presence of CoV-2 pseudotype virus. The percent of infected cells (GFP+) was quantified by flow cytometry and was normalized by dividing by the GFP+ signal in the negative control wells, which lacked test article.

Figure 17C:
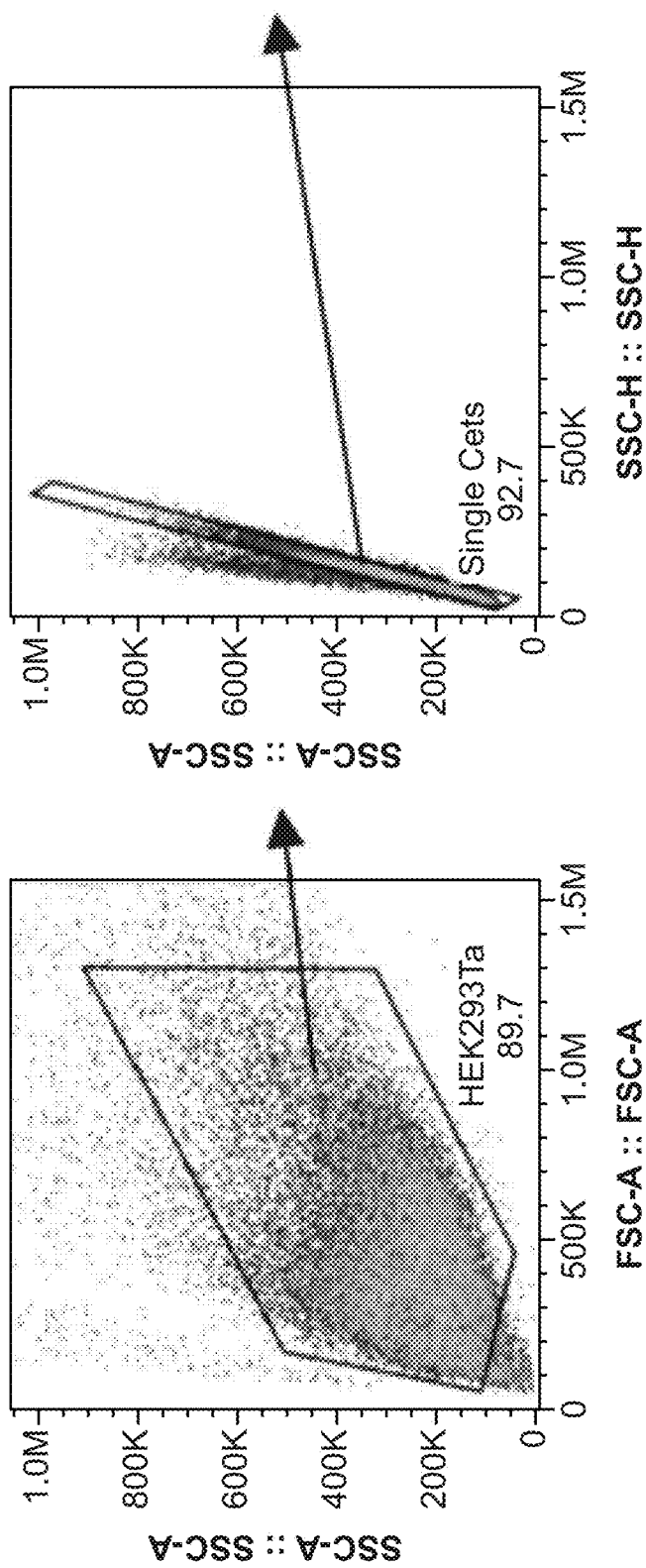
Figure 17C:
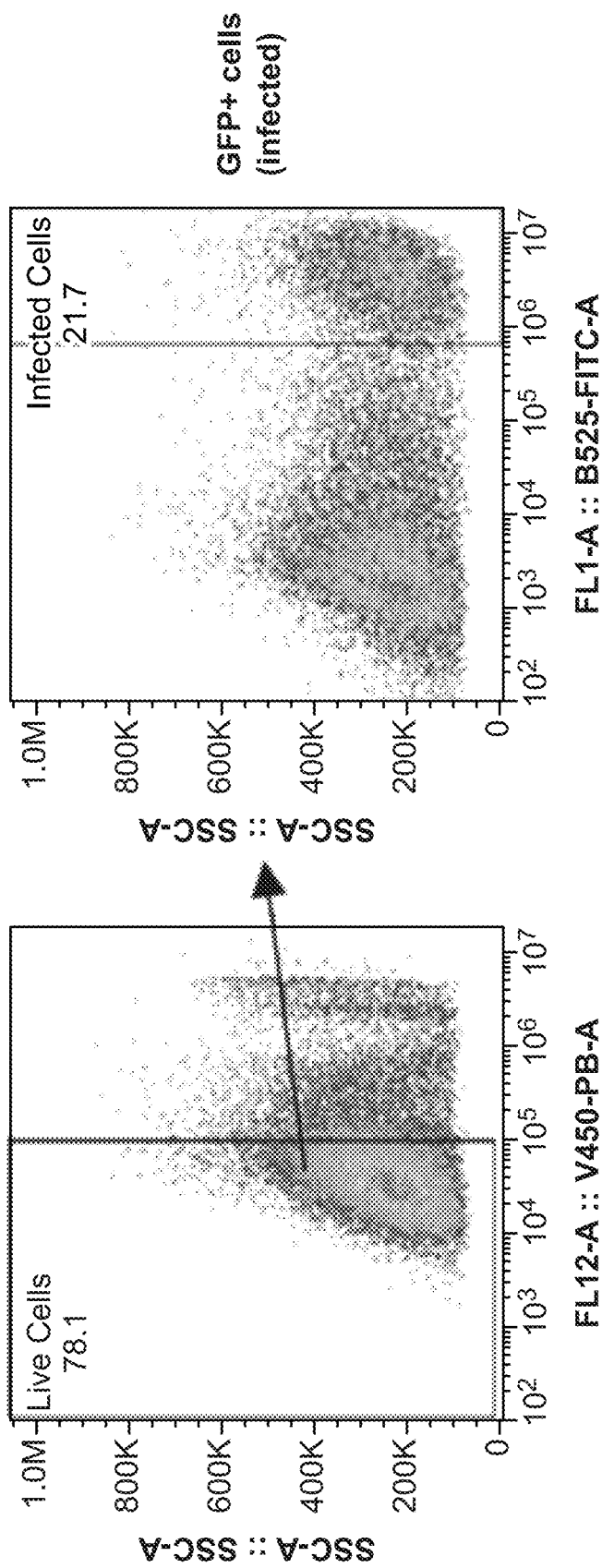

FIG. 17C provides flow gating strategy of the pseudotype virus neutralization assay to identify live, GFP+ cells (those infected with pseudotype virus).

Figure 18A:
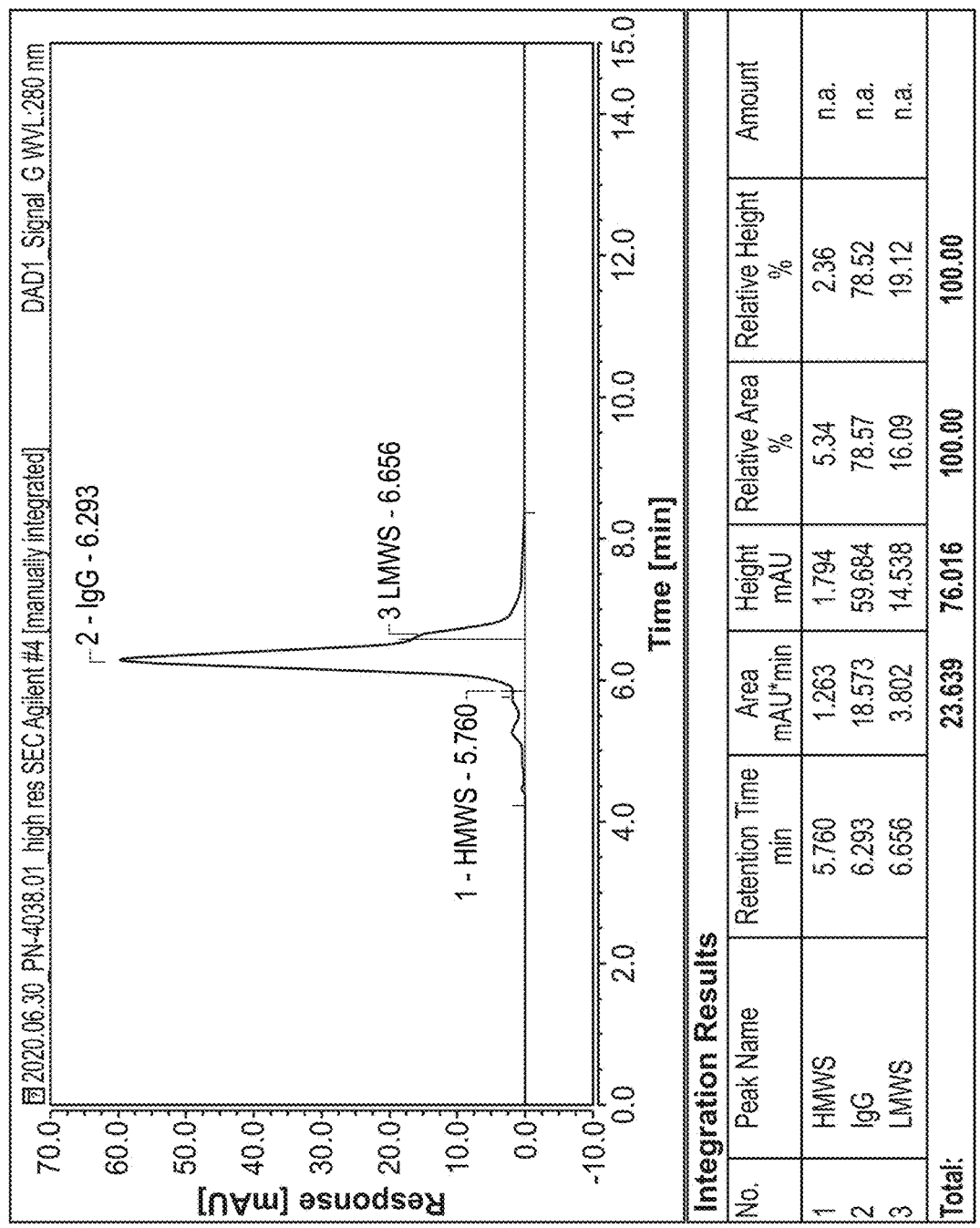
Figure 18B:
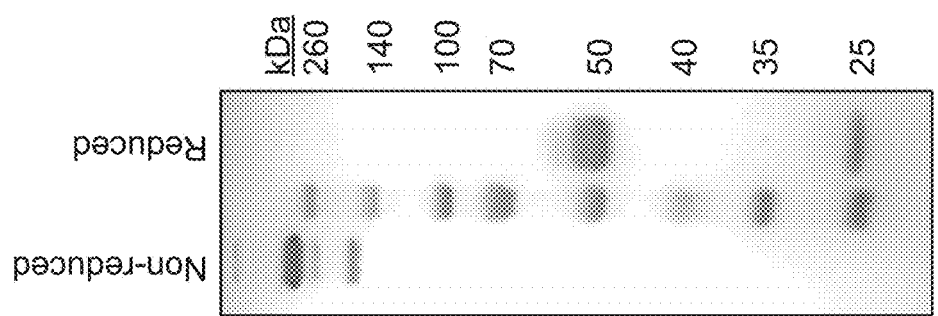
Figure 19B:
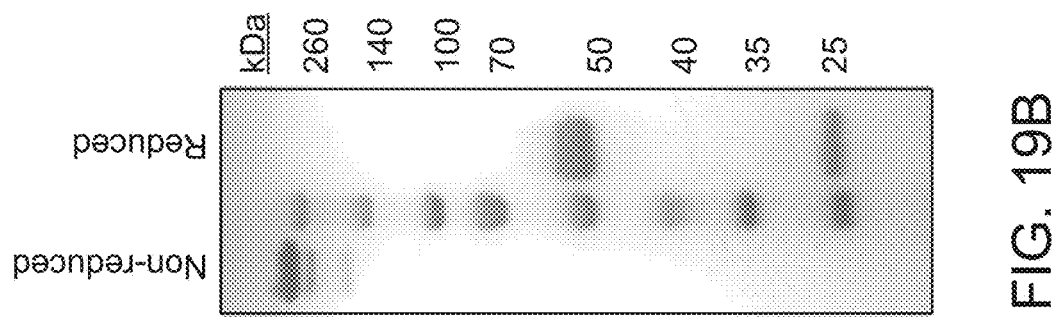
Figure 19A:
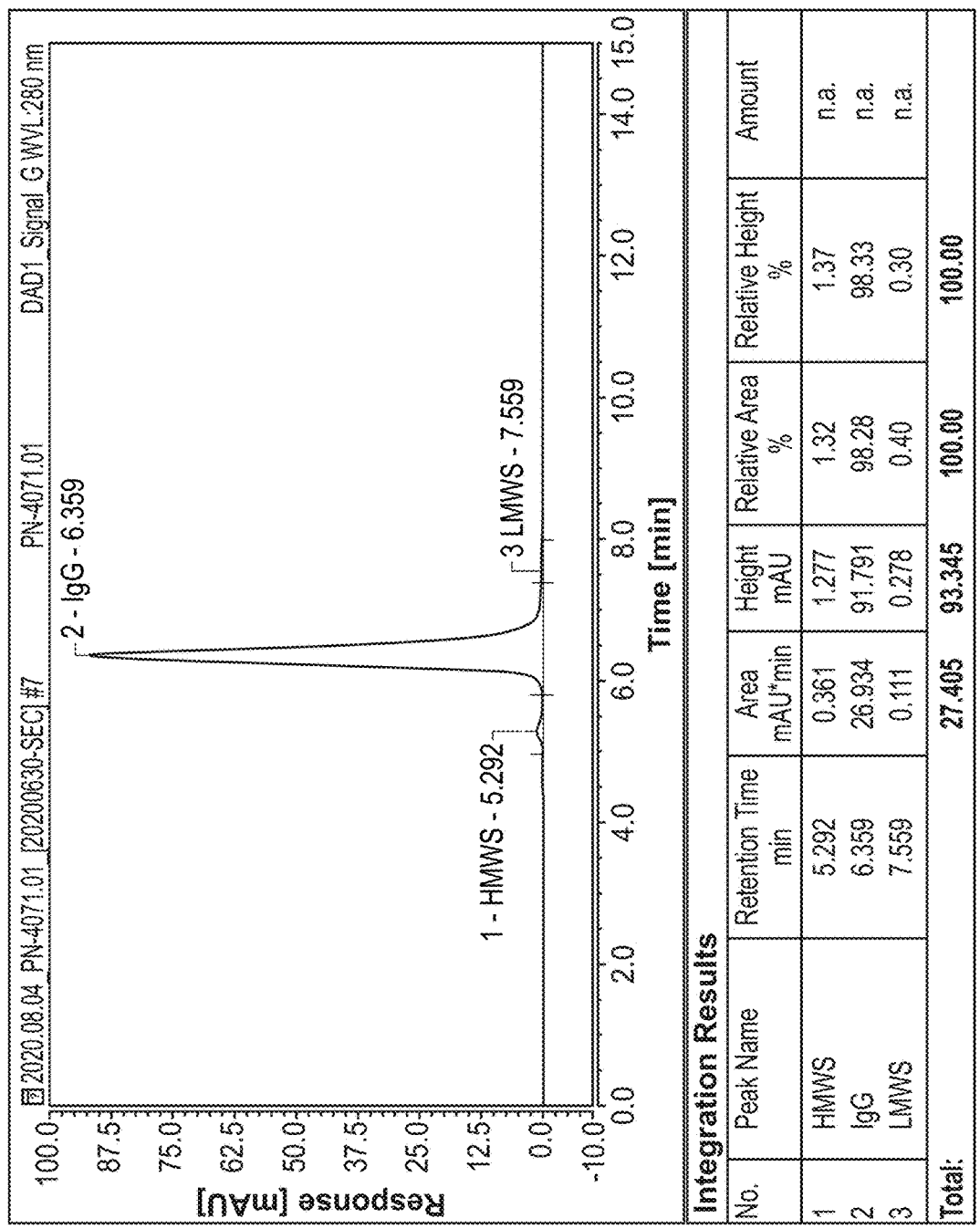
Figure 19C:
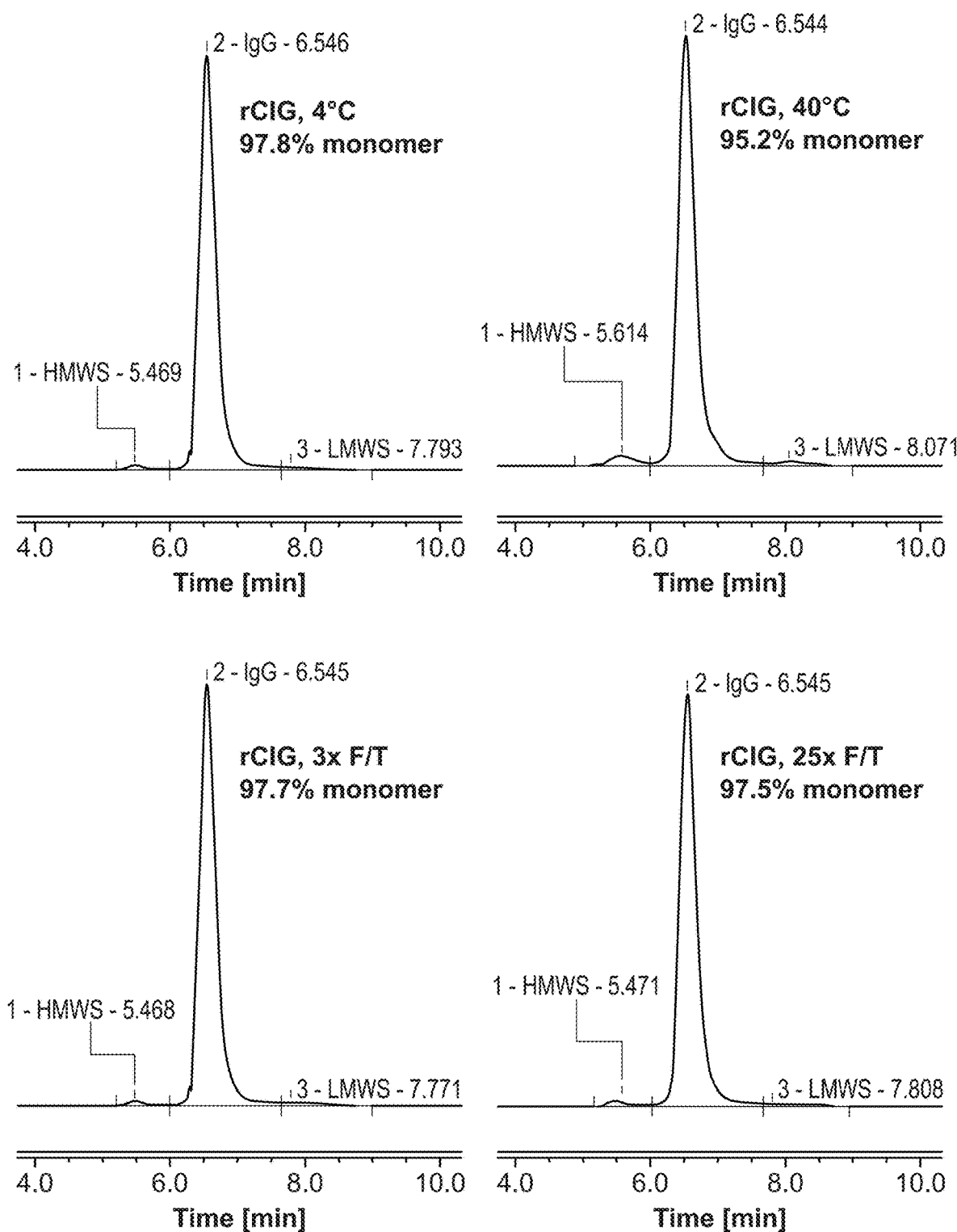
Figure 19D:
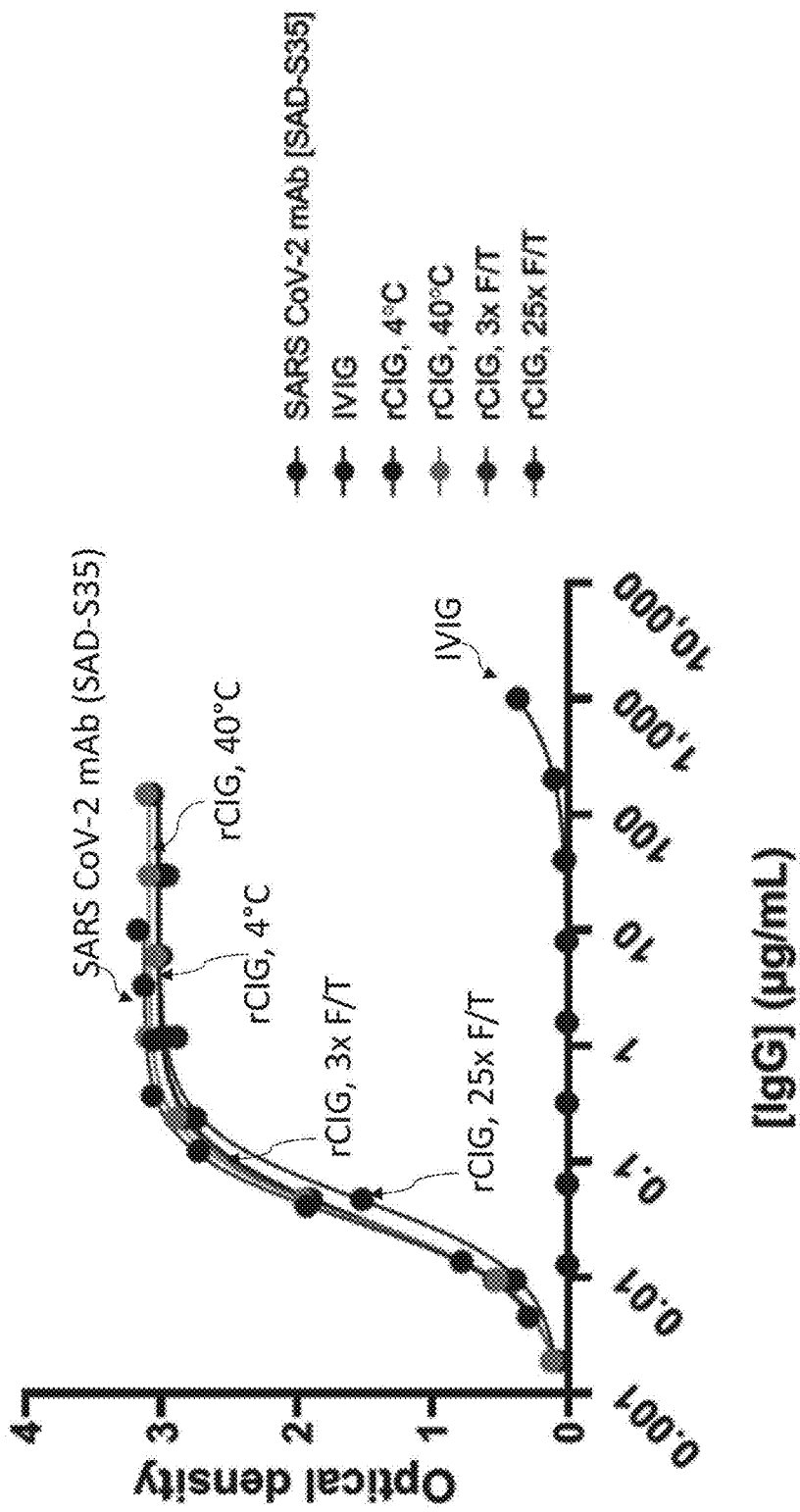

FIGS. 18A and 18B show quality control analysis of purified rCIG protein. (FIG. 18A) SEC-HPLC analysis used to assess the purity of the Protein A-purified protein. (FIG. 18B) SDS-PAGE analysis used to assess the purity of the Protein A-purified protein.

FIG. 19A to 19D show stability, purity and functional assay of polished rCIG protein. (FIG. 19A) SEC-HPLC analysis used to assess the purity of the polished rCIG protein. (FIG. 19B) SDS-PAGE analysis used to assess the purity of the polished rCIG protein. (FIG. 19C) SEC-HPLC ELISA used to assess the purity and function of the rCIG protein after incubation at 4° C. or at 40° C. for 14 days, or after undergoing 3 or 25 freeze-thaw cycles (F/T). 40° C. incubation weakly increased the high molecular weight species with no change in SARS CoV-2 ELISA binding, while 25× F/T had no change in purity but had ~50% reduced binding to SARS CoV-2. (FIG. 19D) SARS-CoV-2 S1 ELISA used to assess the purity and function of the rCIG protein after incubation at 4° C. or at 40° C. for 14 days, or after undergoing 3 or 25 freeze-thaw cycles (F/T). 40° C. incubation weakly increased the high molecular weight species with no change in SARS CoV-2 ELISA binding, while 25× F/T had no change in purity but had ~50% reduced binding to SARS CoV-2.

Figure 20A:
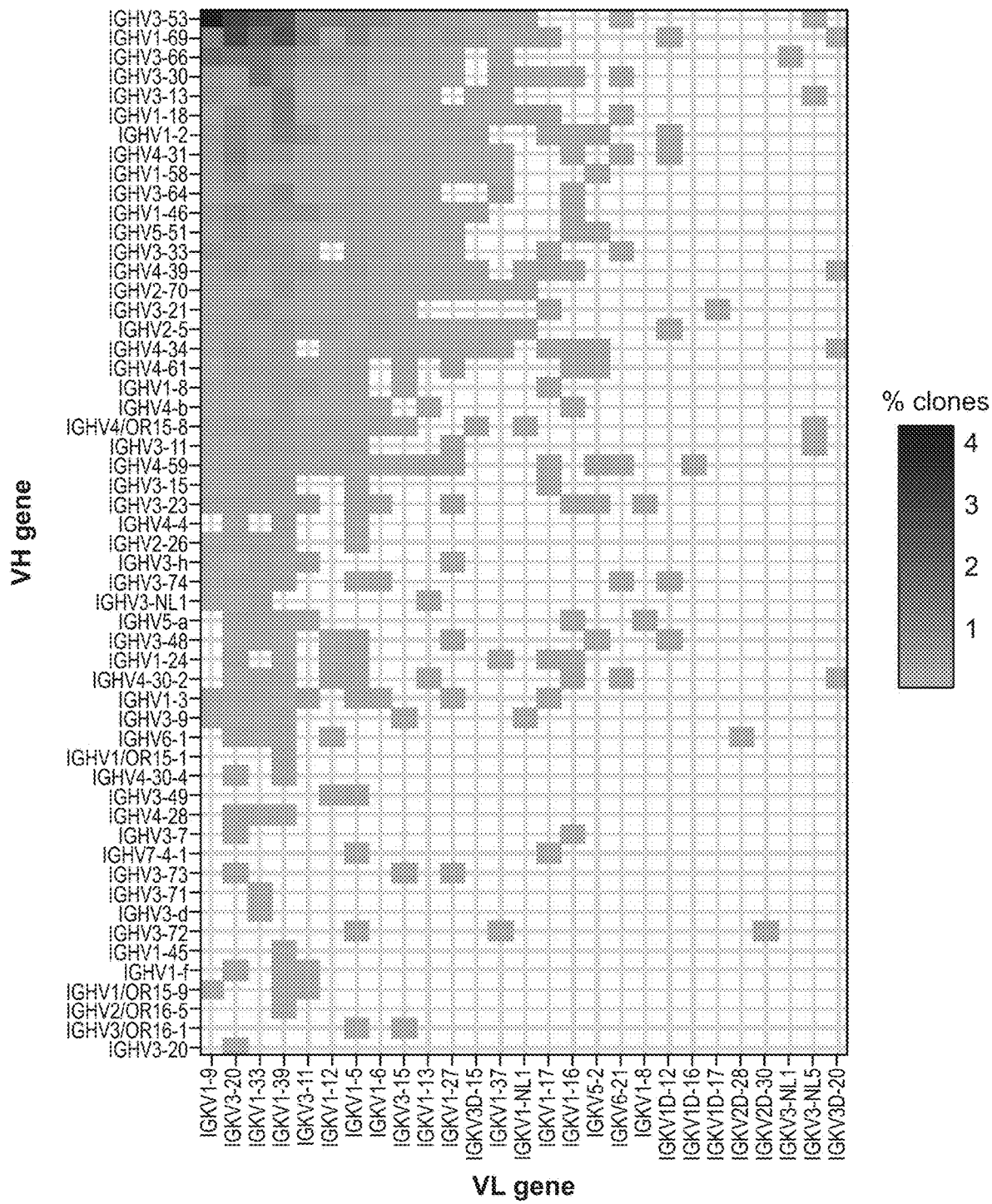

FIG. 20A to 20D show repertoire sequencing analysis of rCIG. FIG. 20A is a heatmap showing antibody variable (V) gene usage from the linked scFv library (the 8 sorted libraries combined). The x-axis and y-axis show light and heavy chain V genes, respectively. The greyscale represents unique clone abundance in the library.

Figure 20B:
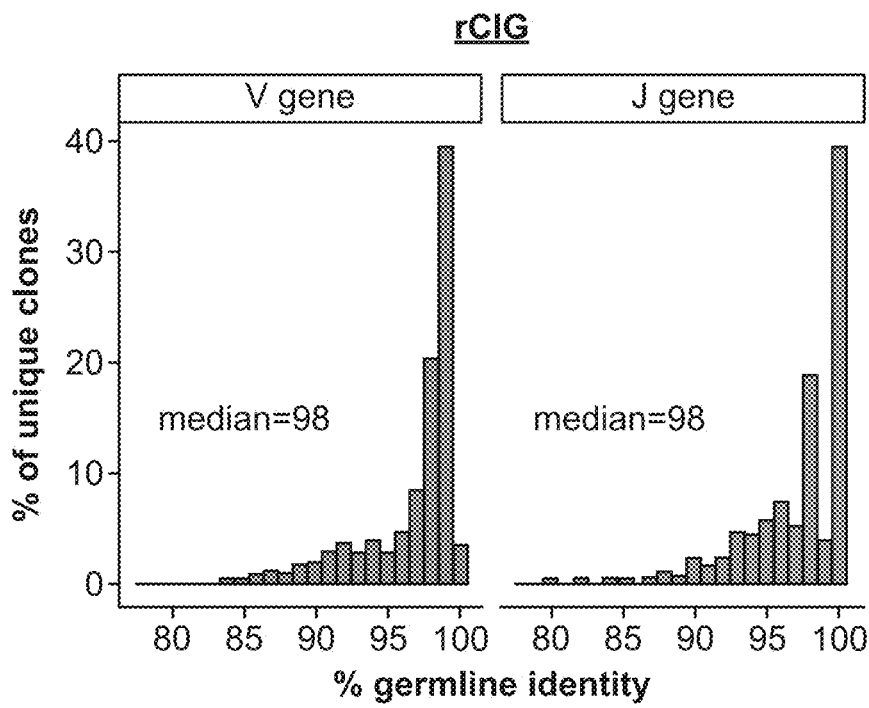

FIG. 20B is a histogram showing distribution of percent germline identity for variable gene (V; left panel) and joining gene (J; right panel), from the final CHO library.

Figure 20C:
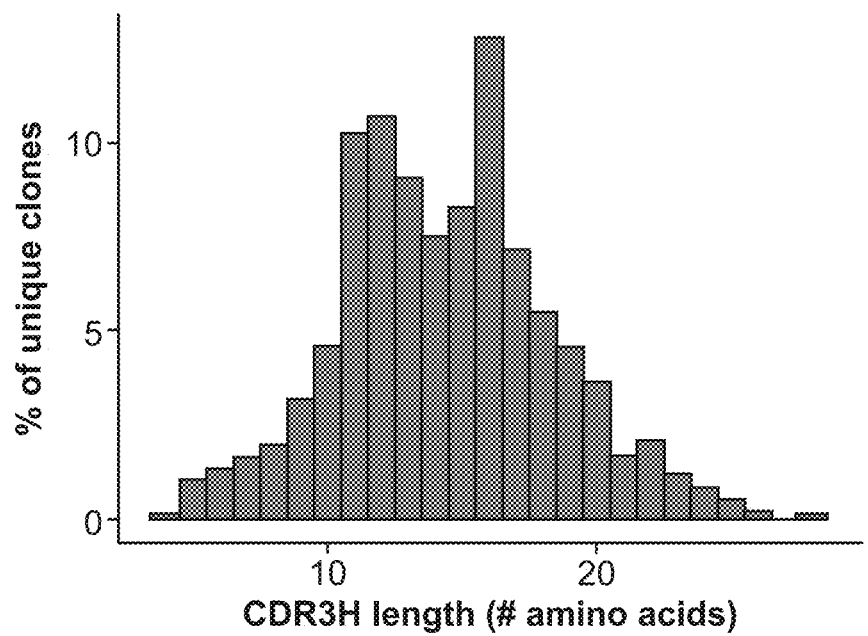

FIG. 20C is a histogram showing the distribution of heavy chain CDR3 amino acid length, from the final CHO library.

Figure 20D:
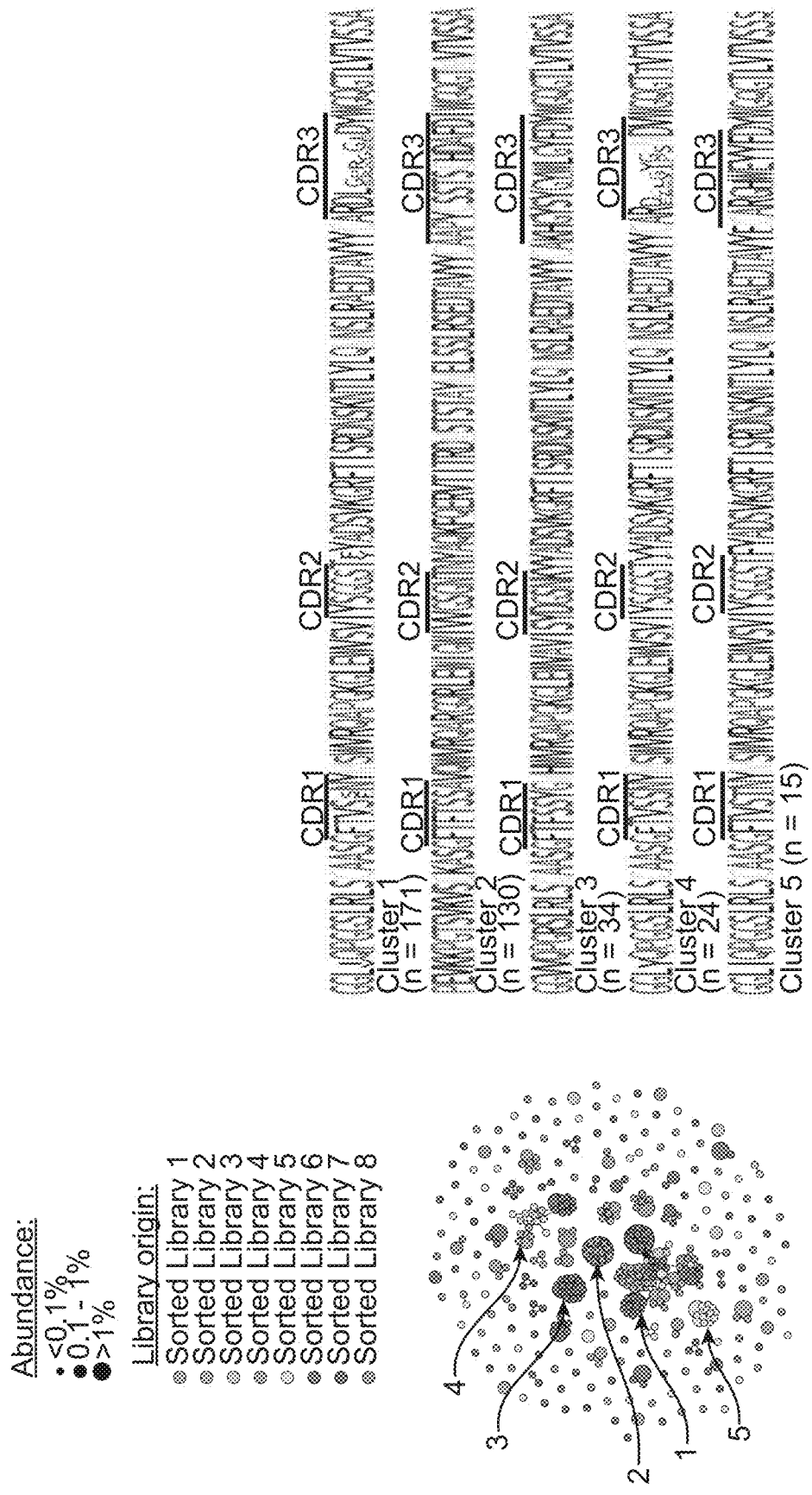

FIG. 20D shows the clonal cluster analysis of rCIG antibodies from FIG. 8C (from the final CHO library) (left). FIG. 20D also shows sequence logos of all heavy chain sequences from the top five clusters (based on clone count). The first 8 amino acids (variable region primer binding sites) are not shown. Figure discloses SEQ ID NOS 25951-25955, respectively, in order of appearance.

Figure 21A:
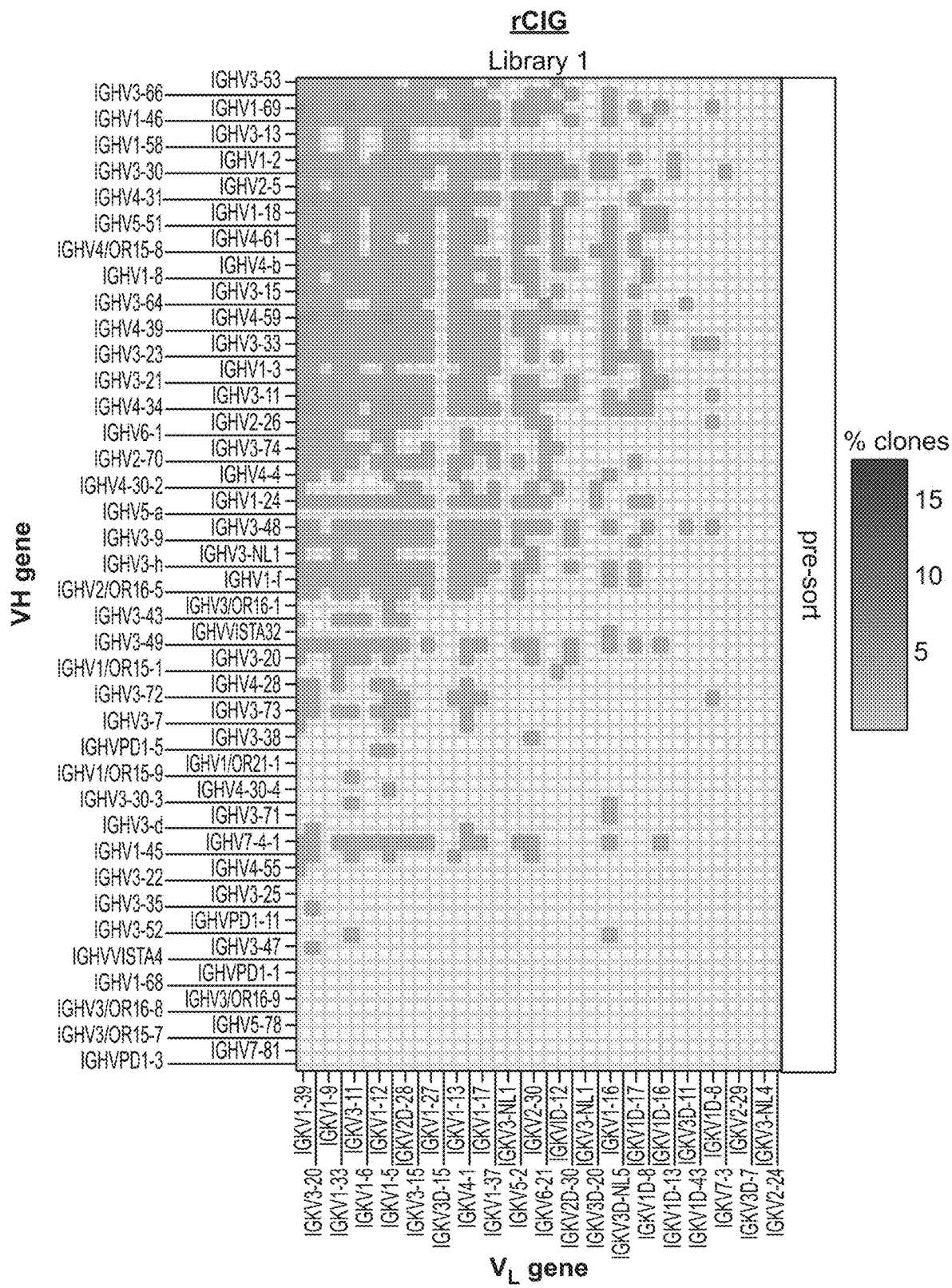
Figure 21B:
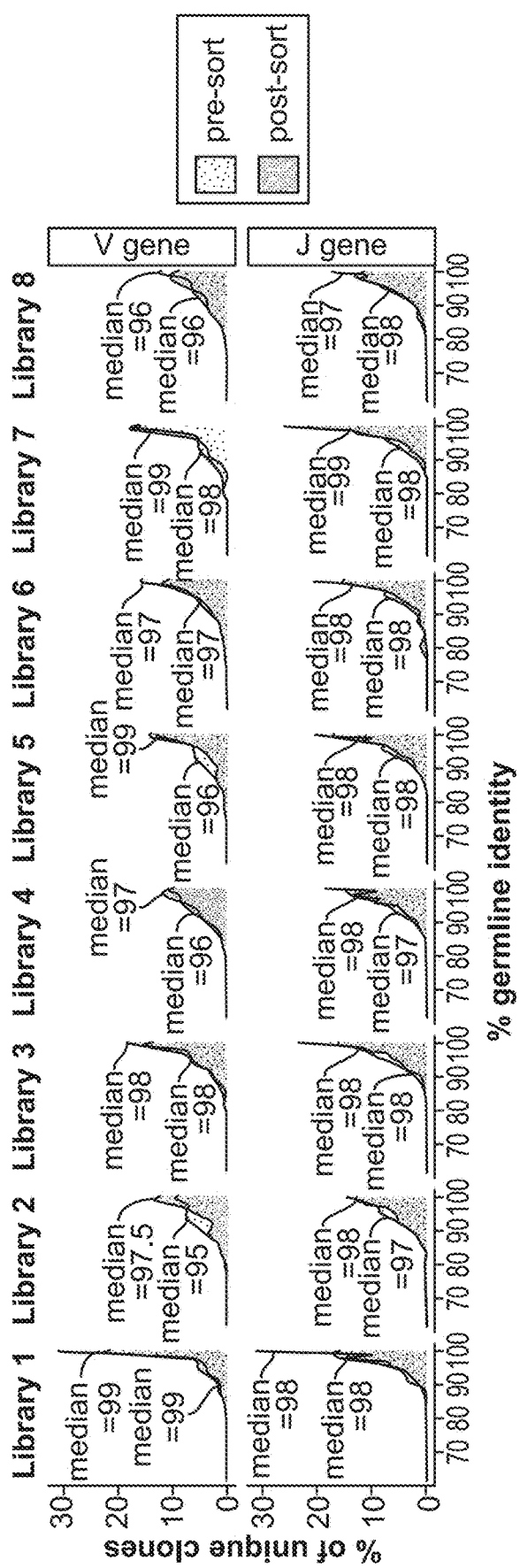
Figure 21C:
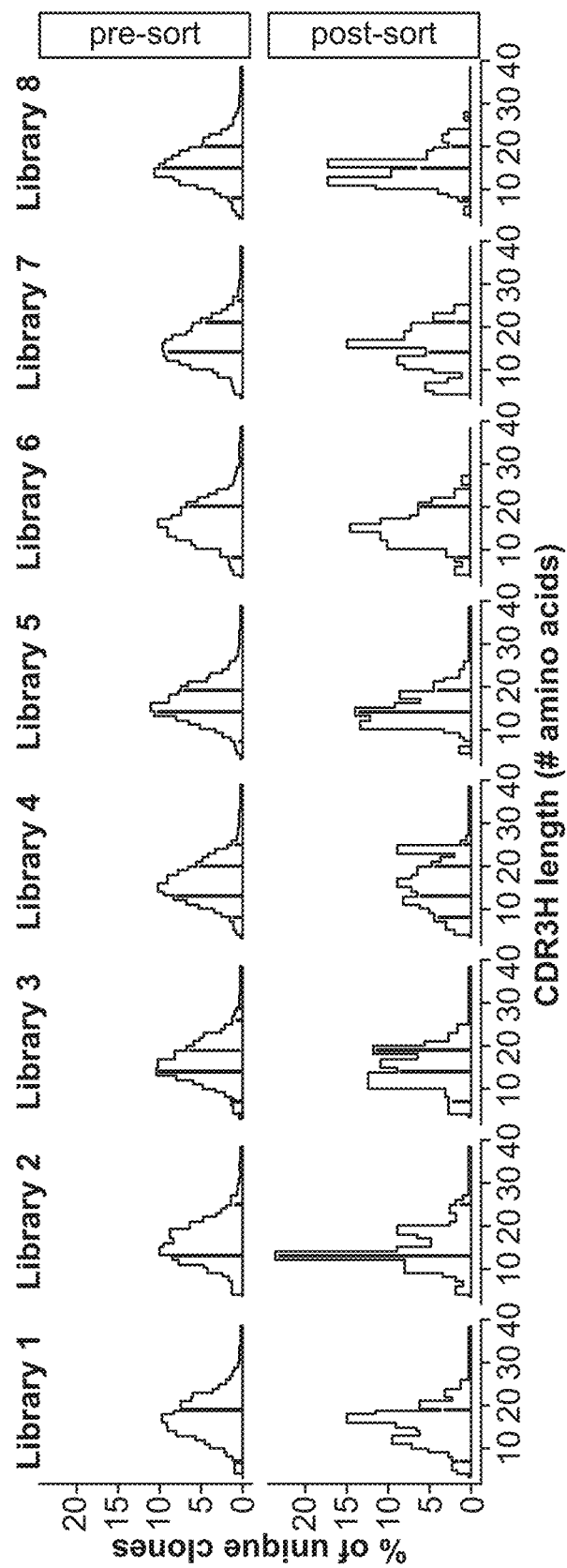

FIG. 21A to 21C shows repertoire sequencing analysis of pre- and post-sort rCIG.

FIG. 21A is a heatmap showing antibody variable (V) gene usage from each pre-sort and post-sort linked scFv library. FIG. 21B is a histogram showing distribution of percent germline identity for variable gene (V; left panel) and joining gene (J; right panel) from each pre-sort and post-sort scFv library. FIG. 21C is a histogram showing the distribution of heavy chain CDR3 amino acid length from each pre-sort and post-sort scFv library.

FIG. 22 shows antibody reactivity to SARS-CoV-2 variants and other coronaviruses. ELISA plates were coated with 2 μg/mL of spike or RBD proteins from known circulating variants of SARS-CoV-2, SARS-CoV, MERS, and other human coronaviruses (HCoV). The binding ability of rCIG, SARS-CoV-2 neutralizing mAb (SAD-S35), and IVIG was determined for each antigen. *, No binding was observed against the indicated antigen. While rCIG and the mAb had poly-variant specific responses to all SARS-CoV-2 variants, only rCIG bound SARS-CoV RBD while the mAb did not. IVIG had no specific responses to SARS-CoV-2, SARS-CoV or MERS but did have a weak response to HCoV-229E and HCoV-NL63.

Figure 23A:
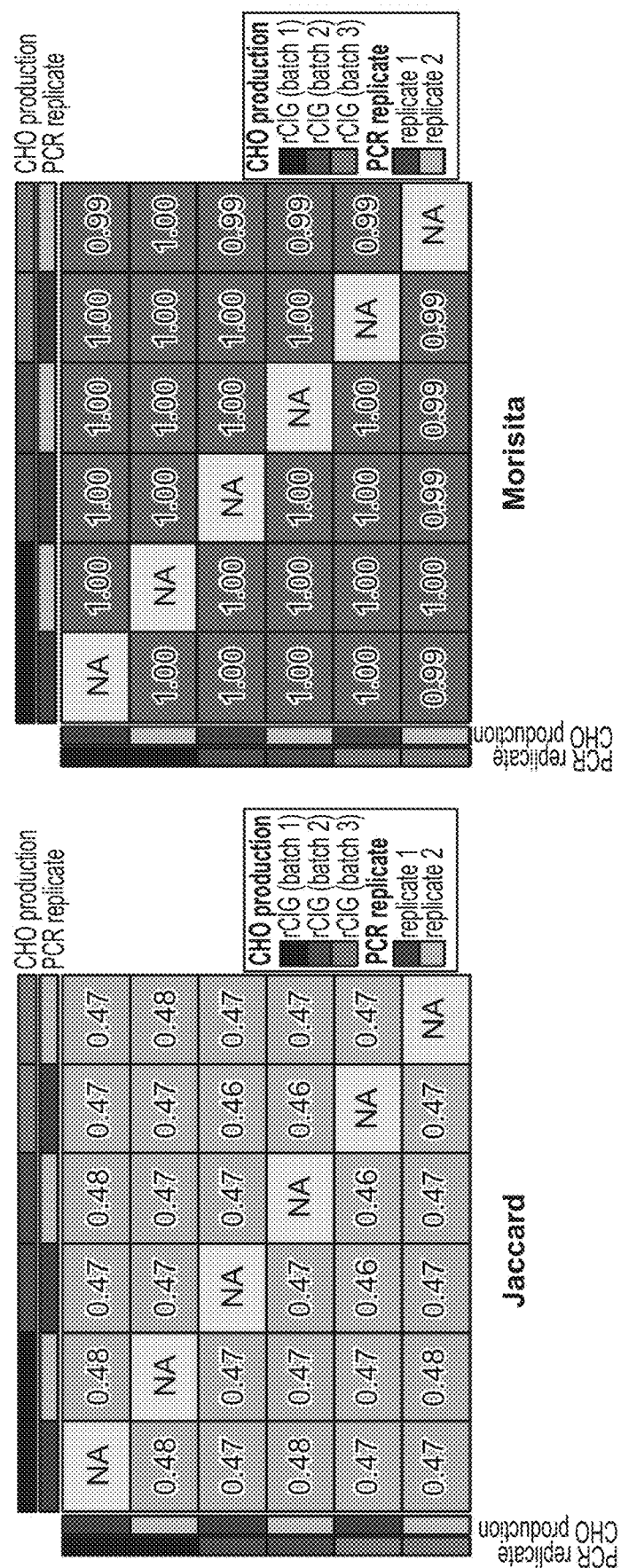
Figure 23C:
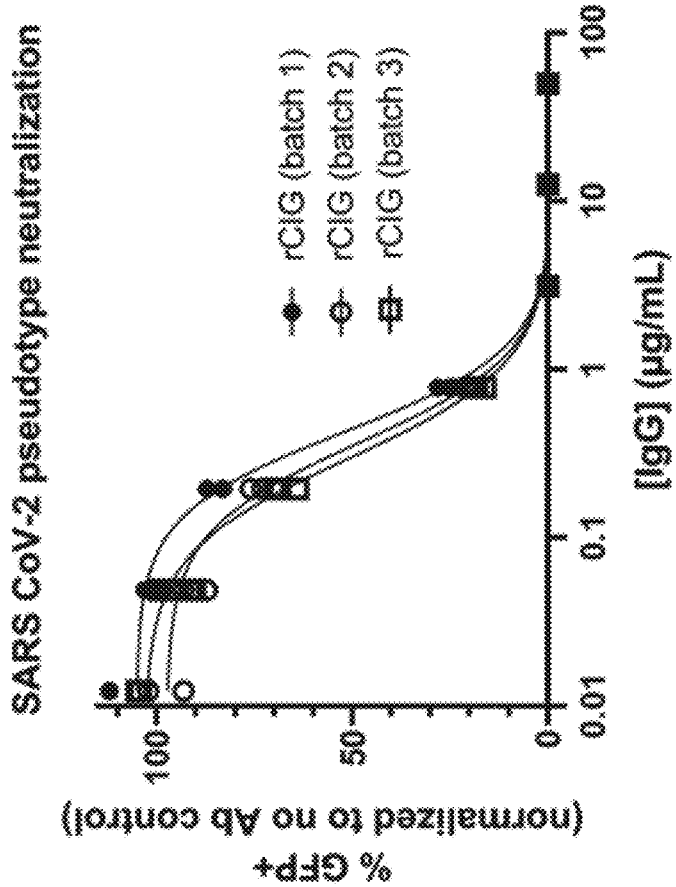
Figure 23B:
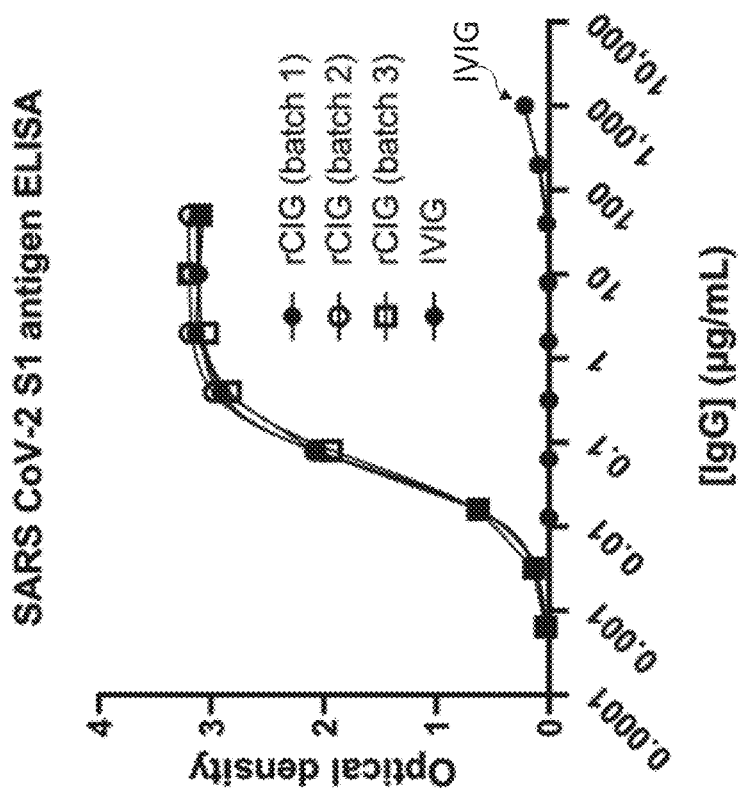

FIGS. 23A and 23B provide data showing batch-to-batch variation of rCIG. RNA antibody sequencing was performed (in duplicate) on RNA isolated from the end of replicate CHO bioreactor production runs. In FIG. 23A, Jaccard (left) and Morisita (right) analyses data are provided to show the amount of antibody clone variation between production batches and between PCR replicates performed on each batch. Wilcoxon rank sum tests showed that the indices from the PCR replicates came from the same population as the indices from the batch replicates (p>0.05), suggesting that the variability inherent to the batches was no worse than the variability between PCR replicates.

FIG. 23B shows binding of the indicated batch of serially diluted rCIG and IVIG to SARS CoV-2 S1 antigen was measured by ELISA.

FIG. 23C. The indicated batch of rCIG was titrated and added to ACE2-expressing cells in the presence of CoV-2 pseudotype virus. The percent of infected cells (GFP+) was quantified by flow cytometry and was normalized by dividing by the GFP+ signal in the negative control wells, which lacked test article. Feltz & Miller's asymptotic test was used to test whether the three bioproduction batch IC50 measurements had a different coefficient of variation from eight IC50 measurements on a fourth bioproduction batch (18% vs. 17%, respectively). A p-value >0.05 suggested that the variation inherent to the batches was no worse than the variation inherent to the pseudotype neutralization assay.

Figure 24A:
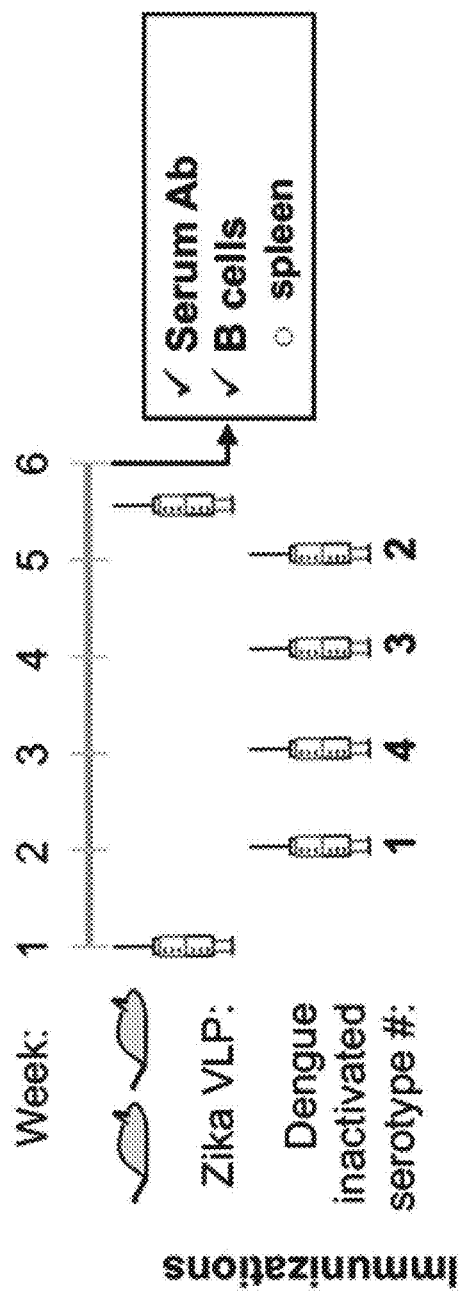
Figure 24B:
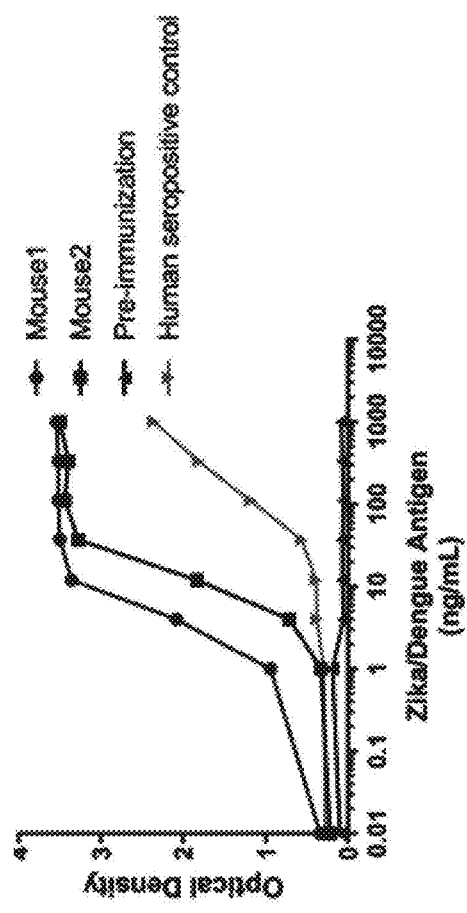

FIGS. 24A and 24B show immunization induced antibody responses to Zika and Dengue in humanized mice. (FIG. 24A) Two Trianni mice were immunized weekly with Zika virus like particles (VLP), inactivated Dengue 1, Dengue 4, Dengue 3, or Dengue 2 as indicated in the figure. (FIG. 24B) After week 5, serum from the mice was tested for antibody response against a mixture of Zika and Dengue antigens and compared to pre-immunization or human seropositive controls to confirm antigen-specific antibody responses.

Figure 25A:
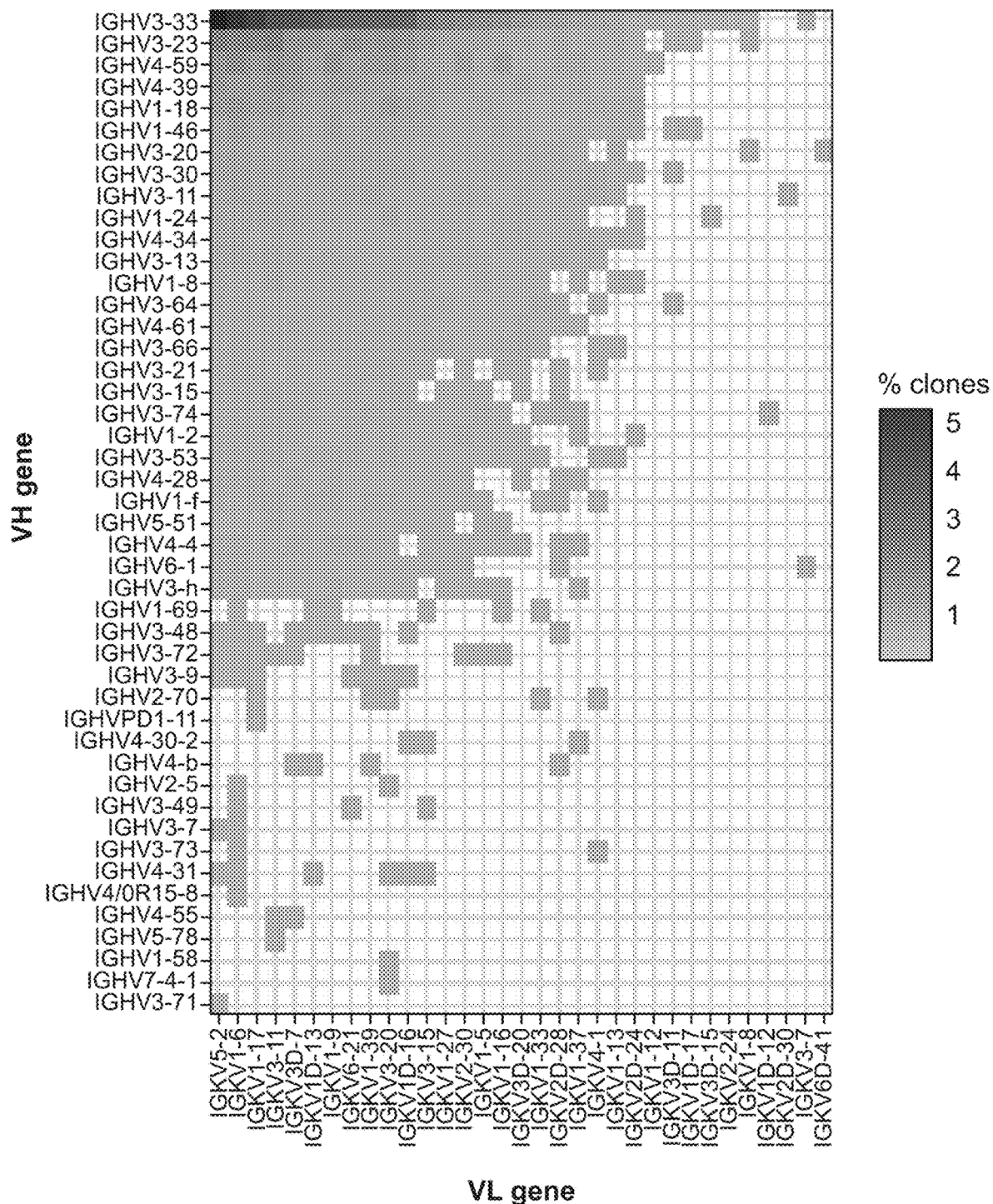

FIG. 25A to 25D show repertoire sequencing analysis results of rZIG. FIG. 25A is a heatmap showing antibody variable (V) gene usage from the linked scFv library. The x-axis and y-axis show light and heavy chain V genes, respectively. The greyscale gradient represents percent unique clone abundance in the library.

Figure 25B:
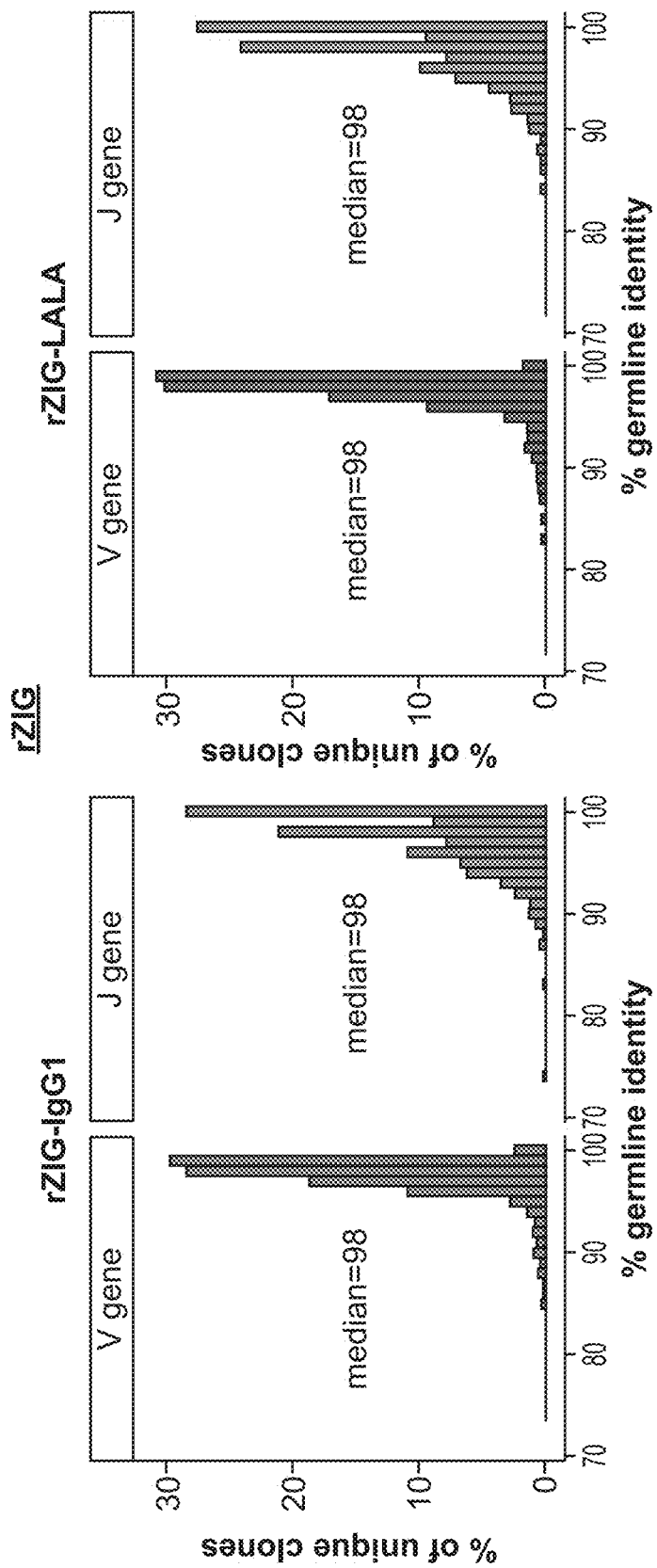

FIG. 25B. For each indicated rZIG library, histogram showing distribution of percent germline identity for variable gene (V; left panel) and joining gene (J; right panel), from the final CHO library.

Figure 25C:
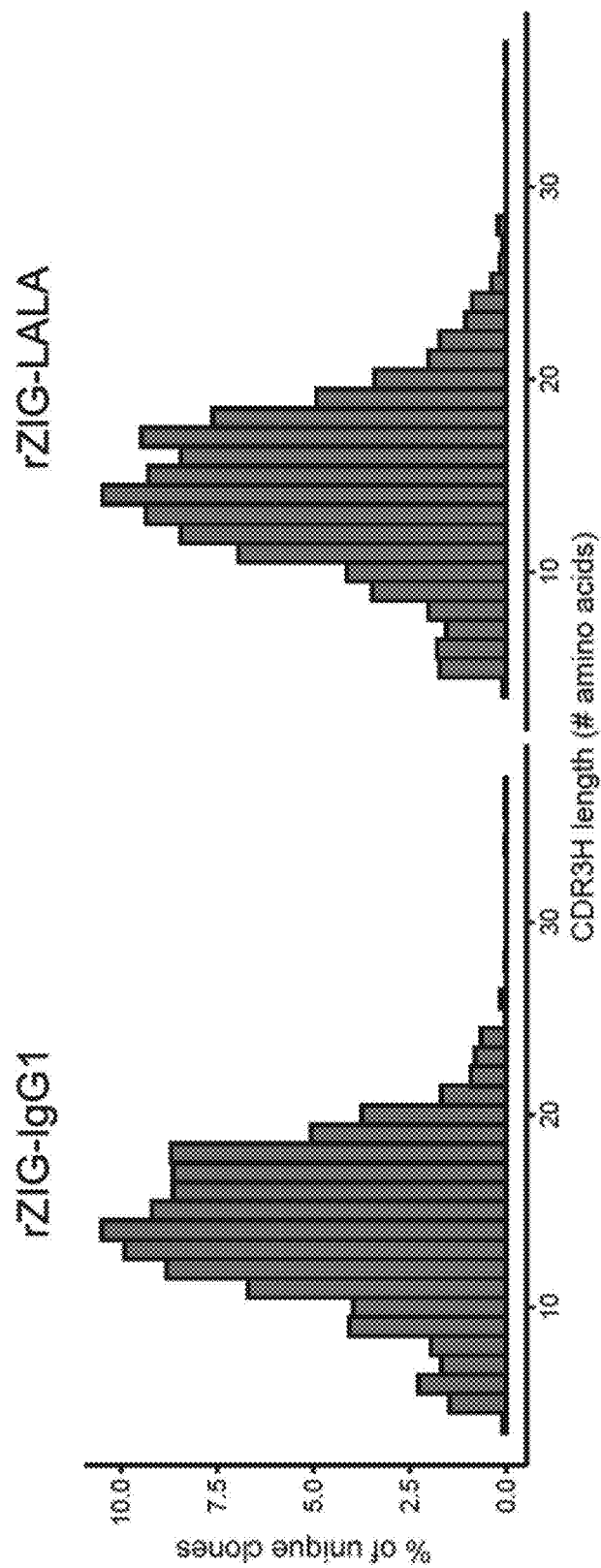

FIG. 25C. For each indicated rZIG library, histogram showing the distribution of heavy chain CDR3 amino acid length, from the final CHO library.

Figure 25D:
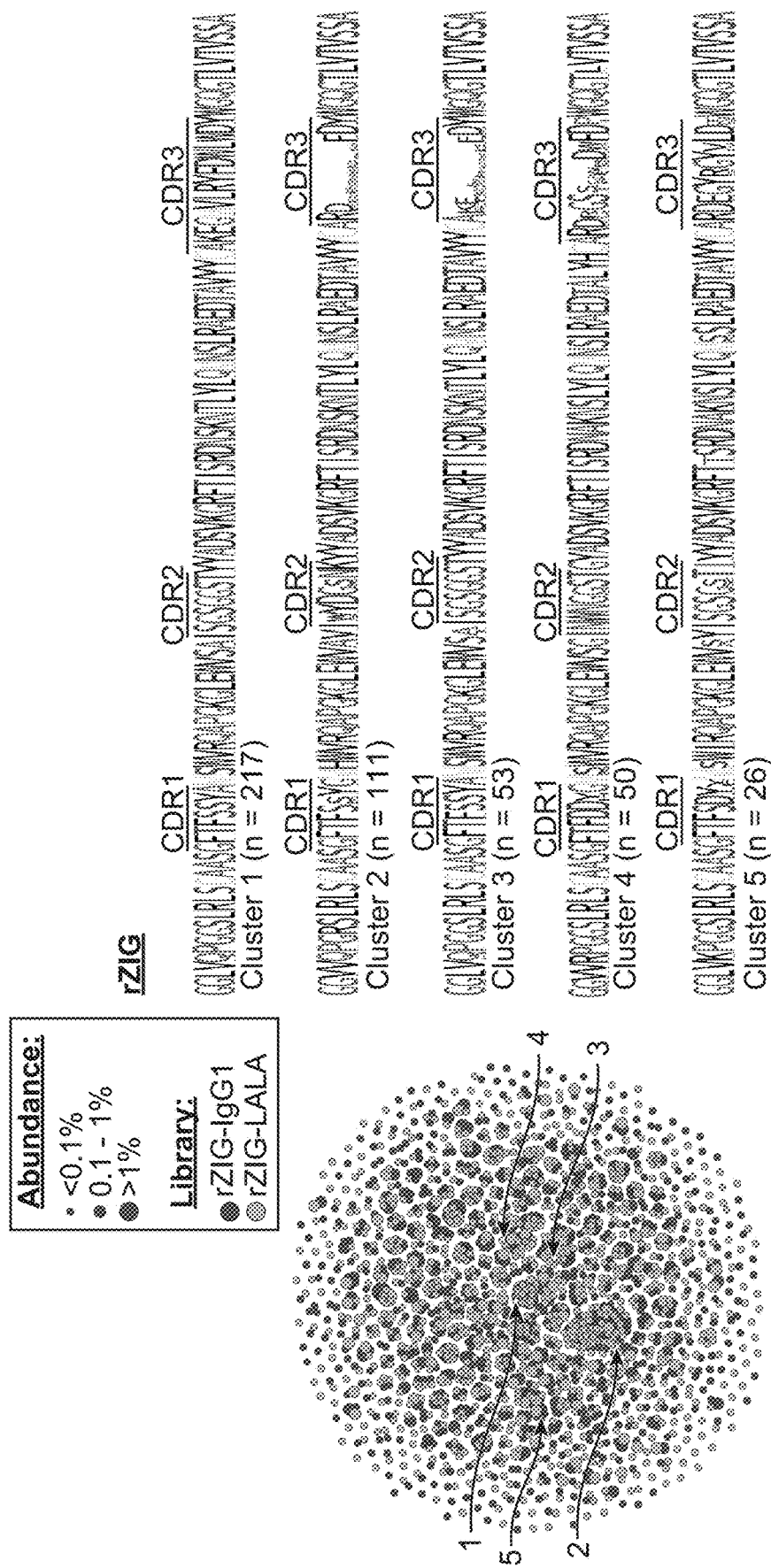

FIG. 25D. Left: The clonal cluster analysis of rZIG antibodies from FIG. 9A (from the final CHO library). Right: Sequence logos of all heavy chain sequences from the top five clusters (based on clone count). The first 8 amino acids (variable region primer binding sites) are not shown. Figure discloses SEQ ID NOS 25956-25960, respectively, in order of appearance.

Figures 26A, 26B:
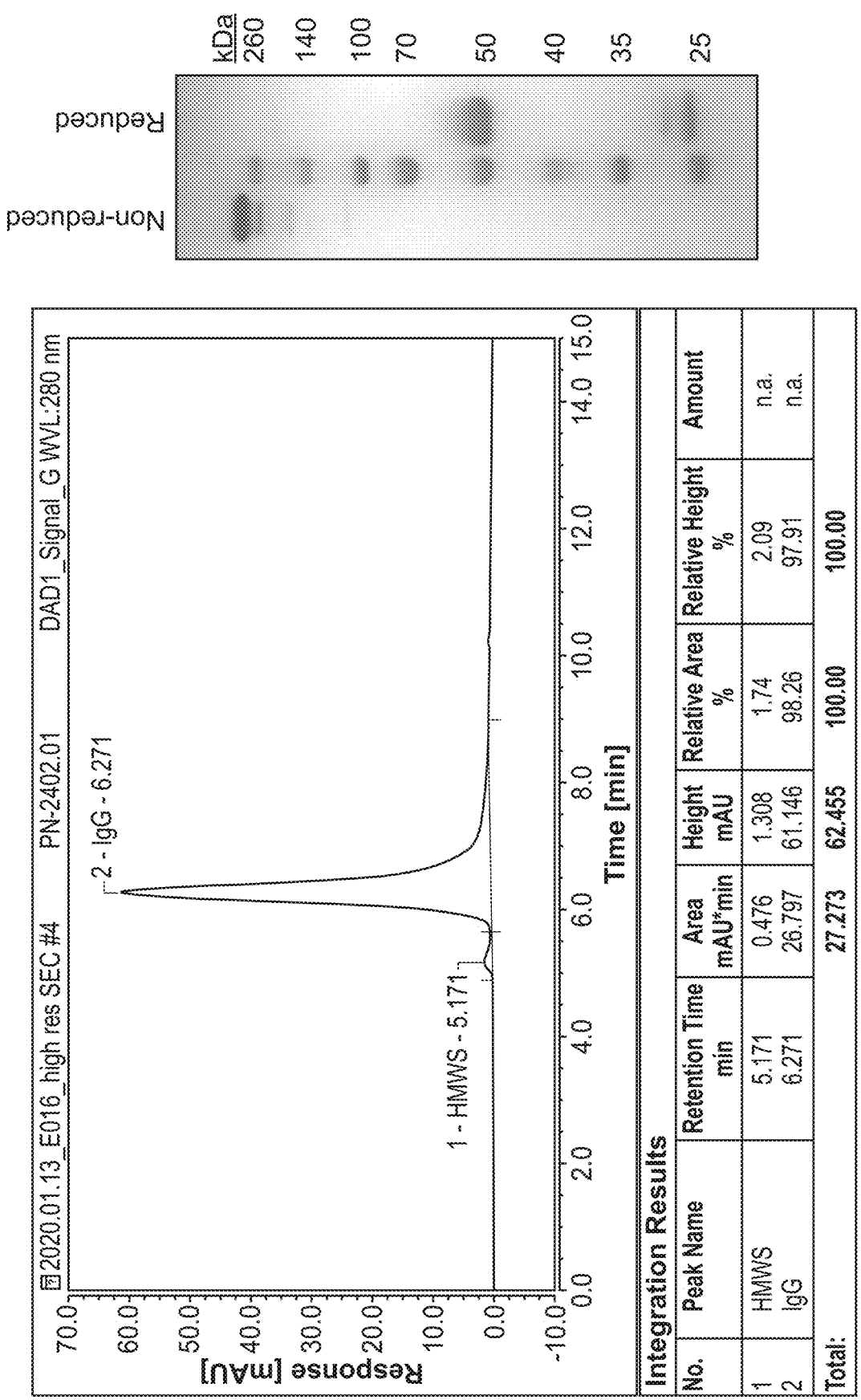

FIG. 26A to 26B show quality control analysis of purified rZIG-IgG1 protein. FIG. 26A is SEC-HPLC analysis used to assess the purity of the Protein A-purified protein. FIG. 26B is SDS-PAGE analysis used to assess the purity of the Protein A-purified protein.

Figure 27A:
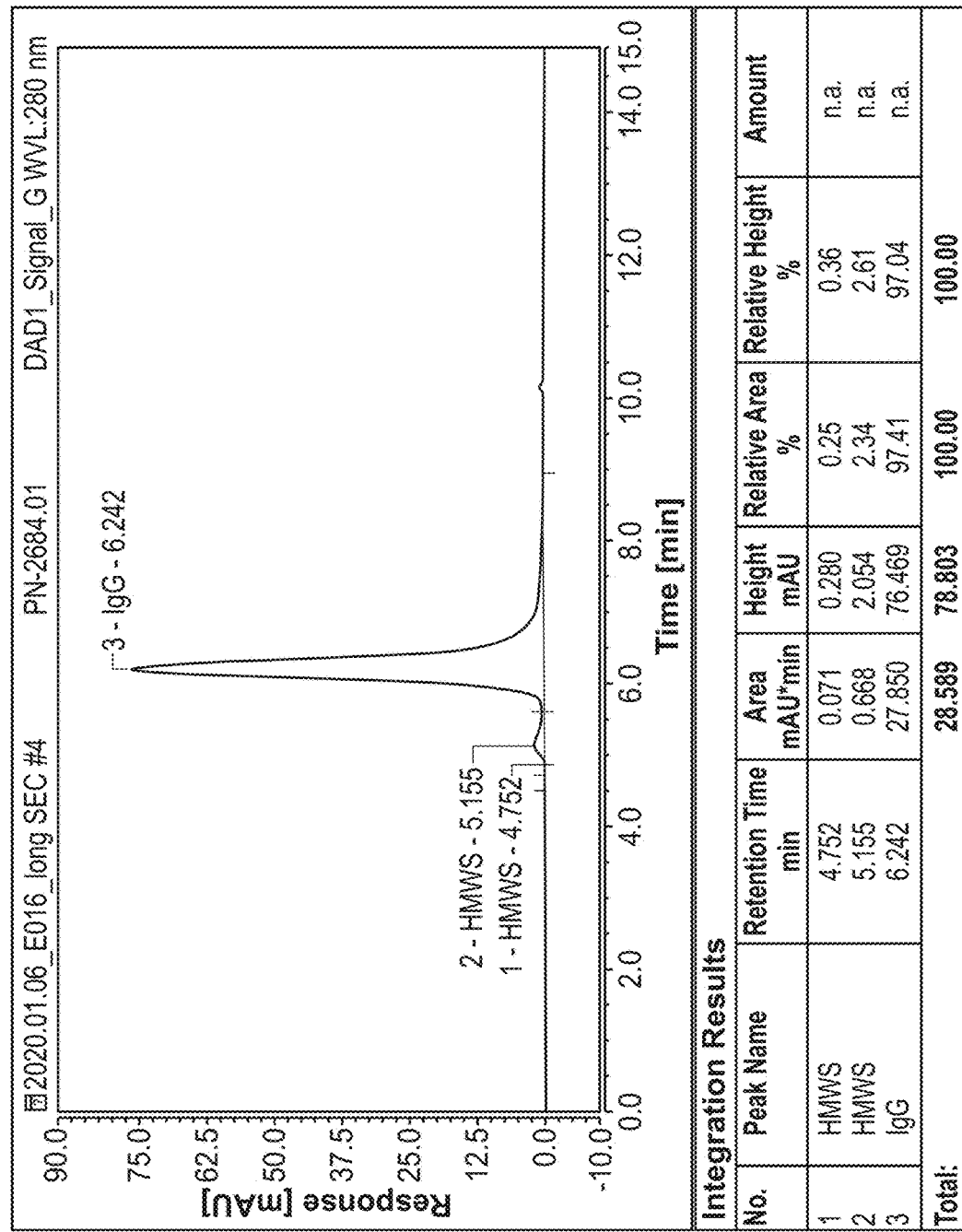
Figure 27B:
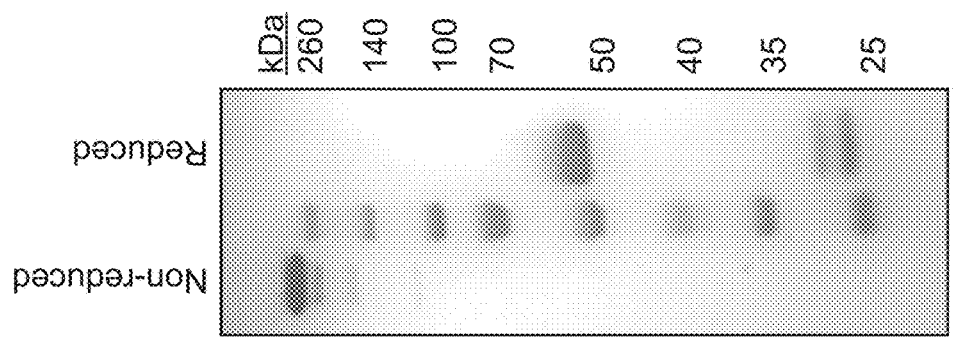

FIG. 27A to 27B show quality control analysis of purified rZIG-LALA protein. FIG. 27A is SEC-HPLC analysis used to assess the purity of the Protein A-purified protein. FIG. 27B is SDS-PAGE analysis used to assess the purity of the Protein A-purified protein.

Figure 28:
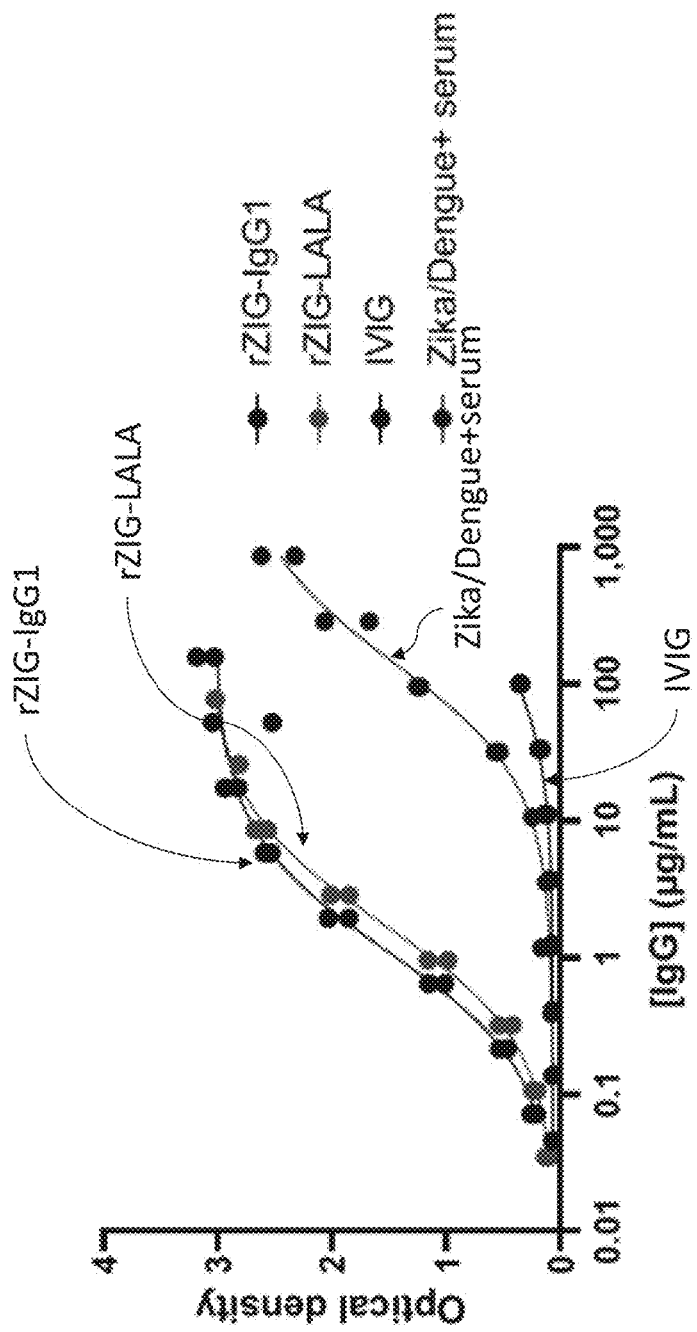

FIG. 28 shows rZIG binding to Zika measured by ELISA. rZIG-IgG1, rZIG-LALA, negative control IVIG, and positive control Zika/Dengue positive serum were serially diluted and added to a Zika envelope-coated plate. Antigen-specific responses were quantified by an anti-human-HRP secondary antibody.

Figure 29:
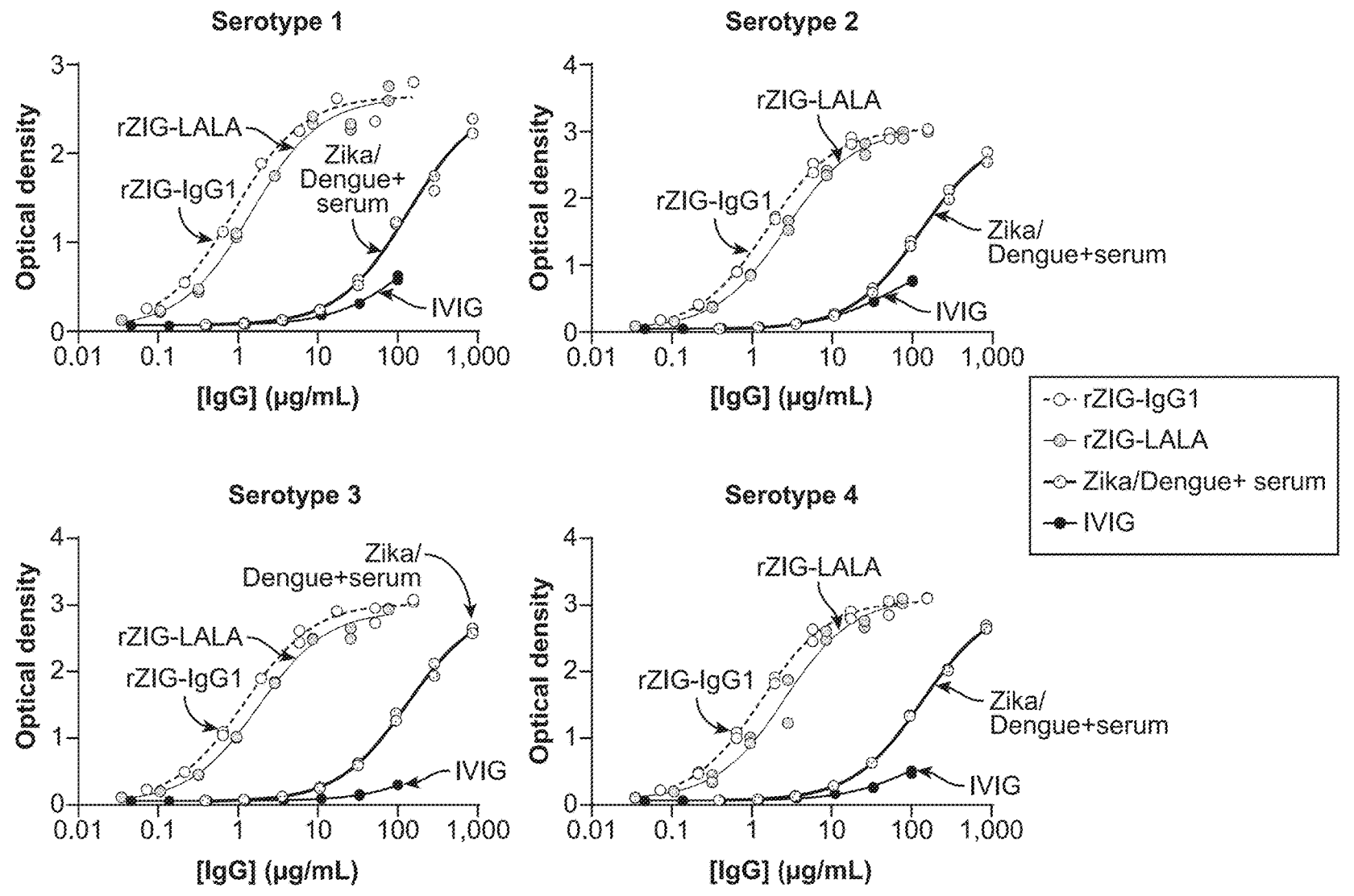

FIG. 29 shows rZIG binding to Dengue serotypes measured by ELISA. rZIG-IgG1, rZIG-LALA, negative control IVIG, and positive control Zika/Dengue positive serum were serially diluted and added to a Dengue serotypes 1, 2, 3, or 4 envelope-coated plates. Antigen-specific responses were quantified by an anti-human-HRP secondary antibody.

Figure 30:
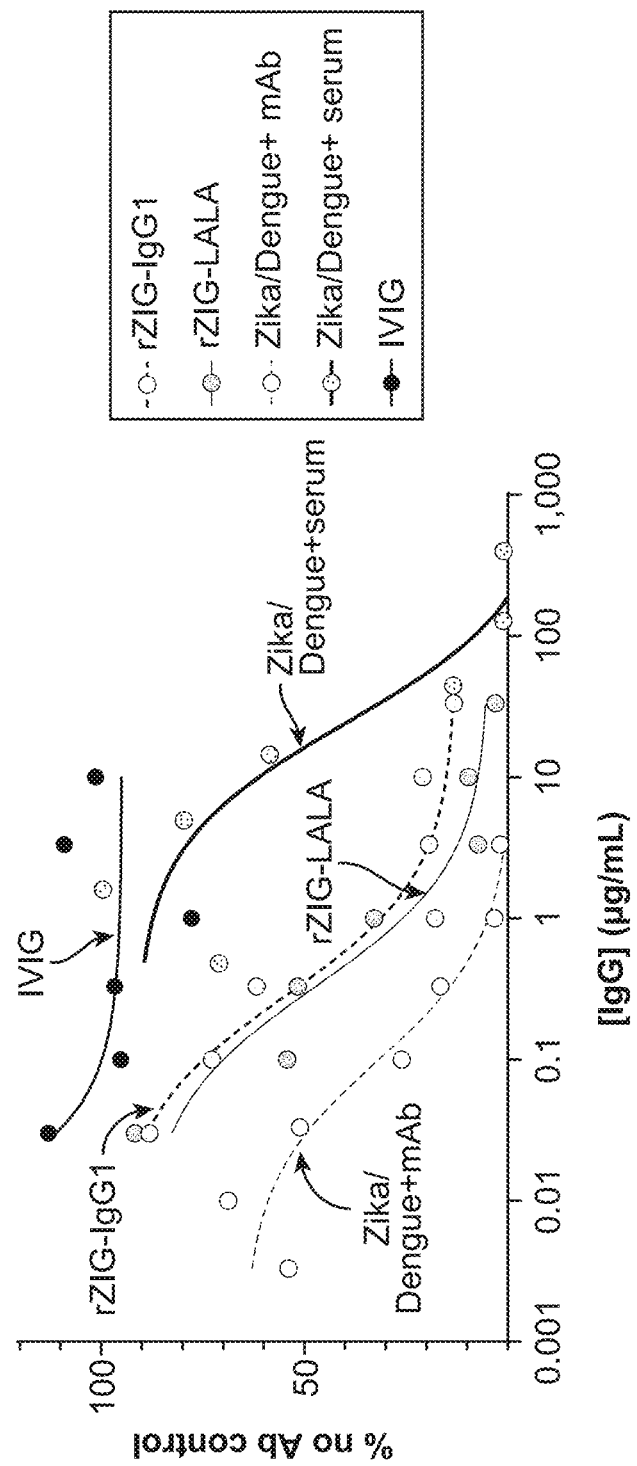

FIG. 30 provides results from Zika pseudotype virus neutralization assay. rZIG-IgG1, rZIG-LALA, negative control IVIG, positive control Zika/Dengue mAb, and positive control Zika/Dengue positive serum were serially diluted, co-incubated with Zika pseudotype virus, and added to BHK/DC-SIGN target cells. Antibody induced neutralization was quantified by the infection-induced luciferase expression divided by luciferase expression in the no Ab control.

Figure 31:
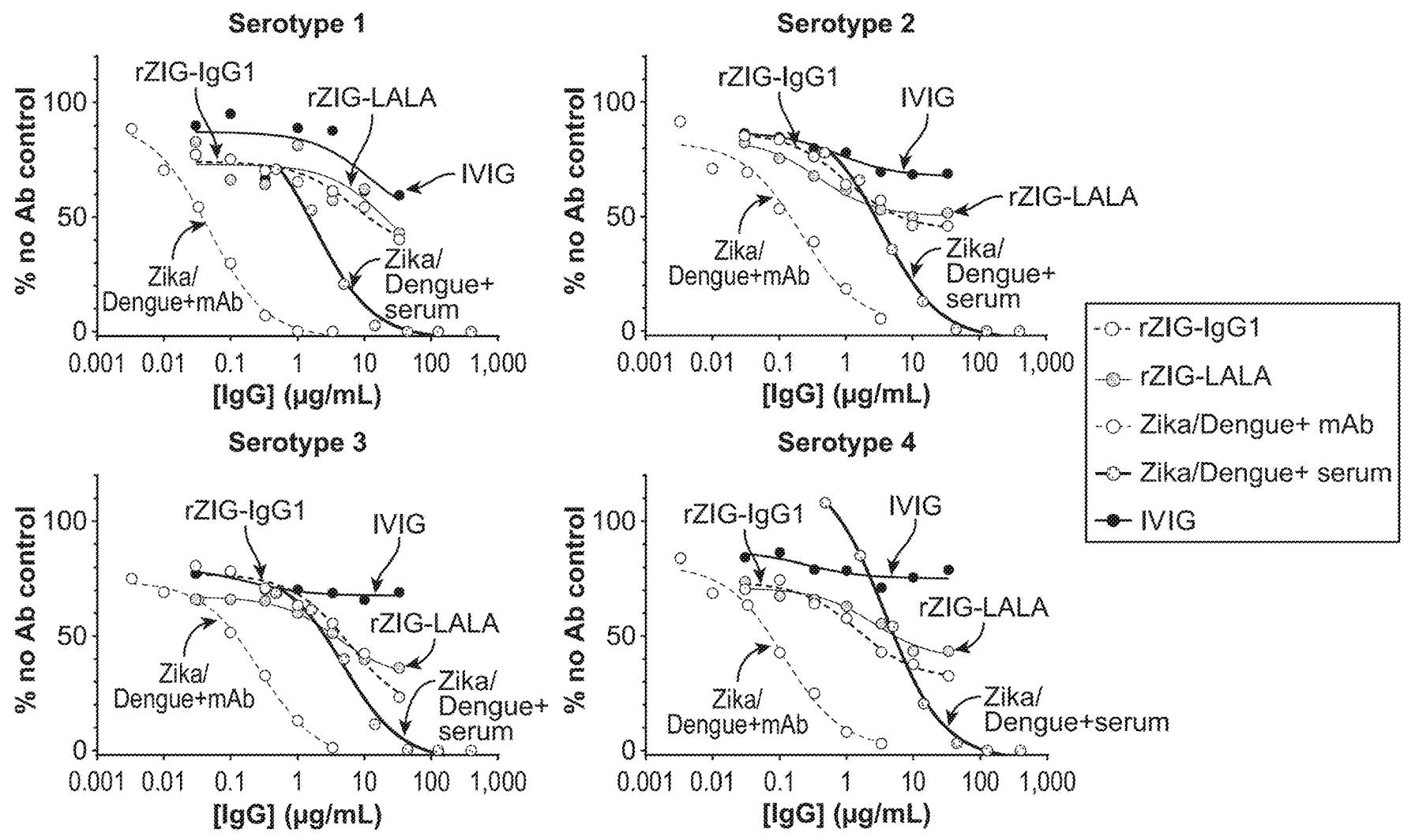

FIG. 31 provides results from Dengue serotype pseudotype virus neutralization assay. rZIG-IgG1, rZIG-LALA, negative control IVIG, positive control Zika/Dengue mAb, and positive control Zika/Dengue positive serum were serially diluted, co-incubated with pseudotype virus expressing the indicated Dengue serotype envelope antigens, and added to BHK/DC-SIGN target cells. Antibody induced neutralization was quantified as "% no Ab control", or infection-induced luciferase expression divided by the luciferase expression in the no Ab control.

FIG. 32 is a schematic of antibody dependent enhancement (ADE) assay. Antibody bound to pseudotype virus can infect cells through the Fc receptor expressed on target cells. By introducing an Fc mutation that prevents FcR binding (e.g. LALA), antibody-induced viral infection is abrogated.

Figure 33B:
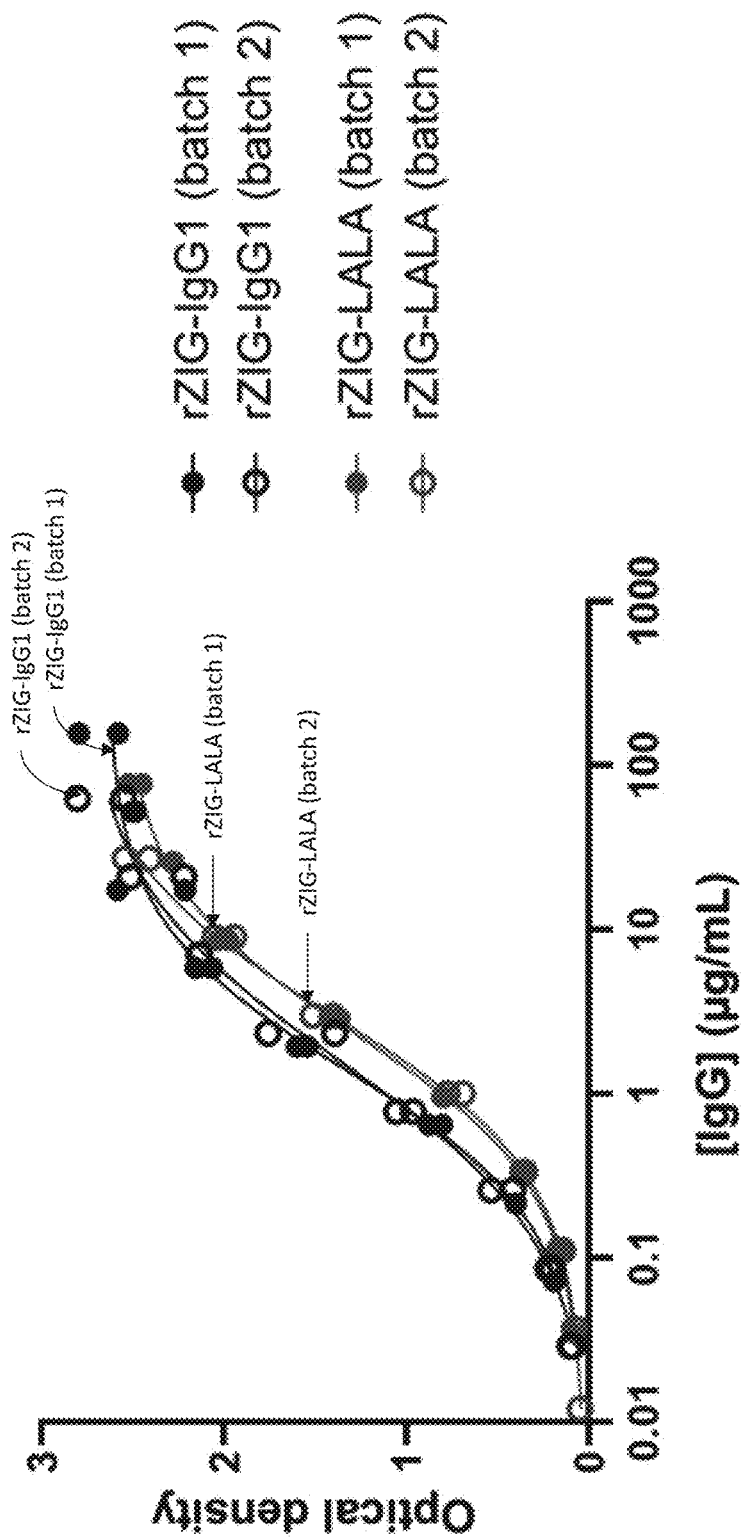

FIGS. 33A and 33B show batch-to-batch variation of rZIG.

FIG. 33A is based on RNA antibody sequencing performed (in duplicate) on RNA isolated from the end of replicate CHO bioreactor production runs. Jaccard (left) and Morisita (right) analyses showed that the amount of antibody clone variation between production batches and between PCR replicates performed on each batch. Wilcoxon rank sum tests showed that the indices from the PCR replicates came from the same population as the indices from the batch replicates, suggesting that the variability inherent to the batches was no worse than the variability between PCR replicates.

FIG. 33B shows binding of the indicated batch of serially diluted rZIG-IgG1 and rZIGLALA to a Zika envelope-coated plate was measured by ELISA.

FIG. 34A to 34D shows results from repertoire sequencing analysis of rHIG.

Figure 34A:
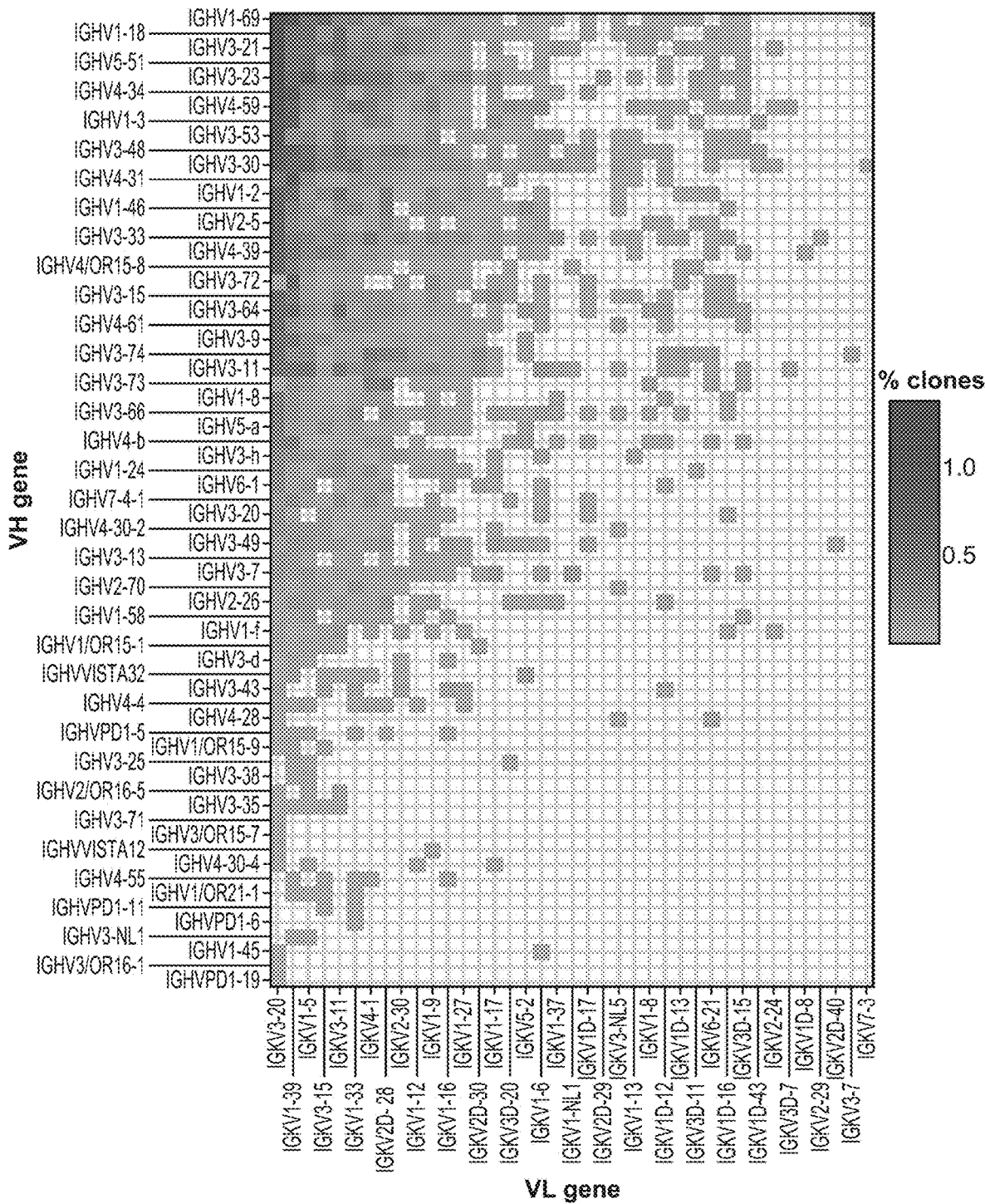

FIG. 34A is a heatmap showing antibody variable (V) gene usage from the linked scFv library. The x-axis and y-axis show light and heavy chain V genes, respectively. The color represents percent unique clone abundance in the library.

Figure 34B:
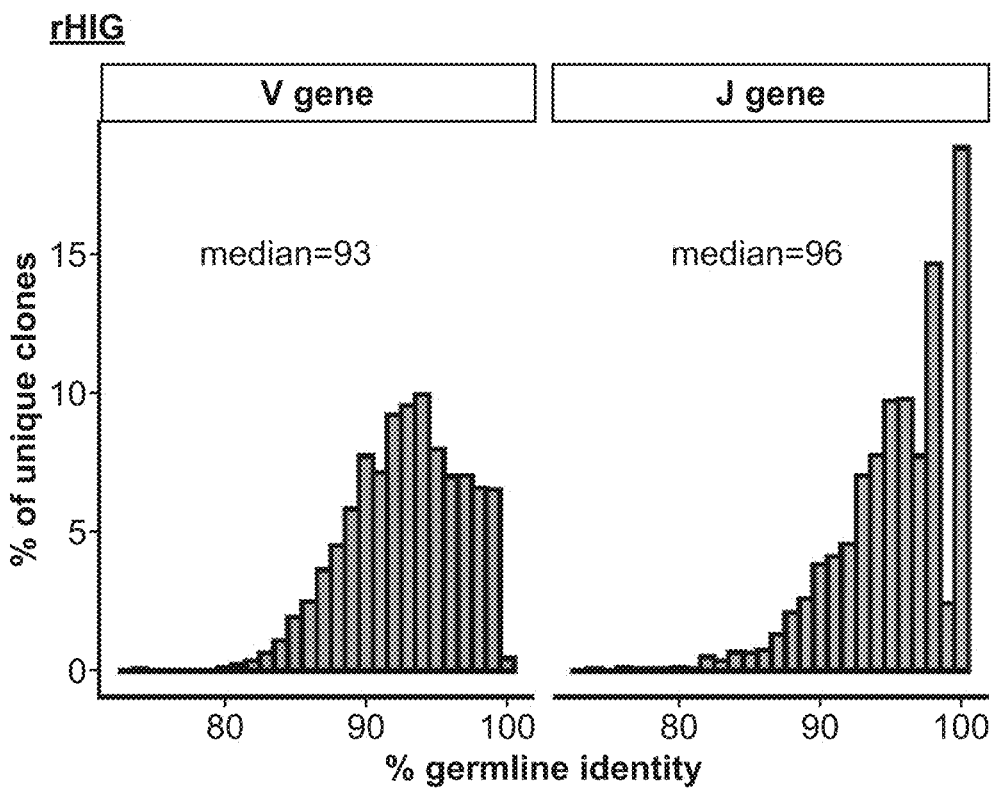

FIG. 34B is a histogram showing distribution of percent germline identity for variable gene (V; left panel) and joining gene (J; right panel), from the final CHO library.

Figure 34C:
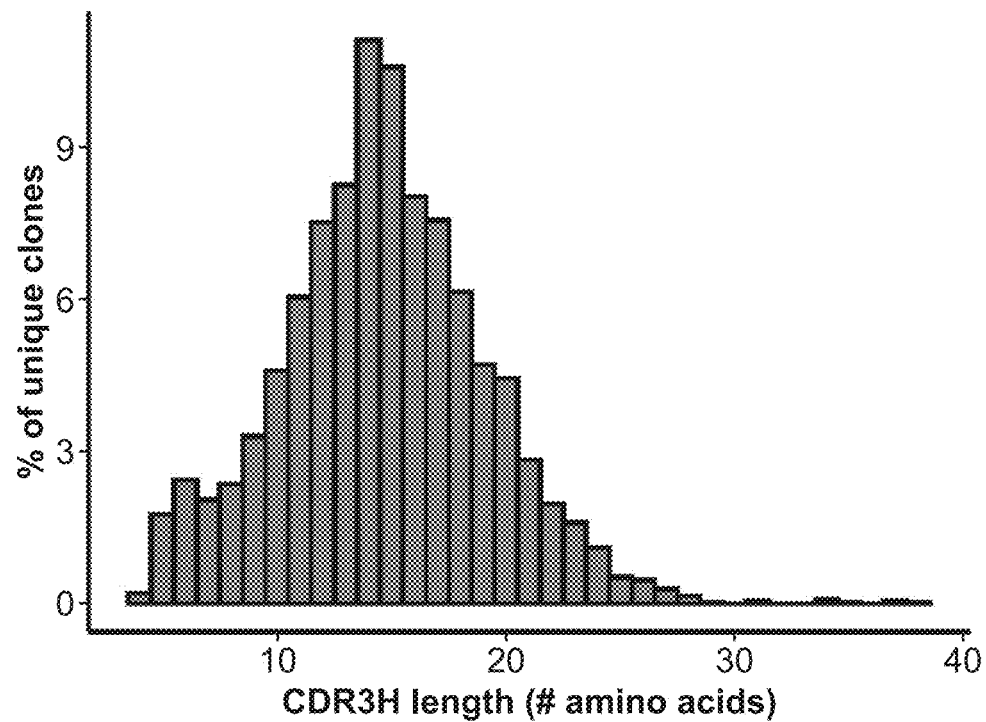

FIG. 34C is a histogram showing the distribution of heavy chain CDR3 amino acid length, from the final CHO library.

Figure 34D:
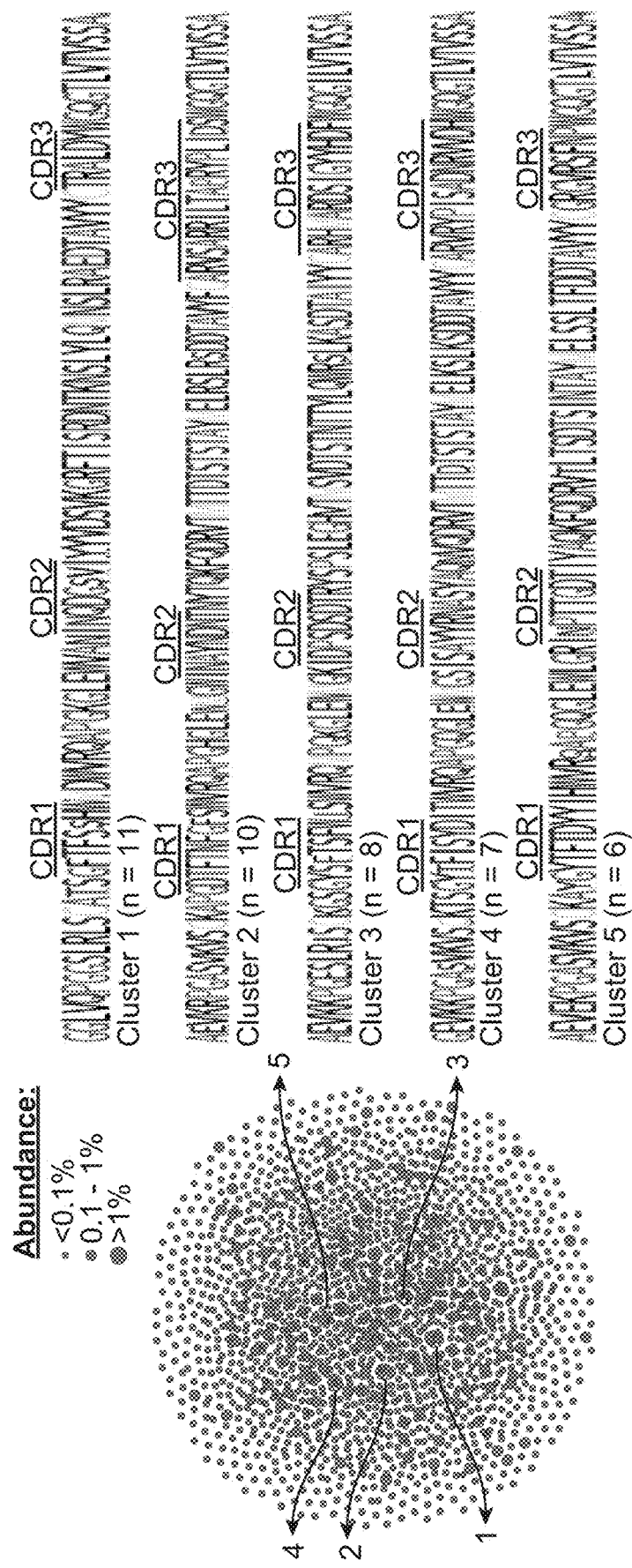

FIG. 34D. Left: The clonal cluster analysis of Rhig antibodies, modified from FIG. 4 (from the final CHO library). Right: Sequence logos of all heavy chain sequences from the top five clusters (based on clone count). The first 8 amino acids (variable region primer binding sites) are not shown. Figure discloses SEQ ID NOS 25961-25965, respectively, in order of appearance.

FIG. 35A to 35D provide results from repertoire sequencing analysis of rPIG.

Figure 35A:
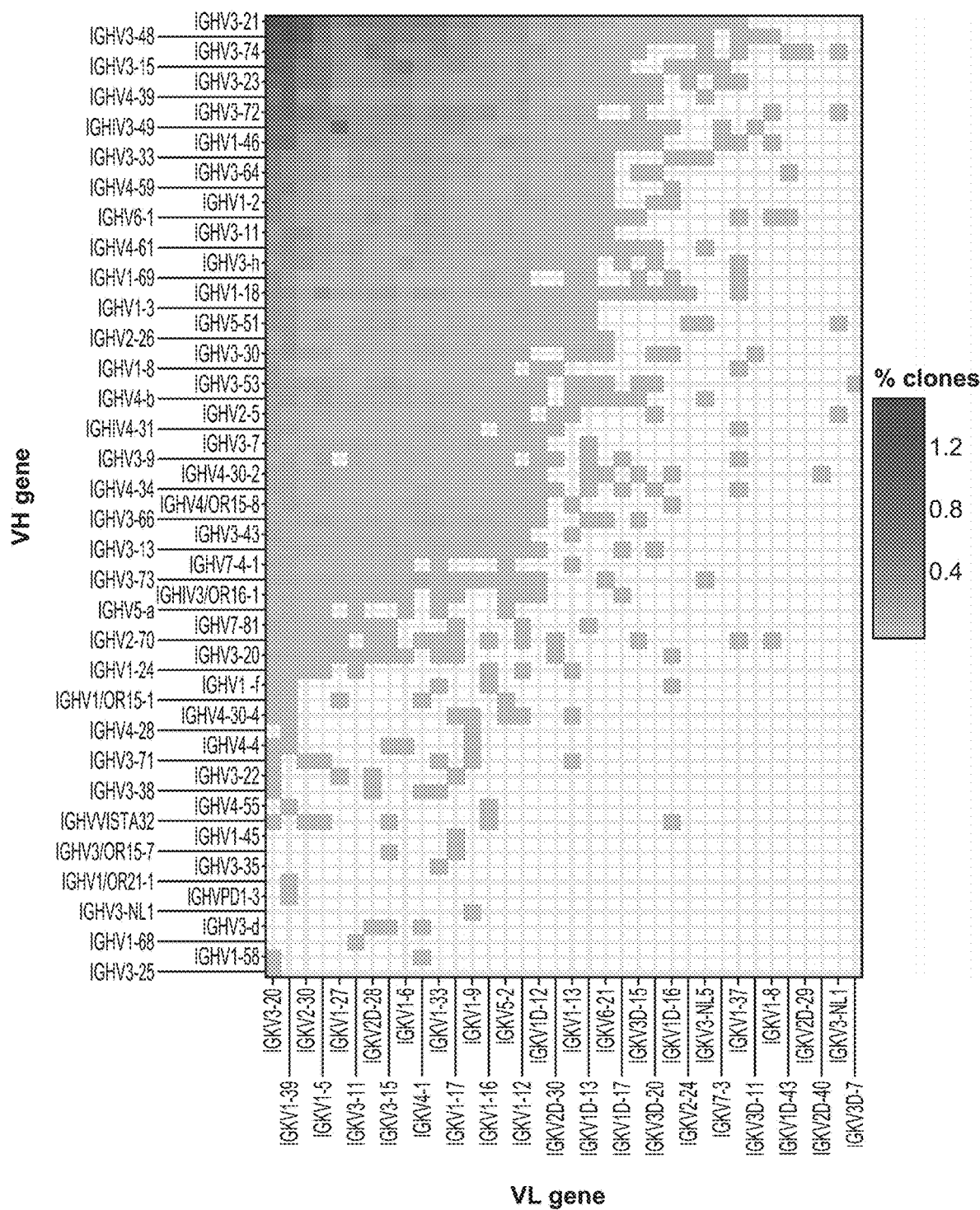

FIG. 35A is a heatmap showing antibody variable (V) gene usage from the linked scFv library. The x-axis and y-axis show light and heavy chain V genes, respectively. The color represents percent unique clone abundance in the library.

Figure 35B:
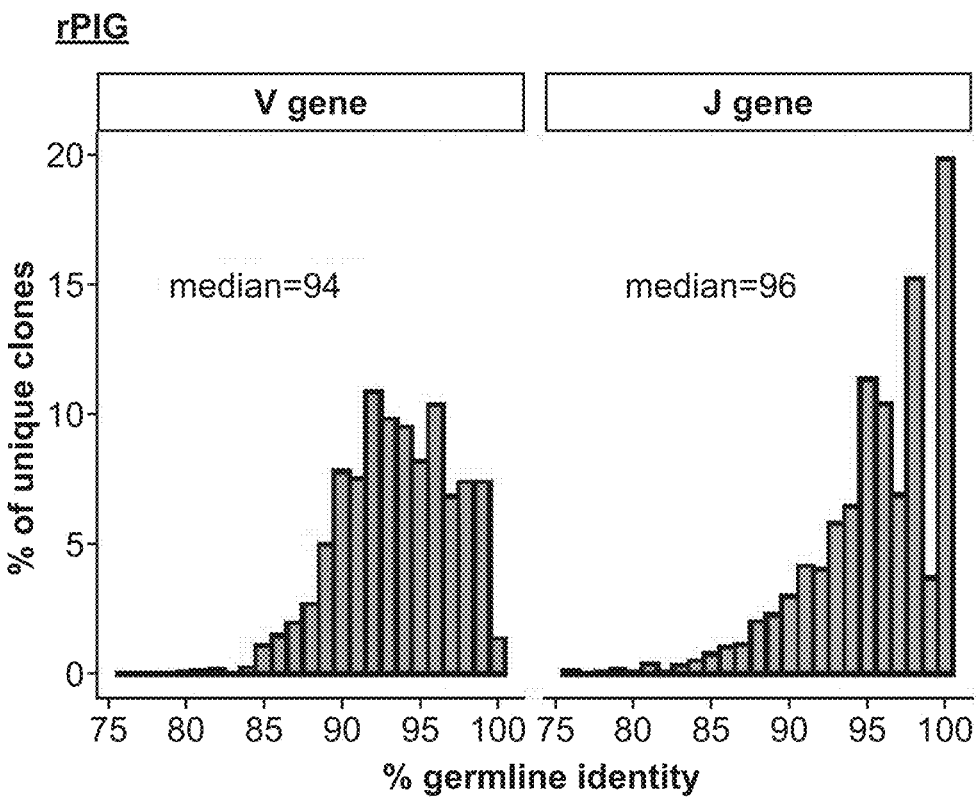

FIG. 35B is a histogram showing distribution of percent germline identity for variable gene (V; left panel) and joining gene (J; right panel), from the final CHO library.

Figure 35C:
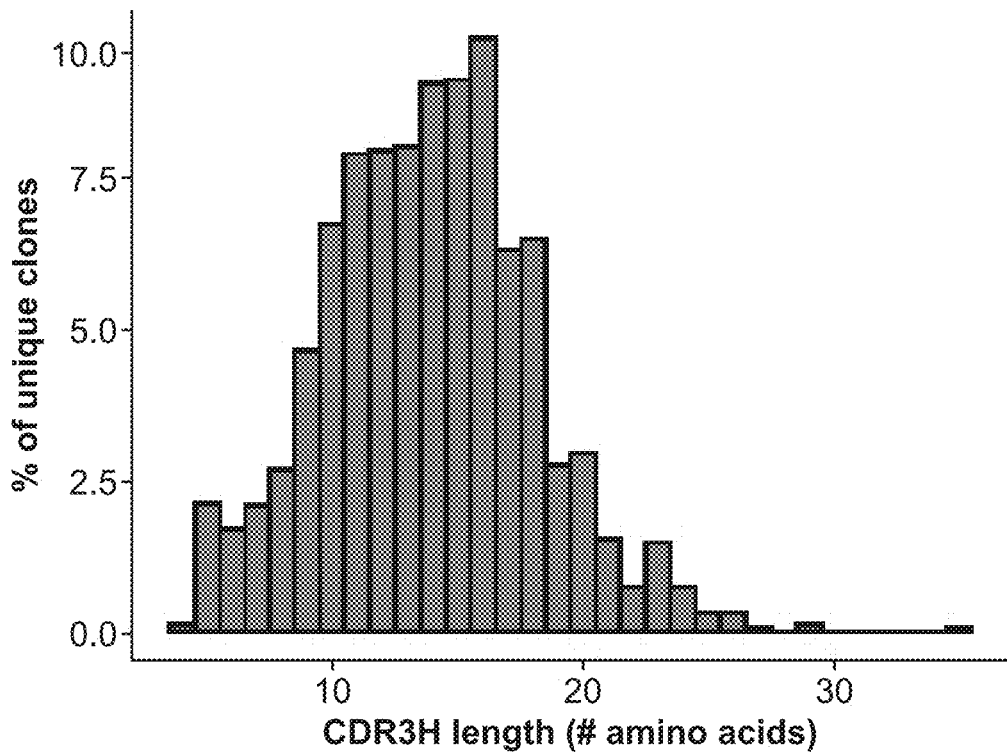

FIG. 35C is a histogram showing the distribution of heavy chain CDR3 amino acid length, from the final CHO library.

Figure 35D:
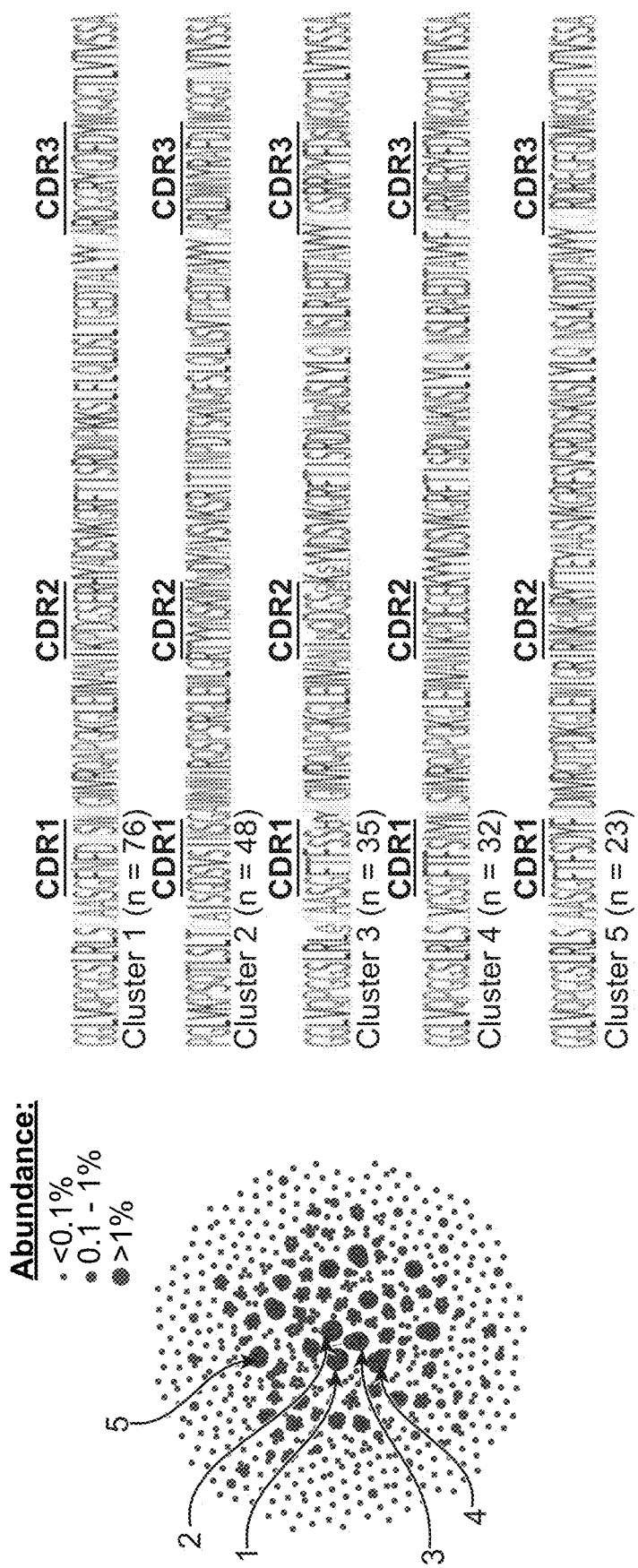

FIG. 35D. (d) Left: The clonal cluster analysis of Rpig antibodies, modified from FIG. 4 (from the final CHO library). Right: Sequence logos of all heavy chain sequences from the top five clusters (based on clone count). The first 8 amino acids (variable region primer binding sites) are not shown. Figure discloses SEQ ID NOS 25966-25970, respectively, in order of appearance.

Figures 36A, 36B:
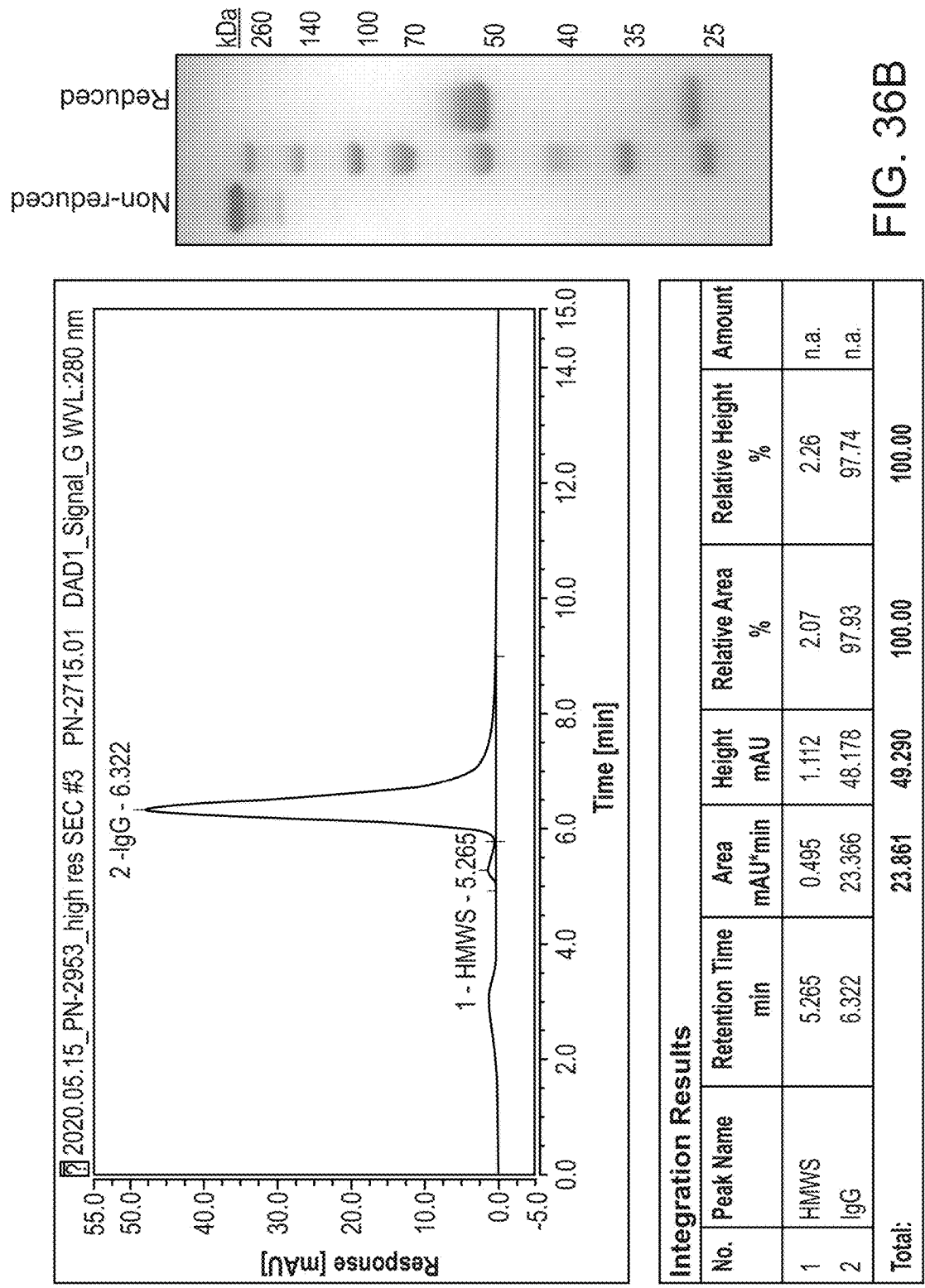

FIGS. 36A and 36B show quality control analysis of purified rHIG protein. FIG. 36A is from SEC-HPLC analysis used to assess the purity of the Protein A-purified protein. FIG. 36B is from SDS-PAGE analysis used to assess the purity of the Protein A-purified protein.

FIGS. 37A and 37B show quality control analysis of purified rPIG protein. FIG. 37A is from SEC-HPLC analysis were used to assess the purity of the Protein A-purified protein. FIG. 37B is from SDS-PAGE analysis used to assess the purity of the Protein A-purified protein.

Figure 38:
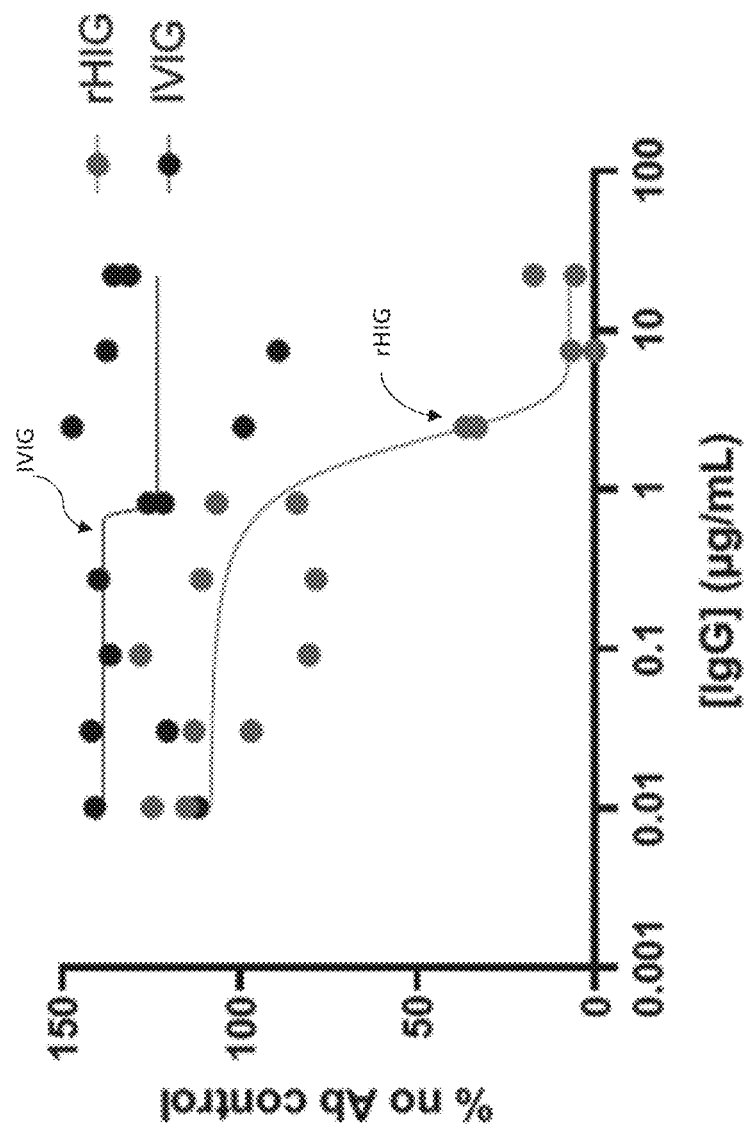

FIG. 38 provides data from *Haemophilus influenzae* serum bactericidal assay (SBA). rHIG and IVIG were serially diluted and co-incubated with $5 \times 10^4$ CFU/mL *Haemophilus influenzae* Eagan strain. After incubation, complement was added, incubated, and test samples were plated on chocolate agar. After 16 hours incubation, bacteria colony counts for each serial dilution were quantified and divided by the bacteria colony counts in the no Ab control.

Figure 39:
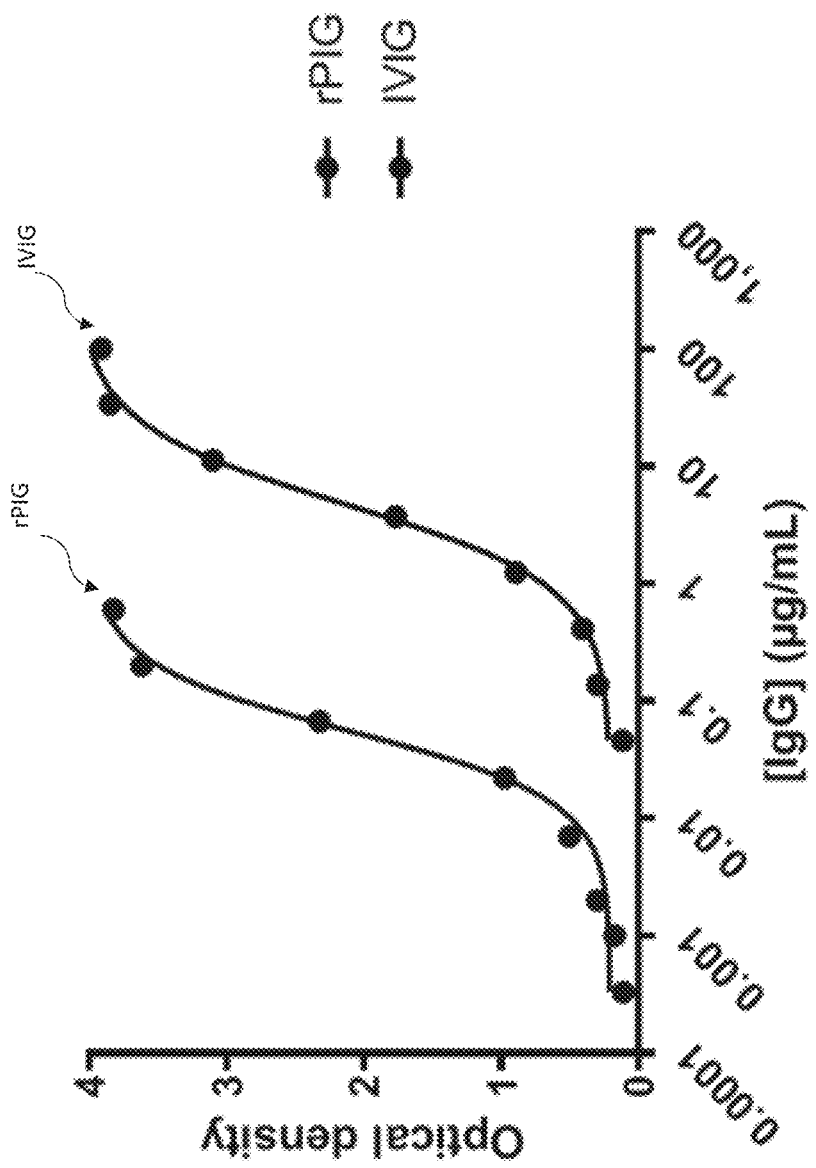

FIG. 39 provides data from Pneumococcal antibody binding assay using ELISA. Binding of serially diluted rPIG and IVIG to a pool of 23 pneumococcal polysaccharides was measured by ELISA.

Figure 40A:
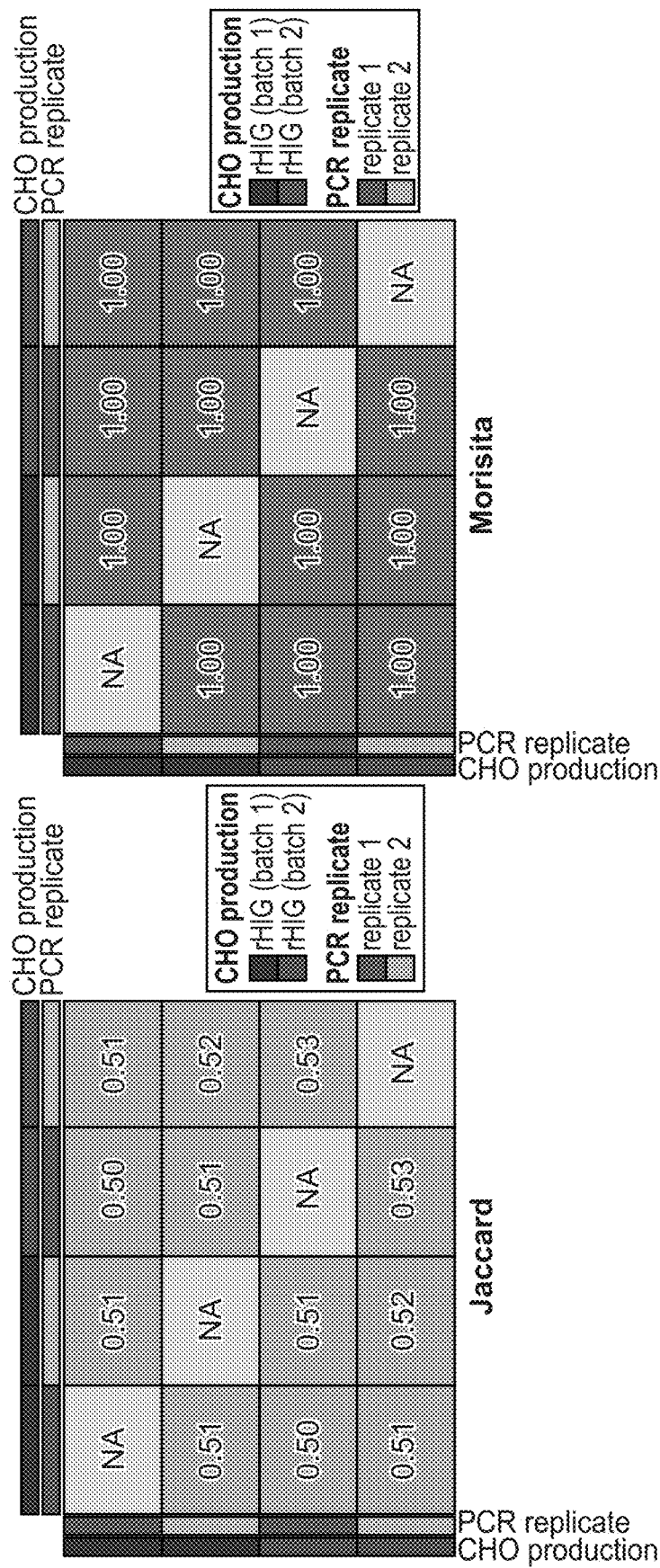
Figure 40B:
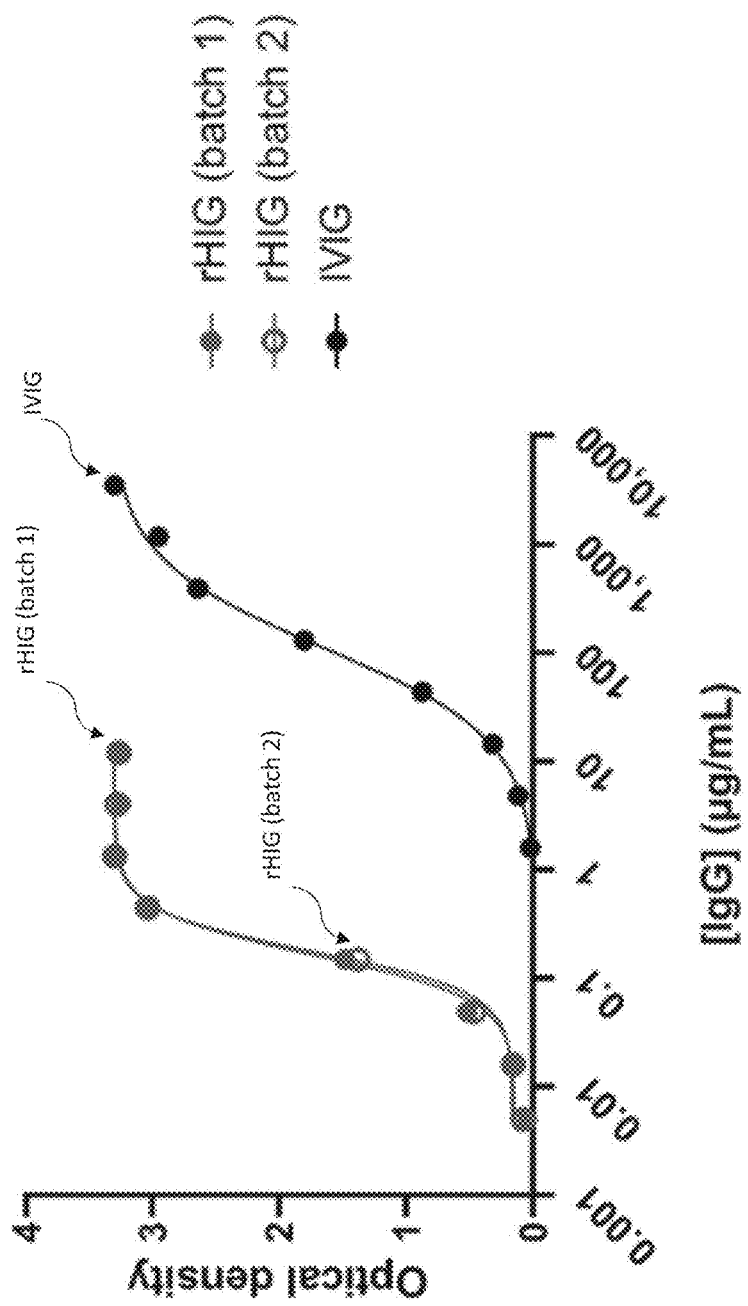

FIG. 40A to 40B show measurement of batch-to-batch variation of rHIG. (FIG. 40A) RNA antibody sequencing was performed (in duplicate) on RNA isolated from the end of replicate CHO bioreactor production runs. Jaccard (left)

and Morisita (right) analyses showed that the amount of antibody clone variation between production batches and between PCR replicates performed on each batch. Wilcoxon rank sum tests showed that the indices from the PCR replicates came from the same population as the indices from the batch replicates (p>0.05), suggesting that the variability inherent to the batches was no worse than the variability between PCR replicates. FIG. 40B show binding of the indicated batch of serially diluted rHIG and IVIG to Hib as measured by ELISA.

Figure 41A:
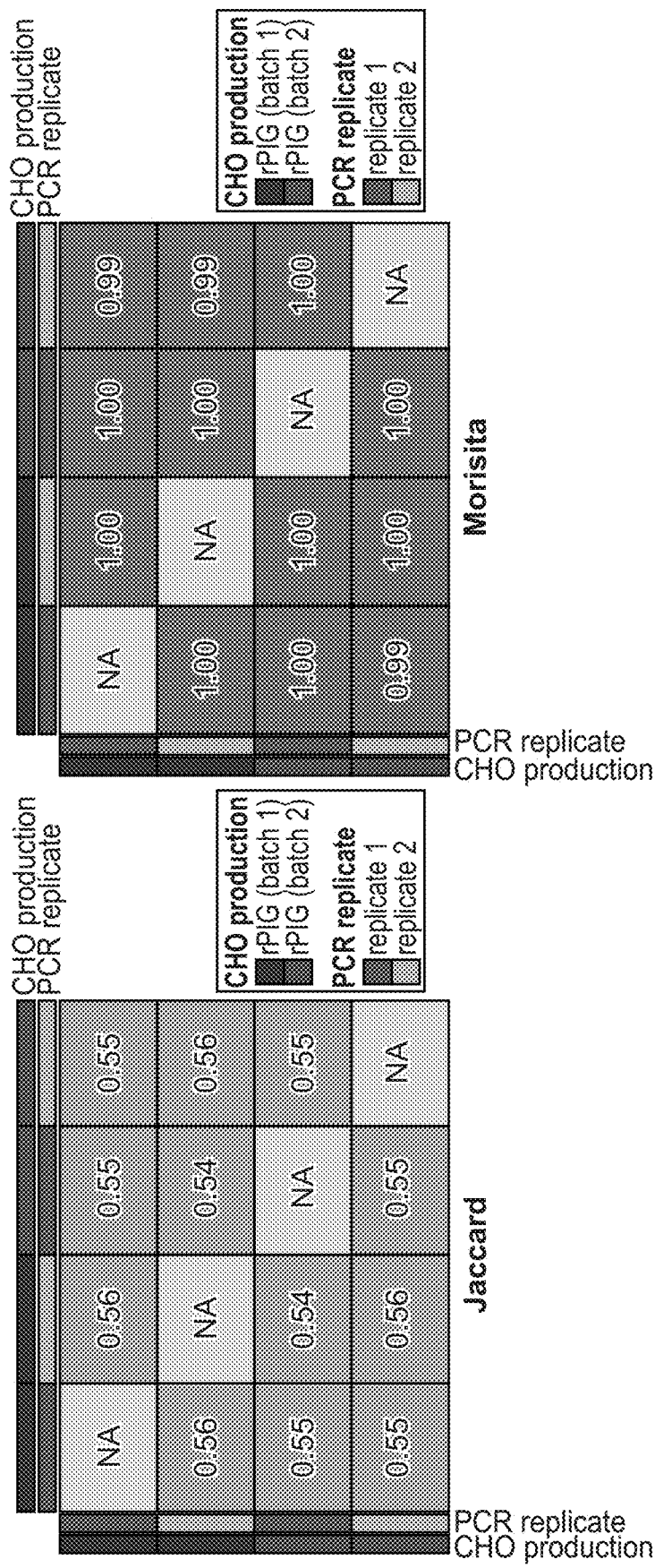
Figure 41B:
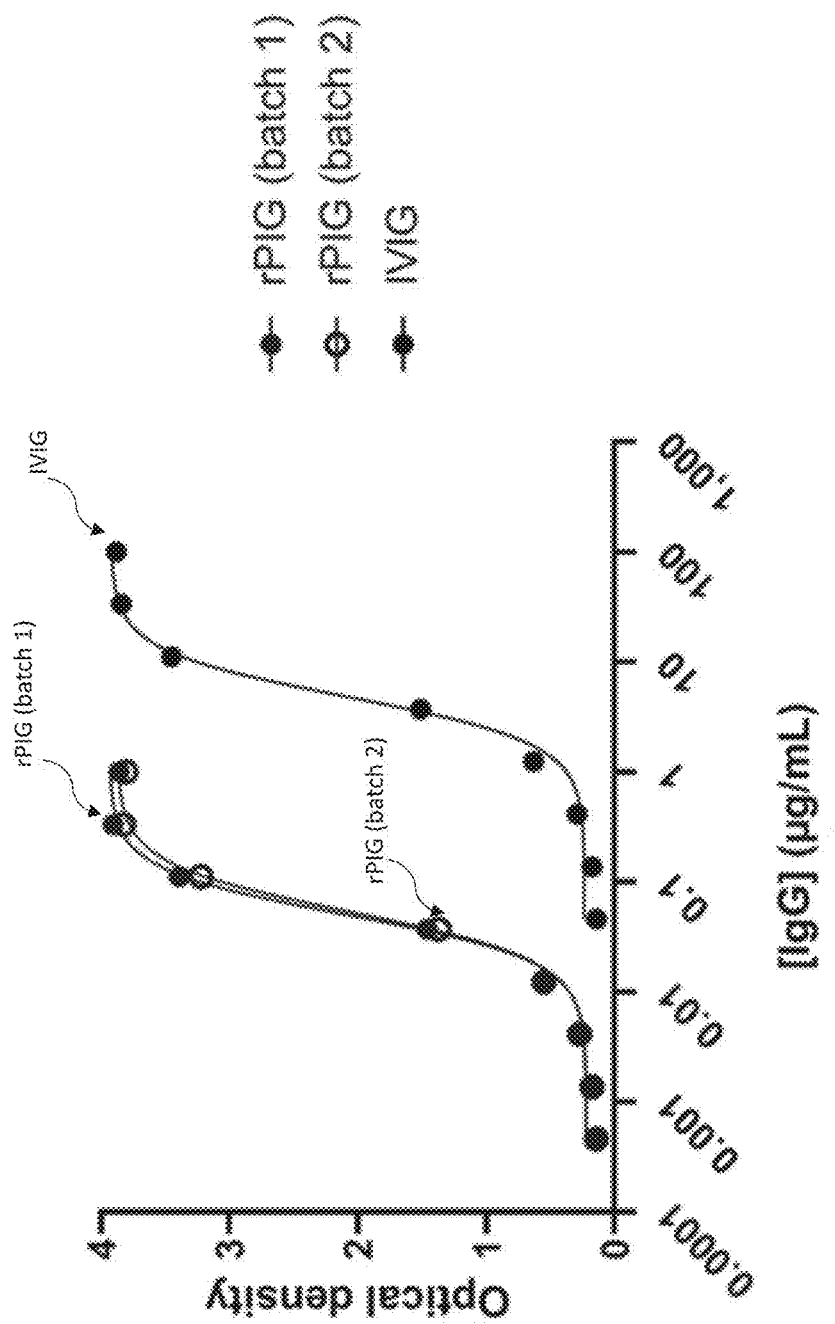

FIG. 41A and FIG. 41B show measurement of batch-to-batch variation of rPIG. (FIG. 41A) RNA antibody sequencing was performed (in duplicate) on RNA isolated from the end of replicate CHO bioreactor production runs. Jaccard (left) and Morisita (right) analyses showed that the amount of antibody clone variation between production batches and between PCR replicates performed on each batch. Wilcoxon rank sum tests showed that the indices from the PCR replicates came from the same population as the indices from the batch replicates (p>0.05), suggesting that the variability inherent to the batches was no worse than the variability between PCR replicates. FIG. 41B shows binding of the indicated batch of serially diluted rPIG and IVIG to a pool of 23 pneumococcal polysaccharides as measured by ELISA.

Figure 42B:
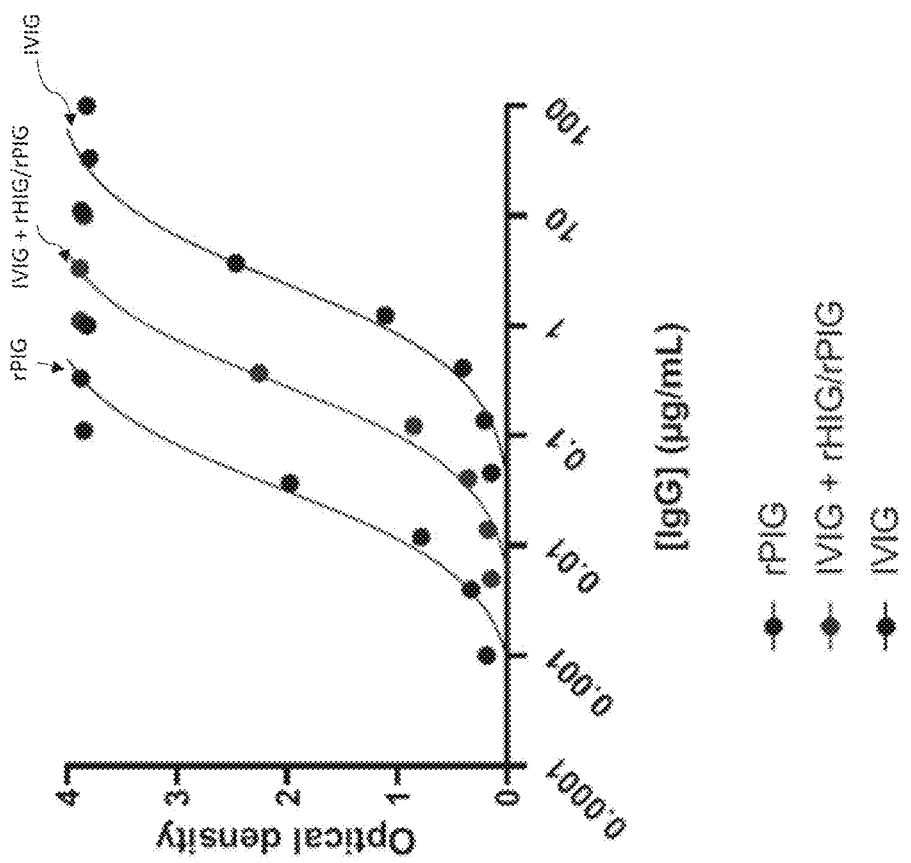
Figure 42A:
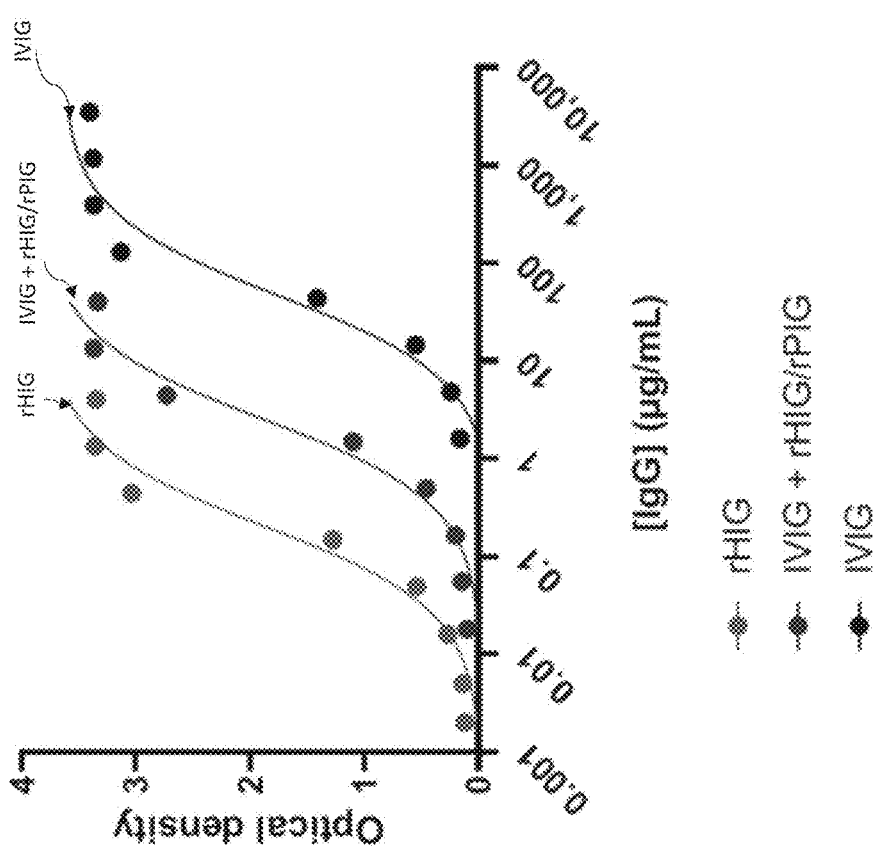

FIGS. 42A and 42B show Pneumococcal or Hib antibody binding of IVIG+rHIG/rPIG by ELISA. FIG. 42A shows binding of serially diluted rHIG, IVIG+rHIG/rPIG, and IVIG to Hib, measured by ELISA. FIG. 42B shows binding of serially diluted rPIG, IVIG+rHIG/rPIG, and IVIG to a pool of 23 pneumococcal polysaccharides, measured by ELISA.

FIG. 43A illustrates procedures for immunizing three Trianni mice weekly with T cells isolated from one human donor with ALD/MDP adjuvant. After week 5, serum from the mice was tested to confirm binding to T cells before a final boost without adjuvant 5 days prior to harvesting the organ B cells.

Figure 43B:
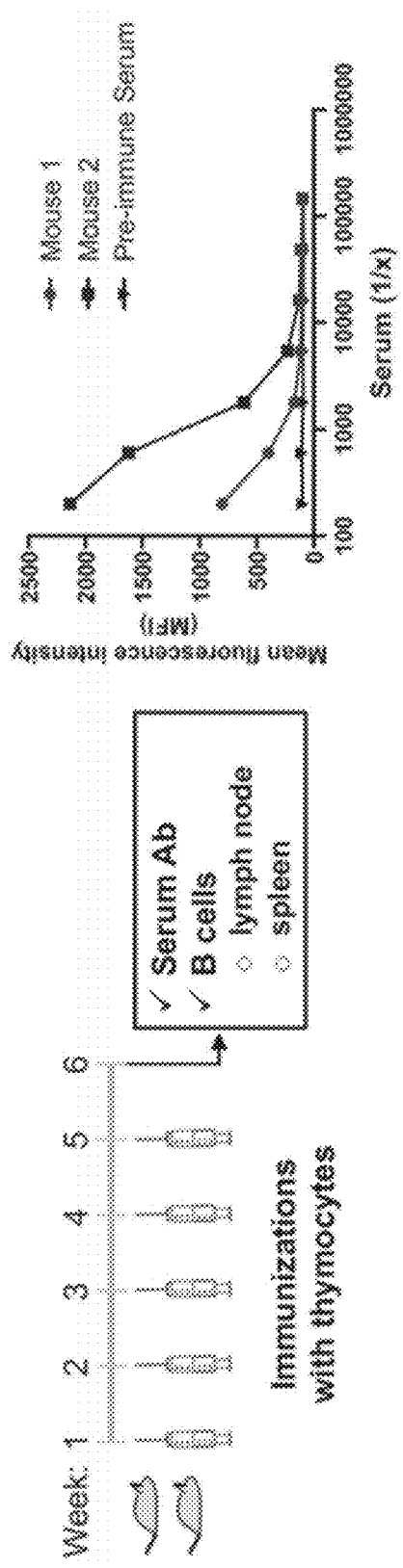

FIG. 43B illustrates procedures for immunizing two Trianni mice weekly with thymocytes isolated from five separate human donors with ALD/MDP adjuvant. After week 5, serum from the mice was tested to confirm binding to T cells before a final boost without adjuvant 5 days prior to harvesting the organ B cells.

Figure 44A:
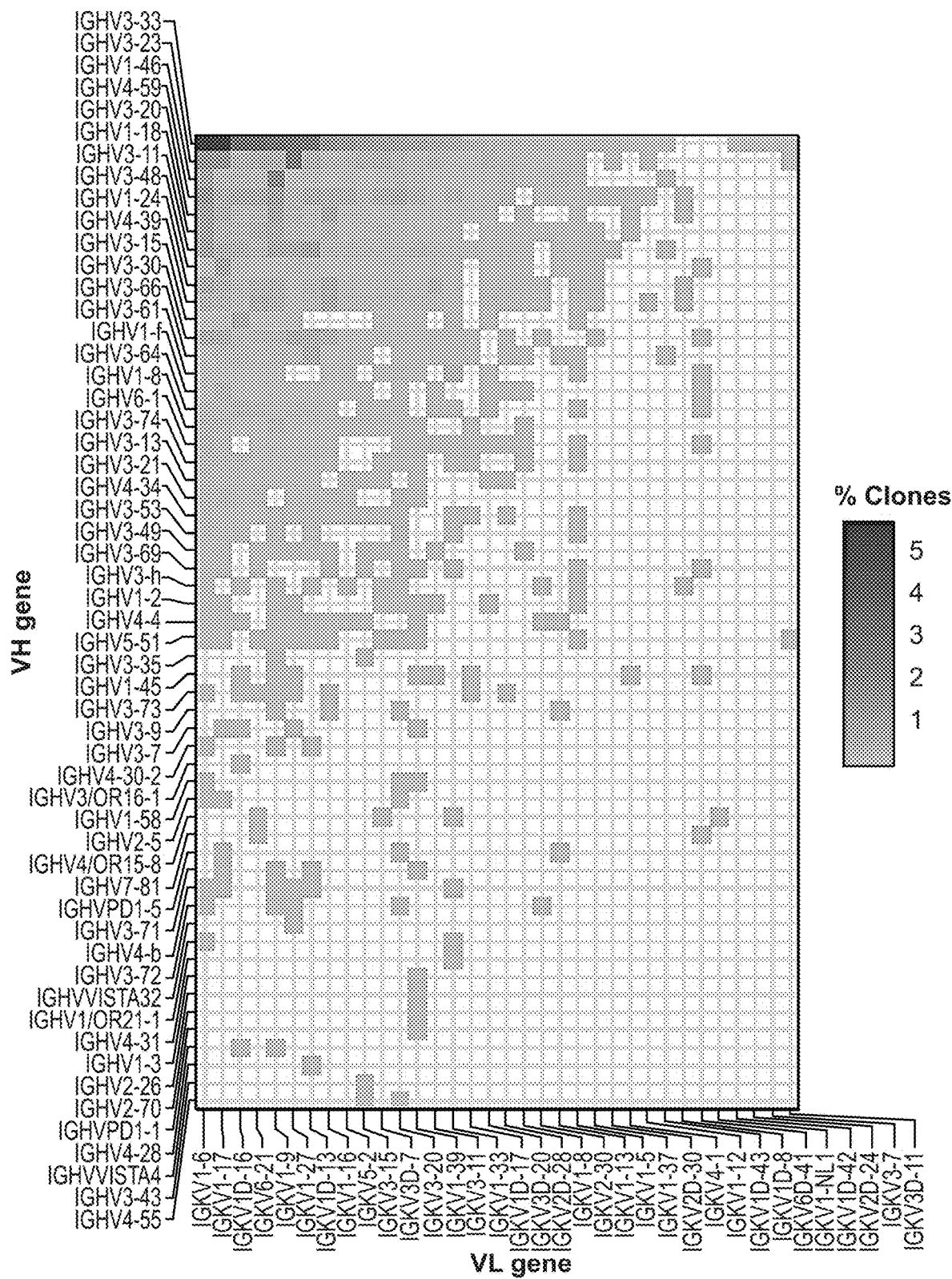

FIG. 44A is a heatmap showing antibody variable (V) gene usage from the linked scFv library (the 4 libraries combined). The x-axis and y-axis show light and heavy chain V genes, respectively. The greyscale represents percent unique clone abundance in the library.

Figure 44B:
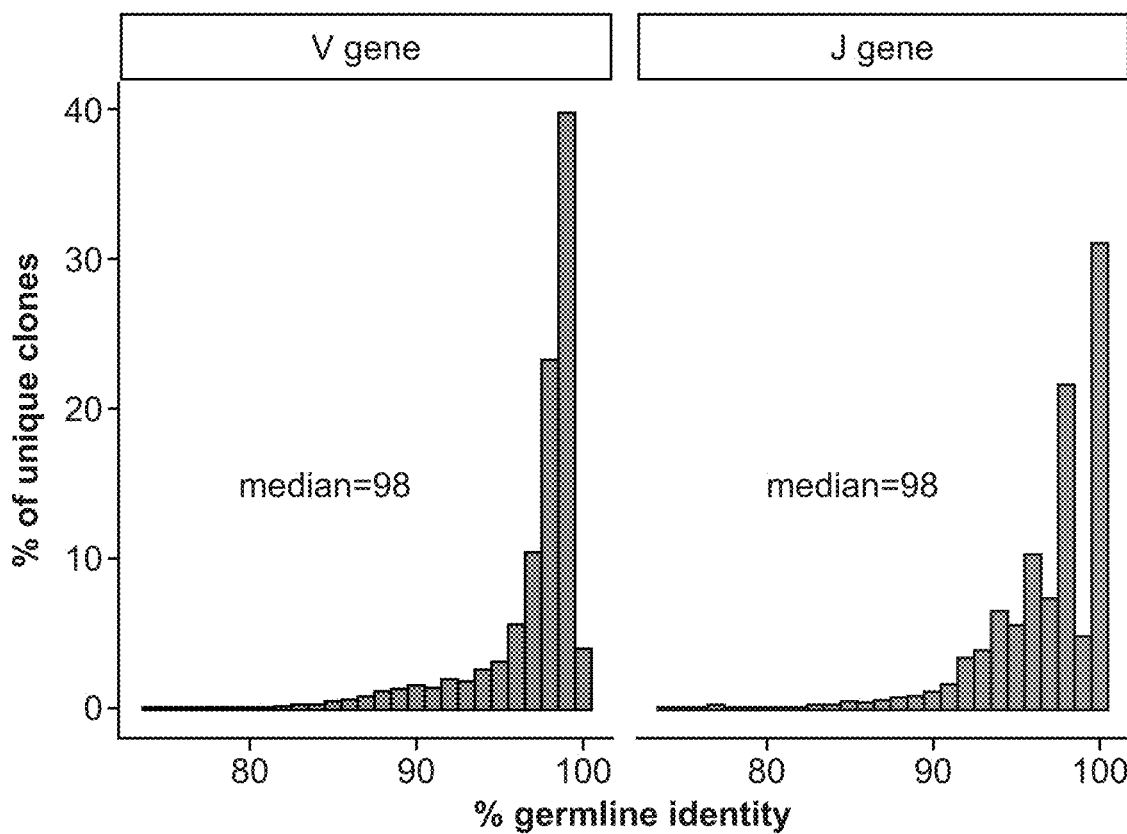

FIG. 44B provides a histogram showing distribution of percent germline identity for variable gene (V; left panel) and joining gene (J; right panel), from the final CHO library.

Figure 44C:
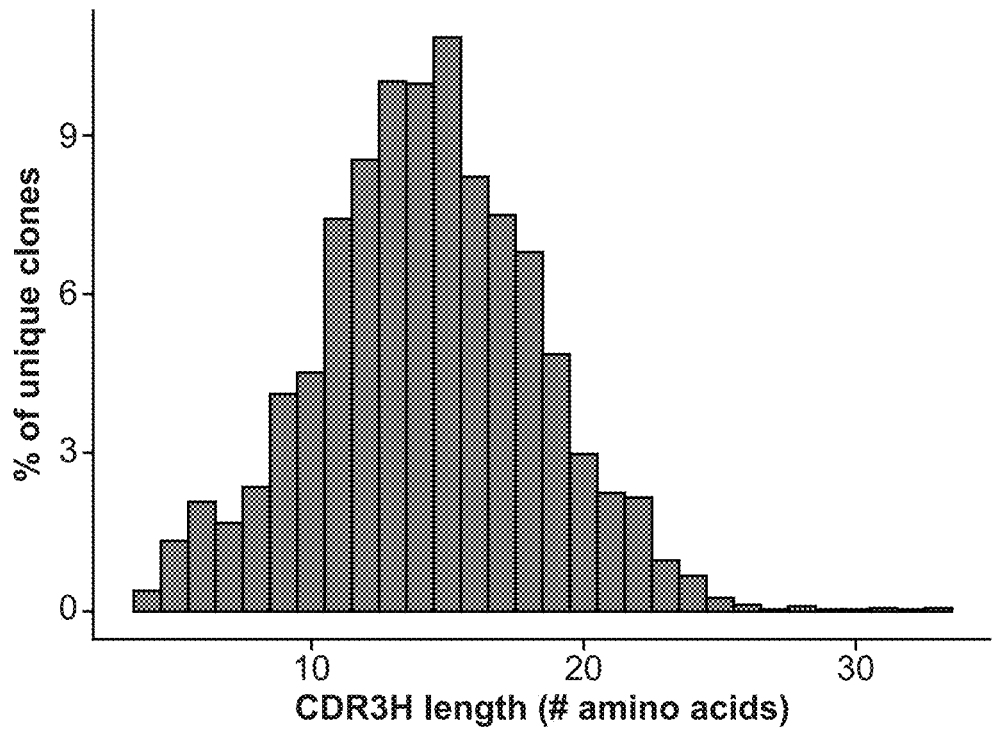

FIG. 44C is a histogram showing the distribution of heavy chain CDR3 amino acid length, from the final CHO library.

Figure 44D:
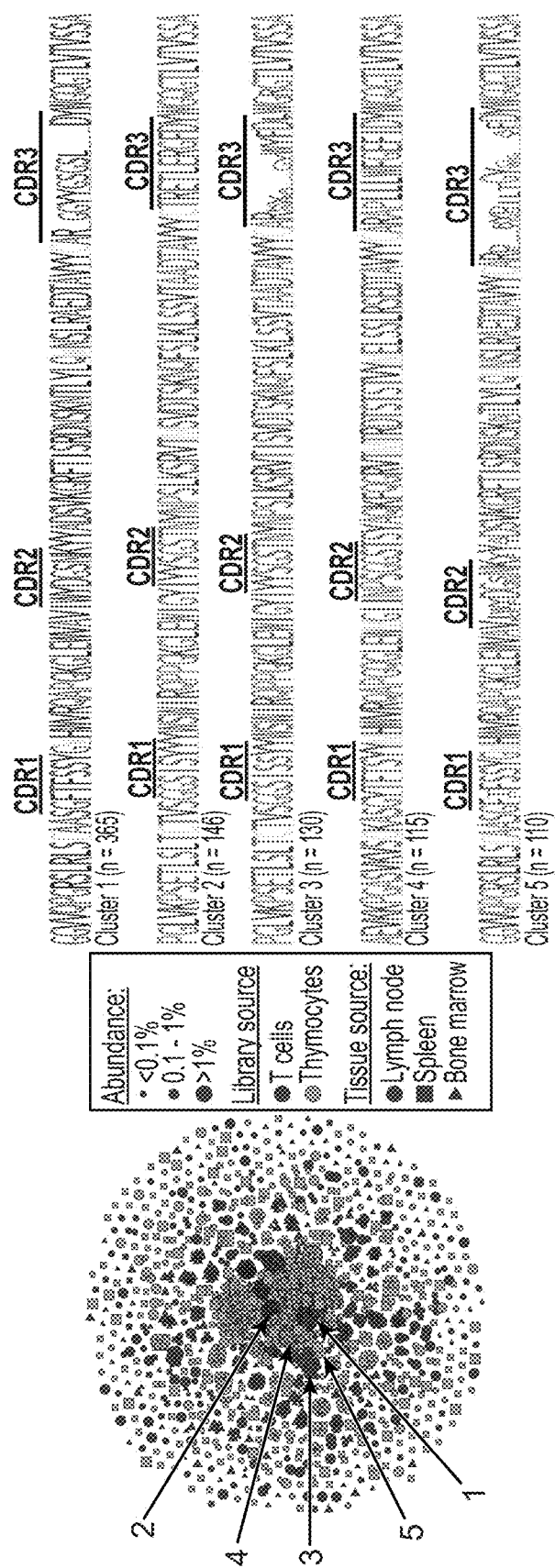

FIG. 44D. Left: The clonal cluster analysis of rhATG antibodies from FIG. 11A (from the CHO libraries). Right: Sequence logos of all heavy chain sequences from the top five clusters (based on clone count). The first 8 amino acids (variable region primer binding sites) are not shown. Figure discloses SEQ ID NOS 25971-25975, respectively, in order of appearance.

Figure 45A:
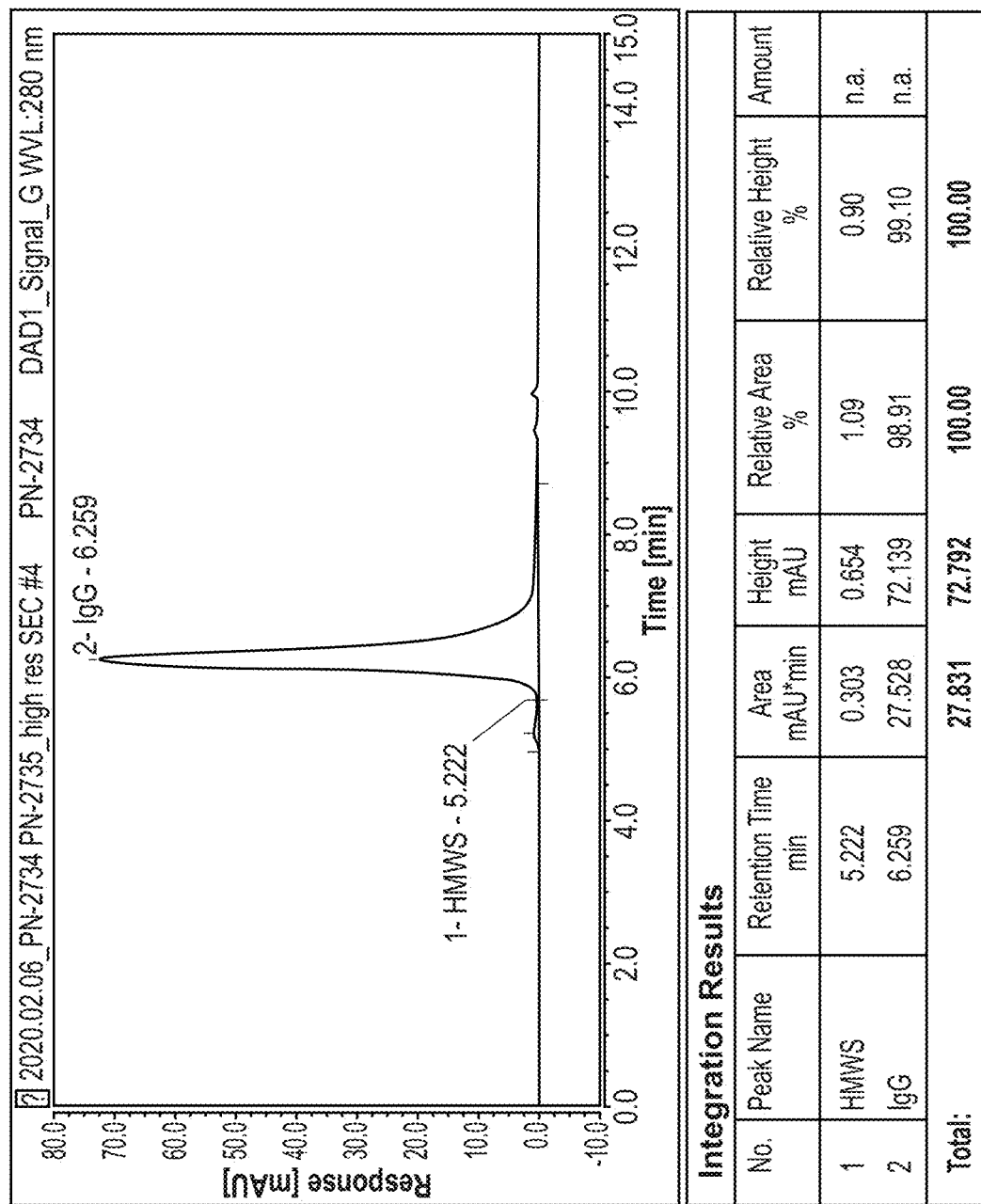
Figure 45B:
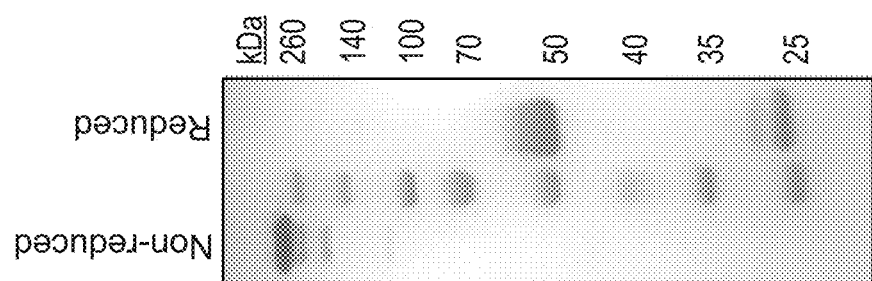

FIG. 45A-45B shows quality control analysis of purified rhATG protein. FIG. 45A shows a result from SEC-HPLC analysis used to assess the purity of the Protein A-purified protein. FIG. 45B shows a result from SDS-PAGE analysis used to assess the purity of the Protein A-purified protein.

Figures 46A, 46B:
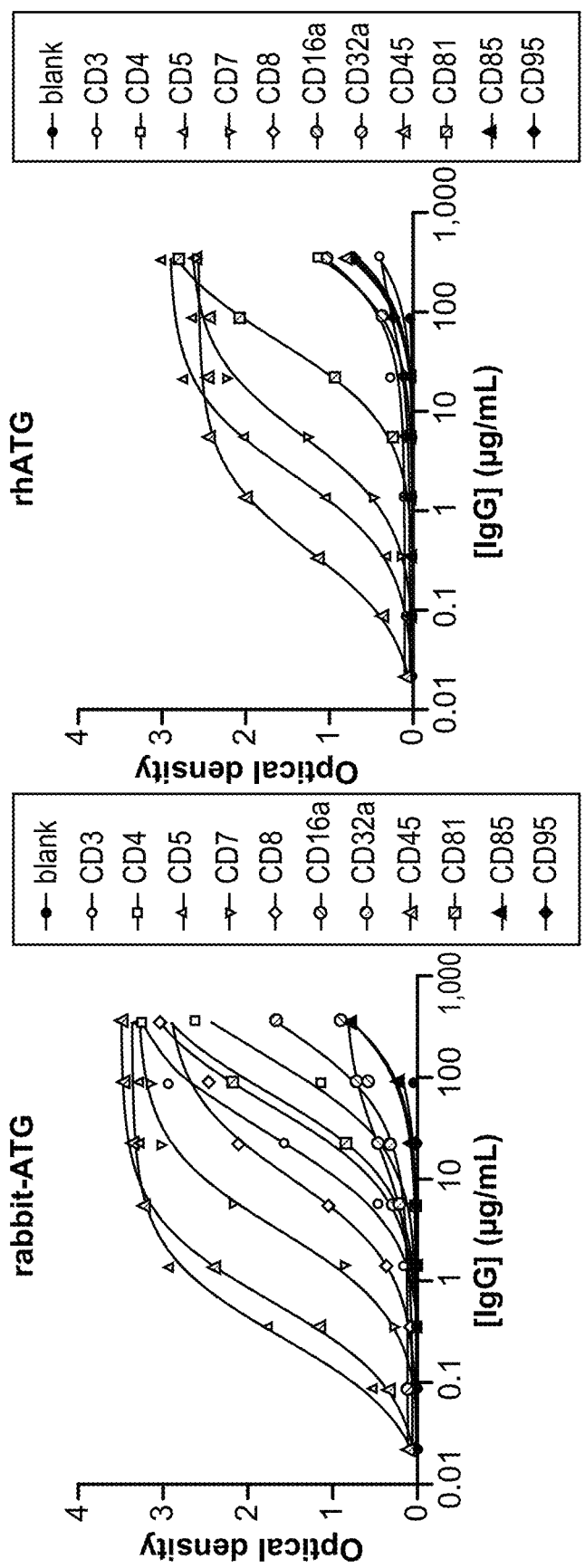

FIG. 46A-46B show ATG immune cell-specific antibody responses measure by ELISA. The indicated Immune cell antigens were coated onto ELISA plates. (FIG. 46A) rabbit-ATG was serially diluted and added to the plate. Antibody bound to antigens were quantified by anti-rabbit-HRP or anti-human-HRP, respectively. (FIG. 46B) h-ATG were serially diluted and added to the plate. Antibody bound to antigens were quantified by anti-rabbit-HRP or anti-human-HRP, respectively.

Figure 47:
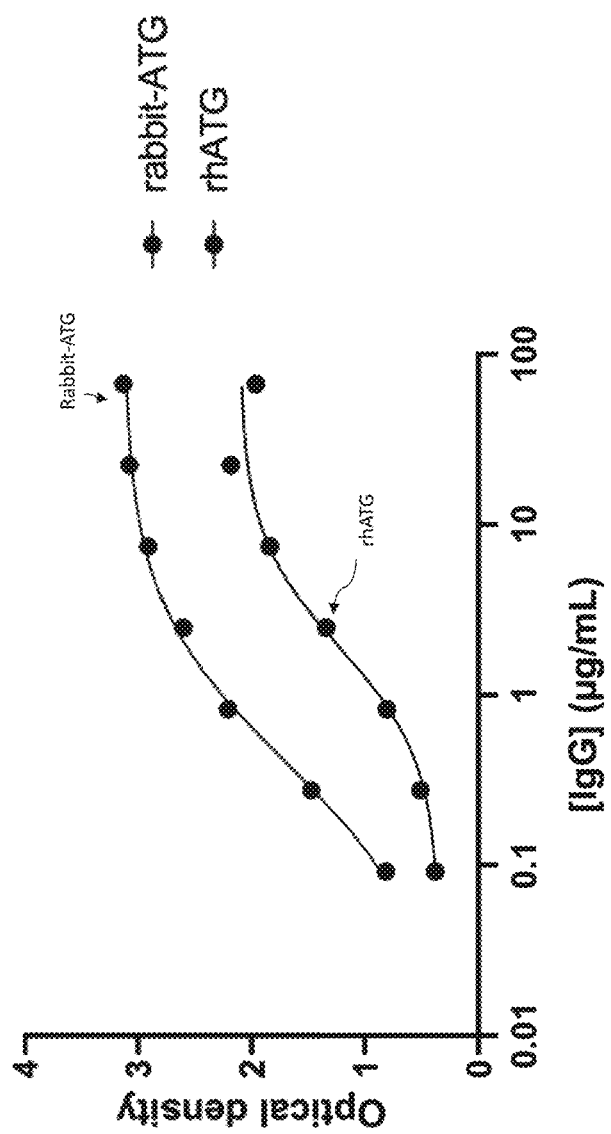

FIG. 47 shows ATG binding to red blood cells by ELISA. RBC-specific antibody response was measured by Immucor Capture-R ELISA. Rabbit-ATG and rhATG were serially diluted and added to the Immucor Capture-R plate. RBC-bound antibodies were quantified by anti-rabbit-HRP or anti-human-HRP, respectively.

Figure 48A:
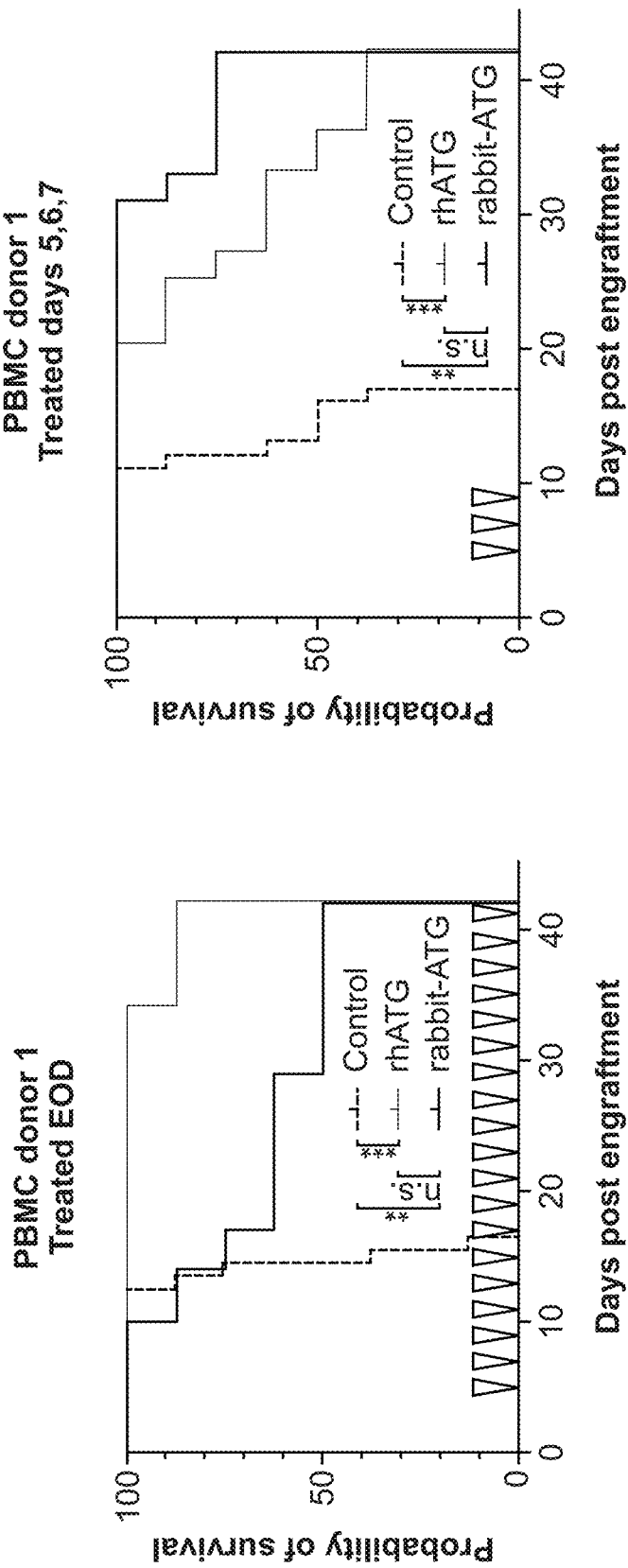
Figure 48B:
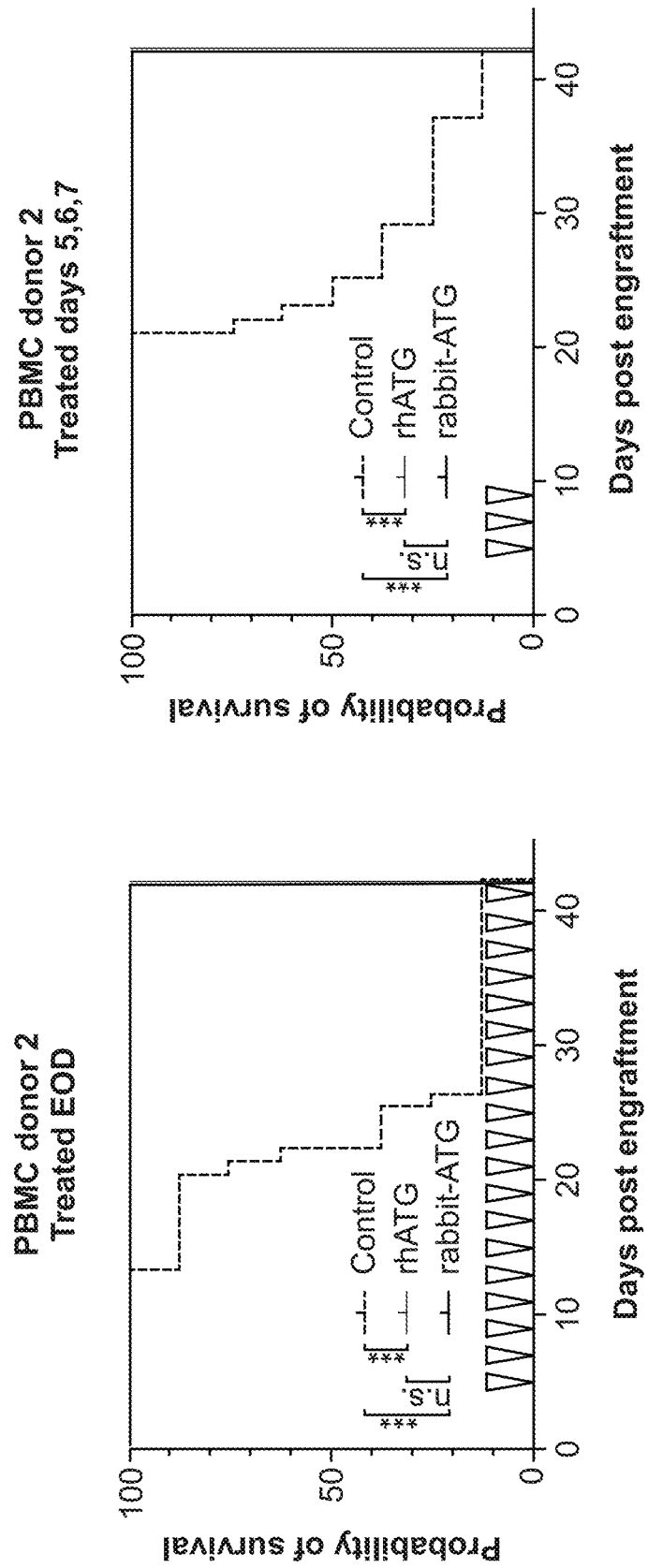

FIGS. 48A and 48B show survival of mice in the GVHD study after ATG treatment. (FIG. 48A) Eight animals per treatment group were engrafted with $10^7$ PBMC from one of two donors. Animals were treated with rhATG, rabbit-ATG, or vehicle control either every other day beginning at day 5 or on days 5, 6, and 7 (treatment days are indicated by triangles), then monitored for progression to GVHD and death.  $p<0.01$, * $p<0.001$, n.s. not significant. (FIG. 48B) Eight animals per treatment group were engrafted with $10^7$ PBMC from one of two donors. Animals were treated with rhATG, rabbit-ATG, or vehicle control either every other day beginning at day 5 or on days 5, 6, and 7 (treatment days are indicated by triangles), then monitored for progression to GVHD and death.  $p<0.01$, * $p<0.001$, n.s. not significant.

Figure 49A:
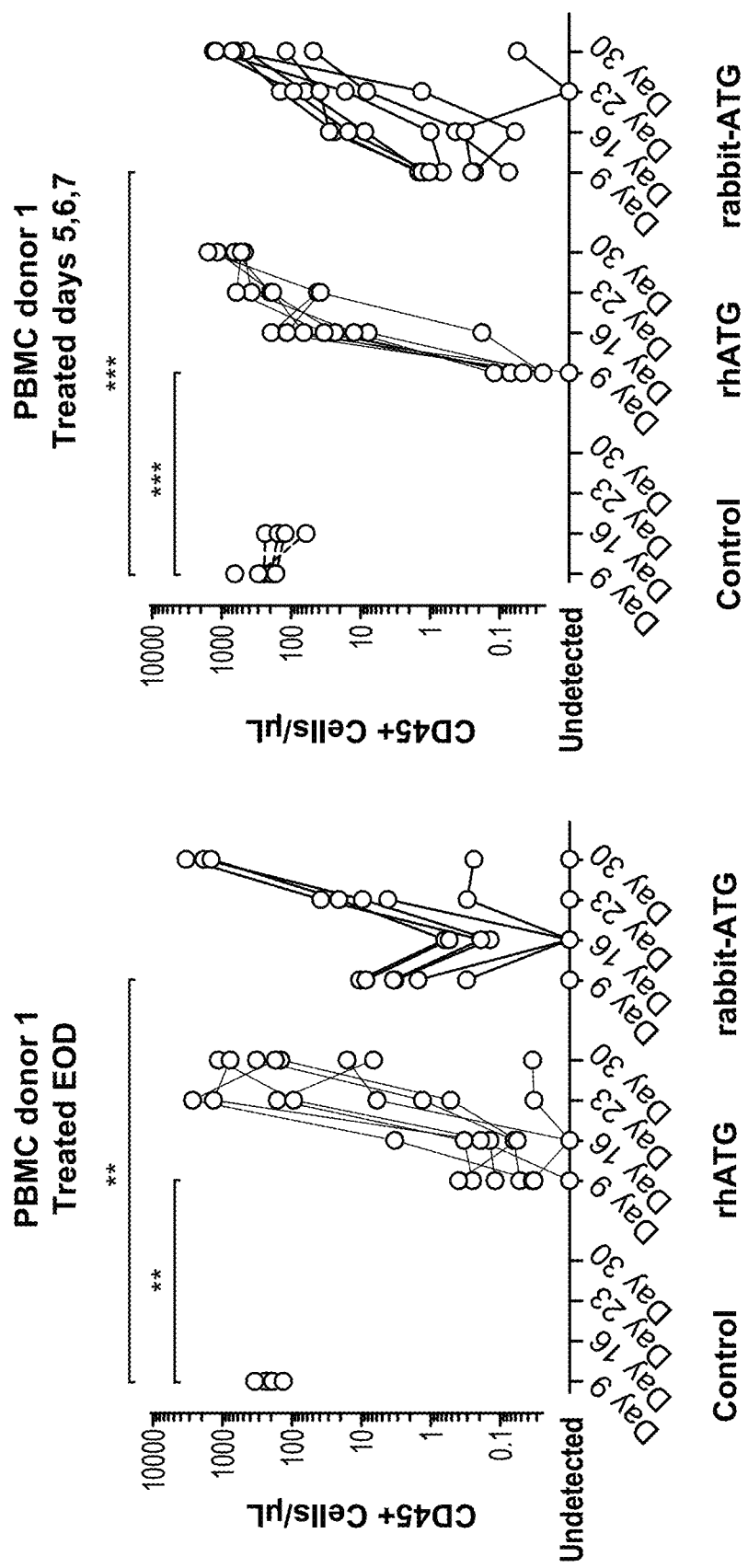
Figure 49B:
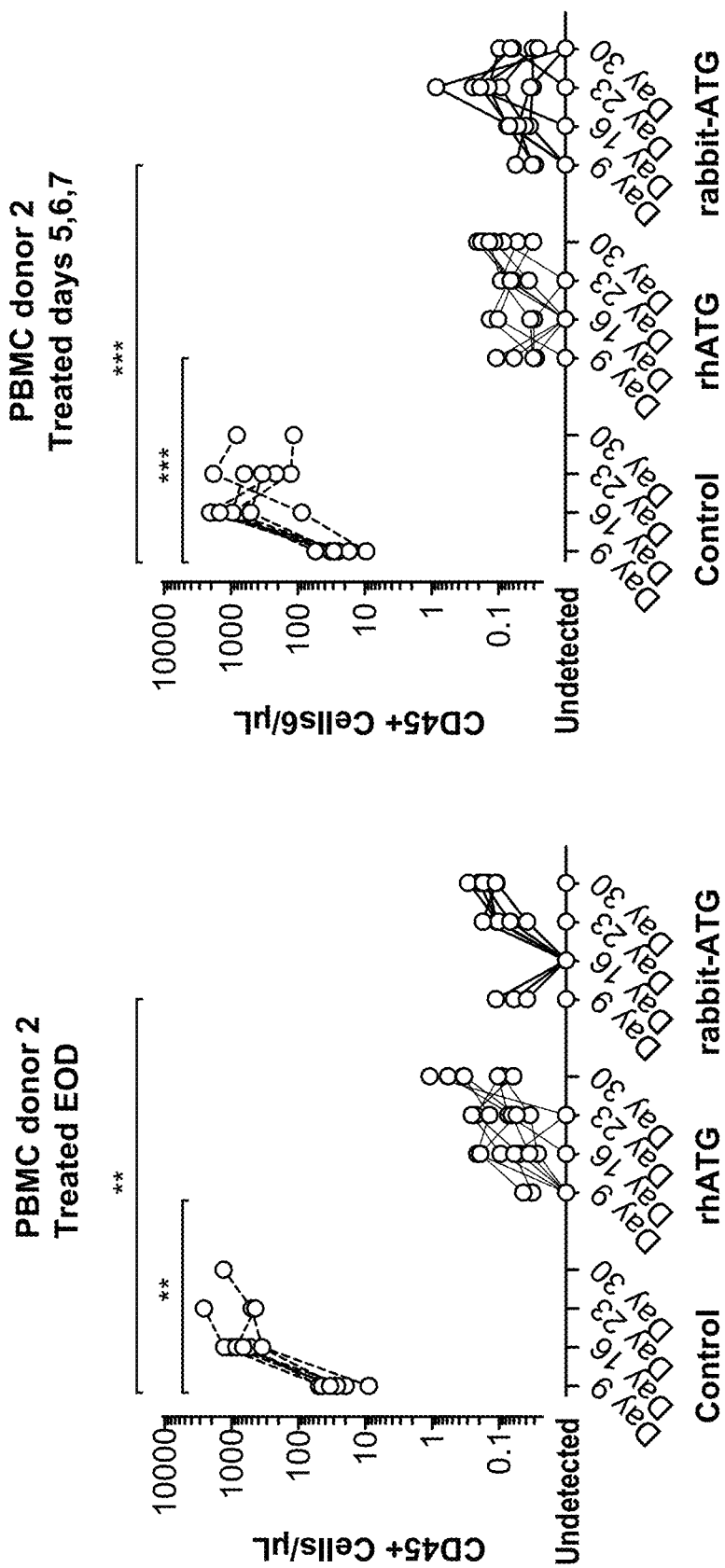

FIGS. 49A and 49B show flow cytometry of CD45+ cells from the ATG GVHD study. (FIG. 49A) Eight animals per treatment group were engrafted with $10^7$ PBMC from one of two donors. Animals were treated with rhATG, rabbit-ATG, or vehicle control either every other day beginning at day 5 or on days 5, 6, and 7. Flow cytometry was used to determine the concentration of CD45+ cells from each alive mouse on Days 9, 16, 23, and 30. Lines connect measurements from each mouse. No CD45+ cells were observed where circles intercept the x-axis.  $p<0.01$, * $p<0.001$.

(FIG. 49B) Eight animals per treatment group were engrafted with $10^7$ PBMC from one of two donors. Animals were treated with rhATG, rabbit-ATG, or vehicle control either every other day beginning at day 5 or on days 5, 6, and 7. Flow cytometry was used to determine the concentration of CD45+ cells from each alive mouse on Days 9, 16, 23, and 30. Lines connect measurements from each mouse. No CD45+ cells were observed where circles intercept the x-axis.  $p<0.01$, * $p<0.001$.

Figure 50A:
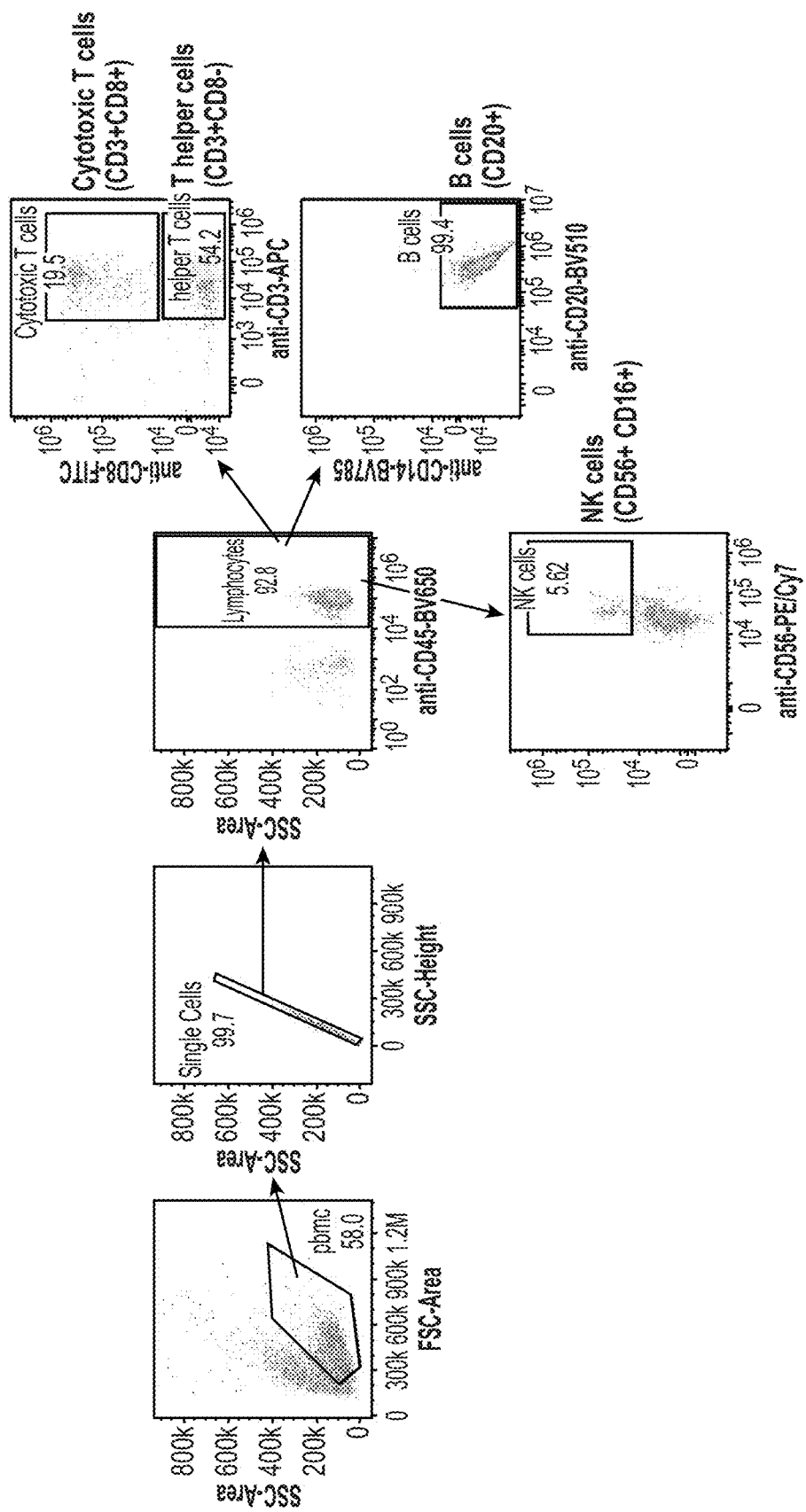
Figure 50B:
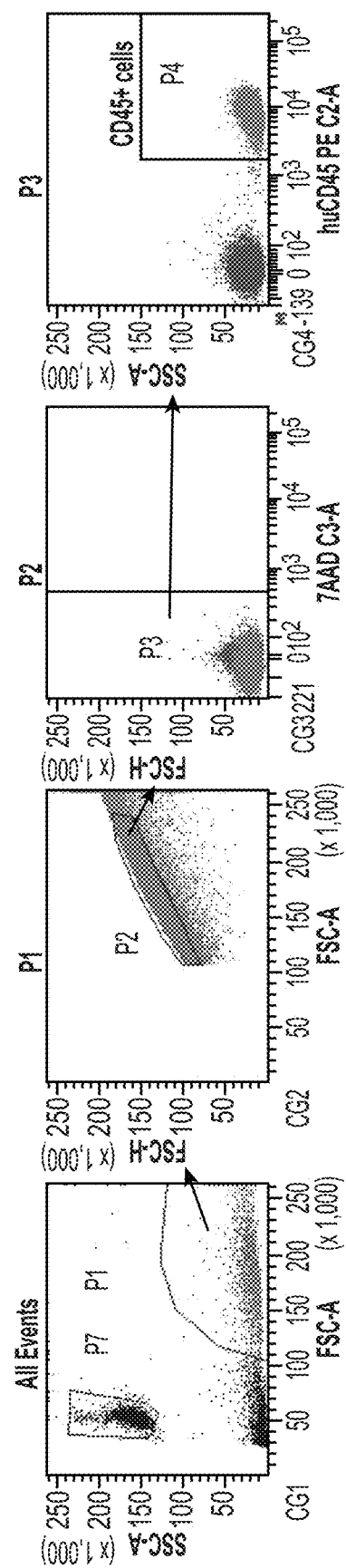

FIGS. 50A and 50B show ATG assay flow gating strategies. (FIG. 50A) Flow gating strategy for the ATG PBMC killing assay to quantify cytotoxic T cells, T helper cells, B cells, and NK cells. (FIG. 50B) Flow gating strategy of the GVH study to quantify CD45+ cells.

Figures 51A, 51B:
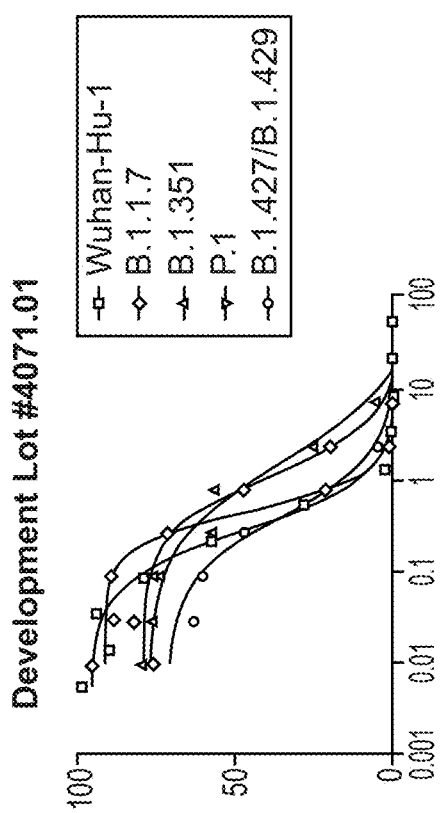

FIGS. 51A and 51B show data from SARS-CoV-2 pseudotype virus neutralization assay. Wuhan-Hu-1 as well as arising SARS-CoV-2 variants (B.1.1.7 (UK), B.1.351 (South Africa), P.1 (Japanese/Brazilian), and B.1.427/B.1.429 (California)) were psudotyped and tested.

FIG. 51A shows % of infected cells normalized to infected cells under a control condition without application of antibodies. FIG. 51B summarizes $IC_{50}$ value (μg/mL) for psudotype virus of the tested SARS-CoV-2 variants.

7. DETAILED DESCRIPTION

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "recombinant polyclonal protein", "recombinant polyclonal protein composition" or "RPP" refers to more than one recombinant antigen binding proteins (ABPs), collectively comprising more than one antigen-binding domains that specifically bind to an antigen or epitope, or multiple antigens and epitopes. The recombinant polyclonal protein or RPP can be antibodies or variants or derivatives thereof. In some embodiments, the antigen-binding domains bind an antigen or epitope with specificity and affinity similar to that of a naturally occurring antibody. In some embodiments, an RPP comprises antibodies. In some embodiments, the RPP consists essentially of antibodies. In some embodiments, an RPP is a mixture of antibodies. In some embodiments, an RPP comprises scFvs. In some embodiments, the RPP comprises an alternative scaffold. In some embodiments, the RPP consists of alternative scaffolds. In some embodiments, the RPP consists essentially of alternative scaffolds. In some embodiments, the RPP comprises an antibody fragment. In some embodiments, the RPP consists of antibody fragments. In some embodiments, the RPP consists essentially of antibody fragments.

The term "antigen binding protein" or "ABP" as used herein refers to a protein comprising one or more antigen-binding domains that specifically bind to an antigen or epitope. In some embodiments, the ABP comprises an antibody. In some embodiments, the ABP consists of an antibody. In some embodiments, the ABP consists essentially of an antibody. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. One example of an antigen-binding domain is an antigen-binding domain formed by a $V_H$-$V_L$ dimer.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of naturally occurring antibodies. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD3 (e.g., Tetranectins), Fynomers, and (LDLR-A module) (e.g., Avimers). Additional information on alternative scaffolds is provided in Binz et al., Nat. Biotechnol., 2005 23:1257-1268; Skerra, Current Opin. in Biotech., 2007 18:295-304; and Silacci et al., J. Biol. Chem., 2014, 289: 14392-14398; each of which is incorporated by reference in its entirety. Alternative scaffolds comprise one type of RPP.

The term "antigen-binding domain" means the portion of an ABP that is capable of specifically binding to an antigen or epitope.

The terms "full length antibody," "intact antibody," and "whole antibody" are used herein interchangeably to refer to an antibody having a structure substantially similar to a naturally occurring antibody structure and having heavy chains that comprise an Fc region.

The term "immunoglobulin" refers to a class of structurally related proteins, e.g., antibodies, generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, Fundamental Immunology 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, J. Allergy Clin. Immunol., 2010, 125:S41-52, incorporated by reference in its entirety. The Fc region may be a naturally occurring Fc region, or an Fc region modified as described elsewhere in this disclosure.

The $V_H$ and $V_L$ regions may be further subdivided into regions of hypervariability ("hypervariable regions (HVRs)" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., Sequences of Proteins of Immunological Interest 5th ed.

(1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J Mol. Biol. 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme); each of which is incorporated by reference in its entirety.

Table 1 provides the positions of CDR1-L (CDR1 of $V_L$), CDR2-L (CDR2 of $V_L$), CDR3-L (CDR3 of $V_L$), CDR1-H (CDR1 of $V_H$), CDR2-H (CDR2 of $V_H$), and CDR3-H (CDR3 of $V_H$), as identified by the Kabat and Chothia schemes. For CDR1-H, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, Immunology, 2008, 45:3832-3839, incorporated by reference in its entirety.

TABLE 1

Residues in CDRs according to Kabat and Chothia numbering schemes.

| CDR | Kabat | Chothia |
| --- | --- | --- |
| CDR1-L | 24-34 | 24-34 |
| CDR2-L | 50-56 | 50-56 |
| CDR3-L | 89-97 | 89-97 |
| CDR1-H (Kabat Numbering) | 31-35B | 26-32 or 34* |
| CDR1-H (Chothia Numbering) | 31-35 | 26-32 |
| CDR2-H | 50-65 | 52-56 |
| CDR3-H | 95-102 | 95-102 |

*The C-terminus of CDR1-H, when numbered using the Kabat numbering convention, varies between 32 and 34, depending on the length of the CDR.

The "EU numbering scheme" is generally used when referring to a residue in an antibody heavy chain constant region (e.g., as reported in Kabat et al., supra).

An "antibody fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (Cm) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is a (GGGGS)$_n$ (SEQ ID NO: 5). In some embodiments, n=1, 2, 3, 4, 5, or 6. See Antibodies from Escherichia coli. In Rosenberg M. & Moore G. P. (Eds.), The Pharmacology of Monoclonal Antibodies vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., FEBS Letters, 1998, 414:521-526 and Muyldermans et al., Trends in Biochem. Sci., 2001, 26:230-245, each of which is incorporated by reference in its entirety.

A "monospecific RPP" is an RPP that comprises a binding site that specifically binds to a single epitope. An example of a monospecific RPP is a naturally occurring IgG molecule which, while divalent, recognizes the same epitope at each antigen-binding domain. The binding specificity may be present in any suitable valency.

A "polyspecific RPP" is an RPP that binds to more than one epitope. An example of a polyspecific RPP is a mixture of antibodies that bind to different serotypes of pneumococcal bacteria.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "polyclonal antibody" refers to a mixture of at least two monoclonal antibodies. Polyclonal antibodies may be either monospecific or polyspecific.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated RPP" or "isolated nucleic acid" is an RPP or nucleic acid that has been separated and/or recovered from a component of its natural environment. Components of the natural environment may include enzymes, hormones, and other proteinaceous or nonproteinaceous materials. In some embodiments, an isolated RPP is purified to a degree sufficient to obtain at least 15 residues of N-terminal or internal amino acid sequence, for example by use of a spinning cup sequenator. In some embodiments, an isolated RPP is purified to homogeneity by gel electrophoresis (e.g., SDS-PAGE) under reducing or nonreducing conditions, with detection by Coomassie blue or silver stain. An isolated RPP includes an RPP in situ within recombinant cells, since at least one component of the RPP's natural environment is not present. In some aspects, an isolated RPP or isolated nucleic acid is prepared by at least one purification step. In some embodiments, an isolated RPP or isolated nucleic acid is purified to at least 80%, 85%, 90%, 95%, or 99% by weight. In some embodiments, an isolated RPP or isolated nucleic acid is purified to at least 80%, 85%, 90%, 95%, or 99% by volume. In some embodiments, an isolated RPP or isolated nucleic acid is provided as a solution comprising at least 85%, 90%, 95%, 98%, 99% to 100% RPP or nucleic acid by weight. In some embodiments, an isolated RPP or isolated nucleic acid is provided as a solution comprising at least 85%, 90%, 95%, 98%, 99% to 100% RPP or nucleic acid by volume.

"Affinity" refers to the strength of the sum total of non-covalent interactions between a single binding site of a molecule (e.g., an RPP) and its binding partner (e.g., an antigen or epitope). Unless indicated otherwise, as used herein, "affinity" refers to intrinsic binding affinity, which reflects a 1:1 interaction between members of a binding pair (e.g., RPP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®).

With regard to the binding of an RPP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the RPP to the target molecule is competitively inhibited by the control molecule.

The term "$k_d$" ($\text{sec}^{-1}$), as used herein, refers to the dissociation rate constant of a particular ABP-antigen interaction. This value is also referred to as the $k_{off}$ value.

The term "$k_a$" ($M^{-1} \times \text{sec}^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D = k_d/k_a$.

The term "$K_A$" ($M^{-1}$), as used herein, refers to the association equilibrium constant of a particular ABP-antigen interaction. $K_A = k_a/k_d$.

An "immunoconjugate" is an RPP conjugated to one or more heterologous molecule(s).

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more RPPs, the term "competes with" or "cross-competes with" indicates that the two or more RPPs compete for binding to an antigen (e.g., pneumococcus polysaccharide). In one exemplary assay, an antigen is coated on a surface and contacted with a first RPP against the antigen, after which a second RPP against the antigen is added. In another exemplary assay, a first RPP against an antigen is coated on a surface and contacted with the antigen, and then a second RPP against the antigen is added. If the presence of the first RPP against an antigen reduces binding of the second RPP, in either assay, then the RPPs compete. The term "competes with" also includes combinations of RPPs where one RPP reduces binding of another RPP, but where no competition is observed when the RPPs are added in the reverse order. However, in some embodiments, the first and second RPPs inhibit binding of each other, regardless of the order in which they are added. In some embodiments, one RPP reduces binding of another RPP to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the RPPs for pneumococcus polysaccharide and the valency of the RPPs. The assays described in this definition are illustrative, and a skilled artisan can utilize any suitable assay to determine if antibodies compete with each other. Suitable assays are described, for example, in Cox et al., "Immunoassay Methods," in Assay Guidance Manual [Internet], Updated Dec. 24, 2014 (www.ncbi.nlm.nih.gov/books/NBK92434/; accessed Sep. 29, 2015); Silman et al., Cytometry, 2001, 44:30-37; and Finco et al., J. Pharm. Biomed. Anal., 2011, 54:351-358; each of which is incorporated by reference in its entirety.

The term "epitope" means a portion of an antigen the specifically binds to an RPP or an ABP. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an RPP or an ABP binds can be determined using known techniques for epitope determination such as, for example, testing for RPP or an ABP binding to an antigen.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in TABLES 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, Proteins: Structures and Molecular Properties 2nd ed. (1993) W. H. Freeman & Co., New York, N.Y. An RPP generated by making one or more conservative substitutions of amino acid residues in a parent RPP is referred to as a "conservatively modified variant."

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminish of any direct or indirect pathological consequences of the disease, preventing reinfection or associated symptom, decreasing the rate of disease progression, amelioration or palliation of the disease state, and remission or improved prognosis. Improvements in any conditions can be readily assessed according to standard methods and techniques known in the art. The population of subjects treated by the method of the disease includes subjects suffering from the undesirable condition or disease, as well as subjects at risk for development of the condition or disease.

As used herein, the term "therapeutically effective amount" or "effective amount" refers to an amount of an RPP or pharmaceutical composition provided herein that, when administered to a subject, is effective to produces the desired effect for which it is administered. The exact dose or amount will depend on the purpose of the treatment, and will be ascertainable by one skilled in the art using known techniques (see, e.g., Lloyd (1999) The Art, Science and Technology of Pharmaceutical Compounding). A therapeutically effective amount can be a "prophylactically effective amount" as prophylaxis can be considered therapy. The term "sufficient amount" means an amount sufficient to produce a desired effect.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an RPP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "pharmaceutical composition" refers to a preparation which is in such form as to permit the biological activity of an active ingredient contained therein to be effective in treating a subject, and which contains no additional components which are unacceptably toxic to the subject.

The term "plasma cell" refers to white blood cells that secrete large volumes of antibodies. They are transported by the blood plasma and the lymphatic system. B cells (for example, either germinal center naïve B cells or memory B cells) differentiate into plasma cells that produce antibody molecules closely modelled after the receptors of the precursor B cell. Once released into the blood and lymph, these antibody molecules bind to the target antigen (foreign substance) and initiate its neutralization or destruction. Terminally differentiated plasma cells express relatively few surface antigens, and do not express common pan-B cell markers, such as CD19 and CD20. Instead, plasma cells are identified through flow cytometry by their additional expression of CD138, CD78, and the Interleukin-6 receptor. In humans, CD27 is a good marker for plasma cells, naive B cells are CD27-, memory B-cells are CD27+ and plasma cells are CD27++. The surface antigen CD138 (syndecan-1) is expressed at high levels. Another important surface antigen is CD319 (SLAMF7). This antigen is expressed at high levels on normal human plasma cells. It is also expressed on malignant plasma cells in multiple myeloma. Compared with CD138, which disappears rapidly ex vivo, the expression of CD319 is considerably more stable.

The term "plasmablast" refers to antibody-secreting cells in the peripheral blood, which differentiate from activated B cells, such as memory B cells, upon stimulation with an antigen. The most immature blood cell that is considered of plasma cell lineage is the plasmablast. Plasmablasts secrete more antibodies than B cells, but less than plasma cells. They divide rapidly and are still capable of internalizing antigens and presenting them to T cells. A cell may stay in this state for several days, and then either die or irrevocably differentiate into a mature, fully differentiated plasma cell. Differentiation of mature B cells into plasma cells is dependent upon the transcription factors Blimp-1/PRDM1 and IRF4.

The term "memory B cell" refers to a B cell sub-type that are formed within germinal centers following primary infection and are important in generating an accelerated and more robust antibody-mediated immune response in the case of re-infection (also known as a secondary immune response). Memory B cells do not secrete antibody until activated by their specific antigen.

The term "naïve B cell" refers to a B cell that has not been exposed to an antigen. Once exposed to an antigen, the naïve B cell either becomes a memory B cell or a plasma cell that secretes antibodies specific to the antigen that was originally bound. Plasma cells do not last long in the circulation, this is in contrast to memory cells that last for very long periods of time.

The term "peripheral blood" refers to blood which travels through peripheral vessels. Peripheral blood is typically obtained by venipuncture (also called phlebotomy), or by finger prick for small quantities.

The term "plasma hyperimmune" refers to a polyclonal antibody preparation similar to intravenous immunoglobulin (IVIg), except that it is prepared from the plasma of donors with high titers of antibody against a specific organism or antigen. The term hyperimmune is often used interchangeably with the terms "hyperimmune gammaglobulin" and "hyperimmune globulins". Some agents against which hyperimmune globulins are available include hepatitis B, rabies, tetanus toxin, varicella-zoster, etc. Administration of hyperimmune globulin provides "passive" immunity to the patient against an agent. This is in contrast to vaccines that provide "active" immunity. However, vaccines take much longer to achieve that purpose while hyperimmune globulin provides instant "passive" short-lived immunity.

The term "activity" refers to a quantitative measurement of an RPP or antibody against an antigen, vaccine, protein, epitope, cell, bacterium, or virus. Activity can be assessed using in vivo or in vitro methods.

The term "recombinant" refers to proteins that result from the expression of recombinant DNA within living cells. Recombinant DNA is the general name for a piece of DNA that has been created by the combination of at least two separate segments of DNA.

The term "neutralization" refers to the ability of specific antibodies to block the site(s) on viruses that they use to enter their target cell. The effect of a neutralizing antibody can be negligible even with large excesses of antibody production if they lack specificity to this antigen. The production of specific antibodies can be learned for a faster response at next exposition. The reduction or destruction of a homologous infectious agent can be partial or complete and can make it no longer infectious or pathogenic to other cells.

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the invention include fragments, analogs, recombinant polypeptides, synthetic polypeptides, and/or fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include CS-9 cells, the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

Recombinant Polyclonal Proteins (RPPs)

The present disclosure provides a RPP (rZIG) that specifically binds one or more Zika antigens. The RPP comprises a plurality of ABPs specifically binding to one or more Zika antigens.

In some embodiments, the RPP comprises at least 100 ABPs each with a cognate pair of heavy chain CDR3 and light chain CDR3 sequences as shown in Table 5. In some embodiments, the RPP comprises at least 100, 500, 1000, 5000, 10,000, or 15,000 ABPs each with a cognate pair of heavy chain CDR3 and light chain CDR3 sequences as shown in Table 5. In some embodiments, the RPP comprises 100 to 500 ABPs, 500 to 1000 ABPs, 1000 to 2500 ABPs, or more than 2500 ABPs. In some embodiments, the RPP comprises 10, 100, 1,000, 10,000, 100,000 or more than 100,000 distinct ABPs.

In some embodiments, the RPP comprises scFvs. In some embodiments, the RPP consists of scFvs. In some embodiments, the RPP comprises antibody fragments. In some embodiments, the RPP consists of antibody fragments. In some embodiments, the RPP comprises recombinant full-length antibodies. In some embodiments, the RPP consists of recombinant full-length antibodies. In some embodiments, the RPP comprises human antibodies. In some embodiments, the RPP comprises humanized antibodies. In some embodiments, the RPP comprises monospecific ABPs. In some embodiments, the RPP comprises bispecific ABPs. In some embodiments, the RPP consists of ABPs of a human IgG1 subtype. In some embodiments, the RPP comprises IgGs, IgAs, or IgMs.

In some embodiments, the RPP comprises antibody fragments. The RPP can be a Fab fragment, a F(ab')$_2$ fragment an Fv fragment, or a combination thereof. A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991.

In some embodiments, the RPP comprises humanized antibodies. A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

An RPP can also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be incorporated into a molecule either covalently or noncovalently to make it an antigen binding protein. CDRs can be obtained by constructing polynucleotides that encode the CDR of interest. Such polynucleotides are prepared, for example, by using the polymerase chain reaction to synthesize the variable region using mRNA of antibody producing cells as a template (see, for example, Larrick et al., Methods: A Companion to Methods in Enzymology 2:106, 1991; Courtenay Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley Liss, Inc. 1995).

The variable region domains of RPPs can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C terminal amino acid to at least one other antibody domain or a fragment thereof. Thus, for example, a $V_H$ domain that is present in the variable region domain may be linked to an immunoglobulin CH1 domain, or a fragment thereof. Similarly, a $V_L$ domain may be linked to a CK domain or a fragment thereof. In this way, for example, the antibody may be a Fab fragment wherein the antigen binding domain contains associated $V_H$ and $V_L$ domains covalently linked at their C termini to a CH1 and CK domain, respectively. The CH1 domain may be extended with further amino acids, for example to provide a hinge region or a portion of a hinge region domain as found in a Fab' fragment, or to provide further domains, such as antibody CH2 and CH3 domains.

The RPP can be ABPs comprising, e.g., the cognate pairs of heavy and light chain CDR3 sequence disclosed herein. For example, CDRs may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain embodiments, the RPP comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

An RPP can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Different RPPs may bind to different domains of disease targets or act by different mechanisms of action. As indicated herein inter alia, the domain regions are designated such as to be inclusive of the group, unless otherwise indicated. For example, amino acids 4-12 refers to nine amino acids: amino acids at positions 4, and 12, as well as the seven intervening amino acids in the sequence. Other examples include antigen binding proteins that inhibit binding of a pathogen to its target cell, i.e., neutralizing activity. An antigen binding protein need not completely inhibit a binding to target cell to find use in the present invention.

The RPPs provided herein can induce various biological effects associated with binding to an antigen that comprises a vaccine. In some embodiments, an RPP provided herein prevents binding of a virus to a cell, which therein prevents entry of the virus into the cell. In some embodiments, the RPP binds to the cell surface of a patient's cells, in order to eliminate cells associated with a pathology.

The RPPs describe herein can include an Fc region, e.g., a dimer Fc polypeptide. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Antigen-binding fragments of RPPs of the invention can be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized antibody comprises the variable domain of a murine antibody (or all or part of the antigen binding site thereof) and a constant domain derived from a human antibody. Alternatively, a humanized antibody fragment may comprise the antigen binding site of a murine antibody and a variable domain fragment (lacking the antigen-binding site) derived from a human antibody. Procedures for the production of chimeric and further engineered antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619, 5,225,539, 5,821, 337, 5,859,205, 6,881,557, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with a vaccine, such that antibodies directed against the vaccine antigen pare generated in the animal.

Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, NJ:191-200, Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. Inter'l Immunol. 5 (1993): 647-656, Choi et al., 1993, Nature Genetics 4: 117-23, Fishwild et al., 1996, Nature Biotech. 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Res. 20: 6287-95, Taylor et al., 1994, Inter'l Immunol. 6: 579-91, Tomizuka et al., 1997, Nature Genetics 16: 133-43, Tomizuka et al., 2000, Pro. Nat'l Acad. Sci. USA 97: 722-27, Tuaillon et al., 1993, Pro. Nat'l Acad. Sci. USA 90: 3720-24, and Tuaillon et al., 1994, J. Immunol. 152: 2912-20.

RPPs of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

Single chain antibodies (scFv) may be formed by linking heavy and light chain variable domain (Fv region) fragments via an amino acid bridge (short peptide linker, e.g., a synthetic sequence of amino acid residues), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108, Bird et al., 1988, Science 242:423-26 and Huston et al., 1988, Proc. Natl. Acad. Sci. USA 85:5879-83). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

An RPP, e.g., ABPs, according to the invention may have a binding affinity for antigen target of less than or equal to 5×10⁻⁷ M, less than or equal to 1×10⁻⁷ M, less than or equal to 0.5×10⁻⁷M, less than or equal to 1×10⁻⁸M, less than or equal to 1×10⁻⁹M, less than or equal to 1×10⁻¹⁰M, less than or equal to 1×10⁻¹¹M, or less than or equal to 1×10⁻¹²M.

The affinity of an RPP, as well as the extent to which the RPP inhibits binding, can be determined by one of ordinary skill in the art using conventional techniques, for example those described by Scatchard et al. (Ann. N.Y. Acad. Sci. 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-65 (1993)).

Sequences of RPPs

CDR polypeptide sequences of recombinant antibodies generated using the methods described herein are provided in the sequence listing.

A summary of the sequences is provided in TABLE 5. ABPs of the RPP provided herein can comprise a cognate pair of heavy chain CDR3 and light chain CDR3 sequences as shown in Table 5, optionally all the cognate pairs.

In some embodiments, the RPP comprises an ABP specifically binding to one or more Zika antigens and comprising a cognate pair of heavy chain CDR3 and light chain CDR3 sequences as shown in Table 5, optionally all the cognate pairs. In particular, the heavy chain CDR3 can comprise a sequence selected from SEQ ID NO: 2, 4, 6, through 25838 (even numbers). The light chain CDR3 can comprise a sequence selected from SEQ ID NO: 1, 3, 5, through 25837 (odd numbers).

In some embodiments, the RPP is recombinantly produced using sequences derived from plasma cells or plasmablasts from at least one donor injected with the antigen or infected with Zika. In some embodiments, the sequences are obtained from antiboidies generated in a mammalian subject injected with a Zika or Denghe antigen. In some embodiments, the mammalian subject is injected or infected with Zika virus or Denghe virus. In some embodiments, the mammalian subject is injected or infected with Zika virus and Denghe virus. In some embodiments, the mammalian subject is injected with inactivated Zika virus or Denghe virus. In some embodiments, the mammalian subject is injected with Zika virus like particles (VLP), inactivated Dengue 1, Dengue 4, Dengue 3, or Dengue. In some embodiments, the donor is a human subject. In some embodiments, the donor is not a human subject. In some embodiments, the donor is a mouse.

In some embodiments, the RPP is recombinantly produced using sequences derived from plasma cells or plasmablasts from at least one donor and the activity of the RPP exceeds by at least tenfold a serum titer activity of the donor against Zika virus or a Zika antigen. In some embodiments, the activity is measured by an in vitro pathogen neutralization assay or an in vitro binding to antigen assay or an in vivo efficacy assay.

TABLE 5

CDR3 heavy and CDR3 light chain sequences

| Sequence | Description |
| --- | --- |
| 1, 3, 5, through 25837 (odd numbers) | Antibodies from Trianni mice immunized with Zika and dengue viruses - light chain CDR3 sequences |
| 2, 4, 6, through 25838 (even numbers) | Antibodies from Trianni mice immunized with Zika and dengue viruses - heavy chain CDR3 sequences |

In some embodiments, the RPP includes an ABP comprising cognate pairs of the heavy and light chain variable regions. In some embodiments, the ABP comprises CDR3 sequences disclosed herein. In some embodiments, the ABP comprises a heavy chain CDR3 having a sequence selected from SEQ ID Nos: 2, 4, 6, through 25838 (even numbers) and a light chain CDR3 has a sequence selected from SEQ ID Nos: 1, 3, 5, through 25837 (odd numbers).

In some embodiments, the ABP comprises a heavy chain CDR3 having the sequence of SEQ ID NO: [n+1] and a light chain CDR3 has the sequence of SEQ ID NO: [n], wherein n is an odd number from 1 to 25837. In some embodiments, the ABP comprises a heavy chain CDR3 having the sequence of SEQ ID NO: [n+1] or a light chain CDR3 has the sequence of SEQ ID NO: [n], wherein n is an odd number from 1 to 25837.

In some embodiments, the ABPs of the RPP comprise a heavy chain CDR1 having the sequence of GFTF $X_1X_2X_3X_4$ (SEQ ID NO: 25839).

In some embodiments, the RPP comprises an ABP comprising a heavy chain CDR1 having the sequence of GFTF [S/D][S/D][Y/H/D][A/G/Y/F] (SEQ ID NO: 25840). In some embodiments, the RPP comprises an ABP comprising a heavy chain CDR1 having a sequence selected from the group consisting of:

GFTFSSYA (SEQ ID NO: 25841);
GFTFSSYG (SEQ ID NO: 25842);
GFTFDD[Y/H]G (SEQ ID NO: 25843); and
GFTFSD[Y/D][Y/F] (SEQ ID NO: 25844)

In some embodiments, each of the ABPs in the RPP comprises a heavy chain CDR1 having the sequence selected from SEQ ID Nos: 25839-25844. In some embodiments, each of at least 5%, 10%, 25%, or 50% of the total ABPs in the RPP comprises a heavy chain CDR1 having the sequence selected from SEQ ID Nos: 25839-25844.

In some embodiments, the RPP comprises an ABP comprising a heavy chain CDR2 having the sequence of I $X_1X_2X_3G$ $X_3X_4X_5$ (SEQ ID NO: 25845).

In some embodiments, the RPP comprises an ABP comprising a heavy chain CDR2 having the sequence of I[W/S/N] [G/Y/W][S/D/N]G[G/S/D/Y][S/N/T] [T/K/I] (SEQ ID NO: 25846). In some embodiments, the RPP comprises an ABP comprising a heavy chain CDR2 having a sequence selected from the group consisting of:

ISGSGGST (SEQ ID NO: 25847);
I[W/S]YDGSNK (SEQ ID NO: 25848);
INWNG[G/D]ST (SEQ ID NO: 25849) and
ISGSG[S/Y]TI (SEQ ID NO: 25850).

In some embodiments, each of the ABPs in the RPP comprises a heavy chain CDR1 having the sequence selected from SEQ ID Nos: 25845-25850. In some embodiments, each of at least 5%, 10%, 25%, or 50% of the total ABPs in the RPP comprises a heavy chain CDR1 having the sequence selected from SEQ ID Nos: 25845-25850.

In some embodiments, the RPP comprises an ABP comprising a heavy chain CDR3 having a seqyebce selected from AKEGMVLRYFDWLWDY (SEQ ID NO: 25851);
RX$_1$X$_2$X$_3$SGX4S X$_5$FDY (SEQ ID NO: 25852);
AX$_1$X$_2$X$_3$X$_4$X$_5$X$_6$VX$_7$X$_8$X$_9$Y (SEQ ID NO: 25853);
ARX$_1$X$_2$GSX$_3$X$_4$X$_5$X$_6$DX$_7$FD X$_8$ (SEQ ID NO: 25854); and
ARDEGYX$_1$GYX$_2$LDX$_3$ (SEQ ID NO: 25855).

In some embodiments, each of the ABPs in the RPP comprises a heavy chain CDR3 having a seqyebce selected from AKEGMVLRYFDWLWDY (SEQ ID NO: 25851);
RX1X$_2$X$_3$SGX$_4$S X$_5$FDY (SEQ ID NO: 25852);
AX$_1$X$_2$X$_3$X$_4$X$_5$X$_6$VX$_7$X$_8$X$_9$Y (SEQ ID NO: 25853);
ARX$_1$X$_2$GSX$_3$X$_4$X$_5$X$_6$DX$_7$FD X$_8$ (SEQ ID NO: 25854); and
ARDEGYX$_1$GYX$_2$LDX$_3$ (SEQ ID NO: 25855).

In some embodiments, each of at least 5%, 10%, 25%, or 50% of the total ABPs om the RPP comprises a heavy chain CDR3 having a seqyebce selected from AKEGMVLRYFDWLWDY (SEQ ID NO: 25851);
RX1X$_2$X$_3$SGX$_4$S X$_5$FDY (SEQ ID NO: 25852);
AX$_1$X$_2$X$_3$X$_4$X$_5$X$_6$VX$_7$X$_8$X$_9$Y (SEQ ID NO: 25853);
ARX$_1$X$_2$GSX$_3$X$_4$X$_5$X$_6$DX$_7$FD X$_8$ (SEQ ID NO: 25854); and
ARDEGYX$_1$GYX$_2$LDX$_3$ (SEQ ID NO: 25855).

In some embodiments, the RPP comprises an ABP comprising a heavy chain CDR3 having a sequence selected from AKEGMVLRYFDWLWDY (SEQ ID NO: 25856);
R[D/E][R/L][SN/L]SG[P/W]S[G/FI]FDY (SEQ ID NO: 25857);
A[K/E/R][E/T][Q/L/T][L/W/I][LN/W/N][G/L]V[V/P/L][F/L/N][D/N]Y (SEQ ID NO: 25858);
AR[D/N][R/G]GS[S/T][G/S/W/F][W/F/Y][R/F/Y]D[W/A]FD[P/I] (SEQ ID NO: 25859); and
ARDEGY[R/S]GY[V/N]LD[T/N/S] (SEQ ID NO: 25860).

In some embodiments, the RPP comprises at least 20, 40, 50, 100 or 200 ABPs comprising:

a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of AKEGMVLRYFDWLWDY (SEQ ID NO: 25856);

a heavy chain CDR1 having the sequence of GFTFSSYG (SEQ ID NO: 25842), a heavy chain CDR2 having the sequence of I[W/S]YDGSNK (SEQ ID NO: 25848), and a heavy chain CDR3 having the sequence of R[D/E][R/L][SN/L]SG[P/W]S[G/H]FDY (SEQ ID NO: 25857);

a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of A[K/E/R][E/T][Q/L/T][L/W/I][LN/W/N][G/L]V[V/P/L][F/L/N][D/N]Y (SEQ ID NO: 25858);

a heavy chain CDR1 having the sequence of GFTFDD[Y/H]G (SEQ ID NO: 25843), a heavy chain CDR2 having the sequence of INWNG[G/D]ST (SEQ ID NO: 25849), and a heavy chain CDR3 having the sequence of AR[D/N][R/G]GS[S/T][G/S/W/F][W/F/Y][R/F/Y]D[W/A]FD[P/I] (SEQ ID NO: 25859); or a heavy chain CDR1 having the sequence of GFTFSD[Y/D][Y/F] (SEQ ID NO: 25844), a heavy chain CDR2 having the sequence of ISGSG[S/Y]TI (SEQ ID NO: 25850), and a heavy chain CDR3 having the sequence of ARDEGY[R/S]GY[V/N]LD[T/N/S] (SEQ ID NO: 25860).

In some embodiments, each of at least 5%, 10%, 25%, or 50% of the total ABPs in the RPP comprises:

a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of AKEGMVLRYFDWLWDY (SEQ ID NO: 25856);

a heavy chain CDR1 having the sequence of GFTFSSYG (SEQ ID NO: 25842), a heavy chain CDR2 having the sequence of I[W/S]YDGSNK (SEQ ID NO: 25848), and a heavy chain CDR3 having the sequence of R[D/E][R/L][SN/L]SG[P/W]S[G/H]FDY (SEQ ID NO: 25857);

a heavy chain CDR1 having the sequence of GFTFSSYA (SEQ ID NO: 25841), a heavy chain CDR2 having the sequence of ISGSGGST (SEQ ID NO: 25847), and a heavy chain CDR3 having the sequence of A[K/E/R][E/T][Q/L/T][L/W/I][LN/W/N][G/L]V[V/P/L][F/L/N][D/N]Y (SEQ ID NO: 25858);

a heavy chain CDR1 having the sequence of GFTFDD[Y/H]G (SEQ ID NO: 25843), a heavy chain CDR2 having the sequence of INWNG[G/D]ST (SEQ ID NO: 25849), and a heavy chain CDR3 having the sequence of AR[D/N][R/G]GS[S/T][G/S/W/F][W/F/Y][R/F/Y]D[W/A]FD[P/I] (SEQ ID NO: 25859); or a heavy chain CDR1 having the sequence of GFTFSD[Y/D][Y/F] (SEQ ID NO: 25844), a heavy chain CDR2 having the sequence of ISGSG[S/Y]TI (SEQ ID NO: 25850), and a heavy chain CDR3 having the sequence of ARDEGY[R/S]GY[V/N]LD[T/N/S] (SEQ ID NO: 25860).

In some embodiments, each of the ABPs comprises a unique heavy chain CDR3 and a unique light chain CDR3 sequence. In some embodiments, each of the ABPs comprises a unique heavy chain CDR3 and light chain CDR3 pair.

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDRs provided herein.

In some embodiments, the RPP comprises about 10, 100, 500, 1,000, 5,000, 10,000, 50,000 or more than 100,000 distinct ABPs, each having a unique sequence. In some embodiments, the RPP comprises at least 10, 100, 500, 1,000, 5,000, 10,000, 20,000, 30,000, 40,000, 50,000 or more than 100,000 distinct ABPs, each having a unique sequence.

In some embodiments, the RPP has a binding titer to a Zika antigen at least 50 times higher than antibodies in a sample obtained from one or more donor exposed to the antigen. The binding titer can be measured by any of the methods known in the art. For example, the binding titer can be measured by anti-Zika-ELISA. In some embodiments, the binding titer of the RPP is at least 10, 100, 200, 300, 400, 500, 600, 700, 800, 900, or 1000 times higher than antibodies in a sample obtained from one or more donor exposed to the Zika antigen. The sample can be a plasma sample.

In some embodiments, the RPP has a Zika neutralization titer at least 50 times higher than antibodies in a sample obtained from one or more donor exposed to the antigen. The neutralization titer can be measured by any of the methods known in the art. For example, the neutralization titer can be measured by an in vitro or in vivo assay. In some embodiments, the neutralization titer of the RPP is at least 10, 100, 200, 300, 400, 500, 600, 700, 800, 900, or 1000 times higher than antibodies in a sample obtained from one or more donor exposed to the Zika antigen. The sample can be a plasma sample.

In some embodiments, the RPP comprises ABPs selected based on their activity. For example, the RPP comprises ABPs selected based on their binding or neutralization activity against Zika virus. In some embodiments, the ABP contains a mix of RPPs selected for their activity against different types or variants of Zika virus.

Nucleic Acids

In one aspect, the present invention provides isolated nucleic acid molecules. The nucleic acids comprise, for example, polynucleotides that encode all or part of an ABP in the RPP, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Polynucleotides encoding antibody polypeptides (e.g., heavy or light chain, variable domain only, CDRs only, or full length) can be isolated from B cells, plasma cells, or plasmablasts of a subject that has been exposed to an antigen, e.g., by being infected by virus or immunized with a vaccine. The nucleic acid can be isolated by conventional procedures such as polymerase chain reaction (PCR) or methods described herein (e.g., single cell OE-RT-PCR).

Polypeptide sequences of the CDR3 from the variable regions of the heavy and light chain variable regions are shown herein. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each RPP of the invention.

Methods for hybridizing nucleic acids are well-known in the art. See, e.g., Curr. Prot. in Mol. Biol., John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Curr. Prot. in Mol. Biol. 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an RPP) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However, it is made, a mutant polypeptide can be expressed and screened for a desired property (e.g., binding to a virus).

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a virus binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide In another aspect, the present invention provides libraries of nucleic acids that encode for RPP or a variant or derivative thereof, derived from B cells, plasmablasts, and plasma cells. These libraries of nucleic acids are generated by isolating plasmablasts and plasma cells into single-cell reaction containers, wherein they are lysed and antibody-specific nucleic acids are purified or captured, for example on solid supports such as beads.

In some embodiments, the library is generated by obtaining a plurality of first linear polynucleotides, each comprising a first sequence encoding a heavy chain variable domain from a cognate pair from the single plasma cell or plasmablast; and a second sequence encoding a light chain variable domain from the cognate pair; and a third sequence linking the first and second sequences and comprising a restriction site; and obtaining a second linear polynucleotide, not operationally linked to the first polynucleotide, comprising a fourth sequence homologous to a portion of the first polynucleotide; and circularizing each of the plurality of first polynucleotides with the second polynucleotide to generate a library of polynucleotides encoding the library of recombinant antibodies, wherein circularization is effected through Gibson Assembly; and expressing the library of recombinant antibodies in mammalian cells comprising the library of polynucleotides encoding the recombinant antibodies, thereby generating the library of recombinant antibodies.

The present invention provides methods for performing capture of transcripts from millions of single cells in parallel. Capture of transcripts is followed by amplification of nucleic acids that encode heavy and light chain immunoglobulins, and subsequent linkage of said nucleic acids into libraries of fused constructs that encode both heavy and light chain immunoglobulins. In such libraries the native pairing of heavy and light chain immunoglobulins, as originally found in the input B cells, plasmablasts, and plasma cells, is maintained. Such methods are performed in parallel on millions of single cells, such that the resulting library of fused heavy and light chain immunoglobulin nucleic acids comprises natively paired sequences for millions of single cells. Such methods are described elsewhere (Adler et al., Mabs 9, 1282-1996, 2017; WO2020/223573 which are incorporated by reference in its entirety herein).

Vectors and Host Cells

The present invention provides vectors, each vector comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

In another aspect of the present invention, expression vectors containing the nucleic acid molecules and polynucleotides of the present invention are also provided, and host cells transformed with such vectors, and methods of producing the polypeptides are also provided. The term "expression vector" refers to a plasmid, phage, virus or vector for expressing a polypeptide from a polynucleotide sequence. Vectors for the expression of the polypeptides contain at a minimum sequence required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes polypeptides and proteins to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific cells or tissues, and viral vectors for the expression of polypeptides in targeted human or animal cells.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both pro-karyotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The invention further provides methods of making polypeptides, e.g., RPP. A variety of other expression/host systems may be utilized. Vector DNA can be introduced into prokaryotic or eukaryotic systems via conventional transformation or transfection techniques. These systems include but are not limited to microorganisms such as bacteria (for example, E. coli) transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Mammalian expression allows for the production of secreted or soluble polypeptides which may be recovered from the growth medium.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Once such cells are transformed with vectors that contain selectable markers as well as the desired expression cassette, the cells can be allowed to grow in an enriched media before they are switched to selective media, for example. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990). Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide can be recovered by conventional protein purification procedures (as defined above).

In some cases, such as in expression using prokaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization; however, a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. Ed., Pierce Chemical Co. (1984); Tam et al., J Am Chem Soc, 105:6442, (1983); Merrifield, Science 232:341-347 (1986); Barany and Merrifield, The Peptides, Gross and Meienhofer, eds, Academic Press, New York, 1-284; Barany et al., Int J Pep Protein Res, 30:705-739 (1987).

The polypeptides and proteins of the present invention can be purified according to protein purification techniques well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification are well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography, isoelectric focusing, gel electrophoresis, and combinations of these techniques. As is generally known in the art, it is believed that the order of conducting the various purification steps may be changed, or that certain steps may be omitted, and still result in a suitable method for the preparation of a substantially purified polypeptide. Exemplary purification steps are provided in the Examples below.

Various methods for quantifying the degree of purification of polypeptide are known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "—fold purification number." The actual units used to represent the amount of binding activity are, of course, be dependent upon the particular assay technique chosen to follow the purification and whether or not the polypeptide or peptide exhibits a detectable binding activity.

In some aspects, the present invention includes libraries of antibody-encoding nucleic acid vectors for site-directed integration into mammalian genomes. Such vectors include plasmids, retroviruses, and lentivirus. These libraries of vectors encode libraries of antibody sequences, which are then be used to engineer mammalian cells for production of RPPs. The libraries of nucleic acid vectors may include 10, 100, 1,000, 10,000, or more than 100,000 different antibody-encoding sequences. The sequences are derived from plasmablasts and plasma cells. These libraries of nucleic acids are generated by isolating plasmablasts and plasma cells into single-cell reaction containers, wherein they are lysed and antibody-specific nucleic acids are purified or captured, for example on solid supports such as beads. The present invention provides methods for performing capture of transcripts from millions of single cells in parallel. Capture of transcripts is followed by amplification of nucleic acids that encode heavy and light chain immunoglobulins, and subsequent linkage of said nucleic acids into libraries of fused constructs that encode both heavy and light chain immunoglobulins. In such libraries the native pairing of heavy and light chain immunoglobulins, as originally found in the input plasmablasts and plasma cells, is maintained. Such methods are performed in parallel on millions of single cells, such that the resulting library of fused heavy and light chain immunoglobulin nucleic acids comprises natively paired sequences for millions of single cells. These paired fused amplicons are then engineered into full-length antibody constructs using Gibson Assembly, restriction endonucleases, or other recombinant DNA techniques.

Engineering into full-length antibody constructs is performed on the full library en masse, such that the antibody sequence content and antibody sequence counts of the library are essentially maintained throughout the process. In some aspects, the library of expression vectors is engineered in two steps, such that the scFv amplicon is subcloned into an intermediate vector, and then a second round of Gibson Assembly, restriction digestion, or other recombinant technique is used to engineer additional domains of the antibody into the linker of the scFv. The method is described in U.S. Pat. No. 9,422,547, which is incorporated by reference in its entirety herein. The native pairing of heavy and light chain immunoglobulins is essentially maintained throughout the process of engineering into full-length expression vector libraries. The vectors are designed in various orientations, for example, two separate promoters drive expression of heavy and light chain immunoglobulins, or one promoter drives expression of both heavy and light chain immunoglobulins, and a translational skip motif is used to separately translate the heavy and light chain immunoglobulins into separate polypeptides. In some embodiments, the expression vectors comprise sequences for site-directed integration into mammalian production cells, for example, CRISPR-Cas9, Flp-In, Cre/Lox, or zinc finger recombination methods. Site-directed integration ensures that each mammalian production cell encodes a single antibody sequence, and decreases variability in expression levels between single production cells.

In another aspect, the present disclosure provides a host cell or a library of host cells, each comprising a polynucleotide encoding an ABP described herein. In some embodiments, the host cell comprises a vector or comprises a polynucleotide stably integrated into its genome. In some embodiments, the host cell comprises a polynucleotide encoding a ABP stably integrated into the genome using a Flp recombinase recognition target (FRT) landing pad or a similar method known in the art. In some embodiments, the host cell is a mammalian or prokaryotic cell. In some embodiments, the host cell is a human cell or a yeast cell. In some embodiments, the host cell is CHO cell.

In some embodiments, the host cell comprises an expression vector or integrated polynucleotide for production of RPP. In some embodiments, a library of host cells can be used produce a RPP described herein. In some embodiments, a library of host cells comprise cells selected based on their production yields or neutralization or binding titers of RPP produced by them. The host cells can be production host cells.

Methods of Producing RPPs

The RPP can be purified from host cells that comprises a gene encoding the RPP. The RPP produced from the host cells can be obtained by elution of filtered supernatant of host cell culture fluid using a Heparin HP column, using a salt gradient, or with protein A resin.

Fully human monoclonal antibodies can be generated by any number of techniques with which those having ordinary skill in the art are familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein. For example, fully human monoclonal antibodies may be obtained from transgenic mice that have been engineered to produce specific human antibodies in response to antigenic challenge. Methods for obtaining fully human antibodies from transgenic mice are described, for example, by Green et al., Nature Genet. 7:13, 1994; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N.Y. Acad. Sci. 764:525-35. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Fully human monoclonal antibodies may be obtained by immunizing the transgenic mice, which may then produce human antibodies specific for the antigen target or targets. Lymphoid cells of the immunized transgenic mice can be used to produce human antibody-secreting hybridomas according to the methods described herein.

Another method for generating human antibodies of the invention includes immortalizing human peripheral blood cells by EBV transformation. See, e.g., U.S. Pat. No. 4,464,456. Such an immortalized B-cell line (or lymphoblastoid cell line) producing an RPP that specifically binds to target or targets can be identified by immunodetection methods as provided herein, for example, an ELISA, and then isolated by standard cloning techniques. The stability of the lymphoblastoid cell line producing an RPP can be improved by fusing the transformed cell lines with a murine myeloma to produce a mouse-human hybrid cell line according to methods known in the art (see, e.g., Glasky et al., Hybridoma 8:377-89 (1989)). Still another method to generate human RPPs is in vitro immunization, which includes priming human splenic B-cells with antigen targets, followed by fusion of primed with a hetero-hybrid fusion partner. See, e.g., Boerner et al., 1991 J Immunol. 147:86-95.

In certain embodiments, B-cells that are producing a RPP are selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing an antibody that specifically binds to the antigen target. B-cells may also be isolated from humans, for example, from a peripheral blood sample.

Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains the antigen target. Binding of the specific antibodies produced by the B-cell to the antigen results in the formation of a complex, which may be visible as an immunoprecipitate.

In some embodiments, specific antibody-producing B-cells are selected by using a method that allows identification natively paired antibodies. For example, a method described in Adler et al., A natively paired antibody library yields drug leads with higher sensitivity and specificity than a randomly paired antibody library, MAbs (2018), which is incorporated by reference in its entirety herein, can be employed. The method combines microfluidic technology, molecular genomics, yeast single-chain variable fragment (scFv) display, fluorescence-activated cell sorting (FACS) and deep sequencing. In short, B cells can be isolated from immunized animals and then pooled. The B cells are encapsulated into droplets with oligo-dT beads and a lysis solution, and mRNA-bound beads are purified from the droplets, and then injected into a second emulsion with an OE-RT-PCR amplification mix that generates DNA amplicons that encode scFv with native pairing of heavy and light chain Ig. Libraries of natively paired amplicons are then electroporated into yeast for scFv display. FACS is used to identify high affinity scFv. Finally, deep antibody sequencing can be used to identify all clones in the pre- and post-sort scFv libraries.

After the B-cells producing the desired antibody are selected, the specific antibody genes may be cloned by isolating and amplifying DNA or mRNA according to methods known in the art and described herein.

The methods for obtaining antibodies of the invention can also adopt various phage display technologies known in the art. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to the RPP or variant or fragment thereof. See, e.g., U.S. Pat. No. 5,223, 409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into E. coli, yeast, or mammalian-based systems for expression. Large amounts of a single-chain protein containing a fusion of the $V_H$ and $V_L$ domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

RPP of the present invention preferably have activity in the cell-based assays described herein and/or the in vivo assay described herein and/or bind to one or more of the antigens described herein. Accordingly, such binding agents can be identified using the assays described herein.

Other antibodies according to the invention may be obtained by conventional immunization and cell fusion procedures as described herein and known in the art.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551.

Human, partially human, or humanized antibodies are suitable for many applications, particularly those involving administration of the antibody to a human subject, other types of antigen binding proteins. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

ABPs may be prepared, and screened for desired properties, by any of a number of conventional techniques. Certain of the techniques involve isolating a nucleic acid encoding a polypeptide chain (or portion thereof) of an RPP of interest, and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example. Furthermore, the antigen binding proteins may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. Expression systems are detailed comprehensively above. In general, host cells are transformed with a recombinant expression vector that comprises DNA encoding a desired polypeptide. Among the host cells that may be employed are prokaryotes, yeast or higher eukaryotic cells. Prokaryotes include gram negative or gram-positive organisms, for example E. coli or Bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

Production cell lines for monoclonal antibodies (mAbs) are typically produced by randomly inserting expression constructs into a mammalian production cell genome, for example, a CHO genome (Rita Costa et al., 2010). However, this canonical method produces cell lines with multiple copies of mAb inserted into the CHO genome. If the polyclonal antibody construct libraries were randomly inserted into the CHO genome, many clones would express multiple antibodies, which would result in frequent non-native pairing between heavy and light chain Ig. Additionally, different genome locations have different transcriptional activity levels (Kito et al., 2002), which could result in heterogeneous, inconsistent and/or unstable bioproduction. Thus, in some aspects the current invention provides a CHO cell line with a Flp recombinase recognition target (FRT) landing pad stably engineered into the genome. Such site-directed genome integration cell lines are then used for stable expression of RPP.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative that do not destroy the binding capability of an antibody comprising the RPP. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions can involve the exchange of a member of one class of amino acids or amino acid mimetics for a member from another class with different physical properties (e.g. size, polarity, hydrophobicity, charge). Such substituted residues can be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art can choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochem., 13(2):222-245 (1974); Chou et al., Biochem., 113(2):211-222 (1974); Chou et al., Adv. Enzymol. Relat Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, ABPs of the invention can be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, Curr. Opin. in Struct. Biol., 7, 463-469).

It will be appreciated that the ABPs of the invention include the humanized antibodies described herein. Humanized antibodies such as those described herein can be produced using techniques known to those skilled in the art (Zhang, W., et al., Molecular Immunology. 42(12): 1445-1451, 2005; Hwang W. et al., Methods. 36(1): 35-42, 2005; Dall'Acqua W F, et al., Methods 36(1): 43-60, 2005; and Clark, M., Immunology Today. 21(8): 397-402, 2000).

Where an antibody comprises one or more of CDR3-H, and/or CDR3-L as described in Table 5, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 Methods Enzymol. 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

Replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (Molecular Cloning, A Laboratory Manual, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., Nucleic Acids Res. 12:9441, (1984); Kunkel Proc. Natl. Acad. Sci. USA 82:488-92 (1985); Kunkel et al., Methods in Enzymol. 154:367-82 (1987); the Anglian Biotechnology Ltd. handbook). Additionally, numerous publications describe techniques suitable for the preparation of antibodies by manipulation of DNA, creation of expression vectors, and transformation and culture of appropriate cells (Mountain A and Adair, J R in Biotechnology and Genetic Engineering Reviews (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of ABPs according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of $E.$ $coli.$ (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and sexual PCR (Crameri, et al., Nature, 391, 288-291, 1998). All of these methods of affinity maturation are discussed by Vaughan et al. (Nature Biotech., 16, 535-539, 1998).

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

Pharmaceutical Compositions

Pharmaceutical compositions containing one or more of the RPPs of the present disclosure are also provided. Such compositions comprise a therapeutically or prophylactically effective amount of the polypeptides or proteins in a mixture with pharmaceutically acceptable materials.

In some embodiments, the pharmaceutical composition comprises an RPP produced using sequences derived from immune cells of a donor exposed to one or more Zika (and/or Dengue virus) antigens. In some embodiments, the pharmaceutical composition comprises RPPs produced using sequences derived from immune cells of multiple donors exposed to one or more Zika (and/or Dengue virus) antigens. The donors can be a human, non-human animal (mouse, humanized mouse, rat, humanized rat, horse, or cow) or both.

In some embodiments, the pharmaceutical composition comprises a first RPP comprising a first ABPs, wherein each of the first ABPs specifically binds to a first antigen, and a second RPP comprising a second ABPs, wherein each of the second ABPs specifically binds to a second antigen. In some embodiments, the first antigen is an antigen of Zika (and/or Dengue virus). In some embodiments, the second antigen is a different antigen of Zika (and/or Dengue virus).

In some embodiments, the pharmaceutical composition comprises about 10, 100, 500, 1,000, 5,000, 10,000, 50,000 or more than 100,000 distinct ABPs, each having a unique sequence. In some embodiments, the pharmaceutical composition comprises at least 10, 100, 500, 1,000, 5,000, 10,000, 20,000, 30,000, 40,000, 50,000 or more than 100,000 distinct ABPs, each having a unique sequence.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

Optionally, the composition additionally comprises one or more physiologically active agents, for example, an antiviral agent, plasma IVIg, etc. In various embodiments, the composition comprises one, two, three, four, five, or six physiologically active agents in addition to an RPP.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

Content of Pharmaceutically Active Ingredient

In typical embodiments, the active ingredient (i.e., the proteins and polypeptides of the present invention) is present in the pharmaceutical composition at a concentration of at least 0.01 mg/ml, at least 0.1 mg/ml, at least 0.5 mg/ml, or at least 1 mg/ml. In certain embodiments, the active ingredient is present in the pharmaceutical composition at a concentration of at least 1 mg/ml, 2 mg/ml, 3 mg/ml, 4 mg/ml, 5 mg/ml, 10 mg/ml, 15 mg/ml, 20 mg/ml, or 25 mg/ml. In certain embodiments, the active ingredient is present in the pharmaceutical composition at a concentration of at least 30 mg/ml, 35 mg/ml, 40 mg/ml, 45 mg/ml or 50 mg/ml. In certain embodiments, the active ingredient is present in the pharmaceutical composition at a concentration of at least 100 mg/ml, 250 mg/ml, 500 mg/ml, 750 mg/ml, 1 g/ml, 5 g/ml, 10 g/ml, or 50 g/ml.

Formulation Generally

The pharmaceutical composition can be in any form appropriate for human or veterinary medicine, including a liquid, an oil, an emulsion, a gel, a colloid, an aerosol or a solid.

The pharmaceutical composition can be formulated for administration by any route of administration appropriate for human or veterinary medicine, including enteral and parenteral routes of administration.

In some embodiments, the pharmaceutical composition is formulated for intravenous, intraperitoneal, intramuscular, or subcutaneous administration. In some embodiments, the pharmaceutical composition is formulated for intravenous injection or intravenous infusion.

In some embodiments, the pharmaceutical composition is formulated for intrathecal or intracerebroventricular administration.

In some embodiments, the pharmaceutical composition is formulated for topical administration.

Pharmacological Compositions Adapted for Injection

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In various embodiments, the unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the active ingredient. In some embodiments, the unit dosage form contains 125 mg, 150 mg, 175 mg, or 200 mg of the active ingredient. In some embodiments, the unit dosage form contains at least 250 mg, 1 g, 10 g, 20 g, 30 g, 40 g, 50 g, 60 g, 70 g, 80 g, 90 g, or 100 g of the active ingredient. In some embodiments, the unit dosage form contains about 250 mg, 1 g, 10 g, 20 g, 30 g, 40 g, 50 g, 60 g, 70 g, 80 g, 90 g, or 100 g of the active ingredient.

In typical embodiments, the pharmaceutical composition in the unit dosage form is in liquid form. In various embodiments, the unit dosage form contains between 0.1 mL and 50 ml of the active ingredient. In some embodiments, the unit dosage form contains 1 ml, 2.5 ml, 5 ml, 7.5 ml, 10 ml, 25 ml, or 50 ml of active ingredient.

In particular embodiments, the unit dosage form is a vial containing 1 ml of the pharmaceutical composition containing an active ingredient (e.g., RPP) at a concentration of 0.01 mg/ml, 0.1 mg/ml, 0.5 mg/ml, or 1 mg/ml. In particular embodiments, the unit dosage form is a vial containing 1 ml of the pharmaceutical composition containing an active ingredient (e.g., RPP) at a concentration of 0.01 mg/ml, 0.1 mg/ml, 0.5 mg/ml, 1 mg/ml, 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml or 50 mg/ml, 100 mg/ml, 250 mg/ml, 500 mg/ml, 750 mg/ml, 1 g/ml, 5 g/ml, 10 g/ml, or 50 g/ml. In some embodiments, the unit dosage form is a vial containing 2 ml of the pharmaceutical composition containing an active ingredient at a concentration of 0.01 mg/ml, 0.1 mg/ml, 0.5 mg/ml, 1 mg/ml, 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml or 50 mg/ml, 100 mg/ml, 250 mg/ml, 500 mg/ml, 750 mg/ml, 1 g/ml, 5 g/ml, 10 g/ml, or 50 g/ml.

In some embodiments, the pharmaceutical composition is formulated for injection of an active ingredient at a single dose or multiple doses of between 0.010 and 5 g/kg body weight. In some embodiments, the pharmaceutical composition is formulated for injection of an active ingredient at a single dose of 0.010 g/kg body weight. In some embodiments, the pharmaceutical composition is formulated for injection at a single dose of 0.01, 0.05, 0.15, 0.20, 0.25, 0.30, 0.35, 0.40, 0.45, 0.50, 0.55, 0.60, 0.65, 0.70, 0.75, 0.80, 0.85, 0.90, 0.95, or 0.1 g/kg body weight.

In some embodiments, the unit dose contains at least 0.1 g, 0.5 g, 1 g, 1.5 g, 2 g, 2.5 g, 3 g, 3.5 g, 4 g, 5 g, 10 g, 20 g, 30 g, 40 g, or 50 g of the active ingredient (e.g., RPP). In some embodiments, the unit dose contains about 0.1 g, 0.5 g, 1 g, 1.5 g, 2 g, 2.5 g, 3 g, 3.5 g, 4 g, 5 g, 10 g, 20 g, 30 g, 40 g, or 50 g of the active ingredient (e.g., RPP).

The amount of active ingredient which can be combined with a carrier material to produce a single dosage form will generally be that amount of the compound which produces a therapeutic effect.

The pharmaceutical compositions may conveniently be presented in unit dosage form.

The unit dosage form will typically be adapted to one or more specific routes of administration of the pharmaceutical composition.

In some embodiments, the pharmaceutical composition in the unit dosage form is in solid form, such as a lyophilate, suitable for solubilization.

In some embodiments, the unit dosage form is suitable for subcutaneous, intradermal, or intramuscular administration include preloaded syringes, auto-injectors, and auto-inject pens, each containing a predetermined amount of the pharmaceutical composition described hereinabove.

In various embodiments, the unit dosage form is a preloaded syringe, comprising a syringe and a predetermined amount of the pharmaceutical composition. In certain preloaded syringe embodiments, the syringe is adapted for subcutaneous administration. In certain embodiments, the syringe is suitable for self-administration. In particular embodiments, the preloaded syringe is a single use syringe.

In certain embodiments, the unit dosage form is an auto-inject pen. The auto-inject pen comprises an auto-inject pen containing a pharmaceutical composition as described herein. In some embodiments, the auto-inject pen delivers a predetermined volume of pharmaceutical composition. In other embodiments, the auto-inject pen is configured to deliver a volume of pharmaceutical composition set by the user.

7.1.1. Mixtures of Plasma IVIg with Recombinant Hyperimmunes

In some embodiments, a recombinant hyperimmune is spiked into conventional plasma IVIg to increase the antipathogen titer of IVIg. In some embodiments, several antipathogen recombinant hyperimmunes are spiked into conventional plasma IVIg. Any number of spike-ins can be mixed with plasma IVIg to generate increased titers against any number of pathogens.

In some embodiments, the spike-in recombinant hyperimmunes are mixed with plasma IVIg by the pharmacist. In some embodiments, the spike-in recombinant hyperimmunes are mixed with plasma IVIg by the manufacturer.

Methods of Treating a Disease Responsive to an RPP

In another aspect, methods are presented for treating a subject having a disease responsive to an RPP. The disease can be a viral infection, e.g., Zika virus or Dengue virus. In some embodiments, the method comprises administering the pharmaceutical composition, the RPP disclosed herein to a patient infected with Zika virus, Dengue virus, or other related viral infection.

In vivo and/or in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

The actual amount administered, and rate and time-course of administration, will depend on the nature and severity of disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, the pharmaceutical composition is administered by injection, infusion, or by topical application. In some embodiments, the pharmaceutical composition is administered by intravenous infusion.

In some embodiments, the pharmaceutical composition is administered at a dose of 0.01, 0.05, 0.15, 0.20, 0.25, 0.30, 0.35, 0.40, 0.45, 0.50, 0.55, 0.60, 0.65, 0.70, 0.75, 0.80, 0.85, 0.90, 0.95, or 0.1 g active ingredient (RPP)/kg body weight.

In some embodiments, the pharmaceutical composition is administered at a dose of about 0.01, 0.05, 0.15, 0.20, 0.25, 0.30, 0.35, 0.40, 0.45, 0.50, 0.55, 0.60, 0.65, 0.70, 0.75, 0.80, 0.85, 0.90, 0.95, or 0.1 g active ingredient (RPP)/kg body weight. In some embodiments, the pharmaceutical composition is administered at a dose of more than 0.01, 0.05, 0.15, 0.20, 0.25, 0.30, 0.35, 0.40, 0.45, 0.50, 0.55, 0.60, 0.65, 0.70, 0.75, 0.80, 0.85, 0.90, 0.95, or 0.1 g active ingredient (RPP)/kg body weight.

In some embodiments, the pharmaceutical composition is administered once a day, 2-4 times a day, 2-4 times a week, once a week, or once every two weeks.

In some embodiments, the pharmaceutical composition is administered once, twice, three times, four times, five times, or more. In some embodiments, the pharmaceutical composition is administered once a day for one, two, three, four, five, or more days. In some embodiments, the pharmaceutical composition is administered until the desired outcome is observed.

In some embodiments, the pharmaceutical composition is administered with plasma IVIg.

In some embodiments, the method further comprises administering one or more additional therapeutic agents. In some embodiments, the additional therapeutic agent is an immune stimulatory or suppressive agent.

In some embodiments, the RPP is administered in an amount sufficient as prophylaxis against infectious disease when administered to a subject. In some embodiments, the RPP is administered in an amount sufficient to clear infectious disease in an individual actively fighting infection.

8. EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B(1992).

Example 1: Generation of rCIG Using Immunized Mice

Two RPPs targeting COVID-19 were produced, one selected for binding to the SARS-CoV-2 receptor binding domain (RBD) and the other for binding to the SARS-CoV-2 spike 51 protein, using Trianni immunized mice as the donors. The heavy and light chain CDR3 sequences are provided in Table 5 above.

First, transgenic mice carrying inserted human immunoglobulin genes were immunized with a protocol comprising adjuvant, RBD, and inactivated SARS-CoV-2 virus. Footpad injections were performed on two Trianni Mice twice weekly for four weeks. Before the final boosts, the serum titer of thymocyte antibodies was assessed by flow cytometry, using a dilution series of RBD and Spike 51 antigen. A strong serum response was observed in the animals, with one animal showing a slightly stronger response. Lymph nodes (popliteal, inguinal, axillary, and mesenteric) were surgically removed after sacrifice. Single cell suspensions for each animal were made by manual disruption followed by passage through a 70 μm filter. Next, the EasySep™ Mouse Pan-B Cell Isolation Kit (Stemcell Technologies) negative selection kit was used to isolate B cells from each sample. The lymph node B cell populations were quantified by counting on a C-Chip hemocytometer (Incyto) and assessed for viability using Trypan blue. The cells were then diluted to 5,000-6,000 cells/mL in phosphate-buffered saline (PBS) with 12% OptiPrep™ Density Gradient Medium (Sigma). This cell mixture was used for microfluidic encapsulation. Approximately one million B cells from each of the six animals were run through an emulsion droplet microfluidics platform.

A DNA library encoding scFv from RNA of single cells, with native heavy-light Ig pairing intact, was generated using the emulsion droplet microfluidics platform or vortex emulsions. The method for generating the DNA library comprises the steps of 1) poly(A)+mRNA capture, 2) multiplexed overlap extension reverse transcriptase polymerase chain reaction (OE-RT-PCR), and 3) nested PCR to remove artifacts and add adapters for deep sequencing or yeast display libraries. The scFv libraries are generated from approximately one million B cells from each animal that achieved a positive titer.

For poly(A)+mRNA capture, a custom designed co-flow emulsion droplet microfluidic chip fabricated from glass (Dolomite) was used. The microfluidic chip has two input channels for fluorocarbon oil (Dolomite), one input channel for the cell suspension mix described above, and one input channel for oligo-dT beads (NEB) at 1.25 mg/ml in cell lysis buffer (20 mM Tris pH 7.5, 0.5 M NaCl, 1 mM ethylenediaminetetraacetic acid (EDTA), 0.5% Tween-20, and 20 mM dithiothreitol). The input channels are etched to 50 μm by 150 μm for most of the chip's length, narrow to 55 μm at the droplet junction, and were coated with hydrophobic Pico-Glide (Dolomite). Three Mitos P-Pump pressure pumps (Dolomite) were used to pump the liquids through the chip. Droplet size depends on pressure, but typically droplets of ~45 μm diameter were optimally stable. Emulsions were collected into chilled 2 ml microcentrifuge tubes and incubated at 40° C. for 15 minutes for mRNA capture. The beads were extracted from the droplets using Pico-Break (Dolomite). In some embodiments, similar single cell partitioning emulsions are made using a vortex.

For multiplex OE-RT-PCR, glass Telos droplet emulsion microfluidic chips were used (Dolomite). mRNA-bound beads were re-suspended into OE-RT-PCR mix and injected into the microfluidic chips with a mineral oil-based surfactant mix (available commercially from GigaGen) at pressures that generate 27 μm droplets. The OE-RT-PCR mix contains 2x one-step RT-PCR buffer, 2.0 mM $MgSO_4$, SuperScript III reverse transcriptase, and Platinum Taq (Thermo Fisher Scientific), plus a mixture of primers directed against the IgK C region, the IgG C region, and all V regions. The overlap region is a DNA sequence that encodes a Gly-Ser rich scFv linker sequence. The DNA fragments were recovered from the droplets using a droplet breaking solution (available commercially from GigaGen) and then purified using QIAquick PCR Purification Kit (Qiagen). In some embodiments, similar OE-RT-PCR emulsions were made using a vortex.

For nested PCR, the purified OE-RT-PCR product was first run on a 1.7% agarose gel for 80 minutes at 150 V. A band at 1200-1500 base pair (bp) corresponding to the linked product was excised and purified using NucleoSpin Gel and PCR Clean-up Kit (Macherey Nagel). PCR was then performed to add adapters for Illumina sequencing or yeast display; for sequencing, a randomer of seven nucleotides is added to increase base calling accuracy in subsequent next generation sequencing steps. Nested PCR was performed with 2× NEBNext High-Fidelity amplification mix (NEB) with either Illumina adapter containing primers or primers for cloning into the yeast expression vector. The nested PCR product was run on a 1.2% agarose gel for 50 minutes at 150V. A band at 800-1100 bp was excised and purified using NucleoSpin Gel and PCR Clean-up Kit (Macherey Nagel).

The OE-RT-PCR products were used as template in a nested PCR to add adapters for yeast surface display. *S. cerevisiae* cells (ATCC) were electroporated (Bio-Rad Gene Pulser II; 0.54 kV, 25 uF, infinite resistance) with the PCR product combined with a linearized vector for in vivo homologous recombination and inducible expression of scFv protein. Transformed yeast were expanded, induced with galactose, and approximately $2 \times 10^6$ induced yeast cells were stained with anti-c-Myc (Thermo Fisher Scientific) followed by a FITC-conjugated secondary antibody (Thermo Fisher Scientific), and biotinylated SARS CoV-2 RBD or Spike (1200 nM final concentration) followed by APC-streptavidin (Thermo Fisher Scientific); an scFv library specific for an unrelated target was used as a negative control. Yeast cells were then sorted (BD Influx) and 20-30× $10^3$ double-positive cells (FITC/APC+) were recovered. For further specificity, a second round of sorting using the same antigen was performed and $50 \times 10^3$ double-positive yeast was recovered.

The flow-sorted scFv were then subjected to sequencing (Illumina). Sequences identified using yeast scFv sorting with SARS-CoV-2 RBD are listed as Sequences 5083 through 6630, and sequences identified using yeast scFv sorting with SARS-CoV-2 Spike S1 are listed as Sequences 6631 through 8390. In some embodiments, sequences comprising Sequences 5083 through 8390 are used to generate an RPPs with binding and neutralization activity against SARS-CoV-2.

In certain embodiments, rCIG is an RPP comprising antibodies derived from one, two, four, eight, twelve, 50, or 100 mice. In certain embodiments, rCIG is an RPP comprising, 10, 100, 1,000, 10,000, 100,000, or more than 100,000 distinct antibody sequences. In certain embodiments, rCIG is an RPP comprising antibodies at various molar ratios, or antibodies comprising substantially similar molar ratios. In certain embodiments, these RPPs comprise therapeutics for COVID-19. In other embodiments, any single antibody from the RPP is used as a therapeutic for COVID-19. In certain embodiments, any single antibody or RPP is used as a therapeutic for any kind of coronavirus infection in human patients.

Example 2: Generation of RPP with Activity Against SARS CoV-2 from Convalescent COVID-19 Human Donors

Overview

Multiple rCIG (recombinant anti-coronavirus 19 hyperimmune gammaglobulin), i.e., RPP antibody pools with activity against COVID-19 antigens, were generated using B cells from convalescent COVID-19 donors. The sequence identifiers of the heavy and light chain CDR3 sequences are provided in Table 5, above, corresponding the sequences found in the sequence listing.

The rCIG drug is a fully recombinant IgG1/IgK polyclonal antibody preparation, comprising >1,000 unique antibody sequences at various ratios. The antibody sequences were derived from COVID-19 convalescent human donor peripheral blood mononuclear cells (PBMCs).

First, COVID-19 patients underwent IRB-approved consent at clinical sites, and approximately 50 mL of blood from each donor was obtained. Each sample was assessed for residual SARS CoV-2 using CDC qPCR assays. Additionally, each serum sample was tested for seroconversion using anti-SARS CoV-2 ELISA. The 16 high-titer convalescent COVID-19 donors were selected and custom microfluidics was used to capture natively paired antibody sequences from millions of donor B cells. The captured, natively paired, nucleic acid sequences were then expressed as yeast scFv libraries, and subjected to flow cytometry to enrich for binders against SARS CoV-2 RBD. Antibody nucleic acid sequences were purified from the sorted yeast clones and then engineered into full-length IgG1 antibody expression constructs, still retaining native pairing between heavy and light chain Ig.

The flow-sorted scFv were subjected to sequencing (Illumina). Sequences identified using yeast scFv sorting with SARS-CoV-2 RBD are listed as Sequences 1 through 4760, and sequences identified using yeast scFv sorting with SARS-CoV-2 Spike S1 are listed as Sequences 4761 through 5082. In some embodiments, sequences comprising Sequences 1 through 5082 are used to generate an RPPs with binding and neutralization activity against SARS-CoV-2. In some embodiments, single antibodies comprising Sequences 1 through 5082 are used as a therapeutic for COVID-19, or any coronavirus infection in patients.

To convert the scFv libraries into full-length CHO expression libraries (RPPs), nested outer PCR primers were used to add adapters with overhangs for Gibson assembly to the 5' and 3' ends of the scFv library. Then NEBuilder HiFi DNA Assembly Master Mix (NEB, Ipswich, Mass., USA) was used to insert the scFv library into a vector containing a single promoter, a secretory leader sequence for light chain Ig and the remainder of the IgG1 constant region, creating a cloned scFv library. This intermediate library was transformed into $E.\ coli$, spread onto LB-ampicillin plates, 0.5-1 million colonies were scraped and pooled for a plasmid purification using ZymoPURE II Plasmid Maxiprep Kits (Zymo Research, Irvine, Calif., USA). To create the full-length antibody library, a second Gibson assembly was performed by linearizing the product of GA1 with BamHI-HF (NEB, Ipswich, Mass., USA) and using it as a vector to insert a synthetic amplicon containing a portion of the light chain Ig constant region, a poly(A) signal for light chain Ig, a promoter for the IgG gene and a secretory leader sequence for the IgG gene. The full-length library was then transformed into $E.\ coli$ and spread on LB-ampicillin plates Over 0.5 million colonies are scraped and plasmid is purified with a ZymoPURE II Plasmid Maxiprep Kits (Zymo Research) to make the full-length recombinant hyperimmune maxiprep library for transfection.

The adherent Flp-In™-CHO cell line was adapted with a genomically integrated FRT site (Thermo Fisher Scientific, Waltham, Mass., USA) to suspension culture. For all steps in the adaptation process, "Ham's F-12" refers to Ham's F-12 (with L-glutamine, Thermo Fisher Scientific, Waltham, Mass., USA) plus 10% FBS (Thermo Fisher Scientific, Waltham, Mass., USA) and "BalanCD" refers to BalanCD CHO Growth A (Irvine Scientific) with 4 mM Glutamax (Thermo Fisher Scientific, Waltham, Mass., USA). To adapt this cell line to suspension, the cells were first passaged into a mixture of 50% Ham's F-12 plus 50% BalanCD in T-flasks. Cells were next passaged into 25% Ham's F-12 plus 75% BalanCD and switched to shaking Erlenmeyer flasks. Cells were then passaged into 10% Ham's F-12, 90% BalanCD+0.2% anti-clumping agent (Irvine Scientific, Santa Ana, Calif., USA) and banked for future use.

100 million of the adapted Flp-In CHO cells were transfected per recombinant hyperimmune library using an Amaxa Nucleofector 4D (SG buffer, pulse DU133; Lonza, Basel, Switzerland). These cells were plated into shaking Erlenmeyer flasks and recovered in an incubator at 37° C. and 125 rpm for 48 hours. After 48 hours, the cells were counted to determine viability, cells were seeded at 1 million cells/mL, and selection was started using 600 µg/mL Hygromycin-B (Gemini Bio, West Sacramento, Calif., USA) in fresh media. Cells were counted and media was changed every 2-3 days during the 7-day selection. The libraries were kept on 600 µg/mL Hygromycin-B (Gemini Bio, West Sacramento, Calif., USA) during expansion until viability exceeded 95%. When cells were >95% viable and doubling every 24 hours, the cell line was banked for liquid nitrogen storage.

CHO cells stably expressing antibody libraries were grown in media consisting of 90% BalanCD CHO Growth A Medium (Irvine Scientific, Santa Ana, Calif.), 9% Ham's F-12 (Thermo Fisher Scientific, Waltham, Mass., USA), 1% FBS (ThermoFisher Scientific), 4 mM Glutamax (Thermo Fisher Scientific, Waltham, Mass., USA), 0.2% anti-clumping agent (Irvine Scientific, Santa Ana, Calif., USA). For small-scale production, cells were seeded at $1\times10^6$ cells/mL into 50 mL media in a 250 mL Erlenmeyer flask and grown at 37° C., 5% $CO_2$, 125 rpm. Cells were continually grown under these conditions and supplemented with 7.5 mL CHO Feed 1 (Irvine Scientific, Santa Ana, Calif., USA) on days 2, 4 and 7 of the production run. Supernatant was harvested on Day 8 by centrifugation followed by filtration through a 0.22 µm 250 mL filter bottle (EMD Millipore, Burlington, Mass., USA) with 1 µm pre-filter (EMD Millipore, Burlington, Mass., USA). Harvested cell culture fluid (HCCF) was stored at 4° C. until Protein A purification. For large-scale production of the plasma cell recombinant hyperimmune, cells were grown in the same media but with some modifications to the production conditions. A seed train was used to scale the cultures from $2\times10^7$ cells to $1.2\times10^{10}$ cells at 37° C. Cells were then seeded at $1\times10^6$ cells/mL in 2 L in a 5 L flask (in triplicate; Day 0). On Day 2 the temperature was shifted from 37° C. to 33° C. Each flask was fed with 300 mL CHO Feed 1 (Irvine Scientific, Santa Ana, Calif., USA) on days 2, 4, 6, 8, 10, and 13 of the culture. Supernatant was harvested on Day 14.

After harvest, HCCF was purified with MabSelect SuRe Protein A resin (GE Life Sciences, Marlborough, Mass., USA) using the following buffers: Equilibration, Chase, Wash 2 (25 mM Tris, 150 mM NaCl, pH 7.4), Wash 1 (25 mM Tris, 1 M NaCl, pH 7.4), Elution (20 mM citric acid, pH 3.0), Neutralization (100 mM Tris, pH 8.0 for small scale, 1 M Tris, pH 9.0 for large scale). The column was sanitized before and after use with 0.1 N NaOH. For the large-scale production of the plasma cell recombinant hyperimmune, an additional Wash 3 consisting of 0.5 M arginine, pH 7.4 was used, followed by an additional wash with Wash 2 before elution. The order of purification steps was: Equilibration, Load, Chase, Wash 1, Wash 2, (large scale: Wash 3, Wash 2), Elution, Neutralization (added manually into tubes used for collection of eluate fractions). The recombinant hyperimmunes (RPPs) were concentrated using Vivaspin 20, 30 kDa molecular weight cut off spin concentrators (Sartorius, Gottingen, Germany) and formulated in PBS (small-scale productions) or 0.2 M glycine, pH 4.5 (large scale production), followed by 0.22 µm filtration.

This processed resulted in integration of a single heavy-light chain-paired transgene into the genomic FRT site of individual CHO cells, creating cell pools, or "research cell banks" (RCBs). In certain embodiments, these RCBs are combined to create a CHO polyclonal master cell bank (MCB).

In certain embodiments, rCIG is an RPP comprising antibodies derived from one, two, four, eight, twelve, 50, or 100 human donors. In certain embodiments, rCIG is an RPP comprising, 10, 100, 1,000, 10,000, 100,000, or more than 100,000 distinct antibody sequences. In certain embodiments, rCIG is an RPP comprising antibodies at various molar ratios, or antibodies comprising substantially similar molar ratios. In certain embodiments, these RPPs comprise therapeutics for COVID-19. In other embodiments, any single antibody from the RPP is used as a therapeutic for COVID-19. In certain embodiments, any single antibody or RPP is used as a therapeutic for any kind of coronavirus infection in human patients.

Upstream GMP manufacturing is carried out using this MCB and standard GMP protocols in single-use fed-batch bioreactors. The rCIG protein is purified with Protein A resin and standard downstream recombinant antibody processing steps, including anion and cation exchange, viral inactivation and filtration, and diafiltration/ultrafiltration (DF/UF). Viral clearance studies and full MCB characterization are performed. A plasma-derived IVIG is used as a reference control for protein quality assessment. Plasma-derived IVIG is the best available reference control, since it comprises a diverse set of antibodies, like rCIG, and serves as a baseline for an immunoglobulin that is not highly reactive against SARS CoV-2. Lot release assays include a battery of assays typically used to assess purity, such as SEC HPLC, CE-SDS, host cell protein, and potency, such as anti-SARS CoV-2 ELISA. Anti-SARS CoV-2 ELISA, SEC HPLC, and CD-SDS is used to infer identity.

Quantitative PCR (qPCR) is used to confirm the absence of SARS CoV-2 RNA present in donor PBMCs.

Host Cell Line Development

A large-scale screen was performed to identify a parental host cell clone for targeted integration of rCIG expression construct libraries.

Figure 1:
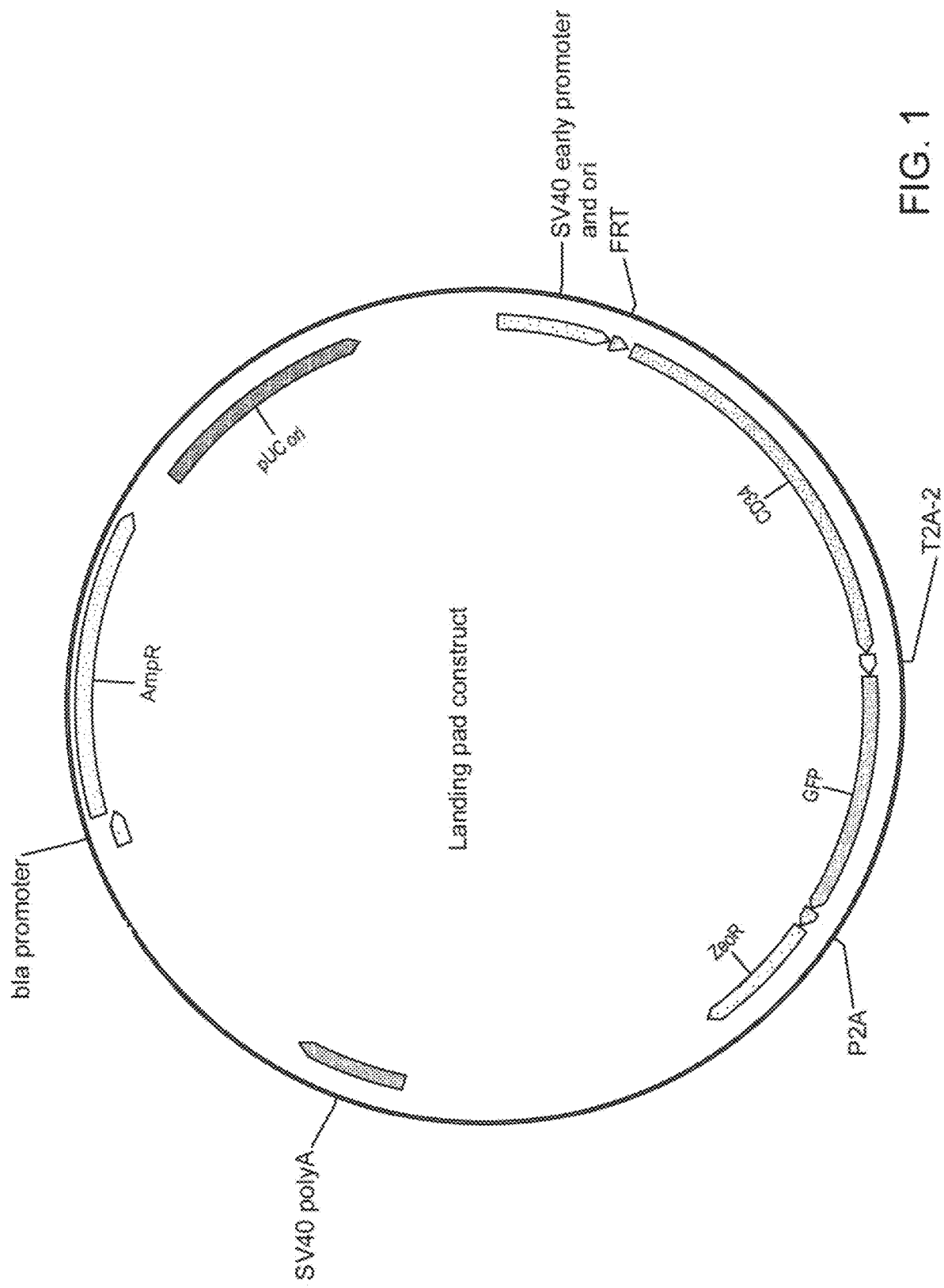

First, a landing pad construct (PMD-4681) was designed and synthesized. PMD-4681 was based on pFRT-lacZeo (ThermoFisher), with some modifications (FIG. 1). In place of the LacZ expression construct a cassette was inserted coding for expression of CD34 and GFP. The CD34, GFP, and downstream Zeocin resistance genes (ZeoR present in original plasmid) were separated by 2A motifs (T2A-2 or P2A) to allow for translation of three separate polypeptide chains. The CD34 sequence was sourced as a gBlock from IDT. The GFP sequence was sourced from ATUM (DasherGFP).

The GMP suspension CHO line CHOZN® GS−/− was obtained from Sigma Aldrich. Cells were sent to Bionova Scientific (Fremont, Calif.) to generate a working cell bank (WCB). A vial of cells from the WCB was thawed from LN2 and expanded. PMD-4681 was linearized using a restriction enzyme and purified via ethanol precipitation. Cells were then transfected with the FRT-GFP-Zeocin landing pad by random integration using Lonza's Nucleofector™ 4D, SE kit. Cells recovered overnight in an incubator and were plated the next day into minipools at 5,000 cells per well, across ten 96-well plates in selective media. The remaining cells were plated and selected together as a bulk pool control. Wells were fed every seven days until at least 80% confluency was reached.

A total of 236 minipools grew out and were screened in parallel for high GFP expression via flow cytometry and low copy number with a Copy Number Variation assay (CNV). Minipools with a copy number less than 2.5 and GFP expression at least 50% of the bulk pool were expanded into shaking adaptation. Expanded pools were also re-tested for GFP expression and confirmed via flow cytometry. Once minipools were expanded, vial aliquots were frozen down.

Minipool vials were thawed and allowed to recover. Cells were then adapted to a liquid counterpart of the semisolid media used for single cell cloning. Minipools were deemed fully adapted when cells would show consistent doubling times and high viability (>90%). Adapted cells were then plated into semisolid media for the Molecular Devices ClonePix3 single cell cloning platform. Single cell imaging was obtained on day 0 of cell plating in semisolid media to confirm monoclonality. Clonal cell colonies reached outgrowth in fourteen days. Clonal cell colonies were picked and deposited as one colony per well of a 96-well plate. Each clone was then expanded, re-adapted to selection media, and cryopreserved. Doubling times were calculated and clones with less than a 30-hour doubling time were chosen for further development. Expanded clones were retested for GFP expression and copy number.

Each clone was then transfected in duplicate using the BioRad Gene Pulser Xcell™ Total System with a monoclonal antibody (mAb)-cyan fluorescent protein (CFP) construct to test expression titer. Transfection conditions were optimized such that clonal lines were >90% viable at time of transfection and at least >70% viable post-transfection. CFP expression was evaluated via flow cytometry 3 days post transfection to determine relative transfection efficiency >35%. After full selection and recovery, cell lines were tested in a 10-day TPP (bioreactor tubes) shaking production run in duplicate. Titers for candidate cell lines ranged 50-100 mg/L. A single clone (CSS-1286) derived from minipool CSS-1144 was selected for further development.

Agilent SureSelect was used to confirm the number of copies and genome location of the landing pad in CSS-1286. SureSelect enriches for a targeted area of interest within the CHO genome and allows for high throughput sequencing using Illumina. In this case, the landing pad site was targeted for enrichment using custom probes.

Genomic DNA was extracted from CSS-1286 and fragmented for sequencing. Complementary oligonucleotide probes ("baits"), were designed to enrich target DNA sequences. When exposed to the genomic DNA library, the baits bound to the sequence of interest and were pulled down via magnetic bead enrichment. Illumina sequencing adapters were then added to the enriched DNA fragments and amplified via PCR, resulting in an enrichment of the fragments of interest. Fragments were analyzed on an Illumina MiSeq.

The data were analyzed using the Horizon Discovery CHO genome sequence as a reference. Sequences were mapped to the reference landing pad sequence. Any chimeric reads, sequences containing both partial landing pad sequences and CHO genome sequences were extracted and mapped back to the CHO genome. This allowed for identification of where the landing pad had inserted into the CSS-1286 genome.

To confirm copy number using an orthogonal method, CSS-1286 was sent to Cergentis for Targeted Locus Amplification (TLA) (Hottentot et al., 2007). Targeted DNA sequences close in physical space were crosslinked. The targeted sequences were then digested and then ligated back together, forming circles of DNA. Inverse PCR was performed, using the targeted sequence as the initial binding region for amplification. This created large libraries of DNA that were then be sequenced using Illumina sequencing. Sequences were then mapped back to the reference Horizon Discovery CHO genome to determine copy number and genome integration location. TLA and SureSelect identified the same single genome location.

Antibody Library Cloning

Figure 2A:
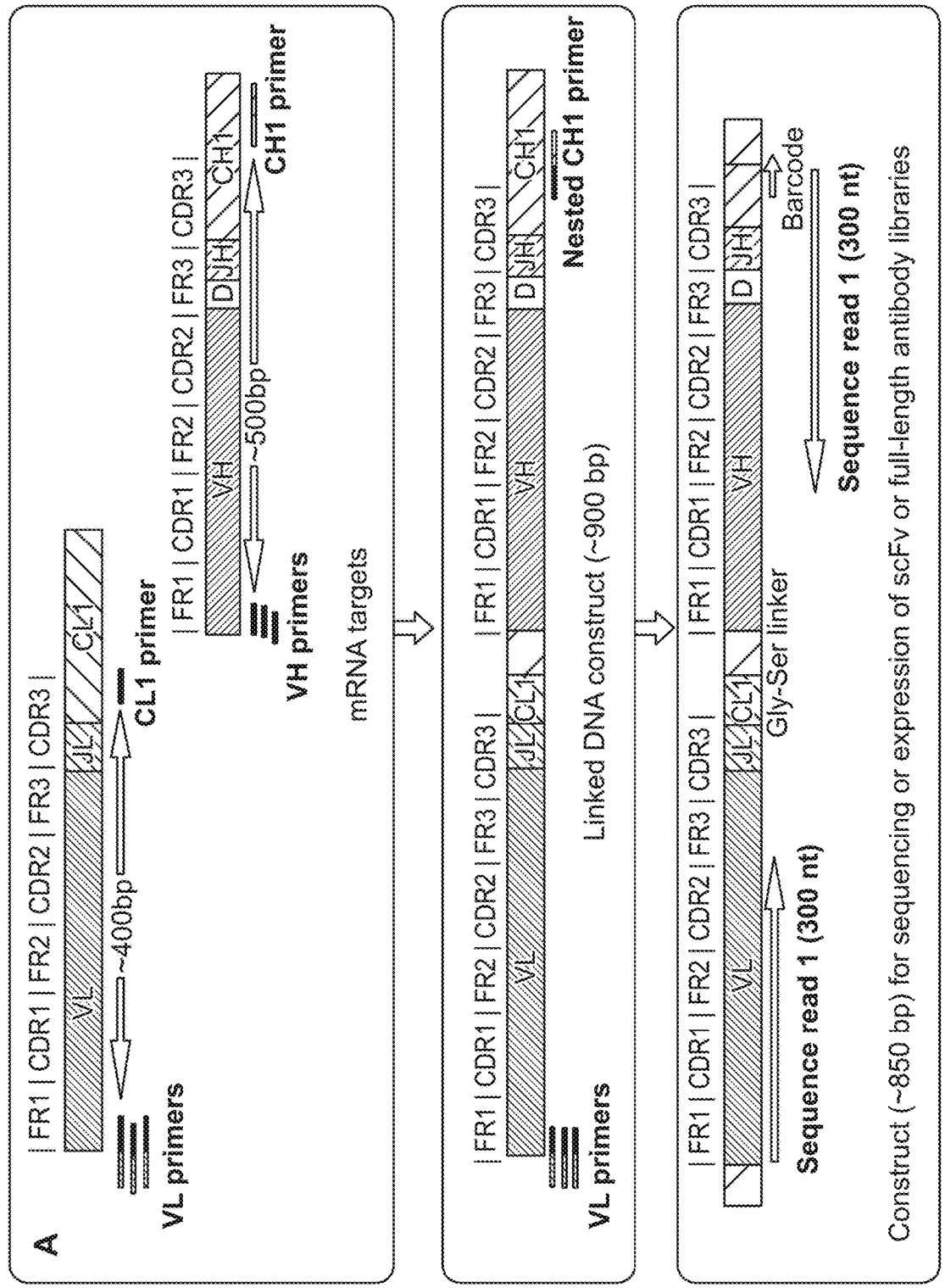
Figure 2B:
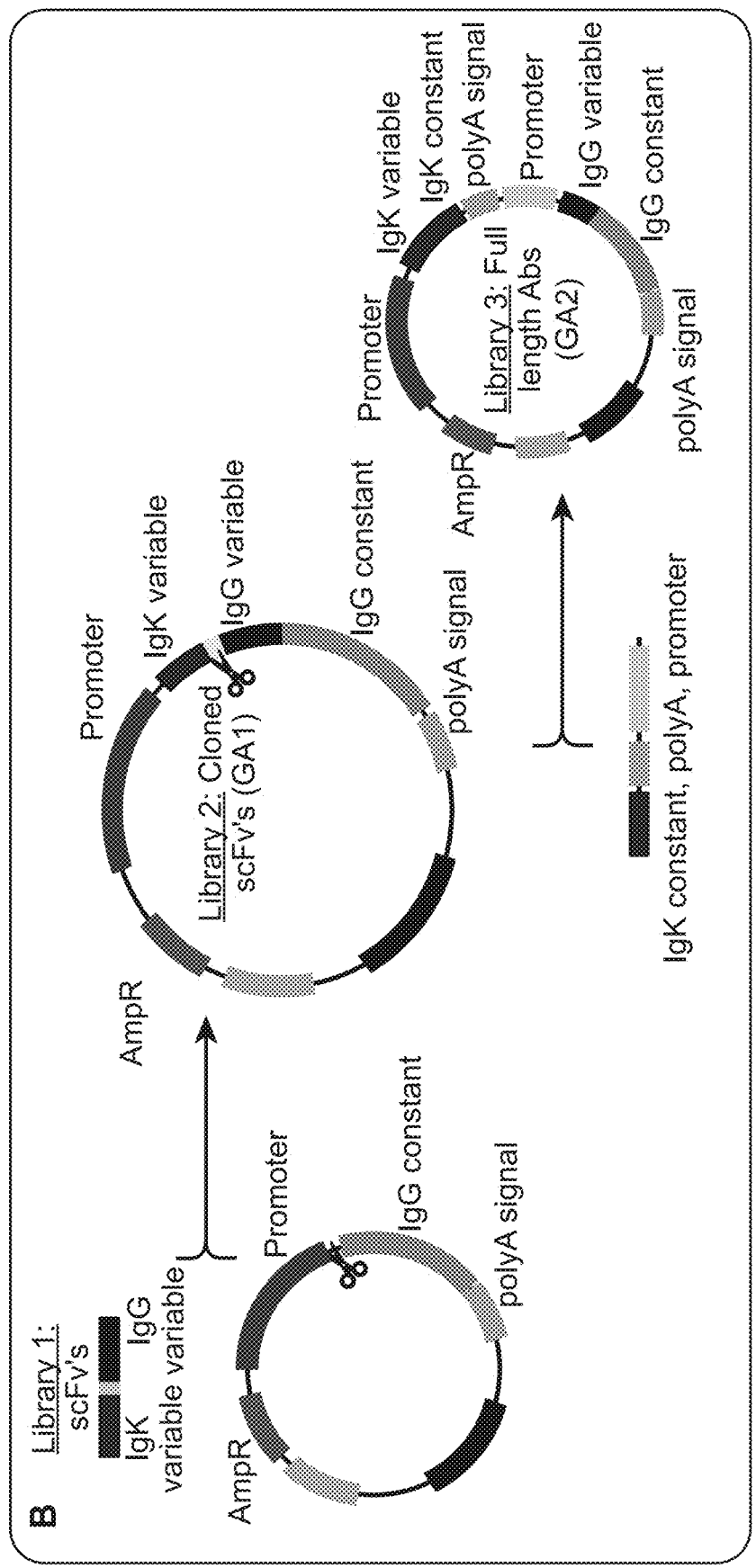

Generation of amplicon libraries comprised three steps: (i) poly(A)+mRNA capture, (ii) multiplexed overlap extension reverse transcriptase polymerase chain reaction (OE-RT-PCR), and (iii) nested PCR to remove artifacts and add adapter sequences for Illumina sequencing or cloning into antibody expression vectors (FIGS. 2A and 2B).

First, PBMCs were collected from 50 human donors (median age 52; range 20-71), either presumed positive by symptoms or confirmed positive by nasal swab test (Roche) at the collection site. No follow-up nasal swab qPCR assay was required to show viral clearance. The median days since onset of symptoms was 23 days (range 12-42). Donors were consented under an IRB protocol by a CRO and shipped to GigaGen overnight at ambient temperature. The serum fraction was isolated for each of the 50 donors. Each serum was assayed for reactivity against SARS CoV-2 Spike protein and SARS CoV-2 RBD protein, using ELISA (FIGS. 3A-3D). 33 of the donors bound to Spike and/or RBD. The 16 highest titer donors were then selected for library generation (Library 1 to 8).

Next, PBMC samples from each of the 16 "high titer" donors were assayed the for SARS CoV-2 virus using CDC qPCR assays (FIGS. 3A-3D). None of the 16 donors showed any detectable SARS CoV-2 RNA. 1.5-2 million B cells were isolated from each of the 16 high titer donors into fluorocarbon oil (Dolomite) emulsion microdroplets with lysis buffer (20 mM Tris pH 7.5, 0.5 M NaCl, 1 mM EDTA, 0.5% Tween-20, and 20 mM DTT) and oligo(dT) beads (New England Biolabs Inc.; NEB), using an emulsion droplet microfluidic chip. Typically, >3 million single cells were processed per hour, with >99% of cell-containing droplets containing single cells. Beads were separated from the droplets using Pico-Break solution (Dolomite). Multiplex OE-RT-PCR was then performed in emulsions, using purified RNA-bound beads as template, to generate single chain variable fragment (scFv) amplicons that linked the heavy and light chain Ig from single B cells (Adler et al., 2017). Pools of 2 high titer donors were amplified in the emulsions, for a total of 8 emulsion reactions.

The OE-RT-PCR products were used as template in a nested PCR to add adapters for yeast surface display. $S.$ $cerevisiae$ cells (ATCC) were electroporated (Bio-Rad Gene Pulser II; 0.54 kV, 25 uF, infinite resistance) with the PCR product combined with a linearized vector for in vivo homologous recombination and inducible expression of scFv protein. Transformed yeast were expanded, induced with galactose, and approximately $2 \times 10^6$ induced yeast cells were stained with anti-c-Myc (Thermo Fisher Scientific) followed by a FITC-conjugated secondary antibody (Thermo Fisher Scientific), and biotinylated SARS CoV-2 RBD or Spike (1200 nM final concentration) followed by APC-streptavidin (Thermo Fisher Scientific); an scFv library specific for an unrelated target was used as a negative control. Yeast cells were then sorted (BD Influx) and $20\text{-}30\times 10^3$ double-positive cells (FITC/APC+) were recovered. For further specificity, a second round of sorting using the same antigen was performed and $50 \times 10^3$ double-positive yeast 2-donor library were recovered.

An average of 1.1% of the expressed antibodies were RBD-specific after the first sort, suggesting that most antibodies in the original convalescent COVID-19 repertoires are not specific to SARS CoV-2. Plasmid scFvs from each of the 8 sorted libraries were subjected to PCR to amplify the scFv and add adapters for Illumina sequencing. A randomer of seven nucleotides was added to increase base calling accuracy in subsequent Illumina sequencing steps. Sequencing on a MiSeq (Illumina) showed that each sorted library comprised a median of 129 antibodies (range: 83 to 209).

Figure 4:
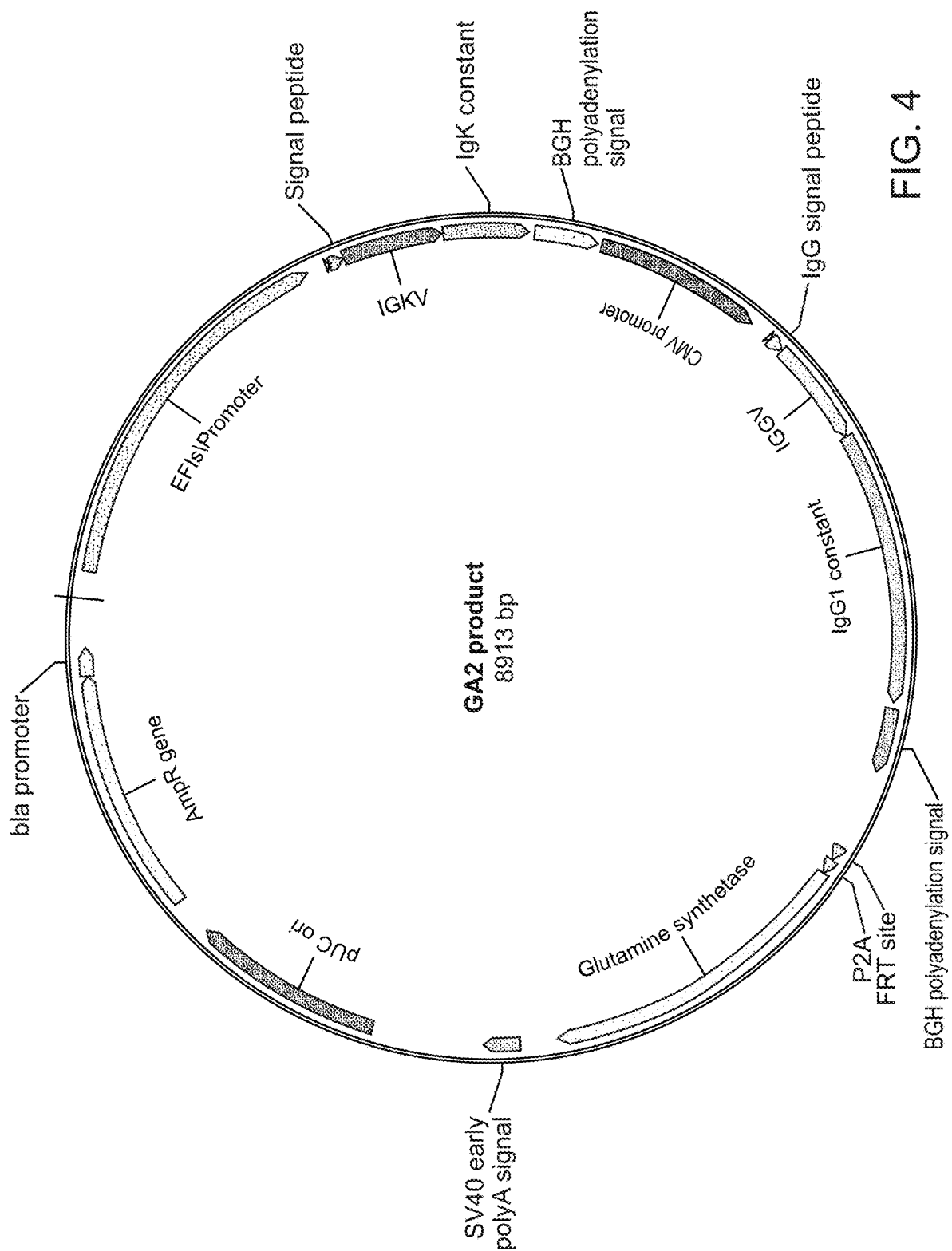
FIG. 4 illustrates a map for a fully assembled antibody expression plasmid.
Figure 7A:
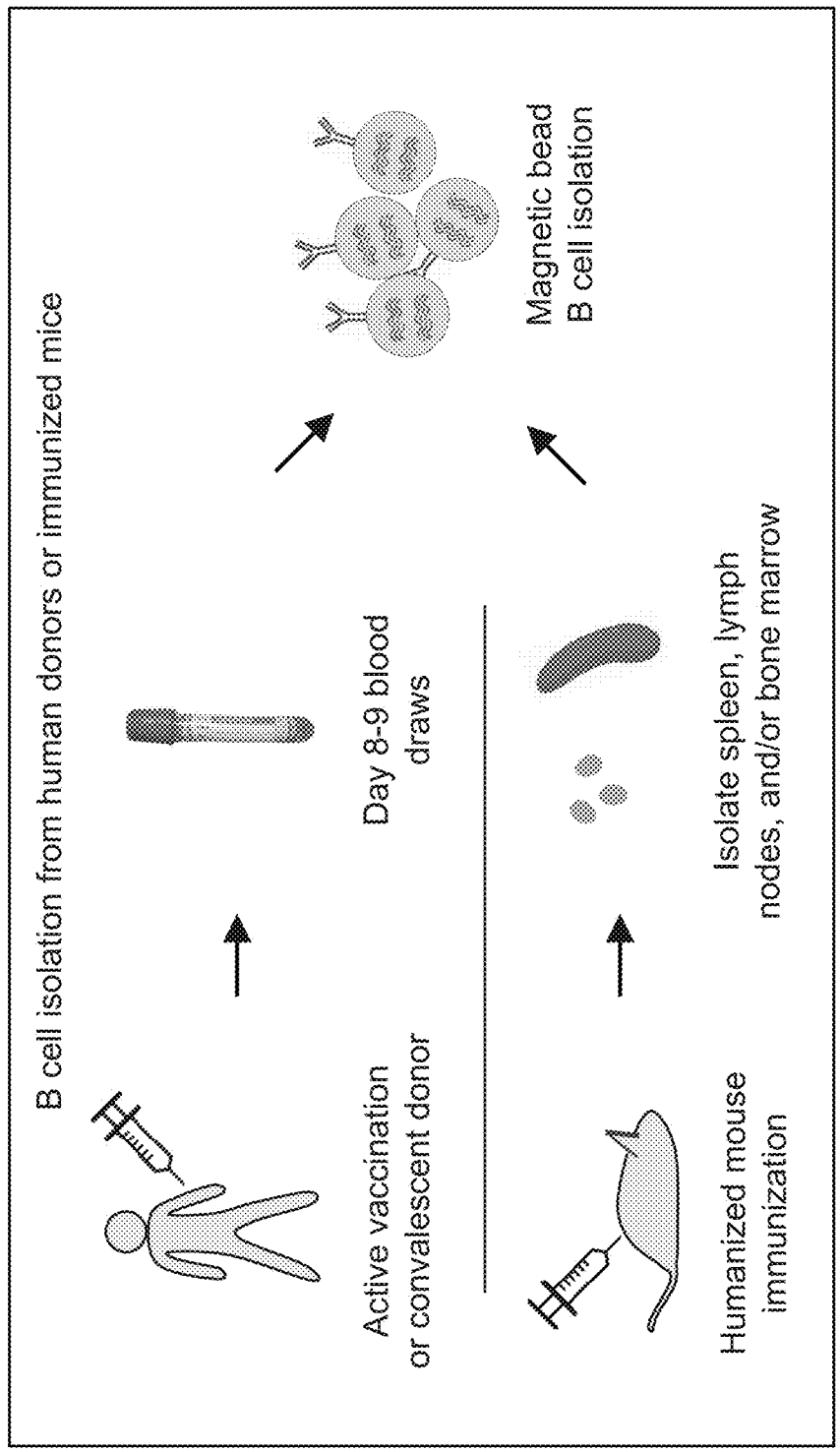
FIG. 7A illustrates the process of isolating B cells from human donors (vaccinated or convalescent) or immunized humanized mice.
Figure 7B:
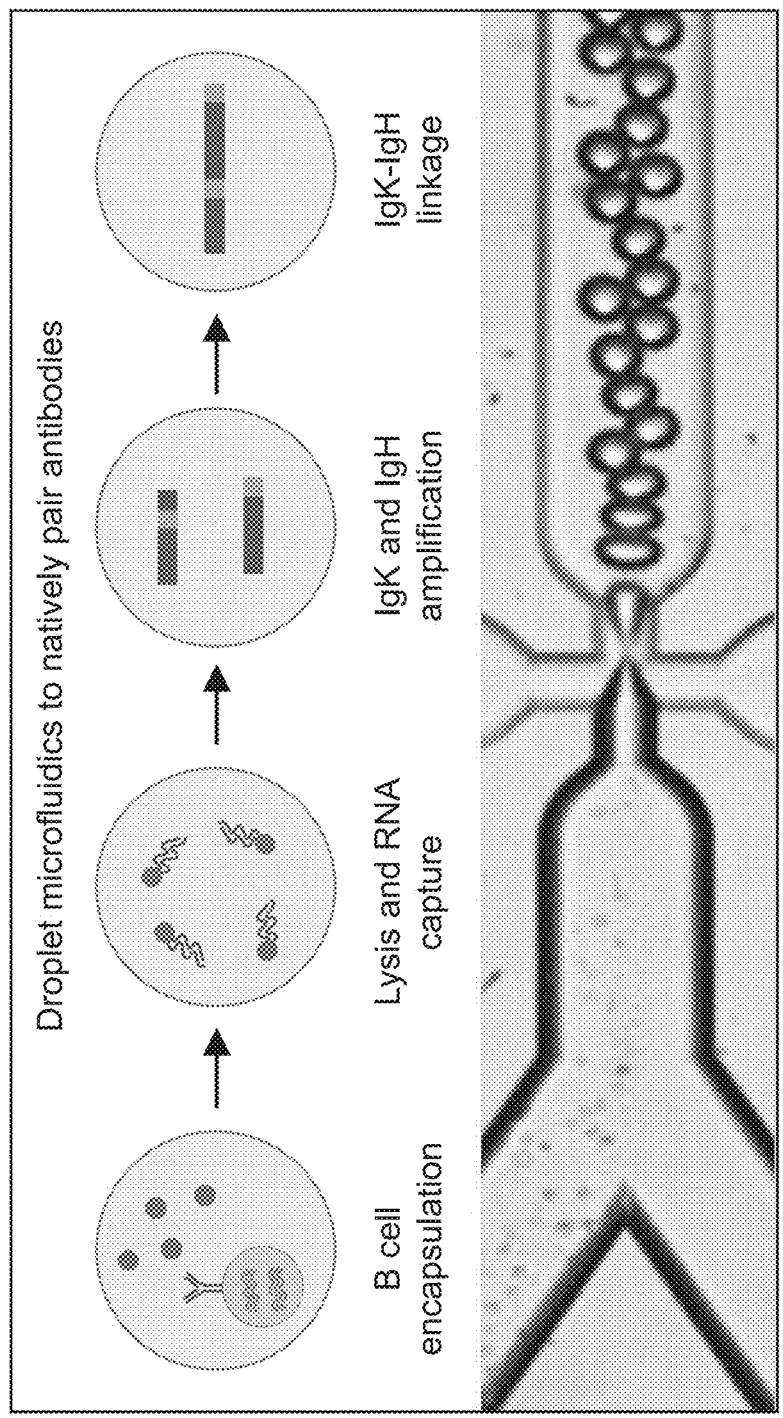
FIG. 7B illustrates the process of capturing natively paired antibody sequences from millions of single cells using droplet microfluidics.
Figure 7E:
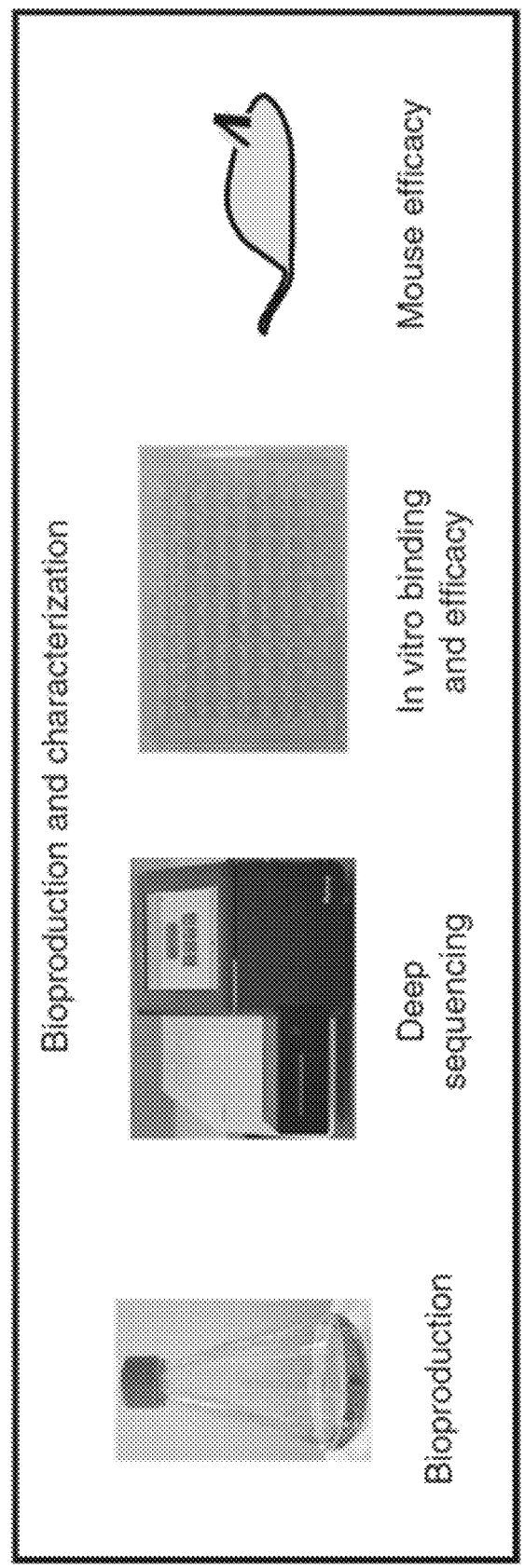
FIG. 7E illustrates bioproduction and characterizations. The libraries were characterized by deep sequencing, in vitro binding and efficacy assays, and/or in vivo mouse efficacy studies.

To convert the 8 sorted scFv libraries into full-length antibody libraries, a cloning pipeline was developed to convert the 8 scFv libraries into full-length CHO expression libraries (FIG. 4). First, nested outer PCR primers added adapters with overhangs for Gibson assembly to the 5' and 3' ends of the scFv library. Then Gibson Assembly (NEB) was used to insert the scFv library into a vector containing a single promoter, a secretory leader sequence for light chain Ig and the remainder of the IgG constant region, creating a cloned scFv library. To create the full-length antibody library, another Gibson Assembly was used to insert a synthetic amplicon containing a portion of the light chain Ig constant region, a poly(A) signal for light chain Ig, a promoter for the IgG gene and a secretory leader sequence for the IgG gene.

The base plasmid for antibody expression was derived from pCDNA5/FRT (ThermoFisher), with some modifications (FIG. 4). The original plasmid (purchased from ThermoFisher) contained a CMV promoter followed by the protein open reading frame and finally a BGH polyadenylation sequence. The assembled antibody expression plasmid (after the second Gibson Assembly) contains an EF1-alpha promoter (sourced from pEF1a-IRES, Takara Bio), followed by an $H.$ $sapiens$ IgG signal peptide, the IgK variable region sourced from the donor B cell, and the IgK constant region. Next is a BGH polyadenylation sequence (same sequence as in the original plasmid), followed by the CMV promoter (from the original plasmid), the IgG signal peptide, IgG variable region sourced from the donor B cell, IgG constant region and a second BGH polyadenylation sequence (from the original plasmid). The hygromycin resistance gene in the original plasmid was replaced with the glutamine synthetase gene (sourced from pCGS3, MilliporeSigma) preceded by a 2A motif The full-length rCIG plasmid libraries were then transformed en masse into $E.$ $coli$ and then spread on LB-carbenicillin plates. >1 million colonies were typically scraped and plasmid was purified with a Maxi prep kit (Qiagen) to make the full-length Maxi prep library, which was then transfected into parental CHO cells, as described below. RCB and MCB Generation The 8 full-length rCIG library maxipreps were used to create 8 polyclonal RCBs, which could be used to produce RPP. First, a vial from the bank of parental CSS-1286 cells was thawed out and recovered. CSS-1286 cells were taken off Zeocin selection the day before transfection. CSS-1286 cells were co-transfected with the full-length rCIG library maxiprep and a recombinase plasmid using the Gene Pulser Xcell™ Total System in growth media. The host cell then expresses the Flp recombinase off the recombinase plasmid to promote recombination of each donor full-length rCIG library into the landing pad site of CSS-1286. Transfected cells were recovered in static flasks for 72 hours at 37° C., 5% $CO_2$ and then subjected to GS selection to produce stable pools of cells expressing rCIG antibodies. The cells were provided a media change with selective media every seven days for approximately 14 days until fully selected.

The selected cells were expanded and cryopreserved, generating 8 polyclonal rCIG RCBs, which could be used to produce RPP. Small-scale production of RPP in shake flasks was performed for each rCIG RCB, and the protein products were subjected to a battery of tests, including anti-SARS CoV-2 ELISA and a Spike:ACE2-inhibition ELISA. The anti-SARS CoV-2 binding ELISA showed that the scFv-sorted rCIG products were typically >10,000-fold more potent than plasma-derived IVIG, and ranged from 147- to 1,394-fold more potent binding than matched convalescent serum/plasma. The potential for SARS CoV-2 neutralization was assessed using a Spike:ACE2-inhibition ELISA and pseudotype neutralization assays. Preliminary results showed that neutralization was generally consistent between the ELISA and pseudotype neutralization methods. Plasma-derived IVIG showed no detectable neutralization. The scFv-sorted rCIG library products were 32.7-1,500-fold more potent than matched convalescent serum/plasma, generally consistent with the trends observed in the anti-SARS CoV-2 binding ELISA experiments. No library that was tested showed anti-RBC agglutination or anti-HLA reactivity.

A mixture of the 8 RCBs is prepared to generate an MCB for GMP production of RPPs, simultaneously maximizing antibody diversity and neutralizing activity, while retaining low off-target reactivity. The mixture of RCBs is generated by thawing the chosen RCBs and then mixing them at a predetermined ratio, i.e., not necessarily in equivalent ratios. A panel of assays is used to characterize rCIG drug candidate produced at small scale from the mixture of RCBs (FIGS. 5 and 6). The MCB is characterized using standard assays, including *mycoplasma*, adventitious viruses, hamster antibodies, and sterility. The MCB is also assessed for phenotypic stability using a standard cell aging protocol.

Bioproduction of rCIG

The MCB are expanded in a seed train. The seed train is used to inoculate large-scale bioreactors, for example, 200 L single use bioreactors (SUBs). Bioproduction of RPP is monitored for a variety of parameters, including viability, IgG titer, glucose, and metabolites. Bioproduction continues for 14 days or until cell viability drops below 80%. The harvested cell culture fluid (HCCF) is then be used for downstream purification.

The GMP downstream process is designed to selectively purify antibody from the harvested cell culture fluid (HCCF), and then further polish the material by removing residual host cell protein (HCP), aggregate, and other impurities. DNA and virus are also inactivated and removed, and the final material is formulated at the desired concentration in the final buffer.

The steps of downstream production include, e.g., standard Protein A purification; subjecting the eluant to a pH 3.5 hold for viral inactivation; and polishing using cation-exchange (CEX), anion-exchange (AEX), and viral clearance filters; ultrafiltration/diafiltration (UF/DF) and sterile filtration for final formulation of the drug substance.

Antibody RNA Sequencing for Process Monitoring

Currently, no technology exists to reliably quantify the individual protein components of mixtures of more than 1,000 proteins. As such, the individual antibody protein components of plasma-derived antibody products such as IVIG remain unknown. Using current technologies, antibody sequencing can only be performed on individual purified proteins, such as monoclonal antibodies. Therefore, lot release metrics for plasma-derived antibody products do not include antibody sequencing.

Like plasma-derived antibody products, rCIG comprise >1,000 different antibodies. Unlike plasma-derived antibody products, rCIG is manufactured from a CHO master cell bank that expresses RNA that encodes >1,000 different antibodies. Unlike protein sequencing, sequencing of RNA mixtures is technologically mature, very high-throughput, and quantitative. Therefore, Illumina sequencing of antibody RNA ("antibody RNA-seq") expressed by CHO cells is used as a method to assesses antibody diversity at the end of bioproduction.

Small-scale (2.5-5 L) engineering runs are used to establish control ranges in the Jaccard and Morisita indices (Rempala & Seweryn, 2013) between the MCB and harvest day. The Jaccard metric assesses the overlap of antibody sequences between two given samples, whereas the Morisita index assesses the quantitative consistency of antibody sequences between two given samples. Thus, Jaccard assesses maintenance of antibody diversity, and Morisita assesses maintenance of antibody frequencies.

Sufficient replicates are performed to generate a median and standard deviation for Jaccard and Morisita indices from production runs that produce protein product above a critical minimal cutoff for rCIG potency. These ranges are used to monitor and assess GMP manufacturing at the 200 L scale.

Example 3: Generation of Recombinant Hyperimmune Globulins from Diverse B-Cell Repertoires Plasma-derived polyclonal antibody therapeutics, such as intravenous immunoglobulin, have multiple drawbacks, including low potency, impurities, insufficient supply and batch-to-batch variation. The present disclosure describes a microfluidics and molecular genomics strategy for capturing diverse mammalian antibody repertoires to create recombinant multivalent hyperimmune globulins. The method generates of diverse mixtures of thousands of recombinant antibodies, enriched for specificity and activity against therapeutic targets. Each hyperimmune globulin product comprised thousands to tens of thousands of antibodies derived from convalescent or vaccinated human donors or from immunized mice. Using this approach, Applicant generated hyperimmune globulins with potent neutralizing activity against severe acute respiratory syndrome coronavirus-2 (SARS-CoV-2) in under 3 months, Fc-engineered hyperimmune globulins specific for Zika virus that lacked antibody-dependent enhancement of disease, and hyperimmune globulins specific for lung pathogens present in patients with primary immune deficiency. To address the limitations of rabbit-derived anti-thymocyte globulin, Applicant generated a recombinant human version and demonstrated its efficacy in mice against graft-versus-host disease.

The technology described here generates recombinant hyperimmune globulins for diverse conditions through high-throughput microfluidics, genomics and mammalian cell engineering. B cells from human donors or mice are run through a microfluidic platform, heavy and light chain immunoglobulin nucleic acid sequences are fused on a single-cell level to create antibody repertoires, antibody repertoires are engineered into full-length expression constructs en masse, and then the full-length antibody expression constructs are stably introduced en masse into Chinese hamster ovary (CHO) cells in a site-directed manner. The technology disclosed herein was applied to develop $10^3$ to $10^4$ diverse recombinant hyperimmune globulin drug candidates to address unmet clinical needs for the COVID-19 pandemic, Zika virus disease, primary immune deficiency (PID) and transplant tolerance. The drug candidates were validated in vivo and/or in vitro for each of the four clinical applications.

Results

Capturing Diverse Antibody Repertoires as CHO Libraries and RPPs

Mammalian antibody repertoires are extremely diverse, comprising as many as $10^7$ antibody clonotypes. Advanced molecular technology is required to capture a substantial fraction of a mammalian donor's diverse antibody repertoire. Applicant used methods for generating millions-diverse libraries of natively paired heavy and light chain immunoglobulin sequences in yeast. That method used microfluidics to isolate millions of single B cells per hour into picoliter droplets for lysis, followed by overlap extension—reverse transcriptase—polymerase chain reaction (OE-RT-PCR), to generate libraries of natively paired single chain variable fragments (scFv).

Because antibody repertoires often contain many antibodies not directed against the target(s) of interest, a variety of enrichment methods (FIG. 7A-7E) were used. For ATG, Zika virus, *Haemophilus influenzae* b (Hib) and *Streptococcus pneumoniae* (pneumococcus), immunogens were administered to human donors or humanized mice before sampling antibody-producing cells. For SARS-CoV-2, convalescent donors were recruited who recently tested positive for COVID-19, made yeast display scFv libraries from donor B cells and sorted the libraries derived from these donors to enrich for antibodies directed against SARS-CoV-2 antigen. In all cases, the output was a library of thousands to tens of thousands of natively paired scFv DNAs, enriched for activity against their respective target(s).

Next, each library of scFv DNAs was used to produce natively paired full-length antibody expression constructs, which were then engineered into mammalian cells for production of recombinant hyperimmune globulins (FIG. 7A-7E). Cloning into full-length antibody expression constructs was performed en masse, that is, to perform all molecular steps on full libraries rather than individual clones. Briefly, the protocol involved a series of two Gibson assemblies, which are referred to as Gibson assembly 1 (GA1) and Gibson assembly 2 (GA2) (FIGS. 12A and 12B). In GA1, the scFv library was inserted into a vector backbone that contained a promoter, a fragment of the IgG1 constant domain and a poly(A) signal. In GA2, the GA1 plasmid was linearlized, and subcloned it into a DNA fragment that contained a fragment of the IgK constant domain, a second poly(A) signal and a second promoter.

Production cell lines for monoclonal antibodies are typically produced by randomly inserting expression constructs into the CHO genome. This method produces cell lines with genomic insertion of multiple copies of the expression construct. If polyclonal antibody construct libraries are inserted randomly into the CHO genome, because each cell might contain several inserted transgenes, many clones would express multiple antibodies, which would result in frequent nonnative pairing between heavy and light chain immunoglobulin. Additionally, different genome locations have different transcriptional activity levels, which could result in heterogeneous, inconsistent and/or unstable bioproduction. Applicant therefore used CHO cell lines engineered with a Flp recombinase recognition target landing pad (FIG. 13E). These cell lines were then used for stable expression of recombinant hyperimmune globulins or RPPs in polyclonal cell banks.

Recombinant Hyperimmune Globulins or RPPs for SARS-CoV-2

To address the urgent unmet clinical need of the COVID-19 pandemic, methods provided herein were to build recombinant hyperimmune globulins against SARS-CoV-2, which is referred to as recombinant coronavirus-2 immune globulin, or rCIG. In March 2020, 50 human donors were recruited from a single clinic in Louisiana who either had tested positive for SARS-CoV-2 by nasal swab PCR testing or had shown symptoms of COVID-19 around the time of a major local outbreak. First, anti-SARS-CoV-2 plasma titer was assessed for each of the donors using the S1 and receptor binding domain (RBD) regions of SARS-CoV-2 spike glycoprotein (FIG. 8A and Table 6). A wide range of half-maximum effective concentration ($EC_{50}$) values was observed among patients who tested positive for COVID-19 (range 0.0056-9.94 mg ml$^{-1}$). 16 donors with high plasma antibody titers was selected and used to build yeast scFv display libraries from pools of two donors, for a total of eight libraries. The libraries comprised a median of 70,940 antibodies (range 54,986-156,592, Table 7).

Applicant used flow sorting to enrich for anti-SARS-CoV-2 antibodies in the eight yeast scFv libraries (FIG. 8B, FIGS. 14A-14B and Table 7). One round of flow sorting suggested that a median of 0.99% of antibodies (range 0.42-2.29%) were directed against SARS-CoV-2. After two rounds of sorting, a median of 62.7% of unsorted antibody sequences were human IgG1 subtype (range 51.5-83.4%), whereas in the sorted libraries a median of 82.4% of antibody sequences were human IgG1 subtype (range 63.6-92.2%), suggesting that the COVID-19 antibody response was generally dominated by IgG1 antibodies. Next, full-length polyclonal antibody preparations were generated from each of the eight scFv libraries. The antibodies were formatted as human IgG1, regardless of the initial IgG subtype. Anti-SARS-CoV-2 enzyme-linked immunosorbent assay (ELISA), spike:ACE2 blocking assays and pseudotype and live virus neutralization assays were used to assess the relative activity of each of the eight antibody libraries (FIG. 8F, FIGS. 15 and 17A-17C and Table 7). The eight scFv-sorted CHO cell banks were used in a way that sought to balance high antibody diversity with high anti-SARS-CoV-2 pseudotype neutralization titer (Table 8) and used the combined cell bank to generate rCIG protein product (FIG. 18A-18B). In preparation for manufacturing rCIG for clinical trials, a comprehensive polishing strategy was developed. Stress testing showed that the polished protein quality and function was highly stable, suggesting that rCIG was amenable to large-scale manufacturing (FIG. 19A-19D). This entire process, from delivery of the first donor sample to laboratory-scale generation of the rCIG protein product, was completed in less than 3 months.

Antibody RNA sequencing of the final CHO cell bank indicated that the rCIG drug candidate comprised a diverse set of 12,500 antibodies (FIG. 8C and Table 9). Additional repertoire analysis of the linked scFv and CHO cell bank libraries for rCIG was performed, including variable gene usage frequency, divergence from germline, CDR3H length distribution and sequence logos of the most abundant clonal clusters (FIG. 20A-20D, FIG. 21A-21C). Anti-SARS-CoV-2 ELISA suggested that the binding titer of rCIG was between 99- and 747-fold higher than corresponding plasma (FIG. 8D, FIG. 15 and Table 7 and 9). ELISAs with several natural variants of SARS-CoV-2 and antigens from related viruses, including SARS-CoV and Middle East respiratory syndrome (MERS) CoV, showed that rCIG bound a broader variety of antigen targets than IVIG or a neutralizing CoV-2 monoclonal antibody (mAb; FIG. 8E, FIG. 22 and Table 9). SARS-CoV-2 pseudotype virus neutralization assay was performed with psudotype virus of several SARS-CoV-2 variants (B.1.1.7 (UK), B.1.351 (South Africa), P.1 (Japanese/Brazilian), and B.1.427/B.1.429 (California)). The result showed that rCIG neutralizes the psudotype virus of the variants in a concentration dependent matter, with an $IC_{50}$ within 6-fold of the $IC_{50}$ determined using the Wuhan-Hu-1 psudoviral particle (FIG. 51 and FIG. 52). The rCIG RPP therefore has broad activity across variants against which individual monoclonal antibodies are not active.

Finally, spike:ACE2 blocking assays, pseudotype virus neutralization assays and live SARS-CoV-2 neutralization assays suggested that the neutralizing titer of rCIG was between 44- and 1,767-fold higher than corresponding convalescent plasma (FIG. 8F, FIGS. 16A and 16B, and Tables 7 and 9).

Antibody RNA sequencing of the CHO cells and SARS-CoV-2 ELISA binding and SARS-CoV-2 pseudotype neu-(possibly inappropriate) choices about viral epitope targets, the potency of an rZIG product produced without enrichment by flow sorting was assessed. To this end, the unsorted scFv library and CHO engineering technology to create rZIG CHO cell banks with a wild type human IgG1 isotype (rZIG-IgG1) or a mutated human IgG1 with abrogated Fc receptor (FcR) binding (rZIG-LALA) were used. Antibody RNA sequencing of IgG sequences in the rZIG cell banks suggested that the rZIG-IgG1 comprised 33,642 antibodies and rZIG-LALA comprised 26,708 antibodies (FIG. 9A and Table 11). A Morisita overlap of 86% and a Jaccard overlap of 58% between the rZIG-IgG1 and rZIG-LALA libraries suggested that the cell banks comprised substantially similar antibody repertoires. Additional repertoire analysis of the linked scFv and CHO cell bank libraries for rZIG was performed, including variable gene usage frequency, divergence from germline, CDR3 length distribution and sequence logos of the most abundant clonal clusters (FIG. 25A-25D). CDR1, CDR2 and CDR3 sequences of 5 clusters provided in FIG. 25D are also summarized in the below table.

| Cluster | CDR1 | CDR2 | CDR3 |
| --- | --- | --- | --- |
| 1 | GFTFSSYA (SEQ ID NO: 25841) | ISGSGGST (SEQ ID NO: 25847) | AKEGMVLRYFDWLWDY (SEQ ID NO: 25856) |
| 2 | GFTFSSYG (SEQ ID NO: 25842) | I[W/S]YDGSNK (SEQ ID NO: 25848) | R[D/E][R/L][S/V/L]SG[P/W]S[G/H]FDY (SEQ ID NO: 25857) |
| 3 | GFTFSSYA (SEQ ID NO: 25841) | ISGSGGST (SEQ ID NO: 25847) | A[K/E/R][E/T][Q/L/T][L/W/I][L/V/W/N][G/L]V[V/P/L][F/L/N][D/N]Y (SEQ ID NO: 25858) |
| 4 | GFTFDD[Y/H]G (SEQ ID NO: 25843) | INWNG[G/D]ST (SEQ ID NO: 25849) | AR[D/N][R/G]GS[S/T][G/S/W/F][W/F/Y][R/F/Y]D[W/A]FD[P/I] (SEQ ID NO: 25859) |
| 5 | GFTFSD[Y/D][Y/F] (SEQ ID NO: 25844) | ISGSG[S/Y]TI (SEQ ID NO: 25850) | ARDEGY[R/S]GY[V/N]LD[T/N/S] (SEQ ID NO: 25860) | tralization of rCIG protein generated from replicate 3-1 bioreactor runs did not show significant batch-to-batch variation in antibody sequence content (Wilcoxon rank sum test, P>0.05) or in vitro pseudotype neutralization (Feltz and Miller's asymptotic test, P>0.05; FIGS. 23A and 23B).

Recombinant Hyperimmune Globulin or RPP for Zika Virus

To address the Zika pandemic, the method described herein was to build recombinant hyperimmune globulins or RPP against Zika virus, which is referred to as recombinant Zika immune globulin, or rZIG. To create rZIG RPP, human-transgenic mice (Trianni) was used that expressed a complete repertoire of human antibody sequences. The mice were immunized with Zika virus antigens (FIGS. 24A and 24B). To explore the ability to engineer an rZIG that would not exhibit antibody-dependent enhancement (ADE), a safety concern for anti-Zika therapeutic antibodies, Applicant additionally boosted with four inactivated dengue virus serotypes.

B cells from the immunized animals and microfluidics technology were used to create an scFv library of natively paired IgGs. The resulting scFv library comprised approximately 119,700 IgG-IgK clonotypes (Table 10). Because enrichment by flow sorting is time-consuming and makes Applicant used these CHO cell banks to produce rZIG-IgG1 and rZIG-LALA hyperimmune globulins at laboratory scale (FIG. 26A-26B, FIG. 27A-27B).

Anti-Zika virus ELISA showed that both rZIG-LALA and rZIG-IgG1 had >75-fold higher titers against Zika virus than a human Zika positive serum sample (FIG. 28 and Table 11). Both rZIG-LALA and rZIG-IgG1 had anti-dengue binding activity across four serotypes, with pooled $EC_{50}$ values showing strong correlation with anti-Zika $EC_{50}$ values (linear regression, $R^2$=0.9993, F-statistic P<0.001; FIG. 9B, FIG. 29 and Table 10). In contrast, although both rZIG-LALA and rZIG-IgG1 had strong activity in a Zika pseudotype neutralization assay (FIG. 30), there was no correlation between Zika and pooled dengue neutralization (linear regression, $R^2$=0.00271, F-statistic P>0.05; FIG. 9C and FIG. 31). Applicant investigated whether the abrogated Fc function of rZIG-LALA could decrease ADE in a Zika pseudotype virus assay (FIG. 32). Both Zika+ human serum and rZIG-IgG1 showed considerable ADE, whereas rZIG-LALA showed no detectable ADE (FIG. 9D). Antibody RNA sequencing of the CHO cells and anti-Zika virus ELISA binding of rZIG-IgG1 and rZIG-LALA protein generated from replicate bioproduction runs did not show significant batch-to-batch variation in antibody sequence content (Wilcoxon rank sum test, P>0.05), and batch-to-batch anti-Zika virus ELISA results were indistinguishable (FIG. 33A-33B).

IVIG Spike-In for Patients with Primary Immunodeficiencies

Plasma-derived IVIG acts as antibody replacement for patients with humoral primary immunodeficiencies ("PID"), who have low serum IgG titers. However, it has insufficient antipathogen activity for certain patients at-risk for PID. To address this unmet clinical need, Applicant manufactured recombinant hyperimmune globulins or RPPs directed against pneumococcus and Hib bacteria, designed as multivalent 'spike-ins' for plasma-derived IVIG, that is, recombinant *Haemophilus* immune globulin (rHIG) and recombinant pneumococcus immune globulin (rPIG). Note that rHIG and rPIG are not replacements for IVIG, but rather supplements meant to increase the efficacy of IVIG. A full recombinant replacement for IVIG would require much broader antipathogen activity.

Healthy human donors were recruited and administered vaccines directed against pneumococcus or Hib. Eight to nine days after vaccination, peripheral blood mononuclear cells (PBMCs) were collected and shipped to our microfluidics processing facility. B cells from the PBMCs were selected and millions of cells were run through the microfluidics platform (Table 12), and then the scFv libraries and the CHO engineering technology were used to create IgG1 CHO cell banks for rHIG and rPIG. Heavy chain antibody RNA sequencing of the cell banks indicated that rHIG comprised 49,206 IgG sequences and rPIG comprised 17,938 IgG sequences (FIG. 10A and Table 13 and 14). Additional repertoire analysis of the linked scFv and CHO cell bank libraries for rHIG and rPIG was performed, including variable gene usage frequency, divergence from germline, CDR3 length distribution and sequence logos of the most abundant clonal clusters (FIGS. 34A-34D and 35A-35D). These CHO cell banks were used to produce rHIG and rPIG hyperimmune globulins at laboratory scale (FIGS. 36A-36B and 37A-37B).

Anti-Hib ELISA indicated that rHIG had 233-fold higher titer than plasma-derived IVIG (FIG. 10B and Table 13). A serum bactericidal assay demonstrated that rHIG was strongly active against two different Hib strains, whereas no bactericidal activity was observed for plasma-derived IVIG (FIG. 10C, FIG. 38 and Table 13). An ELISA against a combination of 23 pneumococcus serotypes showed that rPIG has 85-fold higher titer than plasma-derived IVIG (FIG. 39 and Table 14). ELISA for individual pneumococcus serotypes showed that rPIG was at least fivefold higher titer than plasma-derived IVIG for 13 out of 16 serotypes measured, indicating broadly enriched multivalent reactivity and significantly higher than IVIG overall across all separate ELISAs combined (Wilcoxon signed rank test, P=0.00123; FIG. 10D and Table 14). Finally, semiquantitative serotype-specific opsonophagocytosis assays suggested that rPIG was as effective or more effective than plasma-derived IVIG at cell killing for 15 out of 16 serotypes tested, and had significantly higher activity than IVIG across all separate opsonophagocytosis assays combined (Wilcoxon signed rank test, P=0.00251; FIG. 10D and Table 14). Antibody RNA sequencing of the CHO cells and anti-Hib or antipneumococcal ELISA binding of rHIG or rPIG protein generated from replicate bioproduction runs, respectively, did not show significant batch-to-batch variation in antibody sequence content (Wilcoxon rank sum test, P>0.05), and batch-to-batch antipathogen ELISA results were indistinguishable (FIGS. 40A-40B and 41A-41B).

To simulate the potential clinical application, rHIG and rPIG were mixed in with plasma-derived IVIG (IVIG+rHIG/rPIG) at a ratio of 1:1:8 (rHIG:rPIG:IVIG), producing a product with 18.3-fold higher titer than plasma IVIG for Hib and 8.3-fold higher titer than plasma IVIG for a pool of 23 pneumococcus serotypes (FIGS. 42A-42B and Table 15). A Hib mouse challenge model using IVIG+rHIG/rPIG as prophylactic treatment showed significantly lower bacterial loads in the blood (Welch t-test, P<0.001) and peritoneal fluid (Welch t-test, P<0.001) as compared to plasma IVIG alone (FIG. 10E).

Recombinant Human ATG RPP for Transplant Tolerance

To encourage tolerance of grafts, transplant physicians use a variety immunosuppressive drugs, such as rabbit-ATG, which is manufactured by injecting rabbits with human thymocytes and isolating antibodies from the rabbit serum. However, rabbit-ATG can cause allergic reactions and other complications in humans, and the drug shows significant variation in potency across lots. To improve on rabbit-ATG, a recombinant human ATG, or rhATG RPP, derived from transgenic mice that express human antibodies (Trianni) were used. The mice were immunized with either human T cells or human fetal thymocytes (FIG. 43A-43B). B cells from the immunized animals and the microfluidics technology were used to create four scFv libraries of natively paired IgGs: bone marrow cells from T-cell immunized mice, lymph node cells from T-cell immunized mice, lymph node cells from thymocyte immunized mice and spleen cells from thymocyte immunized mice. The resulting scFv libraries comprised a range of 13,314 to 34,324 IgG-IgK clonotypes (Table 16). Additional repertoire analysis of the linked scFv and CHO cell bank libraries for rhATG was performed, including variable gene usage frequency, divergence from germline, CDR3 length distribution and sequence logos of the most abundant clonal clusters (FIG. 44A-44D). The CHO engineering technology was used to make cell banks from each of the four libraries.

Protein from each of the CHO cell banks was produced, and then pooled in equal mass equivalents to create rhATG (FIG. 45A-45B). Sequencing of individual libraries suggests that the pool comprised 49,885 antibodies (FIG. 11A and Table 17). Then ELISA was performed for a panel of known cell surface antigen targets for rabbit-ATG and observed that rhATG bound several immune cell surface targets, but only a subset of the targets bound by rabbit-ATG (FIG. 46A-46B). To investigate further, in vitro cell killing assays were performed with human PBMCs, which showed that rhATG and rabbit-ATG were not significantly different in cell killing potency against cytotoxic T cells and helper T cells (linear mixed effects model, P>0.05), whereas rhATG is significantly stronger than rabbit-ATG at killing B cells (linear mixed effects model, P<0.01) but significantly weaker than rabbit-ATG at killing natural killer cells (linear mixed effects model, P<0.01; FIG. 11B). Anti-erythrocyte binding assays were also performed, which suggested that rhATG has less off-target activity than rabbit-ATG (FIG. 47).

The efficacy of rhATG in vivo was also studied, using a graft-versus-host (GVH) model in which human PBMCs were grafted onto immune-incompetent mice. Animals (n=8 per PBMC donor) were dosed with rhATG, rabbit-ATG or vehicle control, either every other day for 5 weeks starting 5 days after the PBMC graft, or only on days 5, 6 and 7 after the graft. Two different PBMC donors were tested for each dosing regimen. After 42 days, rhATG was not significantly different from rabbit-ATG for survival (log-rank pairwise tests, P>0.05) and was superior to vehicle control for survival (log-rank pairwise tests, P<0.001), in both dosing schemes across multiple PBMC donors (FIG. 11C and FIG. 48A-48B). In both dosing regimens across both PBMC donors, immune cell (CD45$^+$) expansion was not significantly different between rhATG and rabbit-ATG (linear mixed effects model, P>0.05), whereas for the vehicle control immune cell counts were significantly higher than rhATG at day 9 (Wilcoxon rank sum tests, P<0.01; FIG. 11D and FIG. 49A-49B). The conclusion was that although rhATG and rabbit-ATG did not share identical antigen targets, the drugs had similar efficacy in vivo.

DISCUSSION

Applicant demonstrated the generation of multivalent, $10^3$ to $10^4$ diverse recombinant hyperimmune antibody drugs (RPPs) from convalescent human blood donors, vaccinated human blood donors and humanized mouse repertoires. The drug candidates were validated using in vitro and in vivo methods, highlighting their advantages over plasma-derived incumbents. The technology combines methods in microfluidics, genomics and mammalian cell engineering. Contrasted against previous methods for generating recombinant polyclonal antibodies, our drug candidates had hundreds-fold higher antibody diversity and therefore represented higher fractions of antigen-reactive repertoires. Their advantages over plasma-derived products include higher potency, the ability to scale production without collecting further donors, consistency of production and the ability to modulate pharmacologic problems such as ADE. The technology is fast, producing a master cell bank against a poorly characterized virus (SARS-CoV-2) in less than 3 months. The rCIG product (GIGA-2050) has now been manufactured at a good manufacturing practice (GMP) facility. GMP production was similar to the methods described in this study, except that upstream bioproduction was performed in a single use bioreactor at the 250-liter scale and downstream purification was scaled equivalently.

Emerging viruses are a constant and unpredictable threat to human health. In the past two decades alone, the world has seen outbreaks of Ebola virus, SARS, MERS, 2009 H1N1 swine flu, Zika Virus and SARS-CoV-2, among others. Notwithstanding recent successes in rapid development of SARS-CoV-2 prophylactic vaccines, previous vaccine development efforts required very long development timelines. Development of broadly neutralizing monoclonal antibodies is often confounded by the difficulty of identifying broadly neutralizing epitopes, and escape variants can emerge over time. Because of such issues, convalescent COVID-19 plasma emerged as a promising approach early in the COVID-19 pandemic. However, convalescent plasma is difficult to manufacture at scale because convalescent plasma supply is constrained and each plasma donor supplies enough therapeutic for only 1-2 patients. The conclusion was that rCIG was a promising alternative to COVID-19 convalescent plasma due to significantly higher potency against live virus (Wilcoxon rank sum test, P=0.02869) and the ability to scale GMP production without the need to recruit more donors.

Although Zika virus has been less widespread and less deadly than SARS-CoV-2, Zika can spread from mother to fetus in utero, resulting in birth defects such as microcephaly. As of July 2020, there was no FDA-approved vaccine or therapy for Zika virus. Zika virus disease is complicated by ADE, a phenomenon in which poorly neutralizing antibodies enhance viral infection by bringing virus particles to cells that express FcR. This problem is particularly troublesome for individuals who have been previously infected with dengue, a related flavivirus, since many anti-dengue antibodies are poor neutralizers against Zika virus and vice versa. ADE is a safety concern in the development of plasma-derived hyperimmune globulins and vaccines. The conclusion was that rZIG-LALA was a promising alternative to plasma-derived drugs, due to high neutralizing potency against Zika virus and complete abrogation of the risk of ADE.

Although plasma-derived IVIG reduces rates of serious infections in PID, many patients still suffer frequent serious infections that require hospitalization. In particular, about 78% of serious lung infections are caused by pneumococcus and Hib bacteria. Clinicians have improved outcomes by further increasing IVIG doses, suggesting that, however, bacterial species are often incredibly diverse; for example, there are 90 known pneumococcus serotypes, complicating therapeutic development. The conclusion was that a polyvalent IVIG+rHIG/rPIG product had strong potential to address unmet clinical needs in patients with PID through increased potency against key pathogens.

In 2019, nearly 40,000 solid organ transplants were performed in the USA alone (www.unos.org). Transplantation generally introduces at least some mismatch between the human leukocyte antigen genotypes of the donor and host. This frequently results in some host-versus-graft effects, leading to loss of the graft and other serious complications. The work provided herein suggested that rhATG could one day address unmet clinical needs in transplant tolerance.

Our technology for generating recombinant hyperimmune globulins combines the advantages of recombinant antibodies (purity, consistency, potency) with the advantages of plasma-derived antibodies (proven efficacy, diversity, polyvalence, in vivo affinity maturation). The study disclosed herein has shown how the technology can improve existing plasma-derived products such as IVIG and rabbit-ATG. Polyclonal antibodies contain drugs with different mechanisms of action, potentially increasing efficacy; for example, rCIG may contain some antibodies optimized to block binding of virus to ACE2 and other antibodies optimized to clear virus through complement fixation. In the future, our technology could be used to develop drugs with new mechanisms of action, for example, antitumor antibody mixtures or antiplasma cell mixtures to cure humoral-driven autoimmune disease. It could also be extended to develop recombinant polyclonal IgM or IgA. To strengthen readiness against future pandemics, recombinant hyperimmune globulin cell banks against the most pressing biodefense threats could be produced preemptively.

Methods

Generating Paired Heavy and Light Chain Libraries

Generation of scFv libraries from antibody-producing cells comprises three steps: (1) poly(A)+mRNA capture, (2) multiplexed OE-RT-PCR) and (3) nested PCR. Briefly, a microfluidic device captures single cells in droplets with a mixture of lysis buffer and oligo dT beads (NEB). After the cell is lysed and messenger RNA is bound to the bead, the emulsion is broken and the mRNA-containing beads are purified. Next, an emulsion is created using OE-RT-PCR reagents including a pool of primers directed against the IgK C region, the IgG C region and all V regions (Table 18), and the mRNA-bound beads as a template. The emulsion is subjected to thermal cycling, which creates complementary DNA, amplifies the IgK and IgG variable regions and links them together in an scFv format. Then the emulsion is broken and the linked scFv DNA product is extracted and purified. The purified scFv product is then amplified using nested PCR to remove artifacts and add adapter sequences. Depending on the adapter sequences, the product can be used for deep sequencing, yeast display libraries or full-length CHO expression.

To convert the scFv libraries into full-length CHO expression libraries, nested outer PCR primers were first used to add adapters with overhangs for Gibson assembly to the 5' and 3' ends of the scFv library (for rCIG, this was done after yeast scFv display enrichment, as described in the next section). Then NEBuilder HiFi DNA Assembly Master Mix (NEB) was used to insert the scFv library into a vector containing a single promoter, a secretory leader sequence for light chain immunoglobulin and the remainder of the IgG1 constant region, creating a cloned scFv library (GA1 backbone, FIG. 12A-12E; GenBank accession number MW079271). This intermediate library (GA1 product, FIG. 12A-12E; example plasmid sequence provided as GenBank accession number MW079272) was transformed into *E. coli* and plasmids were purified by either (1) spreading onto LB-ampicillin plates, scraping 0.5-1 million colonies and pooling or (2) inoculating directly into LB-ampicillin broth and growing overnight. Plasmid purification was performed using ZymoPURE II Plasmid Maxiprep Kits (Zymo Research). To create the full-length antibody library, a second Gibson assembly was performed by linearizing the GA1 product with BamHI-HF (rHIG) or NheI-HF (rCIG, rPIG, rhATG and rZIG) (NEB) and using it as a vector to insert a synthetic amplicon (Supplementary FIG. 2, GenBank accession number MW079275) containing a portion of the light chain immunoglobulin constant region, a poly(A) signal for light chain immunoglobulin, a promoter for the IgG gene and a secretory leader sequence for the IgG gene. The full-length library was then transformed into *E. coli* and spread on LB-ampicillin plates. >0.5 million colonies were combined and plasmid was purified with a ZymoPURE II Plasmid Maxiprep Kits (Zymo Research) to make the full-length recombinant hyperimmune globulin maxiprep library for transfection (GA2 product, FIG. 13A-13E; example plasmid sequence provided as GenBank accession number MW079273). When the transformed *E. coli* were inoculated directly into LB-ampicillin medium, a small volume of cells was plated to calculate the total number of transformants. In some cases, ampicillin was used for both plates and medium, whereas in other cases carbenicillin was used instead of ampicillin. Paired heavy and light chain libraries were made only once from each sample.

Enrichment for Antigen Binders by Yeast scFv Display

Polyclonal COVID-19 scFv libraries were sorted to enrich for relevant sequences. Briefly, yeast surface display scFv libraries were generated using COVID-19 scFv DNA libraries and a custom yeast surface display vector transformed by electroporation into EBY100 yeast strain (MYA-4941, ATCC). Surface displayed scFv sequences include a C-terminal myc tag to identify scFv expression with 1 µl per sample of undiluted anti-myc primary (A21281, Thermo Fisher Scientific) and 1 µl per sample of undiluted AF488 secondary antibody (A11039; Thermo Fisher Scientific). Binding to antigen was identified by staining with soluble biotinylated SARS-CoV-2 RBD antigen (SPD-C82E9, Acro Biosystems) at 1,200 nM and APC-streptavidin (SA1005, Thermo Fisher Scientific). Stained yeast libraries were sorted on a FACSMelody (BD Biosciences, with BD fluorescent activated cell sorting (FACS) Chorus software v.1.3.3) and double positive (AF488$^+$/APC$^+$) cells were collected. The gating strategy is outlined in FIG. 14A-14B. The collected cells were expanded and sorted again to further enrich the libraries. After the second round of sorting, cells were expanded a third time before plasmid isolation with a Zymoprep Yeast Plasmid Miniprep kit (Zymo Research). The plasmid libraries were then used as template for barcoding PCR and subsequent analysis by deep sequencing (Illumina). Plasmid from twice-sorted libraries was used as template for PCR toward full-length CHO antibody expression. Yeast scFv sorting was performed only once from each yeast scFv library.

Bioproduction of rHIG and rhATG

Adapted Flp-In-CHO cells stably expressing antibody libraries were grown in media consisting of 90% BalanCD CHO Growth A Medium (Irvine Scientific), 9% Ham's F-12 (Thermo Fisher Scientific), 1% FBS (Thermo Fisher Scientific), 4 mM Glutamax (Thermo Fisher Scientific), 0.2% anticlumping agent (Irvine Scientific), 600 µg ml$^{-1}$ Hygromycin-B (Gemini Bio). Protein production was performed at either small (250 ml) or medium (5 l) scale. For small-scale production, cells were seeded at $1 \times 10^6$ cells per ml into 50 ml of media in a 250 ml Erlenmeyer flask and grown at 37° C., 5% $CO_2$, 125 r.p.m. Cells were continually grown under these conditions and supplemented with 7.5 ml of CHO Feed 1 (Irvine Scientific) on days 2, 4 and 7 of the production run. Supernatant was harvested on days 8 or 9 by centrifugation followed by filtration through a 0.22-µm 250 ml filter bottle (MilliporeSigma) with a 1 µm prefilter (MilliporeSigma). Harvested cell culture fluid (HCCF) was stored at 4° C. (if less than 1 week) or at −80° C. (if more than 1 week) until Protein A purification. For medium-scale production, cells were grown in the same media. Cells were then seeded at $1 \times 10^6$ cells per ml in 2.3 l in a 5 l flask (in duplicate, day 0). Each flask was fed with 345 ml of CHO Feed 1 (Irvine Scientific) on days 2 and 4 of the culture. Cultures were gathered on days 8 or 9. Each of the four rhATG protein libraries were produced separately. Bioproduction was performed twice each for rHIG and rhATG.

Bioproduction of rPIG, rZIG and rCIG

CSS-1286 CHO cells stably expressing antibody libraries were grown in media without glutamine (EX-CELL CHOZN Advanced, MilliporeSigma). Protein production was performed at either small (500 ml flask) or medium (5 l flask) scale. For small-scale production, cells were seeded at $0.5 \times 10^6$ cells per ml into 100 ml media in a 500 ml Erlenmeyer flask and grown at 37° C., 5% $CO_2$, 125 r.p.m. Cells were continually grown under these conditions and supplemented with 15 ml of CHO Feed 1 (MilliporeSigma) on day 3, and 10 ml of CHO Feed 1 (MilliporeSigma) on days 6 and 8 of the production run. Starting on day 3, glucose was measured each day and supplemented to 6 gl$^{-1}$ if below 4 gl$^{-1}$. Supernatant was harvested after cell viability peak and before dropping below 70% viability between days 9 and 11, centrifuged and filtered through a 0.22-µm 250 ml filter bottle (MilliporeSigma) with a 1 µm prefilter (MilliporeSigma). HCCF was stored at 4° C. (if less than 1 week) or at −80° C. (if more than 1 week) until Protein A purification. For medium-scale production, cells were grown in the same media. Cells were seeded at $0.5 \times 10^6$ cells per ml in 2.2 L in a 5 L flask (in duplicate, day 0). Each flask was fed with 330 ml of CHO Feed 1 (MilliporeSigma) on day 3 and 220 ml of CHO Feed 1 (MilliporeSigma) on days 6 and 8 of the production run. Starting on day 3, glucose was measured each day and supplemented to 6 g L$^{-1}$ if below 4 gl$^{-1}$. Cultures were gathered on days 10-12. Bioproduction was performed three times for rCIG and twice each for rZIG and rPIG.

Protein Production and Characterization

After harvest, HCCF was purified using MabSelect PrismA (Cytiva) using 1×PBS (Teknova) for running and wash buffer, 0.1 M Citrate, pH 3.0 (Teknova) for elution and 1 M sodium citrate pH 6.0 (Teknova) for neutralization. The protocol was 10 column volumes (CV) of equilibration, HCCF loading, 10 CV of washing and 5-10 CV of elution followed by cleaning-in-place with 1 M NaOH. HCCF was loaded with a 1-min residence time. Eluted material was neutralized to a pH of roughly 4.5 and centrifuged to remove any precipitation. This material was dialyzed into 0.2 M glycine, pH 4.5 (Teknova) using a 20K molecular weight cutoff dialysis cassette (Thermo Fisher Scientific) and optionally concentrated up to 30 mg ml$^{-1}$ using a 50 kDa molecular weight cutoff spin device (MilliporeSigma). Final material was sterilized with a 0.22 μm filter and quantified by A280 (NanoDrop, Thermo Fisher Scientific). For rhATG, each of the four libraries were purified by Protein A separately and then equally pooled based on mass.

Purity of the protein was determined by size-exclusion-HPLC. Here, 20 μg of material at 1 mg ml$^{-1}$ was injected over a 300 Å, 2.7 μm, 7.8×300 mm size-exclusion column (Agilent) using a mobile phase of 25 mM phosphate, 200 mM NaCl pH 7.0 with 10% acetonitrile at 1 ml min$^{-1}$. The percentage of monomer was determined by integrating the product peaks and reporting the percent area corresponding to roughly 150 kDa. The product was further characterized by running 2 μg on a 12% SDS-PAGE gel under reduced and nonreduced buffering conditions and imaged after staining with SimplyBlue SafeStain (Thermo Fisher Scientific).

Protein production was performed once for each of the bioproduction runs.

Statistical Analysis

All statistical tests were performed on nonnormalized data, two-sided without adjustments to type I error rates. A significance threshold of $\alpha=0.05$ was used for all statistical tests. All statistical analyses were conducted using R v.3.6.2.

For FIG. 8F, a Wilcoxon rank sum test was used to compare the minimum concentration to achieve SARS-CoV-2 live virus neutralization between convalescent plasma measurements (n=16) and rCIG measurements (n=2).

For FIG. 9B, simple linear regression was used to calculate the coefficient of determination ($R^2$) between Zika and dengue ELISA $EC_{50}$ values. $EC_{50}$ values for all dengue serotypes were pooled for the analysis. Significance of the regression model was determined using an F-statistic with 1 and 10 degrees of freedom (d.f.). All measurements were performed in a single experiment. No power analysis was carried out to predetermine an appropriate sample size for this experiment.

For FIG. 9C, simple linear regression was used to calculate the coefficient of determination ($R^2$) between Zika and dengue pseudotype neutralization half-maximum inhibitory concentration ($IC_{50}$) values. $IC_{50}$ values for all dengue serotypes were pooled for the analysis. Significance of the regression model was determined using an F-statistic with 1 and 10 d.f. All measurements were performed in a single experiment. No power analysis was carried out to predetermine an appropriate sample size for this experiment.

For FIG. 10D, fold improvement over IVIG, by assay (ELISA or opsonophagocytosis) was tested using a one-sample Wilcoxon signed rank test, with the null hypothesis that the median equals 1, that is, $H_0=1$. For each assay, all individual serotypes were pooled using a single Wilcoxon signed rank test. Values for each individual serotype were generated by dividing the mean of duplicate rPIG measurements by the mean of duplicate IVIG measurements. All measurements were performed in a single experiment. No power analysis was carried out to predetermine an appropriate sample size for this experiment.

For FIG. 10E, Welch's t-tests were used to compare colony forming units (CFU) Hib per ml between test groups and d.f. were 7.87 for IVIG+rHIG/rPIG (500 mg kg$^{-1}$) and 7.13 for IVIG+rHIG/rPIG (200 mg kg$^{-1}$) in peritoneal fluid, and were 10.87 for IVIG+rHIG/rPIG (500 mg kg$^{-1}$) and 8.03 for IVIG+rHIG/rPIG (200 mg kg$^{-1}$) in blood. All measurements were performed in a single experiment. No power analysis was carried out to predetermine an appropriate sample size for this experiment.

For FIG. 11B, linear mixed effects models were used to compute P values for each of the four cell types, with group and concentration as fixed effects and PBMC donor as a random effect to account for the dependence of repeated measures: the d.f. were 31 for each of the four models. All measurements were performed in a single experiment. No power analysis was carried out to predetermine an appropriate sample size for this experiment.

For FIG. 11C and FIG. 48A-48B, Kaplan-Meier survival models were fit on time to mortality and pairwise log-rank tests were performed to compare median survival between treatment groups. All measurements were performed in a single experiment. No power analysis was carried out to predetermine an appropriate sample size for this experiment.

For FIG. 11D and FIGS. 49A-49B, linear mixed effects models were used to compute P values for trends in CD45$^+$ cell counts in each of the four GVH experiments (2 PBMC donors×2 drug dosing regimens=4 experiments) with day as a fixed effect and PBMC donor as a random effect to account for the dependence of repeated measures. A Wilcoxon rank sum test was used to compare CD45$^+$ cell counts on day 9 for saline negative control versus rhATG and saline negative control versus rabbit-ATG, in each of the four GVH experiments (2 PBMC donors×2 drug dosing regimens=4 experiments). No power analysis was carried out to predetermine an appropriate sample size for this experiment.

For FIGS. 23A-23C, 33A-33B, 40A-40B and 41A-41B, it was assessed whether batch-to-batch variation was more significant than the variability inherent to the assays used to make the measurements.

For rCIG pseudotype neutralization assays (FIG. 23A-23C), Feltz and Miller's asymptotic test was used to determine whether the coefficient of variation of three bioproduction batch $IC_{50}$ measurements (18%) was different from the coefficient of variation of eight $IC_{50}$ measurements on a fourth bioproduction batch (17%).

To assess batch variation in antibody sequence content, the Wilcoxon rank sum test was used to test whether the Jaccard or Morisita indices from PCR replicates from each bioproduction batch came from the same populations as the Jaccard or Morisita indices among bioproduction batches. Sequencing was performed in a single experiment. No power analysis was carried out to predetermine an appropriate sample size for this experiment.

Data Availability

Plasmid and cloning insert sequences are available on GenBank (GA1 backbone, GenBank accession number MW079271; GA1 product, GenBank accession number MW079272; synthetic amplicon insert, GenBank accession number MW079275; GA2 product, example plasmid sequence provided as GenBank accession number MW079273; PMD-4681, GenBank accession number MW079274. Sequencing data are available in the Short Read Archive under project identifier PRJNA649279.

Methods

Sourcing Human Materials

Local ethical regulations were followed and informed consent was obtained for all human sample collection.

rCIG: A contract research organization (CRO; Access Biologics, New Orleans, La., USA) recruited under sample collection protocol #PRO00026464 (Advarra, Columbia, Md., USA) approved by Institutional Review Board (IRB) and included if donors were 12-46 days (average 24 days+/−14 days) from the onset of two or more COVID-19 symptoms (fever, cough, shortness of breath, sore throat, and pneumonia). Sixty mL of whole blood was collected in ACD tubes, de-identified, and transported overnight to GigaGen for processing. 16 donors with high SARS CoV-2 Spike antigen-specific antibodies by ELISA (as described below) were included in rCIG and were predominantly Caucasian (87.5%), female (75%), aged 49 (+/−17 years), collected 21 days (+/−6 days) from onset of symptoms, and were approximately equally distributed, with 6 donors with 2 symptoms, 6 donors with 3 symptoms, and 4 donors with 4 symptoms.

rHIG: A contract research organization (BloodCenter Wisconsin, Milwaukee, Wis., USA) vaccinated two donors (Donor 1, a 26-year-old Caucasian female, and Donor 2, a 21-year-old Asian male) with PedvaxHIB vaccine (Merck, Kenilworth, N.J., USA). Leukapheresis was performed eight or nine days later to obtain PBMCs. In parallel, plasma was isolated from separate blood draws on the day of leukapheresis and prior to vaccination. ELISA was performed against Hib (Alpha Diagnostics, San Antonio, Tex., USA; see methods below) on the plasma samples to confirm a response to the vaccine as compared to plasma from the same donors prior to vaccination. Sample collection protocols were approved by IRB protocol #PRO00028063 (Medical College of Wisconsin/Froedtert Hospital IRB) to GigaGen. Informed consent was obtained from all participants and samples were shipped to GigaGen de-identified.

rPIG: A contract research organization (AllCells, Alameda, Calif., USA) vaccinated three donors (Donor 1, 57-year-old Caucasian male; Donor 2, 44-year-old Caucasian male; Donor 3, 35-year-old Caucasian/Asian male) with Pneumovax®23 vaccine (Merck, Kenilworth, N.J., USA). 60 mL blood draw was performed eight days later. Plasma and pan-B cells were isolated from whole blood (see methods below). ELISA was performed against a mixture of all 23 pneumococcal polysaccharides (Alpha Diagnostics, San Antonio, Tex., USA; see methods below) on the plasma samples to confirm response to the vaccine. Sample collection protocols were approved by IRB protocol #7000-SOP-045 (Alpha IRB, San Clemente, Calif., USA) to AllCells. Informed consent was obtained from all participants and samples were shipped to GigaGen de-identified.

Processing Human Materials

For whole blood, PBMCs and plasma were isolated using density gradient centrifugation SepMate tubes with Lymphoprep medium (StemCell Technologies, Vancouver, BC, Canada). To isolate pan-B cells from PBMCs (from either whole blood or a leukopak), the Human EasySep Pan-B Cell Enrichment Kit (StemCell, Vancouver, BC, Canada) was used. After isolation, the cells were cryopreserved using CryoStor® CS10 (StemCell Technologies, Vancouver, BC, Canada). Immediately prior to generating paired heavy and light chain libraries, cells were thawed, washed in cold DPBS+0.5% BSA, assessed for viability with Trypan blue on a disposable hemocytometer (Bulldog Bio, Portsmouth, N.H., USA) or with AOPI on a Cellometer K2 (Nexcelom Bioscience, Lawrence, Mass., USA), and then re-suspended in 12% OptiPrep™ Density Gradient Medium (Sigma, St. Louis, Mo., USA) at 5,000-10,000 cells per µl. This cell mixture was used for microfluidic encapsulation as described below.

Immunization of Trianni Mouse® Mice

Local ethical regulations were followed for mouse immunizations, by Antibody Solutions IACUC (Sunnyvale, Calif., USA).

Humanized mice were engineered by Trianni (San Francisco, Calif., USA). Trianni mice were bred and obtained from Charles River Laboratories (Wilmington, Mass., USA). All mice were male and 12-15 weeks old at the start of the immunization process. Antibody Solutions (Santa Clara, Calif., USA) performed all Trianni Mouse immunizations. Local ethical regulations were followed for mouse immunizations by the Antibody Solutions IACUC. The mice were ear marked for identification by the breeder and housed in individually ventilated cages (Innovive, San Diego, Calif., USA) and racks with HEPA filtered air at a density of up to 5 mice per cage. The animal room was lighted entirely with artificial fluorescent lighting, with a controlled 12 h light/dark cycle (7 am to 7 pm light). The normal temperature and relative humidity ranges in the animal rooms were 20-22.2° C. and 30-70%, respectively. The animal rooms were set to have up to 10 air exchanges per hour. Sunnyvale municipal tap water and rodent chow (Teklad Global, Indianapolis, Ind., USA) were provided ad libitum.

rZIG: Two Trianni humanized mice were immunized consecutively weekly with Zika VLP, inactivated Dengue 1, inactivated Dengue 4, inactivated Dengue 3, then inactivated Dengue 2 with alhydrogel/muramyl dipeptide (ALD/MDP) adjuvant. Animals were checked for antibody titer and boosted with Zika VLPs without adjuvant 5 days before harvest (Antibody Solutions, Santa Clara, Calif., USA).

rhATG: Two Trianni humanized mice were immunized weekly with human thymocytes from 5 de-identified specimens acquired from a CRO (Vitalant Research Institute, San Francisco, Calif., USA) for 5 weeks with ALD/MDP adjuvant and boosted on week 6 without adjuvant. Three Trianni mice were immunized weekly for 5 weeks with Pan T cells (StemCell, Vancouver, Canada) in ALD/MDP isolated from PBMCs from 1 de-identified donor (StemCell), checked for an elevated antigen-specific antibody titer, and boosted with the same cells 5 days before harvest without adjuvant (Antibody Solutions, Santa Clara, Calif., USA).

After sacrifice, spleen, lymph nodes, and/or bone marrow were harvested and processed into a single cell suspension. Samples from multiple mice were pooled together by tissue and pan-B cells were isolated from spleen and lymph node tissue using the EasySep Mouse Pan-B Cell Enrichment Kit (StemCell Technologies, Vancouver, BC, Canada). CD138+ cells were isolated from bone marrow using Miltenyi CD138+ mouse microbeads (Miltenyi, Bergisch Gladbach, Germany). After isolation, the cells were cryopreserved using CryoStor® CS10 (StemCell Technologies, Vancouver, BC, Canada).

Generating Paired Heavy and Light Chain Libraries

Generation of scFv libraries from antibody-producing cells (Adler et al., 2017) comprises three steps: (i) poly(A)+ mRNA capture, (ii) multiplexed overlap extension reverse transcriptase polymerase chain reaction (OE-RT-PCR), and (iii) nested PCR. Briefly, a microfluidic device captures single cells in droplets with a mixture of lysis buffer and oligo dT beads (NEB, Ipswich, Mass., USA). After the cell is lysed and mRNA is bound to the bead, the emulsion is broken, and the mRNA-containing beads are purified. Next, an emulsion is created using OE-RT-PCR reagents and the beads as template. The emulsion is subjected to thermal cycling which creates cDNA, amplifies the IgK and IgG variable regions, and links them together in an scFv format. Then the emulsion is broken and the linked scFv DNA product is extracted and purified. The purified scFv product is then amplified using nested PCR to remove artifacts and add adapter sequences. Depending on the adapter sequences, the product can be used for deep sequencing, yeast display libraries, or full-length CHO expression.

To convert the scFv libraries into full-length CHO expression libraries, nested outer PCR primers were first used to add adapters with overhangs for Gibson assembly to the 5' and 3' ends of the scFv library (for rCIG, this was done after yeast scFv display enrichment, as described in the next section). Then NEBuilder HiFi DNA Assembly Master Mix (NEB, Ipswich, Mass., USA) was used to insert the scFv library into a vector containing a single promoter, a secretory leader sequence for light chain Ig and the remainder of the IgG1 constant region, creating a cloned scFv library. This intermediate library was transformed into E. coli and plasmids were purified by either (a) spreading onto LB-ampicillin plates, scraping 0.5-1 million colonies and pooling or (b) inoculating directly into LB-ampicillin broth and growing overnight. Plasmid purification was performed using ZymoPURE II Plasmid Maxiprep Kits (Zymo Research, Irvine, Calif., USA). To create the full-length antibody library, a second Gibson assembly was performed by linearizing the product of GA1 with BamHI-HF (rHIG) or NheI-HF (rCIG, rPIG, rhATG, and rZIG) (NEB, Ipswich, Mass., USA) and using it as a vector to insert a synthetic amplicon containing a portion of the light chain Ig constant region, a poly(A) signal for light chain Ig, a promoter for the IgG gene and a secretory leader sequence for the IgG gene. The full-length library was then transformed into E. coli and spread on LB-ampicillin plates. >0.5 million colonies were combined and plasmid with a ZymoPURE II Plasmid Maxiprep Kits (Zymo Research, Irvine, Calif., USA) was purified to make the full-length recombinant hyperimmune maxiprep library for transfection. When the transformed E. coli were inoculated directly into LB-ampicillin broth, a small volume of cells was plated to calculate the total number of transformants. In some cases ampicillin was used for both plates and broth, in other cases carbenicillin was used instead. Paired heavy and light chain libraries were made only once from each sample.

Enrichment for Antigen Binders by Yeast scFv Display

Polyclonal COVID-19 scFv libraries were sorted (Adler et al., 2017) to enrich for relevant sequences. Briefly, yeast surface display scFv libraries were generated using COVID-19 scFv DNA libraries and a custom yeast surface display vector transformed by electroporation into EBY100 yeast strain (MYA-4941; ATCC, Manassas, Va., USA). Surface displayed scFv sequences include a C-terminal myc tag to identify scFv expression with an anti-myc primary (A21281; Thermo Fisher Scientific, Waltham, Mass., USA) and AF488 secondary antibody (A11039; Thermo Fisher Scientific, Waltham, Mass., USA). Binding to antigen was identified by staining with soluble biotinylated SARS CoV-2 receptor binding domain antigen (SPD-C82E9; Acro Biosystems, Newark, Del., USA) at 1200 nM and APC-streptavidin (SA1005; Thermo Fisher Scientific, Waltham, Mass., USA). Stained yeast libraries were sorted on a FACSMelody (BD Biosciences, San Jose, Calif., USA) and double positive (AF488+/APC+) cells were collected. The gating strategy is outlined in Supplementary Figure S2. The collected cells were expanded and sorted again to further enrich the libraries. After the second round of sorting, cells were expanded a third time prior to plasmid isolation with a Zymoprep Yeast Plasmid Miniprep kit (Zymo Research, Irvine, Calif., USA). The plasmid libraries were then used as template for barcoding PCR and subsequent analysis by deep sequencing (Illumina, San Diego, Calif., USA). Plasmid from twice-sorted libraries was used as template for PCR towards full-length CHO antibody expression. Yeast scFv sorting was performed only once from each yeast scFv library.

Cell Line Used for rHIG and rhATG

The adherent Flp-In™-CHO cell line with a genetically integrated FRT site (Thermo Fisher Scientific, Waltham, Mass., USA) was adapted to suspension culture. For all steps in the adaptation process, "Ham's F-12" refers to Ham's F-12 (with L-glutamine, Thermo Fisher Scientific, Waltham, Mass., USA) plus 10% FBS (Thermo Fisher Scientific, Waltham, Mass., USA), and "BalanCD" refers to BalanCD CHO Growth A (Irvine Scientific, Santa Ana, Calif., USA) with 4 mM Glutamax (Thermo Fisher Scientific, Waltham, Mass., USA). To adapt this cell line to suspension, the cells were first passaged into a mixture of 50% Ham's F-12 plus 50% BalanCD in T-flasks. Cells were next passaged into 25% Ham's F-12 plus 75% BalanCD and switched to shaking Erlenmeyer flasks. Cells were then passaged into 10% Ham's F-12, 90% BalanCD+0.2% anti-clumping agent (Irvine Scientific, Santa Ana, Calif., USA) and banked for future use.

Approximately 100 million of the adapted Flp-In CHO cells were transfected per recombinant hyperimmune globulin library using an Amaxa Nucleofector 4D (SG buffer, pulse DU133; Lonza, Basel, Switzerland). These cells were plated into shaking Erlenmeyer flasks and recovered in an incubator at 37° C., 5% $CO_2$, 125 rpm. After 48 hours, the cells were counted to determine viability, cells were seeded at 1 million cells/mL, and selection was started using 600 µg/mL Hygromycin-B (Gemini Bio, West Sacramento, Calif., USA) in fresh media. Cells were counted and media was changed every 2-3 days during the 7-day selection. The libraries were kept on 600 µg/mL Hygromycin-B (Gemini Bio, West Sacramento, Calif., USA) during expansion until viability exceeded 95%. When cells were >95% viable and doubling every 24 hours, the adapted Flp-In™-CHO cell line was banked for liquid nitrogen storage. Before banking, cells were sampled from each library, RNA was purified, and antibody RNA-seq (Illumina, San Diego, Calif., USA) was performed to assess the diversity of the libraries (Table 13 and 17).

Cell Line Used for rPIG, rZIG, and rCIG

A landing pad construct (FIG. 13E, PMD-4681; GenBank accession number MW079274) was designed and cloned at GigaGen. PMD-4681 was based on pFRT-lacZeo (Thermo Fisher Scientific, Waltham, Mass., USA), with some modifications. In place of the LacZ expression construct a cassette was inserted coding for expression of CD34 and GFP. The CD34, GFP, and downstream Zeocin resistance genes (ZeoR present in pFRT-lacZeo) were separated by 2A motifs (T2A or P2A) to allow for translation of three separate polypeptide chains. The CD34 sequence was sourced as a gBlock from IDT (Coralville, Iowa, USA). The GFP sequence was sourced from ATUM (DasherGFP; Newark, Calif., USA).

The GMP suspension CHO line CHOZN® GS-/- was obtained from MilliporeSigma (St. Louis, Mo., USA). PMD-4681 was linearized using ScaI-HF and purified via ethanol precipitation. Cells were transfected with the linearized DNA using Amaxa Nucleofector 4D, SE kit, pulse CM-150 (Lonza, Basel, Switzerland). Cells recovered overnight in an incubator and were plated the next day into minipools at approximately 5,000 cells per well, across ten 96-well plates in selective media. The remaining cells were plated and selected together as a bulk pool control. Wells were topped off with fresh media every seven days until at least 80% confluency was reached.

A total of 236 minipools grew out and were screened in parallel for high GFP expression via flow cytometry and low copy number with a quantitative PCR Copy Number Variation (CNV) assay. Minipools with a copy number less than 2.5 and GFP expression at least 50% of the bulk pool were expanded into shaking adaptation. Expanded pools were re-tested for GFP expression via flow cytometry.

Cells were then adapted to BalanCD CHO Growth A in preparation for plating into semi-solid media. Minipools were deemed fully adapted when cells showed consistent doubling times and high viability (>90%). Adapted cells were plated into semisolid media for the Molecular Devices (Fremont, Calif., USA) ClonePix3 single cell cloning platform. Single cell imaging was obtained on day 0 of cell plating in semisolid media to confirm monoclonality. After 14 days, clonal cell colonies were picked and deposited as one colony per well of a 96-well plate. Each clone was then expanded, re-adapted to selection media, and cryopreserved. Doubling times were calculated and clones with less than a 30-hour doubling time were chosen for further development. Expanded clones were retested for GFP expression and copy number.

Remaining clones were transfected in duplicate using the Gene Pulser Xcell Total System (BioRad, Hercules, Calif., USA) per guidelines from MilliporeSigma (St. Louis, Mo., USA) for use with CHOZN GS with a monoclonal antibody (mAb)-cyan fluorescent protein (FrostyCFP, ATUM, Newark, Calif., USA) construct to test expression titer. CFP expression was evaluated via flow cytometry 3 days post transfection to confirm transfection efficiency >35%. After full selection and recovery, cell lines were tested in a 10-day fed batch TPP shaking production run in duplicate. Titers for candidate cell lines ranged from 50-100 mg/L. A single clone (CSS-1286) was selected to use for recombinant hyperimmune expression.

For transfection of recombinant hyperimmune globulins into CSS-1286, approximately 50 million cells were transfected per recombinant hyperimmune globulin library using the BioRad Gene Pulser Xcell Total System (Hercules, Calif., USA), per guidelines from MilliporeSigma (St. Louis, Mo., USA) for use with CHOZN GS. The cells were plated into T-75 flasks (approximately 10 million cells per flask) and recovered in an incubator at 37° C., 5% $CO_2$ for 72 hours. After 72 hours, the cells were counted to determine viability and then seeded into 100 mL fresh media without glutamine (EX-CELL CD CHO Fusion, MilliporeSigma, St. Louis, Mo., USA) in a 500 mL Erlenmeyer flask. Cells were counted and media was changed every 2-3 days during the ~14-day selection. When cells were >95% viable and doubling every 24 hours, the cell line was banked for liquid nitrogen storage. Before banking, cells were sampled from each library, RNA was purified, and antibody RNA-seq (Illumina, San Diego, Calif., USA) was performed to assess the diversity of the libraries (Tables 9, 11, 14).

Bioproduction of rHIG and rhATG RPP

Adapted Flp-In™-CHO cells stably expressing antibody libraries were grown in media consisting of 90% BalanCD CHO Growth A Medium (Irvine Scientific, Santa Ana, Calif., USA), 9% Ham's F-12 (Thermo Fisher Scientific, Waltham, Mass., USA), 1% FBS (Thermo Fisher Scientific, Waltham, Mass., USA), 4 mM Glutamax (Thermo Fisher Scientific, Waltham, Mass., USA), 0.2% anti-clumping agent (Irvine Scientific, Santa Ana, Calif., USA), 600 µg/mL Hygromycin-B (Gemini Bio, West Sacramento, Calif., USA). Protein production was performed at either small (250 mL) or medium (5 L) scale. For small-scale production, cells were seeded at $1\times10^6$ cells/mL into 50 mL media in a 250 mL Erlenmeyer flask and grown at 37° C., 5% $CO_2$, 125 rpm. Cells were continually grown under these conditions and supplemented with 7.5 mL CHO Feed 1 (Irvine Scientific, Santa Ana, Calif., USA) on Days 2, 4 and 7 of the production run. Supernatant was harvested on Day 8 or 9 by centrifugation followed by filtration through a 0.22 µm 250 mL filter bottle (MilliporeSigma, St. Louis, Mo., USA) with 1 µm pre-filter (MilliporeSigma, St. Louis, Mo., USA). Harvested cell culture fluid (HCCF) was stored at 4° C. (if less than 1 week) or at −80° C. (if more than one week) until Protein A purification. For medium-scale production, cells were grown in the same media. Cells were then seeded at $1\times10^6$ cells/mL in 2.3 L in a 5 L flask (in duplicate; Day 0). Each flask was fed with 345 mL CHO Feed 1 (Irvine Scientific, Santa Ana, Calif., USA) on Days 2 and 4 of the culture. Cultures were harvested on Day 8 or 9. Each of the four rhATG protein libraries were produced separately.

Bioproduction of rPIG, rZIG, and rCIG RPP

CSS-1286 CHO cells stably expressing antibody libraries were grown in media without glutamine (EX-CELL CHOZN Advanced; MilliporeSigma, St. Louis, Mo., USA). Protein production was performed at either small (250 mL) or medium (5 L) scale. For small-scale production, cells were seeded at $0.5\times10^6$ cells/mL into 100 mL media in a 500 mL Erlenmeyer flask and grown at 37° C., 5% $CO_2$, 125 rpm. Cells were continually grown under these conditions and supplemented with 15 mL CHO Feed 1 (MilliporeSigma, St. Louis, Mo., USA) on Day 3, and 10 mL CHO Feed 1 (MilliporeSigma, St. Louis, Mo., USA) on Days 6 and 8 of the production run. Starting on Day 3, glucose was measured each day and supplemented to 6 g/L if below 4 g/L. Supernatant was harvested after cell viability peak and before dropping below 90% viability between Days 9-11, centrifuged and filtered through a 0.22 µm 250 mL filter bottle (MilliporeSigma, St. Louis, Mo., USA) with 1 µm pre-filter (MilliporeSigma, St. Louis, Mo., USA). HCCF was stored at 4° C. (if less than 1 week) or at −80° C. (if more than one week) until Protein A purification. For medium-scale production, cells were grown in the same media. Cells were seeded at $0.5\times10^6$ cells/mL in 2.2 L in a 5 L flask (in duplicate; Day 0). Each flask was fed with 330 mL CHO Feed 1 (MilliporeSigma, St. Louis, Mo., USA) on Day 3 and 220 mL CHO Feed 1 (MilliporeSigma, St. Louis, Mo., USA) on Days 6 and 8 of the production run. Starting on Day 3, glucose was measured each day and supplemented to 6 g/L if below 4 g/L. Cultures were harvested on Day 10-12.

RPP Protein Production and Characterization

After harvest, HCCF was purified using a 1 mL or 5 mL HiTrap MabSelect PrismA Protein A Column (GE Life Sciences, Marlborough, Mass., USA) using the following buffers: 1×PBS pH 7.0-7.4 (Teknova, Hollister, Calif., USA) for running and wash buffer, 0.1 M Citrate Buffer, pH 3.0 (Teknova, Hollister, Calif., USA) for elution buffer, 1 M Sodium Citrate, pH 6.0 (Teknova, Hollister, Calif., USA) for neutralization. The column was washed at 10 mL/min until UV was stable, then sample was injected at 5 mL/min. The column was washed with 10 column volumes at 10 mL/min. Protein was eluted using elution buffer at 5 mL/min, collecting 1 mL fractions. Fractions were then pooled. Pooled sample was neutralized slowly using 1 M Sodium Citrate to a pH of ~5.0. Neutralized sample was centrifuged at 5000×g to remove any precipitation, then dialyzed overnight into 0.2 M glycine, pH 4.5 (Teknova, Hollister, Calif., USA) using a 20K MWCO Dialysis Cassette (Thermo Fisher Scientific, Waltham, Mass., USA). Buffer was changed once, then sample was removed, spun down to remove any precipitant, filtered through a 0.22 μm filter and quantified by A280 (NanoDrop; Thermo Fisher Scientific, Waltham, Mass., USA). For rhATG, each of the four libraries were purified by Protein A separately and then equally pooled based on mass.

Purity of the protein was determined by SEC-HPLC. 20 μg of material at 1 mg/mL was injected over a 300 Å, 2.7 μm, 7.8×300 mm size exclusion column (Agilent, Santa Clara, Calif., USA) using a mobile phase of 25 mM phosphate, 200 mM NaCl pH 7.0 with 10% acetonitrile at 1 mL/min. The percent monomer was determined by integrating the product peaks and reporting the percent area corresponding to ~150 kDa. The product was further characterized by running 2 μg on a 12% SDS-PAGE gel under reduced and non-reduced buffering conditions, and imaged after staining with SimplyBlue SafeStain (Thermo Fisher Scientific, Waltham, Mass., USA).

Medium-Scale Production, Polishing, and Stress Testing of rCIG

For bioreactor production at 3 L scale, a seed train protocol was devised to mimic the number of passages required for production at up to 2,000 L scale. For each bioreactor production run, a single vial of rCIG cell bank was thawed at 37° C. and the contents of the vial were transferred to 10 mL of EX-CELL CD CHO Fusion media (MilliporeSigma, St. Louis, Mo., USA). The cells were then centrifuged for 5 minutes at 500×g. The supernatant was aspirated and discarded, and the cells were re-suspended in 5 mL of EX-CELL CD CHO Fusion. The entire volume of cells was seeded into a 250 mL non-baffled, vented shake flask at a final volume of 50 mL. The shake flask was incubated at 37° C., 5% $CO_2$, >80% humidity and 125 RPM (25 mm orbital diameter). Three days post thaw the viable cell density (VCD) was $4.0$-$6.0\times10^6$ vc/mL with a viability ≥90%. At this point the cells were passaged using EX-CELL CD CHO Fusion into a 1000 mL shake flask at a seeding density of $0.4\times10^6$ vc/mL. In a similar manner, the culture was passaged once more into a 1000 mL shake flask, and then two more times into 1000 mL spinner flasks. The final passage before bioreactor inoculation was done in EX-Cell Advanced CHO Fed Batch media (MilliporeSigma, St. Louis, Mo., USA).

Three days after completing the fifth passage, three 3 L Mobius single-use bioreactors (MilliporeSigma, St. Louis, Mo., USA) were seeded using the culture. Each bioreactor was prepared with 1300 mL of EX-Cell Advanced CHO Fed Batch media and then seeded at a VCD of $0.4\pm0.1\times10^6$ vc/mL. Additional media was added if required to have an initial working volume of 1600 mL. Each bioreactor was controlled using the following set points: temperature setpoint Days 0-4 setpoint 37° C.; temperature Days 4-14 setpoint 32° C.; dissolved oxygen setpoint 30%; pH Days 0-3 7.0±0.2; pH Days 3-14 7.0±0.1. EX-Cell Advanced CHO Feed (MilliporeSigma, St. Louis, Mo., USA) and Cellvento 4Feed COMP (MilliporeSigma, St. Louis, Mo., USA) were added on Days 3, 5, 7, 9, and 11. Feed volumes were determined as a percentage of the current bioreactor volume, such that EX-Cell Advanced CHO Feed was added at 4% of the volume of the bioreactor and Cellvento 4Feed COMP was added at 2% of the volume of the bioreactor. Glucose levels were monitored daily, and starting on Day 3 were maintained above 4 g/L by adding a 45% Glucose solution until levels reached 6 g/L. The bioreactors were harvested after 14 days of culture. 5-10 million cells were collected from each bioreactor for antibody repertoire sequencing (FIG. 23A-23B).

For purification and polishing, an empty column was packed with MabSelect Sure PrismA resin (Cytiva, Marlborough, Mass., USA) and equilibrated with 20 mM phosphate, 150 mM NaCl, pH 7.4. Harvested cell-culture fluid was loaded at 20-40 g/L, washed with 20 mM phosphate, 500 mM NaCl, pH 7.4 and 50 mM phosphate, pH 6.0, and eluted with 50 mM sodium acetate, pH 3.5. The pH of the Protein A eluate was adjusted to 3.5 using 1 M acetic acid and the material was subjected to a 1 hour viral hold, after which it was adjusted to pH 5 using 1 M Tris-HCl, pH 9 and filtered to remove particulate. A second column was packed with POROS XS (Thermo Fisher Scientific, Waltham, Mass., USA) cation exchange (CEX) resin and equilibrated with 50 mM sodium acetate, pH 5.0. The filtered neutralized low pH hold pool was loaded on this column at 14-21 g/L, washed with 50 mM sodium acetate, 100 mM sodium chloride, pH 5.0, and eluted over a 20 CV gradient to 50 mM sodium acetate, 400 mM sodium chloride, pH 5.0. The product eluted with several distinct peaks, of which only the first was collected. The pooled CEX eluate was diluted with 20 mM tris-acetate, pH 7.4 to <8 mS/cm, then flowed through a Sartobind Q (Sartorious, Gottingen, Germany) anion-exchange membrane. The flowthrough was concentrated using a 30K molecular weight cutoff cellulose acetate tangential flow filtration cartridge (MilliporeSigma, St. Louis, Mo., USA), then diafiltered with 200 mM glycine pH 4.5 and sterile-filtered.

For stress testing, polished rCIG at 15 mg/mL in 200 mM glycine, pH 4.5 was incubated at 40° C. for 14 days. Separately, aliquots were subjected to 3 or 25 freeze-thaw cycles in a −80° C. freezer or dry ice/ethanol bath. The stressed samples were run on SEC-HPLC and SARS CoV-2 S1 ELISA and compared to a control that was stored at 4° C.

Deep Antibody Repertoire Sequencing

Deep antibody sequencing libraries were prepared as described previously (Adler et al., 2017), quantified using a KAPA quantitative PCR Illumina Library Quantification Kit (Roche, Mannheim, Germany), and diluted to 17.5 pM. Libraries were sequenced on a MiSeq (Illumina, San Diego, Calif., USA) using a 500 cycle MiSeq Reagent Kit v2, according to the manufacturer's instructions. To make sequencing libraries, tailed-end PCR was used to add Illumina sequencing adapters to the 5' and 3' ends of the constructs of interest. For scFv libraries (after droplet emulsion breaking or yeast plasmid isolation), a forward read of 340 cycles was used to capture the light chain CDR3 sequence, and a reverse read of 162 cycles was used to capture the linked heavy chain CDR3 sequence. For CHO libraries, the full-length heavy chain sequence was obtained using overlapping forward and reverse reads of 251 cycles. To determine the number of antibody clones in the final CHO cell libraries and for generating the clonal cluster analysis figures, 5-10 million CHO cells were harvested prior to a production run. For the batch-to-batch variation analysis, 5-10 million CHO cells were harvested at the conclusion of the replicate production runs, and a median of 855,746 sequence reads were obtained for each sequencing library (range: 658,013 to 1,113,968).

To determine the Fc subtype of a library, the heavy chain was amplified with a primer that binds further into the constant domain to add the Illumina sequencing adapter to the 3' end; the first 60 bp of the constant domain was sequenced to determine the subtype, which was linked to the corresponding CDR3H that was simultaneously sequenced. Each library was sequenced one time.

Sequence analysis, including error correction, reading frame identification, and FR/CDR junction calls was performed using our previously reported bioinformatics pipeline (Adler et al., 2017). Reads with E>1 (E is the expected number of errors) were discarded, to retain sequences for which the most probable number of base call errors is zero. Clones are defined as sequences with unique CDR3 amino acid sequences (CDR3K+CDR3H for scFv clones, CDR3H only for CHO clones). A more conservative clone count is also provided (combined CDR3), where unique clones were combined if they had 1 amino acid difference for 5-6 amino acid long CDR3s, or if they had 1-2 amino acid differences for >6 amino acid long CDR3s; this applies to a concatenation of CDR3K+CDR3H for scFv clones or CDR3H only for CHO clones).

For the clonal cluster analysis, USEARCH (Edgar, 2010) to compute the total amino acid differences between each pairwise alignment of full-length heavy chain sequences with abundance ≥0.01% in each CHO cell bank. Then the R package graph (version 1.2.4.1) was used to generate clustering plots for the pairwise alignments. The sequences were represented as "nodes", with the color (and sometimes shape) defined in the respective figures. The size of the nodes reflects the frequency of the clone (small, <0.1%; medium, 0.1-1%; large, >1%). "Edges" are the links between nodes, which indicate pairwise alignments with <5 amino acid differences. The layout with graphopt (niter=3000, charge=0.03) option was used to format the output. To visualize the sequences within a library, the top five clusters containing the highest number of connected nodes/sequences were selected. These sequences were aligned and visualized as sequence logos using the R package msa 1.16.0.

To assess antibody repertoire overlap between libraries, Jaccard and Morisita indices were computed using the R package tcR (version 2.3.2). Shannon entropy and Simpson diversity indices were calculated using the R package vegan 2.5.5. Heavy chain V and J gene identities were measured using the USEARCH[49]-local algorithm with the germline database as reference. For the heatmaps showing the pairing of VH and VL genes, the germline divergence histograms, and the histograms showing the distribution of heavy chain CDR3 length, each unique clone was plotted once (i.e., not scaled by sequencing read abundance).

To estimate the error rate due to RNA/cDNA amplification, a region of the heavy chain constant domain from the rCIG libraries (the region used to determine the heavy chain subtype) was sequenced, after performing the same amplification process as the final polyclonal libraries. The total error rate for this region was 0.3%, then using Illumina's quality (Q) score for each sequenced base, the estimated sequencing error rate for this region was determined to be 0.052%. Thus, the estimated maximum error rate from our amplification process is 0.3%-0.052%=0.248% (which may still contain some error due to natural sequence variation in the constant domain).

Sequencing data are available in the Short Read Archive (SRA) under project identifier PRJNA649279.

In vitro Efficacy Studies rCIG: Anti-SARS CoV-2 antibody reactivities were measured using a protocol based on published ELISA methods (Amanat et al., 2020). In brief, SARS CoV-2 Spike and RBD (wild type and variant proteins; Sino Biological, Wayne, Pa., USA) were used to coat ELISA plates at 2 µg/mL. Serial dilutions of antibody preparations including test plasma and recombinant products, positive control monoclonal antibodies (CR3022; Absolute Antibody, San Diego, Calif., USA, and SAD-535; Acro Biosystems, Newark, Del., USA) and negative control IVIG (Gamunex; Grifols, S. A., Sant Cugat, Spain) were performed in dilution buffer (1×PBS+0.05% Tween+0.3% dry milk) in singlet. Quantitative measurements were performed on a plate reader (Molecular Devices, Fremont, Calif., USA) and analyzed using Softmax Pro (Version 7.1; Molecular Devices, Fremont, Calif., USA) to calculate the EC50 concentrations of samples. The concentration of total IgG was calculated by Cedex Bioanalyzer Human IgG assay (Roche, Mannheim, Germany).

Blocking of binding between Spike RBD and ACE2 was demonstrated by ELISA (BPS Bioscience, San Diego, Calif., USA). In brief, SARS CoV-2 Spike RBD protein was coated onto an ELISA plate, serial dilutions of test plasma and recombinant products, positive control monoclonal antibodies (CR3022; Absolute Antibody, San Diego, Calif., USA, and SAD-S35; Acro Biosystems, Newark, Del., USA) and negative control IVIG (Gamunex; Grifols, S. A., Sant Cugat, Spain) were performed in singlet in dilution buffer (1×PBS+0.05% Tween+0.3% dry milk). After incubation, ACE2-His was added at 2.5 ng/mL. After further incubation, anti-His-horseradish peroxidase was added. The plate was developed for a chemiluminescent readout. Quantitative measurements were performed on a plate reader (Molecular Devices, Fremont, Calif., USA) and analyzed using Softmax Pro (Version 7.1; Molecular Devices, Fremont, Calif., USA) to calculate the EC50 concentrations of samples.

The SARS CoV-2 pseudotype virus neutralization assay was performed in a 96-well plate using ACE2 expressing HEK-293T target cells (CRL-11268; ATCC, Manassas, Va., USA) transiently transfected with TMPRSS-2 expression plasmid. The GFP reporter pseudotype virus expressing SARS-CoV-2 spike (Integral Molecular, Philadelphia, Pa., USA) was mixed with test plasma, test rCIG, positive control monoclonal antibodies (CR3022; Absolute Antibody, San Diego, Calif., USA, and SAD-S35; Acro Biosystems, Newark, Del., USA) and negative control IVIG (Gamunex; Grifols, S. A., Sant Cugat, Spain) at a five-fold dilution series in singlet. After one-hour incubation, $4 \times 10^4$ cells target cells were added to each well and incubated at 37° C. for 48 hours. After incubation, the media was removed from all wells without disturbing the adherent cells. TrypLE (Thermo Fisher Scientific, Waltham, Mass., USA) was added to each well and incubated for 3 minutes at 37° C. Media was added to stop trypsinization and cells were stained with DAPI and passed through a 30-40 µm filter (Pall Corporation, Port Washington, N.Y., USA) before quantifying GFP+ cells using a Cytoflex LX (Beckman Coulter, Indianapolis, Ind., USA). Flow cytometry data were analyzed by FlowJo (BD Biosciences, San Jose, Calif., USA).

SARS CoV-2 microneutralization assays were performed at the Regional Biocontainment Laboratory at Duke University Medical Center (Durham, N.C., USA) in a 96-well plate format using Vero E6 cells (CRL-1586; ATCC, Manassas, Va., USA) infected with 100 TCID50 dose of the 2019-nCoV/USA-WA1/2020 strain. Test and control samples were initially diluted to 1:50, then a 12-step, two-fold serial dilution of test antibodies was performed before infection of the cells; every test or control was run in duplicate. IVIG (Gamunex; Grifols, S. A., Sant Cugat, Spain) was used as negative control. Cell-only control wells were included alongside virus-only treated wells. Following 4 days of infection, culture media was removed, and cell monolayer was fixed with 10% neutral buffered formalin (NBF) and stained with 0.1% Crystal Violet. Absorbance at 590 nm or visual inspection was used to measure the monolayer condition/level of infection. Neutralization was reported as the lowest concentration of sample that prevents cytopathic effect in the monolayer of cells.

rZIG: Zika- and Dengue-specific antibodies were measured by ELISA. A 96-well microtiter plate was coated with either 2 µg/ml Zika or Dengue Serotype 1, 2, 3, or 4 recombinant envelope proteins (ProSpec Bio, East Brunswick, N.J., USA) in 1× carbonate coating buffer (BioLegend, San Diego, Calif., USA) and incubated overnight at 4° C. After blocking the coated plate with ultrablock buffer (Bio-Rad, Hercules, Calif., USA) and washing with PBS+ 0.05% Tween-20 (Teknova, Hollister, Calif., USA), eight-step three-fold serial dilutions in assay buffer (1×PBS+ 0.05% Tween+0.3% dry milk) were performed on rZIG-IgG1, rZIG-LALA, Zika/Dengue+serum positive control (Seracare, Milford, Mass., USA), and a negative control IVIG (Gamunex; Grifols, S. A., Sant Cugat, Spain). Dilutions were added in duplicate and incubated at 37° C. for 1 hour. Next, 1:2500 secondary rabbit anti-human IgG horseradish peroxidase conjugate (Southern Biotech 6140-05, Birmingham, Ala., USA) was added, and the plate was washed and developed using 3,3',5,5'-tetramethylbenzidine (TMB) substrate solution (Thermo Fisher Scientific, Waltham, Mass., USA). The reaction was halted after 8 minutes using sulfuric acid stopping solution (Southern Biotech, Birmingham, Ala., USA). Quantitative absorbance measurements were performed on a SpectraMax i3x plate reader (Molecular Devices, Fremont, Calif., USA) at 450 nm and 620 nm. Standard curves (OD450-620) were artificially set to max out at 2.97 absorbance value. EC50 values were calculated by non-linear regression analysis using GraphPad Prism v8 (San Diego, Calif., USA).

Zika and Dengue in vitro pseudotype neutralization assays were performed at Vitalant Research Institute (VRI, San Francisco, Calif., USA). rZIG, a Zika/Dengue-specific immune sera (UWIS; de-identified sample screened positive for Zika and Dengue 1-4 by University of the West Indies), monoclonal antibody positive control (UWI-mAb1; IgG1 isotype cloned from de-identified donor by University of the West Indies, found to be cross-reactive to Zika and Dengue 1-4), and IVIG negative control (Gamunex; Grifols, S. A., Sant Cugat, Spain) were co-incubated with reporter virus particles (RVPs; Integral Molecular, Philadelphia, Pa., USA) expressing both luciferase and flavivirus-specific glycoproteins as previously described. Briefly, BHK/DC-SIGN cells (CRL-325; ATCC, Manassas, Va., USA) were seeded in black 96-well plates and then incubated with a 7-step, 3-fold serial dilution of antibodies pre-incubated for one hour at 37° C. with RVPs and tested in duplicate. After 72 hours cells were lysed and luciferase activity measured using lysis buffer and firefly luciferase substrate following manufacturer's guidelines (Promega, Madison, Wis., USA). Infection-induced relative light units (RLU) in the presence of test articles were calculated as the RLU of the test article divided by the RLU of a no-serum control infection. The amount of protein required to inhibit 50% of the maximum untreated Zika or Dengue RLUs (IC50) was calculated by non-linear regression analysis using GraphPad Prism v8 (San Diego, Calif., USA).

Zika pseudotype assays for in vitro antibody-dependent enhancement (ADE) were performed at VRI. rZIG, the Zika/Dengue-specific immune sera UWIS, the monoclonal antibody positive control UWI-mAb1, and IVIG negative control (Gamunex; Grifols, S. A., Sant Cugat, Spain) were serially diluted and co-incubated with Zika pseudotype RVPs at 37° C. for 1 hour before addition to K562 chronic myelogenous leukemia cells (CCL-243; Manassas, Va., USA) in U-bottom 96-well plates in triplicate. After a 72 hour incubation at 37° C., cells were harvested, lysed, and infection-induced relative light units (RLU) in the presence of test articles were calculated as the RLU of the test article divided by the RLU of a no antibody control infection (to determine the reported fold-increase in infection).

rHIG: The Human Anti-Hib-PRP IgG ELISA kit (#980-100-PHG, Alpha Diagnostics, San Antonio, Tex., USA) was used for anti-Hib ELISA titers. Serial dilutions of test articles were performed in Low NSB (non-specific binding) sample diluent in singlet. IVIG (Gamunex; Grifols, S. A., Sant Cugat, Spain) was used as a reference control. Quantitative measurements were performed on a plate reader (Molecular Devices, Fremont, Calif., USA) at 450 nm. EC50 values were calculated using SoftMax Pro v8 (Molecular Devices, Fremont, Calif., USA).

In vitro serum bactericidal assay neutralization studies for Hib were performed at ImQuest (Frederick, Md., USA). The *Haemophilus influenzae* strain ATCC 10211 was obtained from ATCC (Manassas, Va., USA) as a lyophilized stock and was propagated as recommended by the supplier. The Eagan strain was obtained from Zeptometrix (Buffalo, N.Y., USA). Colonies from an overnight incubation on chocolate agar plates were inoculated into growth media (Brain Heart Infusion, or BHI broth; BD Biosciences, San Jose, Calif., USA, with 2% Fildes enrichment; Remel, San Diego, Calif., USA) and allowed to achieve an optical density of 625 nm ($OD_{625}$) of approximately 0.4. The culture was adjusted to an OD625 of 0.15, which is equivalent to approximately $5 \times 10^8$ colony forming units (CFU)/mL. The culture was further diluted to $5 \times 10^4$ CFU/mL in dilution buffer (Hanks Balanced Salt Solution; Gibco, Waltham, Mass., USA, with 2% Fildes enrichment; Remel, San Diego, Calif., USA). The density of the bacterial culture used in the assay was confirmed by plating 50 µL of the $5 \times 10^3$ and $5 \times 10^2$ dilutions in duplicate on chocolate agar and enumerating the colonies following incubation at 37° C./5% CO2 for 24 hours. rHIG and IVIG (Gamunex; Grifols, S. A., Sant Cugat, Spain) reference control were diluted three-fold in buffer, starting at 200 µg/mL such that a total of ten total dilutions were evaluated in singlet. 10 µL of each dilution of test article was added in duplicate to a 96-well microtiter plate. ATCC 10211 bacteria at a concentration of approximately $5 \times 10^4$ CFU/mL were then added to the plate in a volume of 20 µL, such that the total in-well bacterial density would be $1 \times 10^4$ CFU/20 Following an incubation of 15 minutes at 37° C./5% CO2, 25 µL of baby rabbit complement (Pel-Freez; Rogers, Ark., USA) and 25 µL of dilution buffer was added to each well. The plate was incubated at 37° C./5% CO2 for 60 minutes. Following the incubation, 5 µL of each reaction mixture was diluted in 45 µL of dilution buffer and the entire 50 µL was plated on chocolate agar plates. The plates were incubated for approximately 16 hours at 37° C./5% CO2. Following incubation, bacterial colonies were enumerated. The fold-dilution of the test article that killed >50% of the bacteria is the serum bactericidal index (SBI).

rPIG: The Human Anti-S. Pneumococcal vaccine (Pneumovax/CPS23) IgG ELISA kit (Alpha Diagnostics #560-190-23G, San Antonio, Tex., USA) was used in parallel with the human anti-*S. pneumoniae* CWPS/22F IgG ELISA kit (#560-410-C22, Alpha Diagnostics, San Antonio, Tex., USA) for initial assessment of anti-pneumococcal titers against a pool of all 23 polysaccharides included in the vaccine.

Serotype-specific antibodies were measured by ELISA and opsonophagocytosis. The concentrations of serotype-specific IgG antibody were calculated using the standard reference serum, lot 007SP (National Institute for Biological Standards and Control; Hertfordshire, UK), using the standardized pneumococcal reference ELISA as previously described. Briefly, 96-well flat-bottomed microtiter plates were coated with capsular polysaccharide antigens (LGC Standards, Teddington, UK) from pneumococcal serotypes 1, 3, 4, 5, 6A, 6B, 7F, 9V, 12F, 14, 18C, 19A, 19F, 22F, 23F, and 33F. All samples were tested in duplicate and double absorbed with CWPS and with purified serotype 22F polysaccharide to neutralize the anti-cell wall polysaccharide and nonspecific homologous antibodies to serotype 22F, except for the 22F assay which was absorbed with CWPS Multi, as described in the WHO reference ELISA protocol. Plates were washed, and a titration of rPIG and reference control IVIG (Gamunex; Grifols, S. A., Sant Cugat, Spain) was performed. Plates were incubated and washed again, and prediluted alkaline phosphatase-conjugated goat anti-human IgG (Thermo Fisher Scientific, Waltham, Mass., USA) was added to each well. After another incubation, the plates were washed a final time and p-nitrophenyl phosphate substrate (MilliporeSigma, St. Louis, Mo., USA) was added. Following a final incubation, the reaction was stopped by adding 3 M NaOH (Thermo Fisher Scientific, Waltham, Mass., USA) to each well. Plates were read using a microtiter plate reader (SPECTROstar Omega; BMG Labtech, Buckinghamshire, UK) at 405 and 620 nm.

The opsonophagocytic indices (OI) to the same pneumococcal serotypes were evaluated by multiplexed opsonophagocytic assay, as previously described. In brief, frozen aliquots of target pneumococci were thawed, washed twice with opsonization buffer B (HBSS with Ca and Mg, 0.1% gelatin, and 10% fetal bovine serum), and diluted to the proper bacterial density (approximately $2 \times 10^5$ CFUs/mL each serotype). Equal volumes of four bacterial suspensions chosen for simultaneous analysis were pooled. Duplicate serially diluted test articles (20 µL/well) were mixed with 10 µL of bacterial suspension in each well of a microplate. After 30 minutes of incubation at room temperature with shaking at 700 rpm, 10 µL of 3- to 4-week-old rabbit complement (Pel-Freeze, Rogers, Ark., USA) and 40 µL of differentiated HL60 cells ($10^7$ cells; CCL-240, ATCC, Manassas, Va., USA) were added. Plates were incubated in a 37° C./5% CO2 incubator with shaking at 700 rpm. After being incubated for 45 minutes, plates were placed on ice for 20 minutes, and an aliquot of the final reaction mixture (10 µL) was spotted onto four different Todd-Hewitt broth with 0.5% yeast extract and 0.75% agar (THY) plate. When the fluid was absorbed into the agar, an equal volume of overlay agar containing one of four antibiotics (optochin, spectinomycin, streptomycin, or trimethoprim) was applied to each THY agar plate. After overnight incubation at 37° C., the number of bacterial colonies in the agar plates was enumerated. IVIG was used as reference control (Gamunex; Grifols, S. A., Sant Cugat, Spain). The OI was defined as the test product dilution that kills 50% of bacteria and was determined by linear interpolation.

rhATG: To assess relative amount and specificity of rhATG, an ELISA was performed on antigens known to be expressed on thymocytes and previously described as having rabbit-ATG reactivity.[41] Rabbit-ATG positive control was from Sanofi Genzyme (Thymogobulin; Cambridge, Mass., USA). T cell antigens (CD3, CD4, CD5, CD7, CD8, CD16a, CD32a, CD45, CD81, CD85 CD95) were purchased from Sino Biological (Wayne, Pa., USA) and individually coated onto 96-well ELISA plates (Thermo Fisher Scientific, Waltham, Mass., USA) at 1 µg/mL in 1× carbonate coating buffer (BioLegend, San Diego, Calif., USA). After an overnight incubation at 4° C., coated plates were washed and blocked (Bio-Rad, Hercules, Calif., USA) for 1 hour. Polyclonal products were diluted to 200 µg/mL of total IgG and an 8-step 1:3 titration in assay buffer (1×PBS+0.05% Tween+0.3% dry milk) was performed. The antibody titrations were added to each antigen and incubated for 1 hour at 37° C. 1:2500 polyclonal HRP goat anti-rabbit IgG (E28002; Novodiax, Hayward, Calif., USA) or 1:2500 mouse anti-human IgG HRP (109-035-088; Jackson ImmunoResearch, West Grove, Pa., USA) were diluted 1:2500 and incubated on the plate for 1 hour. Plates were washed, developed using 1-step ultra TMB substrate (Thermo Fisher Scientific, Waltham, Mass., USA), and stopped with 1 N HCl. Plates were read by a spectrophotometer (Molecular Devices, Fremont, Calif., USA) at 450 nm and analyzed with Softmax Pro (v7; Molecular Devices, Fremont, Calif., USA).

To assess off-target antibody binding a red blood cell antigen binding assay was performed, using the Capture-R kit (Immucor, Norcross, Ga., USA). Using a dilution of test article (Thymoglobulin or rhATG) or positive control from the Immucor kit, samples were added to the plate and incubated for 1 hr at 37° C. in singlets. ELISA plates were washed and incubated with 1:2500 polyclonal HRP goat anti-rabbit IgG (E28002; Novodiax, Hayward, Calif., USA) or 1:2500 mouse anti-human IgG HRP (109-035-088; Jackson ImmunoResearch, West Grove, Pa., USA). Subsequently, plates were washed and developed with ultra-TMB substrate (Thermo Fisher Scientific, Waltham, Mass.) and the reaction was stopped with 3 M NaOH (Thermo Fisher Scientific, Waltham, Mass., USA) and read the plate on a spectrophotometer at 450 nm.

To determine in vitro function of rhATG, peripheral blood mononuclear cells were isolated from whole blood acquired from a CRO (StemCell Technologies, Vancouver, Canada) and frozen. PBMCs were thawed, washed, and plated at $1.5 \times 10^5$ cells/well in singlets. Thymoglobulin or rhATG were diluted five-fold starting at 40 µg/mL total IgG and co-incubated with each donor PBMC. Cells were co-incubated overnight at 37° C. After incubation, cells were washed, FcR blocked, and stained for CD45 (clone H130; BioLegend #304008, San Diego, Calif., USA), CD3 (clone UCHT1; BioLegend #300439, San Diego, Calif., USA), CD8 (clone BW135/80; Miltenyi #130-113-157, Bergisch Gladbach, Germany), CD20 (clone 2H7; BioLegend, San Diego, Calif.), CD56 (clone 5.1H11; BioLegend #362509, San Diego, Calif., USA), and CD16 (clone 3G8; BioLegend #302017, San Diego, Calif., USA). 1 µL of each antibody was used per $1.5 \times 10^5$ cells. Flow cytometry was performed using a Cytoflex LX (Beckman Coulter, Indianapolis, Ind., USA) with CytExpert (2.3.1.22) and a consistent collection volume of 150 seconds per well was implemented for every sample. The data were analyzed by FlowJo v10 (BD Biosciences, San Jose, Calif., USA). Cell counts after antibody co-incubation relative to no-antibody control (% cells) were calculated. Results were graphed in GraphPad Prism v8 (San Diego, Calif., USA). The gating strategy is outlined in FIG. 50A.

In Vivo Mouse Efficacy Studies

Ethical approval was obtained by Institutional Animal Care and Use Committees (IACUCs) at either SSI (Copenhagen, Denmark) for the Hib challenge model or Jackson Laboratory (Sacramento, Calif., USA) for the GVH model.

IVIG+rHIG/rPIG: For IVIG+rHIG/rPIG in vivo challenge studies, the *Haemophilus* influenza strain ATCC 10211 was grown on chocolate agar plates overnight at 35° C. and 5% CO2. Single overnight colonies were resuspended in sterile saline to $1.5 \times 10^8$ CFU/mL. This suspension was diluted in BHI broth to $1.5 \times 10^7$ CFU/mL and further diluted in BHI broth with 5% mucin and 2% hemoglobin to $1.5 \times 10^4$ CFU/mL. In an IACUC-approved protocol (SSI, Copenhagen, Denmark), Balb/cJ mice (Taconic, Rensselaer, N.Y., USA; n=6 per group) were inoculated with single 0.5 mL intraperitoneal doses of $10^5$ CFU/mL ATCC 10211, and then randomized into treatment groups by animal identifier. All mice were female, age 6-8 weeks. The temperature and humidity were registered daily in the animal facilities. The temperature was 22° C.+/−2° C. and can be regulated by heating and cooling. The humidity was 55 +/−10%. The air changes per hour were approximately 8-12 times (70-73 times per hours inside cages), and light/dark period was in 12-hours interval of 6 am-6 pm/6 pm-6 am. The mice had free access to domestic quality drinking water and food (Teklad Global diet 2916C, Envigo, Indianapolis, Ind., USA) and occasionally peanuts and sunflower seeds (Koge Korn A/S, Koge, Denmark). The mice were housed in IVC cages, 6-8 mice per cage, with bedding from Tapvei. Further, the animals were offered Enviro-Dri nesting material and cardboard houses (Bio-Serv, Flemington, N.J., USA).

Approximately 1 hour before inoculation, mice were treated orally with 45 µL Nurofen (30 mg/kg) as pain relief. Twenty-four hours prior to Hib inoculation, mice were intravenously administered 200 mg/kg IVIG+rHIG/rPIG mixture, 500 mg/kg IVIG+rHIG/rPIG mixture, 500 mg/kg IVIG (Gamunex; Grifols, S. A., Sant Cugat, Spain), or saline (no treatment). For the ciprofloxacin positive control, one hour after Hib inoculation, mice were dosed with 20 mg/kg ciprofloxacin. Mice were scored for clinical signs of infection, then after 6 hours all animals were sacrificed and blood and peritoneal fluid was collected for CFU determination by serial dilution and plating of 0.02 ml spots on chocolate agar plates.

rhATG was tested for ability to delay GVHD in immunodeficient NOD scid gamma (NSG) mice (genotype: NOD.Cg-Prkdc$^{scid}$ Il2rg$^{tm1Wjl}$/SzJ), compared against rabbit-ATG (Thymoglobulin; Sanofi Genzyme, Cambridge, Mass.) and a vehicle control. All mice were female, age 6-8 weeks. The mice were ear notched for identification and housed in individually ventilated polysulfonate cages with HEPA filtered air at a density of up to 5 mice per cage. The animal room was lighted entirely with artificial fluorescent lighting, with a controlled 12 hour light/dark cycle (6 am to 6 pm light). The normal temperature and relative humidity ranges in the animal rooms were 22-26° C. and 30-70%, respectively. The animal rooms were set to have up to 15 air exchanges per hour. Filtered tap water, acidified to a pH of 2.5 to 3.0, and standard rodent chow was provided ad libitum.

Each animal was grafted with approximately $1 \times 10^7$ PBMC of a single human donor. On Day 5 after PBMC engraftment, animals were randomized by weight and dosed intravenously every other day for two weeks with 5.5 mg/kg rhATG (n=8), 6.5 mg/kg Thymoglobulin (n=8), or a vehicle control (n=8), or Days 5, 6, and 7 post-engraftment with 5.5 mg/kg rhATG (n=8), 6.5 mg/kg Thymoglobulin (n=8), or a vehicle control (n=8). Two PBMC donors were tested for each dosing regimen (2 PBMC donors ×2 dosing regimens×3 treatment groups×8 animals per group=96 animals). Animals were assessed for clinical signs of mortality daily. Mice were euthanized by CO2 asphyxiation before final study take down if they showed >20% weight loss from their starting weight or a combination of the following clinical signs: >10-20% weight loss from their starting weight, cold to touch, lethargic, pale, hunched posture and scruffy coat. 50 µL of blood was drawn from all alive animals on Days 9, 16, 23, and 30 post-engraftment via retro-orbital bleed, and flow cytometry stained for Human (hu)CD45-PE (clone HI30; BioLegend #304008, San Diego, Calif., USA) and 7AAD (BioLegend, San Diego, Calif., USA); 50 µL of CountBright beads (Thermo Fisher Scientific, Waltham, Mass., USA) were added to each sample prior to acquisition. Flow cytometric data acquisition was performed using the BD Biosciences FACSCanto flow cytometer (San Jose, Calif., USA), and data were acquired and analyzed using BD Biosciences FACSDiva™ software (version 8; San Jose, Calif., USA); lymphocytes, singlet, live cells, and CD45+ cells were gated and cell numbers quantified relative to CountBright beads. The gating strategy is outlined in FIG. 50B.

9. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

10. EQUIVALENTS

Whereas various specific embodiments have been illustrated and described, the above specification is not restrictive. It will be appreciated that various changes can be made without departing from the spirit and scope of the invention(s). Many variations will become apparent to those skilled in the art upon review of this specification.

SEQUENCE LISTING

The patent contains a lengthy sequence listing. A copy of the sequence listing is available in electronic form from the USPTO web site (https://seqdata.uspto.gov/?pageRequest=docDetail&DocID=US11718660B2). An electronic copy of the sequence listing will also be available from the USPTO upon request and payment of the fee set forth in 37 CFR 1.19(b)(3).

The invention claimed is:

1. A method of treating a subject in need thereof, the method comprising administering to the subject an effective amount of a pharmaceutical composition comprising:

a mixture of at least 100 unique recombinant antibodies wherein the mixture is capable of neutralizing Zika virus with an IC50 lower than 0.001 mg/ml using an in vitro neutralization assay, and a pharmaceutically acceptable excipient, wherein the mixture of at least 100 unique recombinant antibodies has been generated by the process of
  a. isolating single cells from a blood sample from a donor exposed to an antigen of Zika virus;
  b. amplifying polynucleotides, wherein each of the polynucleotides encodes a cognate pair of heavy chain and light chain variable regions from one of the single cells by overlap extension reverse transcriptase polymerase chain reaction (OE-RT-PCR);
  c. cloning the polynucleotides obtained from the amplification into an expression vector, thereby obtaining constructs encoding antibody fragments;
  d. expressing the antibody fragments from the constructs;
  e. generating antibody expression constructs using the subset of the constructs, wherein each of the antibody expression constructs encodes a light chain variable region, a kappa or lambda-type light chain constant region, a heavy chain variable region, and a heavy chain constant region,
  f. introducing the antibody expression constructs into a cell line, and
  g. expressing antibodies from the antibody expression constructs in the cell line, thereby obtaining the at least 100 unique recombinant antibodies;

wherein each of the at least 100 unique recombinant antibodies is an antibody comprising a cognate pair of heavy chain and light chain variable regions from a single cell out of a blood sample from a donor exposed to an antigen of Zika virus.

2. The method of claim 1, wherein the subject has a viral infection.

3. The method of claim 1, further comprising administration of one or more additional therapeutic agents.

4. The method of claim 1, wherein the subject has Zika viral infection.

5. The method of claim 1, wherein the effective amount is 0.01, 0.05, 0.15, 0.20, 0.25, or 0.30 g/kg body weight.

6. The method of claim 1, wherein the pharmaceutical composition is administered by intravenous infusion.

* * * * *